US008101770B2

(12) United States Patent
Charrier et al.

(10) Patent No.: US 8,101,770 B2
(45) Date of Patent: Jan. 24, 2012

(54) PYRIDONES USEFUL AS INHIBITORS OF KINASES

(75) Inventors: Jean-Damien Charrier, Wantage (GB); Steven Durrant, Abingdon (GB); Sharn Ramaya, Burghfield Common (GB); Juan-Miguel Jimenez, Abingdon (GB); Alistair Rutherford, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 969 days.

(21) Appl. No.: 11/304,057

(22) Filed: Dec. 15, 2005

(65) Prior Publication Data

US 2006/0183911 A1 Aug. 17, 2006

Related U.S. Application Data

(60) Provisional application No. 60/636,754, filed on Dec. 16, 2004, provisional application No. 60/673,870, filed on Apr. 22, 2005.

(51) Int. Cl.
*C07D 401/00* (2006.01)
*A61K 31/44* (2006.01)

(52) U.S. Cl. .................................. 546/268.1; 514/336
(58) Field of Classification Search ............... 546/268.1; 514/336
See application file for complete search history.

(56) References Cited

U.S. PATENT DOCUMENTS

| | | | |
|---|---|---|---|
| 4,004,012 A | 1/1977 | Lesher et al. |
| 4,072,746 A | 2/1978 | Lesher et al. |
| 4,107,315 A | 8/1978 | Lesher et al. |
| 4,225,715 A | 9/1980 | Lesher et al. |
| 4,271,168 A | 6/1981 | Lesher et al. |
| 4,313,951 A | 2/1982 | Lesher et al. |
| 4,514,400 A | 4/1985 | Campbell |
| 4,539,321 A | 9/1985 | Campbell |
| 4,563,528 A | 1/1986 | Gomez-Parra et al. |
| 5,521,179 A | 5/1996 | Bernstein et al. |
| 6,118,002 A | 9/2000 | Vander-Roest et al. |
| 6,265,350 B1 | 7/2001 | Schnatterer et al. |
| 6,403,596 B1 | 6/2002 | Liverton et al. |
| 6,452,008 B2 | 9/2002 | Muraoka et al. |
| 6,706,717 B2 | 3/2004 | Barrish et al. |
| 2004/0023973 A1 | 2/2004 | Nagato et al. |

FOREIGN PATENT DOCUMENTS

| | | |
|---|---|---|
| CA | 1103253 | 8/1980 |
| CA | 1103254 | 8/1980 |
| EP | 0462800 A2 | 12/1991 |
| EP | 0481802 A1 | 4/1992 |
| EP | 1 325 921 A2 | 7/2003 |
| GB | 2064533 A1 | 11/1980 |
| JP | 61140583 | 6/1986 |
| WO | WO 98/24780 A1 | 6/1998 |
| WO | 9965901 A1 | 12/1999 |
| WO | WO 00/56737 A2 | 9/2000 |
| WO | 02053543 A1 | 11/2002 |
| WO | WO 2004/016609 A1 | 2/2004 |
| WO | 2006065946 A1 | 6/2006 |
| WO | 2006099268 A2 | 9/2006 |

OTHER PUBLICATIONS

Graham L. Patrick "Introduction to Medicinal Chemistry", 3rd Edition, 2005, Oxford University Press, Inc., New York, NY, pp. 200-206.*
F. Zaragoza Dörwald "Side Reactions in Organic Synthesis: A Guide to Successful Synthesis Design" 2005 Wiley-VCH Verlag GmbH & Co. KGaA, Weinheim.*
V. Gomez-Parra et al, "An Improved Synthesis of Amrinone by Phase-Transfer Catalysis", Arch. Pharm., 317, 183-185, (1984).
H. Niedrich et al., "Untersuchungen zur Synthese von 3-Amino-5-(pyrid-4-yl)-1,2-dihydro-pyrid-2-on (Cordemcura) aus technischen Pyridinbasengemischen", Pharmazie, 41, 173-175, (1986).
A.A. Krause et al., "Synthesis of 3-(N-R) Carbamoyl-5(PYRID-4-YL)Pyridine-2(1H)-Thiones and their derivatives", Khim. Geterotsikl. Soedin, 67-70, (1992).
Walker et al., "Synthesis of Benzo[f]quinolines and Ergolines from 5-Phenyl-6-methyl-2-pyridones", Journal of Organic Chemistry, 26, 4441-4455, (1961).
Sadiq et al., "Possible contribution of acetylamrinone and its enhancing effects on platelet aggregation under shear stress conditions in the onset of thrombocytopenia in patients treated with amrionone", Thrombosis Research, 111, 357-361, (2003).
E. Allen et al., "Hemodynamic Effects of N-Acetylamrinone in a porcine model of group B streptococcal sepsis", Drug Metabolism and Disposition, 24, 1028-1031, (1996).
Pappas et al., "HPLC micromethod for amrinone and metabolites in patients receiving concurrent cephalosporin therapy", Clinical Chemistry, 42:5, 761-765, (1996).
Laganiere et al., "Amrinone and N-acetylamrinone assay in human plasma using solid-phrase extraction and reversed phase chromatography", Journal of Pharmaceutical & Biomedical Analysis, 12:3, 407-411, (1994).
Lawless et al., "Simplified Assay of Amrinone in Plasma by High-Performance Liquid Chromatography", Therapeutic Drug Monitoring, 12:570, 570-573, (1990).
R.A. Hamilton et al., "Effect of the acetylator phenotype on amrinone pharmacokinetics" Clinical Pharmacology and Therapeutics, 40, 615-619, (1986).
H. Niedrich et al., "Untersuchungen zur Reinigung und Charakterisierung von Cordemcura", Pharmazie, 41, 176-179, (1986).
J.F. Baker et al., "Metabolism of Amrinone in Animals", Drug Metabolism and Disposition, 10(2), 168-172, (1982).
M.P. Kullberg et al., "High-performance liquid chromatographic analysis of amrinone and its N-acetyl derivative in plasma", Journal of Chromatography, 187, 264-270, (1980).
M.P. Kullberg et al., Amrinone metabolism, Clinical Pharmacology and Therapeutics, 29, 394-401, (1981).
H. Migulla et al., "Mikromethode zur Bestimmung von Amrinon und Actylamrinon in Plasma und Urin durch HPLC", Pharmazie, 49, 290-291, (1994).

* cited by examiner

*Primary Examiner* — Rita Desai
*Assistant Examiner* — John Mabry
(74) *Attorney, Agent, or Firm* — Rory C. Stewart

(57) ABSTRACT

The present invention relates to compounds useful as inhibitors of protein kinases. The invention also provides pharmaceutically acceptable compositions comprising said compounds and methods of using the compositions in the treatment of various disease, conditions, or disorders. The invention also provides processes for preparing the compounds of the invention and intermediate compounds useful in these processes.

25 Claims, No Drawings

PYRIDONES USEFUL AS INHIBITORS OF KINASES

CROSS-REFERENCE TO RELATED APPLICATIONS

This application claims the benefit of U.S. Provisional Application 60/673,870, filed Apr. 22, 2005 and U.S. Provisional Application 60/636,754, filed Dec. 16, 2004, which are incorporated herein in their entirety.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders. The invention also provides processes for preparing the compounds of the invention and intermediate compounds useful in these processes.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

The Tec family of non-receptor tyrosine kinases plays a central role in signaling through antigen-receptors such as the TCR, BCR and Fcε receptors (reviewed in Miller A, et al., Current Opinion in Immunology 14; 331-340 (2002). Tec family kinases are essential for T cell activation. Three members of the Tec family, Itk, Rlk and Tec, are activated downstream of antigen receptor engagement in T cells and transmit signals to downstream effectors, including PLC-γ. Deletion of Itk in mice results in reduced T cell receptor (TCR)-induced proliferation and secretion of the cytokines IL-2, IL-4, IL-5, IL-10 and IFN-γ (Schaeffer et al, Science 284; 638-641 (1999)), Fowell et al, Immunity 11; 399-409 (1999), Schaeffer et al Nature Immunology 2, 12; 1183-1188 (2001))). The immunological symptoms of allergic asthma are attenuated in Itk−/− mice. Lung inflammation, eosinophil infiltration and mucous production are drastically reduced in Itk−/− mice in response to challenge with the allergen OVA (Mueller et al, Journal of Immunology 170: 5056-5063 (2003)). Itk has also been implicated in atopic dermatitis. This gene has been reported to be more highly expressed in peripheral blood T cells from patients with moderate and/or severe atopic dermatitis than in controls or patients with mild atopic dermatitis (Matsumoto et al, International archives of Allergy and Immunology 129; 327-340 (2002)).

Splenocytes from Rlk−/− mice secrete half the IL-2 produced by wild type animals in response to TCR engagement (Schaeffer et al, Science 284; 638-641 (1999)), while combined deletion of Itk and Rlk in mice leads to a profound inhibition of TCR-induced responses including proliferation and production of the cytokines IL-2, IL-4, IL-5 and IFN-γ (Schaeffer et al Nature Immunology 2, 12; 1183-1188 (2001)), Schaeffer et al, Science 284; 638-641 (1999)). Intracellular signaling following TCR engagement is effected in Itk/Rlk deficient T cells; inositol triphosphate production, calcium mobilization, MAP kinase activation, and activation of the transcription factors NFAT and AP-1 are all reduced (Schaeffer et al, Science 284; 638-641 (1999), Schaeffer et al Nature Immunology 2, 12; 1183-1188 (2001)).

Tec family kinases are also essential for B cell development and activation. Patients with mutations in Btk have a profound block in B cell development, resulting in the almost complete absence of B lymphocytes and plasma cells, severely reduced Ig levels and a profound inhibition of humoral response to recall antigens (reviewed in Vihinen et al Frontiers in Bioscience 5:d917-928). Mice deficient in Btk also have a reduced number of peripheral B cells and greatly decreased levels of IgM and IgG3. Btk deletion in mice has a profound effect on B cell proliferation induced by anti-IgM, and inhibits immune responses to thymus-independent type II antigens (Ellmeier et al, J Exp Med 192:1611-1623 (2000)).

Tec kinases also play a role in mast cell activation through the high-affinity IgE receptor (FcεRI). Itk and Btk are expressed in mast cells and are activated by FcεRI cross-linking (Kawakami et al, Journal of Immunology; 3556-3562 (1995)). Btk deficient murine mast cells have reduced degranulation and decreased production of proinflammatory cytokines following FcεRI cross-linking (Kawakami et al. Journal of leukocyte biology 65:286-290). Btk deficiency also results in a decrease of macrophage effector functions (Mukhopadhyay et al, Journal of Immunology; 168, 2914-2921 (2002)).

Accordingly, there is a great need to develop compounds useful as inhibitors of protein kinases. In particular, it would be desirable to develop compounds that are useful as inhibitors of Tec family (e.g., Tec, Btk, Itk/Emt/Tsk, Bmx, Txk/Rlk) protein kinases, particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of protein kinases. In certain embodiments, these compounds are effective as inhibitors of Tec family (e.g., Tec, Btk, Itk/Emt/Tsk, Bmx, Txk/Rlk) protein kinases. These compounds have the formula I as defined herein or a pharmaceutically acceptable salt thereof.

These compounds and pharmaceutically acceptable compositions thereof are useful for treating or preventing a variety of diseases, disorders or conditions, including, but not limited to, an autoimmune, inflammatory, proliferative, or hyperproliferative disease or an immunologically-mediated disease. The compositions are also useful in methods for preventing thrombin-induced platelet aggregation. The compounds provided by this invention are also useful for the study of kinases in biological and pathological phenomena; the study of intracellular signal transduction pathways mediated by such kinases; and the comparative evaluation of new kinase inhibitors.

Also provided by this invention are processes for preparing compounds of this invention and intermediate compounds useful in these processes.

DETAILED DESCRIPTION OF THE INVENTION

This invention describes compounds of Formula I:

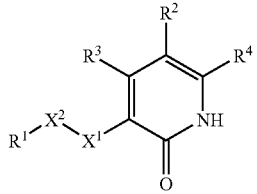

Formula I or a pharmaceutically accepted salt thereof, wherein
each $R^3$ and $R^4$ is independently H, halogen or $C_{1-4}$ aliphatic optionally substituted with halogen, $C_{1-2}$ aliphatic, $OCH_3$, $NO_2$, $NH_2$, $CN$, $NHCH_3$, $SCH_3$, or $N(CH)_2$.
$R^2$ is a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; $R^2$ is optionally substituted with $J^R$;
each $X^1$ and $X^2$ is independently —C(O)—, —NR—, or —SO₂— wherein one of $X^1$ or $X^2$ is —NR— and the other of $X^1$ or $X^2$ is —C(O)— or —SO₂—;
R is H, unsubstituted $C_{1-6}$ aliphatic;
$R^1$ is -T-Q;

T is a bond or $C_{1-6}$ aliphatic, wherein up to three methylene units of the chain are optionally and independently replaced by G or G' wherein G is —NR⁵—, —O—, —S—, —SO—, —SO₂—, —CS—, or —CO—; G' is cyclopropyl, C≡C, or C=C; T is optionally substituted with $J^T$;
Q is independently hydrogen, a $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; Q is optionally substituted with $J^Q$;
$R^5$ is optionally substituted R, $C_{6-10}$ aryl, $C_{3-10}$ cycloaliphatic, 5-14 membered heteroaryl, or 5-14 membered heterocyclyl; or two $R^5$ groups, together with the atom(s) to which they are attached, form an optionally substituted 3-7 membered monocyclic or 8-14 membered bicyclic ring;
the optional substituents $J^R$, $J^T$, and $J^Q$ are defined herein.

Certain embodiments of this invention provide that
when $R^2$ is 4-pyridyl or 3-pyridyl, $R^3$ is H, $X^1$ is —NR—, R is H, and $X^2$ is —C(O)—; then
  a) $R^1$ is not CH(CH₃)OC(=O)CH₃; CH₂C(=O)CH₃; or CH₂C(=O)CH₃;
  b) $R^1$ is not $C_{1-6}$alkyl or O($C_{1-6}$alkyl);
when $R^2$ is 4-pyridyl, $R^3$ and $R^4$ are H, $X^1$ is —NR—, R is H, and $X^2$ is —C(O)—, then
  a) when T is a bond, Q is not methyl, imidazole, OCH₃, or H;
  b) when T is —CH₂—, Q is not 3-OH-phenyl, 4-OH-phenyl, 4-pyridyl, 3-NO₂-phenyl, OH, —O(C=O)CH₃, or —C(=O)CH₃;
  c) when T is —CH(CH₃)—, Q is not —OC(=O)CH₃;
  d) when T is —CH₂CH₂—, Q is not 2-pyridyl or —COOH;
  e) when T is CH(CH₃)OC(=O)—, Q is not CH₃;
when $R^2$ is 4-pyridyl, $R^3$ is H, $R^4$ is not H, $X^1$ is —NR—, R is H, and $X^2$ is —C(O)—, then
  a) when T is a bond, Q is not CH₃;
  b) $R^1$ is not CH(CH₃)OC(=O)CH₃;
when $R^2$ is 2,4-pyrimidyl, $R^3$ and $R^4$ are H, $X^1$ is —NR—, R is H, and $X^2$ is —C(O)—, then
  a) $R^1$ is not methyl, NHCH₃, or —NHC(=O)NH₂;
when $R^2$ is 4-pyridyl, $R^3$ and $R^4$ are H, $X^1$ is —NR—, R is H, and $X^2$ is —SO₂—, then
  a) when T is a bond, Q is not optionally substituted $C_{6-10}$ aryl or $C_{5-10}$ heteroaryl;
when $R^2$ is 4-thiazolyl, $R^3$ is H, $R^4$ is CH₃, $X^1$ is —C(O)—, $X^2$ is —NR—, R is H, then
  a) when T is —CH₂CH₂—, Q is not N(CH₃)₂;
when $R^2$ is unsubstituted phenyl, $R^3$ and $R^4$ are H, $X^1$ is —NR—, R is H, and $X^2$ is —C(O)—,
  then, when T is $C_1$ aliphatic wherein 1 methylene unit of the chain is replaced by G; G is —NR⁵—; and $R^5$ is H; then Q is not 2,6-di-isopropylphenyl;
when $R^2$ is unsubstituted phenyl, $R^3$ is H, $R^4$ is CH₃, $X^1$ is —C(O)—, $X^2$ is —NR—, R is H, then
  a) when T is a bond, Q is not CH₃ or CH₂CH₃;
  b) when T is —CH₂CH₂—, Q is not unsubstituted phenyl or N(CH₂CH₃)₂;
  c) when T is —CH₂CH₂CH₂—, Q is not N(CH₂CH₃)₂;
  d) $R^1$ is not NH₂;
when $R^2$ is unsubstituted phenyl, $R^3$ is H, $R^4$ is CH₃, $X^1$ is —NR—, R is H, $X^2$ is —C(O)—, then
  a) when T is —O—CH₂—, Q is not unsubstituted phenyl;
when $R^2$ is 4-OCH₃ phenyl, $R^3$ is H, $R^4$ is CH₃, $X^1$ is —NR—, R is H, $X^2$ is —C(O)—, then
  a) when T is a bond, Q is not CH₃;

when $R^2$ is a 6-membered heteroaryl with 2 nitrogens; $R^3$ is H, methyl, or ethyl; $R^4$ is methyl or ethyl; $X^1$ is —NR—, R is H, $X^2$ is —C(O)—, then
  a) $R^1$ is not $CH_3$;
when $X^1$ is —C(O)—, $X^2$ is —NR—, and R is H, then $R^1$ is not H or methyl;
when $R^2$ is

$R^3$ and $R^4$ are H, $X^1$ is —NR—, R is H, and $X^2$ is —C(O)—, then $R^1$ is not $CH_3$;
when $R^2$ is unsubstituted phenyl, $R^3$ and $R^4$ are H, $X^1$ is —C(O)—, $X^2$ is —NR—, R is H, then $R^1$ is not

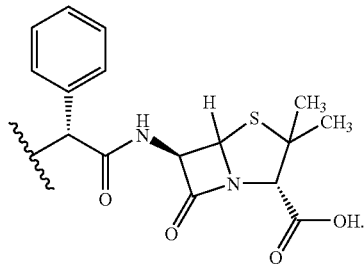

Other embodiments of this invention provide that when $R^2$ is 4-pyridyl, 3-pyridyl, or

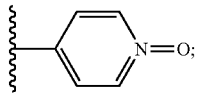

$R^3$ is H, $X^1$ is —NR—, R is H, and $X^2$ is —C(O)—; then
  a) $R^1$ is not H, $C_{1-6}$alkyl, $O(C_{1-6}$alkyl), $CH(CH_3)OC(=O)CH_3$, or imidazole;
  b) when T is —$CH_2$—, Q is not 3-OH-phenyl, 4-OH-phenyl, 4-pyridyl, 3-$NO_2$-phenyl, OH, $OC(=O)CH_3$, or —$C(=O)CH_3$;
  c) when T is —$CH_2CH_2$—, Q is not 2-pyridyl or —COOH;
when $R^2$ is 2,4-pyrimidyl, $R^3$ and $R^4$ are H, $X^1$ is —NR—, R is H, and $X^2$ is —C(O)—, then
  a) $R^1$ is not methyl, $NHCH_3$, or —$NHC(=O)NH_2$;
when $R^2$ is 4-pyridyl, $R^3$ and $R^4$ are H, $X^1$ is —NR—, R is H, and $X^2$ is —$SO_2$—, then
  a) when T is a bond, Q is not optionally substituted $C_{6-10}$ aryl or $C_{5-10}$ heteroaryl;
when $R^2$ is 4-thiazolyl, $R^3$ is H, $R^4$ is $CH_3$, $X^1$ is —C(O)—, $X^2$ is —NR—, R is H, then
  a) when T is —$CH_2CH_2$—, Q is not $N(CH_3)_2$;
when $R^2$ is optionally substituted phenyl, $R^3$ is H, $X^1$ is —NR—, R is H, and $X^2$ is —C(O)—, then,
  a) when T is $C_1$aliphatic wherein 1 methylene unit of the chain is replaced by G; G is —$NR^5$—; and $R^5$ is H; then Q is not 2,6-di-isopropylphenyl;
  b) when T is —O—$CH_2$—, Q is not unsubstituted phenyl;
  c) when T is a bond, Q is not $CH_3$;
when $R^2$ is unsubstituted phenyl, $R^3$ is H, $X^1$ is —C(O)—, $X^2$ is —NR—, R is H, then a) when T is a bond, Q is not $CH_3$ or $CH_2CH_3$;
  b) when T is —$CH_2CH_2$—, Q is not unsubstituted phenyl or $N(CH_2CH_3)_2$;
  c) when T is —$CH_2CH_2CH_2$—, Q is not $N(CH_2CH_3)_2$;
  d) $R^1$ is not $NH_2$ or

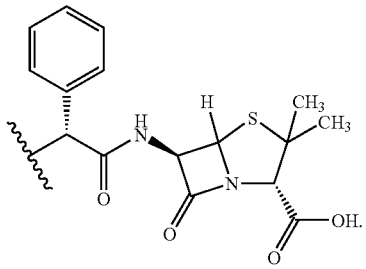

when $R^2$ is a 6-membered heteroaryl with 2 nitrogens; $R^3$ is H, methyl, or ethyl; $R^4$ is methyl or ethyl; $X^1$ is —NR—, R is H, $X^2$ is —C(O)—, then $R^1$ is not $CH_3$;
when $X^1$ is —C(O)—, $X^2$ is —NR—, and R is H, then $R^1$ is not H or methyl.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "optionally interrupted" refers to the replacement of one atom within an alkylidene chain with another atom. Unless otherwise specified, the second atom can replace the first atom at any position, including terminal atoms. For example, a $C_{1-3}$ alkyl chain optionally interrupted with —O— can form —OCH$_2$CH$_3$, —CH$_2$—OCH$_3$, or CH$_2$CH$_2$OH. Unless otherwise specified, the terminal groups are bonded to hydrogen on the terminal side.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

It should be understood that ring systems herein may be linearly fused, bridged, or spirocyclic.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents (e.g $J^R$, $J^T$, and $J^Q$) on the unsaturated carbon atom of an aryl or heteroaryl group are selected from halogen; —R$^\circ$; $C_{1-6}$alkyl, optionally substituted with R$^\circ$, wherein up to three methylene units of the chain are optionally and independently replaced by, —NR$^\circ$—, —O—, —S—, —SO—, SO$_2$—, or —CO— in a chemically stable arrangement; —OCF$_3$; —SCF$_2$; $C_{1-4}$haloalkyl; —CH$_2$-halogen; $C_{6-10}$aryl, optionally substituted with R$^\circ$; a 5-12 membered heteroaryl optionally substituted with R$^\circ$; 3-12 membered heterocyclic ring optionally substituted with R$^\circ$; —O(Ph) optionally substituted with R$^\circ$; —CH═CH(Ph), optionally substituted with R$^\circ$; —CH≡CH(Ph), optionally substituted with R$^\circ$, —C$_{1-6}$alkyl-(5-12 membered heterocyclyl), optionally substituted with R$^\circ$; —C$_{1-6}$alkyl-(C$_{6-10}$aryl), optionally substituted with R$^\circ$, —C$_{1-6}$alkyl-(5-10 membered heteroaryl), optionally substituted with R$^\circ$; C$_{3-10}$cycloaliphatic optionally substituted with R$^\circ$; —C$_{1-6}$alkyl-(C$_{3-10}$cycloaliphatic), optionally substituted with R$^\circ$; —(C$_{1-6}$alkyl)-OR$^\circ$, optionally substituted with R$^\circ$; —(C$_{1-6}$alkyl)-N(R$^\circ$)$_2$, optionally substituted with R$^\circ$; —(C$_{1-6}$alkyl)-SR$^\circ$, optionally substituted with R$^\circ$; —NO$_2$; —CN; —OR$^\circ$; —SR$^\circ$; —N(R$^\circ$)$_2$; —NR$^\circ$C(O)R$^\circ$; —NR$^\circ$C(S)R$^\circ$; —NR$^\circ$C(O)N(R$^\circ$)$_2$; —NR$^\circ$C(S)N(R$^\circ$)$_2$; —NR$^\circ$CO$_2$R$^\circ$; —NR$^\circ$NR$^\circ$C(O)R$^\circ$; —NR$^\circ$NR$^\circ$C(O)N(R$^\circ$)$_2$; —NR$^\circ$NR$^\circ$CO$_2$R$^\circ$; —C(O)C(O)R$^\circ$; —C(O)CH$_2$C(O)R$^\circ$; —CO$_2$R$^\circ$; —C(O)R$^\circ$; —C(S)R$^\circ$; —C(O)N(R$^\circ$)$_2$; —C(S)N(R$^\circ$)$_2$; —OC(O)N(R$^\circ$)$_2$; —OC(O)R$^\circ$; —C(O)N(OR$^\circ$)R$^\circ$; —C(NOR$^\circ$)R$^\circ$; —S(O)$_2$R$^\circ$; —S(O)$_3$R$^\circ$; —SO$_2$N(R$^\circ$)$_2$; —S(O)R$^\circ$; —NR$^\circ$SO$_2$N(R$^\circ$)$_2$; —NR$^\circ$SO$_2$R$^\circ$; —N(OR$^\circ$)R$^\circ$; —C(═NH)—N(R$^\circ$)$_2$; —P(O)$_2$R$^\circ$; —PO(R$^\circ$)$_2$; —OPO(R$^\circ$)$_2$; and —(CH$_2$)$_{0-2}$NHC(O)R$^\circ$;

Each R$^\circ$ is independently selected from hydrogen, NH$_2$, NH(C$_{1-4}$aliphatic), N(C$_{1-4}$aliphatic)$_2$, halogen, OH, O(C$_{1-4}$aliphatic), NO$_2$, CN, CO$_2$H, CO$_2$(C$_{1-4}$aliphatic), O(haloC$_{1-4}$aliphatic), haloC$_{1-4}$aliphatic, optionally substituted C$_{1-6}$ aliphatic wherein up to 2 methylene units are optionally replaced by O, N, or S, optionally substituted 5-8 membered heterocyclyl, unsubstituted 5-6 membered heteroaryl, unsubstituted 3-6 membered cycloaliphatic, unsubstituted phenyl, unsubstituted —O(Ph), unsubstituted —CH$_2$(Ph), unsubstituted —CH$_2$(5-7 membered heterocyclyl), or unsubstituted —CH$_2$(5-6 membered heteroaryl); or, notwithstanding the definition above, two independent occurrences of R$^\circ$, on the same substituent or different substituents, taken together with the atom(s) to which each R$^\circ$ group is bound, form an optionally substituted 3-12 membered saturated, partially unsaturated, or fully unsaturated monocyclic or bicyclic ring having 0-4 heteroatoms independently selected from nitrogen, oxygen, or sulfur;

Optional substituents on the aliphatic group of R° or on the ring formed by 2 R° groups are selected from $NH_2$, $NH(C_{1-4}$ aliphatic), $N(C_{1-4}$aliphatic$)_2$, halogen, $C_{1-4}$aliphatic, OH, $O(C_{1-4}$aliphatic), $NO_2$, CN, $CO_2H$, $CO_2(C_{1-4}$aliphatic), $O($haloC$_{1-4}$ aliphatic), and halo$C_{1-4}$aliphatic, wherein each of the foregoing $C_{1-4}$aliphatic groups of R° is unsubstituted;

An aliphatic or heteroaliphatic group, or a non-aromatic heterocyclic ring may contain one or more substituents. Suitable substituents (e.g $J^R$, $J^T$, and $J^Q$) on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), =NOH, and =NR*, where each R* is independently selected from hydrogen and an optionally substituted $C_{1-6}$ aliphatic. Optional substituents on the aliphatic group of R* are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), and halo($C_{1-4}$ aliphatic), wherein each of the foregoing $C_{1-4}$aliphatic groups of R* is unsubstituted.

Optional substituents (e.g $J^R$, $J^T$, and $J^Q$) on the nitrogen of a non-aromatic heterocyclic ring or on the nitrogen of the heteroaryl ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, and —NR$^+$SO$_2$R$^+$; wherein R$^+$ is hydrogen, an optionally substituted $C_{1-6}$ aliphatic, optionally substituted phenyl, optionally substituted —O(Ph), optionally substituted —CH$_2$(Ph), optionally substituted —(CH$_2$)$_2$(Ph); optionally substituted —CH=CH(Ph); or an unsubstituted 5-6 membered heteroaryl or heterocyclic ring having one to four heteroatoms independently selected from oxygen, nitrogen, and sulfur, or, notwithstanding the definition above, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloaliphatic ring having 0-3 heteroatoms independently selected from nitrogen, oxygen, or sulfur. Optional substituents on the aliphatic group or the phenyl ring of R$^+$ are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), and halo($C_{1-4}$ aliphatic), wherein each of the foregoing $C_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule, wherein one or more methylene units may optionally and independently be replaced with a group including, but not limited to, CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S; or NR.

As detailed above, in some embodiments, two independent occurrences of R° (or R$^+$, or any other variable similarly defined herein), are taken together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

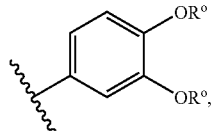

these two occurrences of R° are taken together with the oxygen atoms to which they are bound to form a fused 6-membered oxygen containing ring:

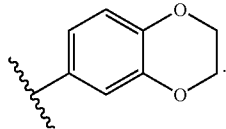

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Unless otherwise stated, structures depicted herein are also meant to include an N-oxide derivative or a pharmaceutically acceptable salt of each of the compounds of formula I.

According to one embodiment of this invention, T is $C_{1-3}$aliphatic optionally interrupted with zero or one G groups wherein G is selected from O, NR$^5$, and S.

In some embodiments, T is —$C_{1-2}$aliphatic-G- wherein G is O or NR$^5$, and G is bound to Q in a chemically stable arrangement. In other embodiments, G is bound to X$^2$ in a chemically stable arrangement. In yet other embodiments T is $C_{1-3}$aliphatic optionally interrupted with zero G groups.

In some embodiments, T is $C_{1-3}$aliphatic optionally interrupted with zero or one G' groups. In other embodiments, T is $C_{1-3}$aliphatic optionally interrupted with zero or one G or G' groups.

In some embodiments, T is —CH$_2$—; in other embodiments T is a bond.

According to one embodiment of the invention, each R$^3$ and R$^4$ is independently H. In some embodiments, both R$^3$ and R$^4$ are H.

According to some embodiments R$^2$ is a 5-8 membered monocyclyl optionally substituted with up to 5 J$^R$ groups. In certain embodiments, R$^2$ is a 5-6 membered aryl or heteroaryl optionally substituted with up to 5 J$^R$ groups. In other embodiments R$^2$ is a 5-6 membered heteroaryl optionally substituted with up to 5 J$^R$ groups, preferably R$^2$ is a 6 membered heteroaryl having 1 or 2 nitrogen atoms wherein R$^2$ is optionally substituted with up to 5 J$^R$ groups.

In some embodiments, R$^2$ is C$_{3-8}$cycloaliphatic optionally substituted with up to five J$^R$ groups. In other embodiments, R$^2$ is C$_{3-8}$cycloalkyl optionally substituted with up to five J$^R$ groups. In certain embodiments, R$^2$ is C$_{3-8}$cycloalkenyl optionally substituted with up to five J$^R$ groups. In other embodiments, R$^2$ is cyclopentyl, cyclopentenyl, cyclohexyl, cyclohexenyl, cycloheptyl, or cycloheptenyl, optionally substituted with up to five J$^R$ groups.

In some embodiments R$^2$ is a pyridine ring optionally substituted with up to 5 J$^R$ groups. In some embodiments, R$^2$ is 2-pyridinyl, 3-pyridyl, or 4-pyridyl optionally substituted with up to five J$^R$ groups. In certain embodiments, R$^2$ is a pyrimidine ring optionally substituted with up to five J$^R$ groups. In some embodiments, R$^2$ is a 2,4 pyrimidinyl. In other embodiments, R$^2$ is a 5-membered heteroaryl ring optionally substituted with up to five J$^R$ groups. In some embodiments, R$^2$ is thiophene or pyrazole optionally substituted with up to five J$^R$ groups. In yet other embodiments R is phenyl optionally substituted with up to 5 J$^R$ groups.

In some embodiments R$^2$ is optionally substituted with up to 5 J$^R$ groups; in other embodiments, up to 3 J$^R$ groups; in yet other embodiments, 0 or 1 J$^R$ groups.

In some embodiments of this invention, J$^R$ is selected from C$_{1-6}$alkyl, C$_{6-10}$aryl, —C$_{1-6}$alkyl-C$_{6-10}$aryl, C$_{1-4}$haloalkyl, —OR°, —N(R°)$_2$, —SR°, 3-12 membered heterocyclyl, —(C$_{1-6}$alkyl)-OR°, —(C$_{1-6}$alkyl)-N(R°)$_2$, —(C$_{1-6}$alkyl)-SR°, —C(O)OR°, —NR°COR°, —COR°, —CON(R°)$_2$, —SO$_2$R°, —SO$_2$N(R°)$_2$, and C$_{1-6}$alkyl wherein up to three methylene units of the chain are independently replaced by, —NR°—, —O—, —S—, —SO—, SO$_2$—, or —CO— in a chemically stable arrangement.

In certain embodiments, J$^R$ is selected from oxo or ═NOH.

In other embodiments J$^R$ is —OR°, —N(R°)$_2$, —SR°, NO$_2$, CN, —(C$_{1-6}$alkyl)-OR°, —(C$_{1-6}$alkyl)-N(R°)$_2$, or —(C$_{1-6}$alkyl)-SR°.

In some embodiments, each J$^R$ is independently selected from optionally substituted 5-8 membered heterocyclyl, optionally substituted —NR(C$_{1-4}$alkyl)N(R°)$_2$, optionally substituted —NR(C$_{1-4}$alkyl)OR°, —N(R°)$_2$, or optionally substituted —NH(5-6 membered heterocyclyl). In certain embodiments J$^R$ is —NH(C$_{1-4}$alkyl)N(R°)$_2$; in other embodiments —NH(C$_{1-4}$alkyl)NHR° or —NH(C$_{1-4}$alkyl)NH$_2$; In some embodiments J$^R$ is —NR(CH$_2$CH$_2$)N(R°)$_2$; In other embodiments J$^R$ is —N(CH$_3$)CH$_2$CH$_2$N(R°)$_2$;

In other embodiments, each J$^R$ is independently selected from optionally substituted —NH(5-6 membered heterocyclyl).

In certain embodiments, each J$^R$ is 5-6 membered heterocyclyl contains 1-2 nitrogen atoms. In some embodiments, the 5-6 membered heterocyclyl is selected from pyrrolidine, piperidine, or piperazine.

In some embodiments J$^R$ is optionally and independently substituted with R°.

In one embodiment of this invention, each X$^1$ and X$^2$ is independently —C(O)— or —NR— wherein one of X$^1$ or X$^2$ is —NR— and the other of X$^1$ or X$^2$ is —C(O)—.

In some embodiments X$^1$ is —C(O)— and X$^2$ is —NR—.

In other embodiments X$^1$ is —NR— and X$^2$ is —C(O)—.

In one embodiments of this invention, Q is a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur.

In certain embodiments Q is C$_{6-10}$ aryl, C$_{3-10}$ cycloaliphatic, 5-14 membered heteroaryl, or 5-14 membered heterocyclyl. In other embodiments Q is C$_{6-10}$ aryl or 5-14 membered heteroaryl. In yet other embodiments Q is a 5-6 membered aryl or heteroaryl. In some embodiments, Q is 5-8 membered heterocyclyl; in certain embodiments, 5-6 membered heterocyclyl; In certain embodiments Q is phenyl.

In some embodiments of this invention, Q is substituted with up to 5 J$^Q$ groups wherein J$^Q$ is CN, C$_{1-6}$alkyl, C$_{6-10}$aryl, —C$_{1-6}$alkyl-C$_{6-10}$aryl, C$_{1-4}$haloalkyl, —OR°, —N(R°)$_2$, —SR°, —(C$_{1-6}$alkyl)-OR°, —(C$_{1-6}$alkyl)-N(R°)$_2$, —(C$_{1-6}$alkyl)-SR°, —C$_{1-6}$alkyl-(C$_{3-10}$heterocyclyl), —C(O)OR°, —NR°COR°, —COR°, —CON(R°)$_2$, —SO$_2$R°, —SO$_2$N(R°)$_2$, or C$_{1-6}$alkyl wherein up to three methylene units are optionally and independently replaced by, —NR°—, —O—, —S—, —SO—, SO$_2$—, or —CO— in a chemically stable arrangement.

In some embodiments, J$^Q$ is selected from C$_{1-6}$alkyl, CN, C$_{1-4}$haloalkyl, —OR°, —N(R°)$_2$, —SR°, —(C$_{1-6}$alkyl)-OR°, —(C$_{1-6}$alkyl)-N(R°)$_2$, —(C$_{1-6}$alkyl)-SR°, C$_{6-10}$aryl, —C$_{1-6}$alkyl-C$_{6-10}$aryl, C$_{3-10}$cycloaliphatic, —C$_{1-6}$alkyl-(C$_{3-10}$cycloaliphatic), C$_{3-10}$heterocyclyl, —C$_{1-6}$alkyl-(C$_{3-10}$heterocyclyl), —C(O)OR°, —NR°COR°, —COR°, —CON(R°)$_2$, —SO$_2$R°, —SO$_2$N(R°)$_2$, or C$_{1-6}$alkyl wherein up to three methylene units are optionally and independently replaced by, —NR°—, —O—, —S—, —SO—, SO$_2$—, —CO—, cyclopropyl, C≡C, or C═C in a chemically stable arrangement; each J$^Q$ is optionally and independently substituted with R°.

In some embodiments, J$^Q$ is —SO$_2$N(R°)$_2$, —SO$_2$R°, —NR°C(O)OR°, —C≡C—R°, —C═C—R°, phenyl, —O-Ph, —O—CH$_2$Ph, C$_{5-6}$heteroaryl, C$_{3-7}$heterocyclyl, or C$_{3-7}$cyclyoaliphatic.

In certain embodiments, J$^Q$ is CN, C$_{1-6}$alkyl, —CF$_3$, —OCF$_3$, —OR°, —N(R°)$_2$, —SR°, —CH$_2$-halogen, —SCF$_2$, —(C$_{1-6}$alkyl)-N(R°)$_2$, C$_6$aryl, C$_{5-6}$heteroaryl, —C(O)OR°, —NR°—COR°, or —CON(R°)$_2$.

In some embodiments R$^2$ is optionally substituted with up to 5 J$^Q$ groups; in other embodiments, up to 3 J$^Q$ groups; in yet other embodiments, 0 or 1 J$^Q$ groups.

In some embodiments R° is selected from methyl, ethyl, n-propyl, isopropyl, cyclopropyl, sec-butyl, n-butyl, t-butyl, OH, halogen, —CH$_2$-pyrrolidine, COCH$_3$, —(C$_{1-4}$alkyl)$_{0-1}$-O(C$_{1-4}$alkyl), —(C$_{1-4}$alkyl)$_{0-1}$-O(C$_{1-4}$alkyl)OH, —(C$_{1-4}$alkyl)$_{0-1}$-O(C$_{1-4}$alkyl)OH, —(C$_{1-4}$alkyl)$_{0-1}$-NH(C$_{1-4}$alkyl), —(C$_{1-4}$alkyl)$_{0-1}$N(C$_{1-4}$alkyl)$_2$, or —(C$_{1-4}$alkyl)$_{0-1}$-NH$_2$.

In some embodiments, the variables are as depicted in the Table I compounds.

Accordingly, representative examples of compounds of formula I are depicted in Table I.

TABLE I
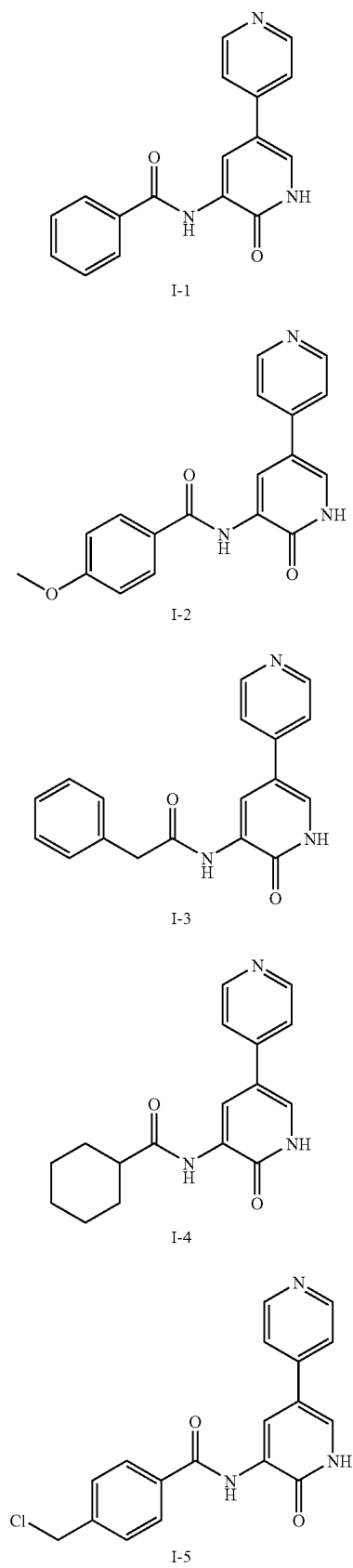
TABLE I-continued
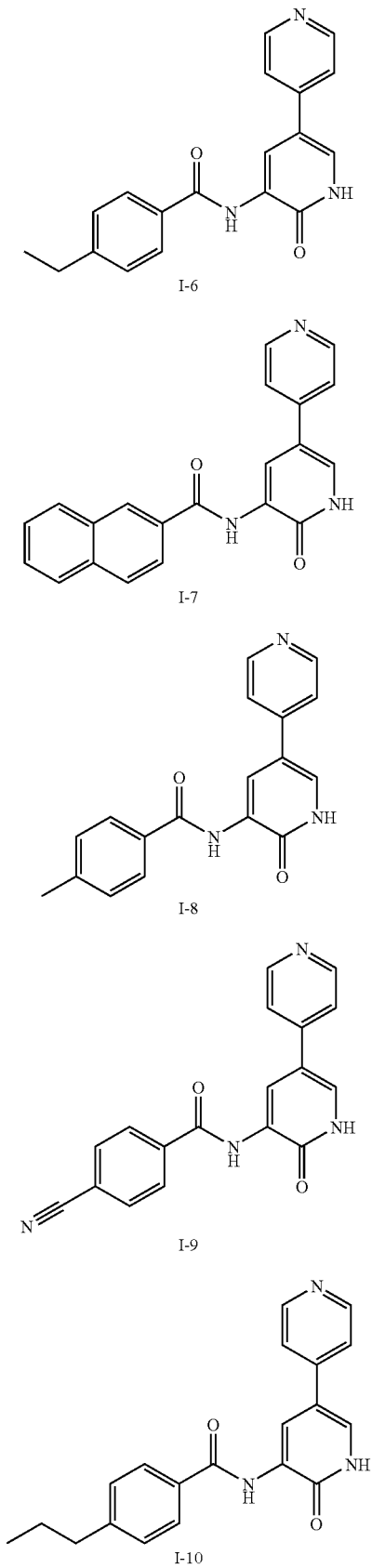

TABLE I-continued
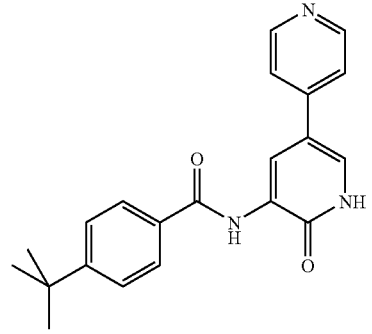
I-11
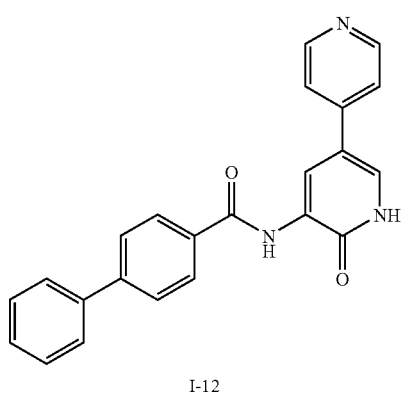
I-12
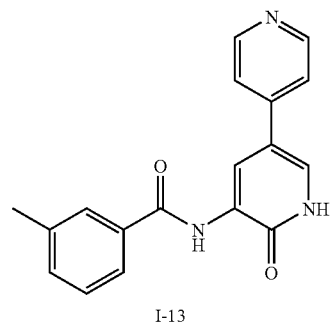
I-13
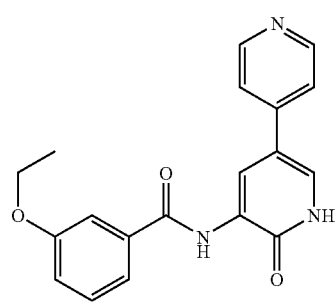
I-14
TABLE I-continued
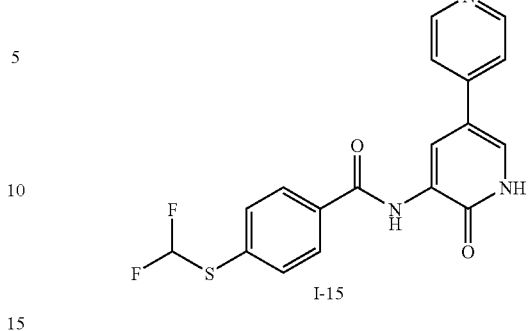
I-15
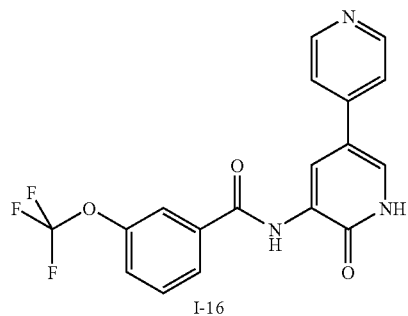
I-16
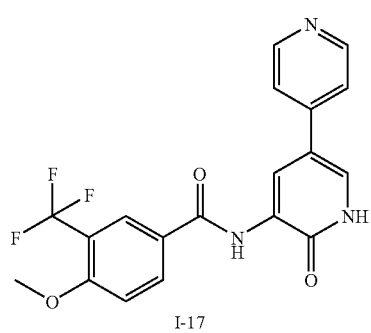
I-17
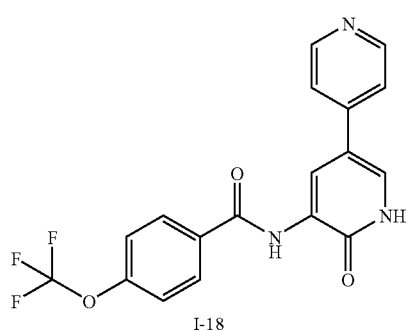
I-18
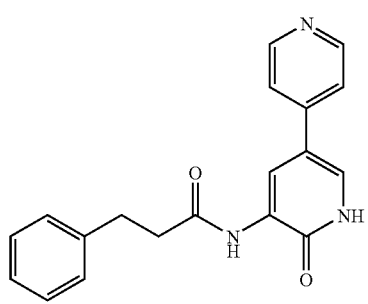
I-19

TABLE I-continued
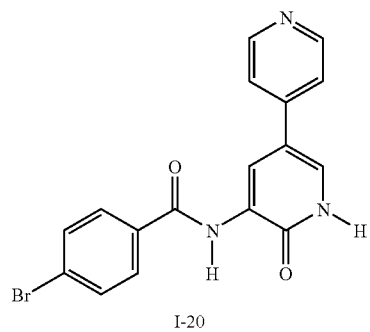
I-20
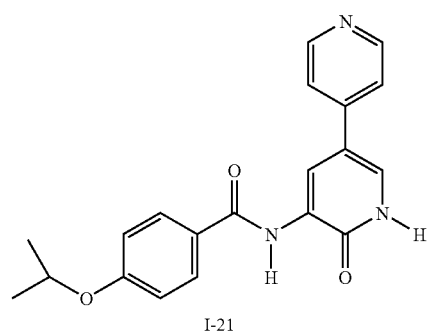
I-21
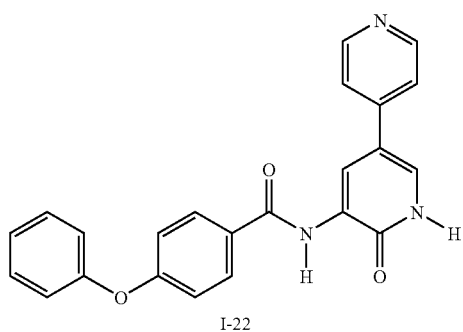
I-22
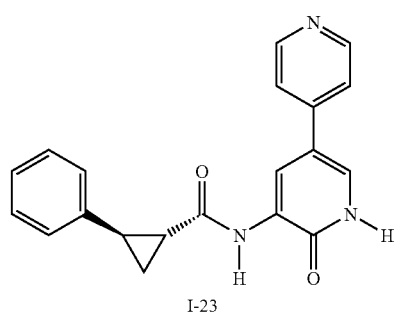
I-23
TABLE I-continued
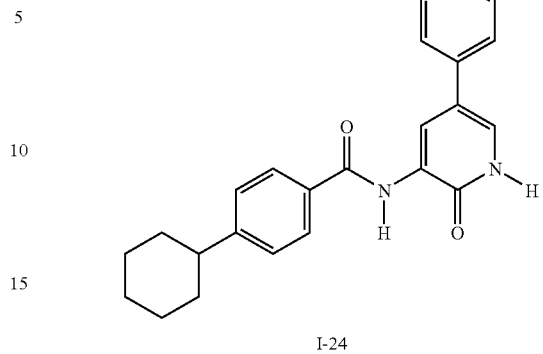
I-24
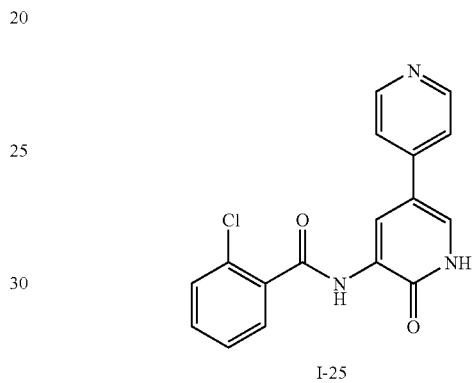
I-25
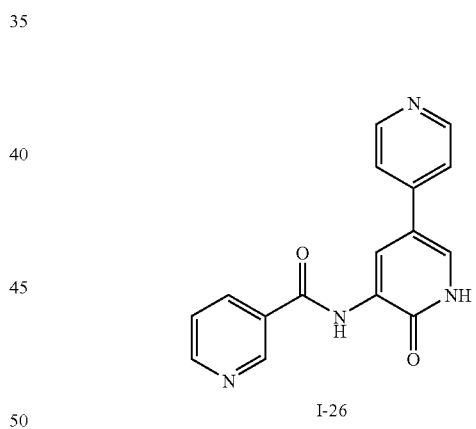
I-26
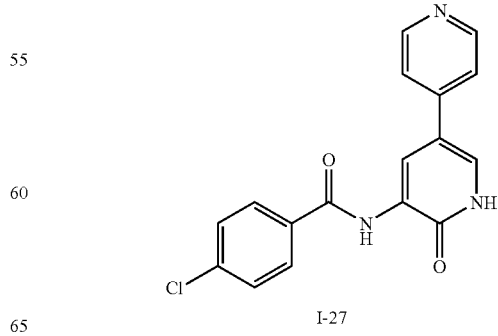
I-27

TABLE I-continued
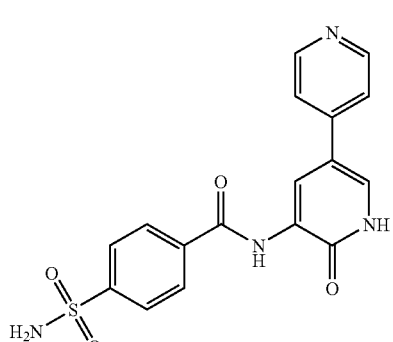
I-28
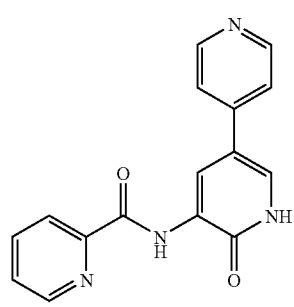
I-29
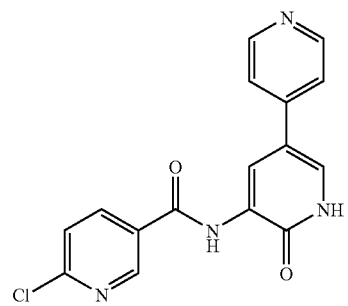
I-30
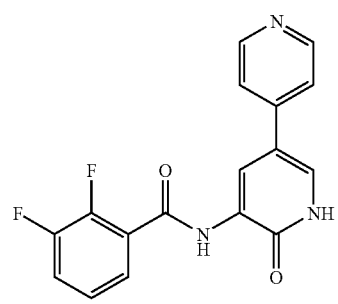
I-31
TABLE I-continued
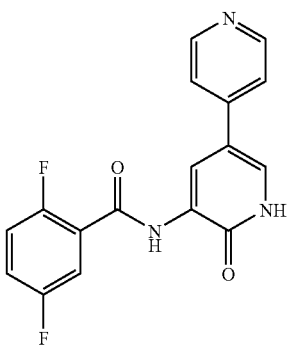
I-32
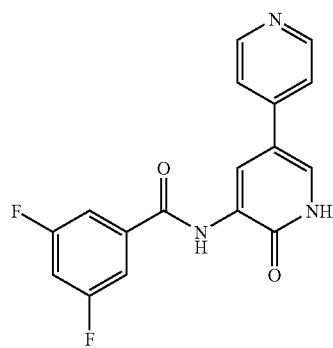
I-33
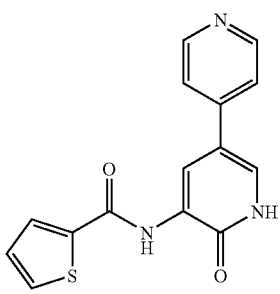
I-34
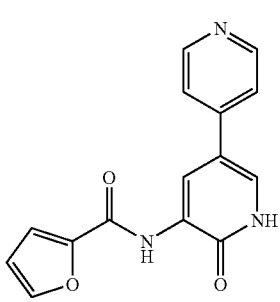
I-35

TABLE I-continued
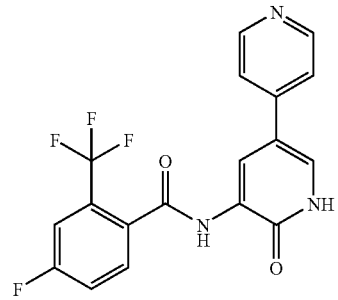
I-36
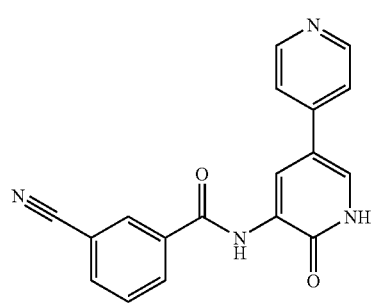
I-37
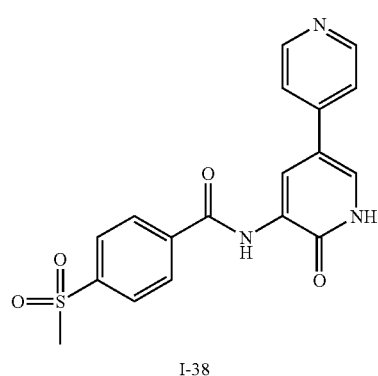
I-38
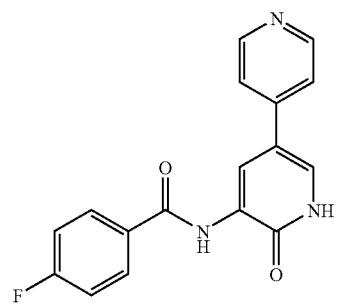
I-39
TABLE I-continued
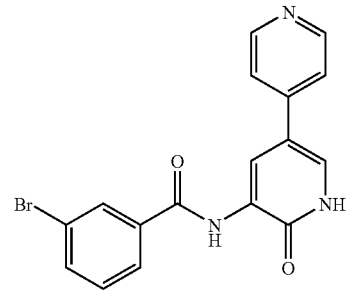
I-40
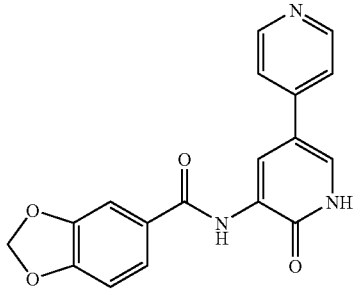
I-41
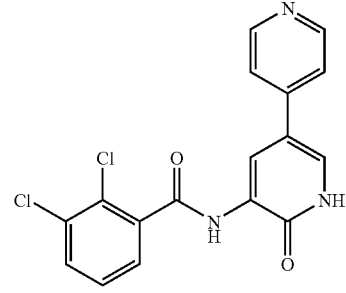
I-42
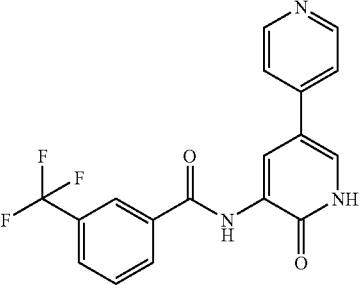
I-43
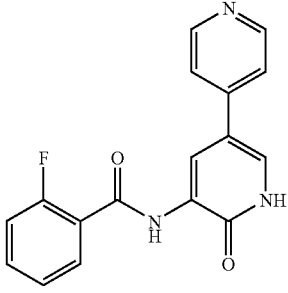
I-44

TABLE I-continued
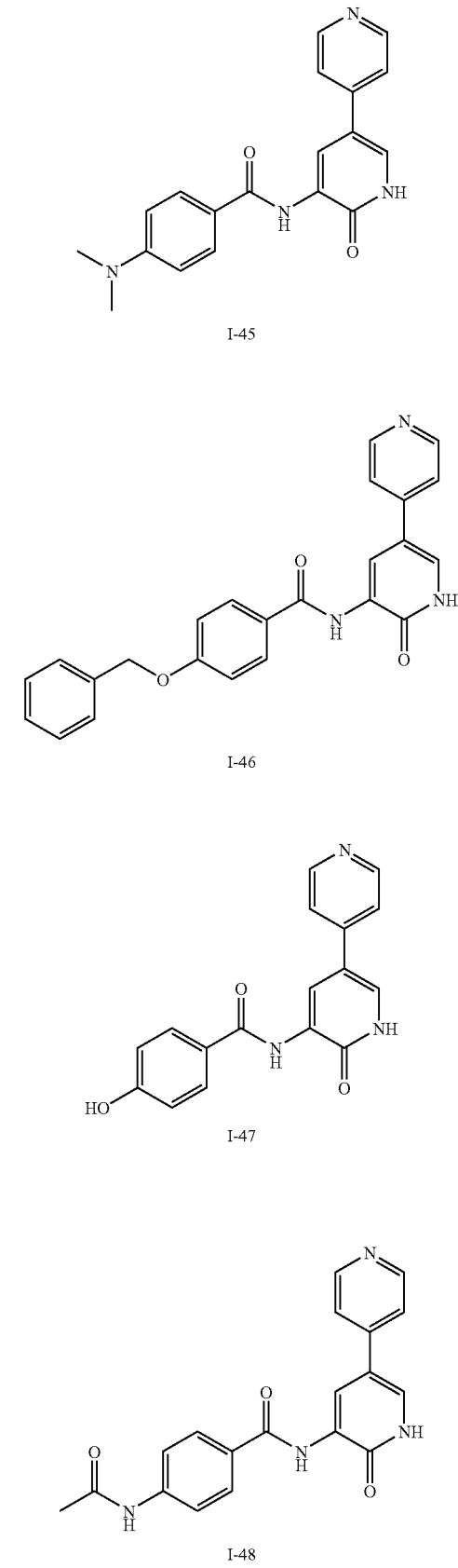
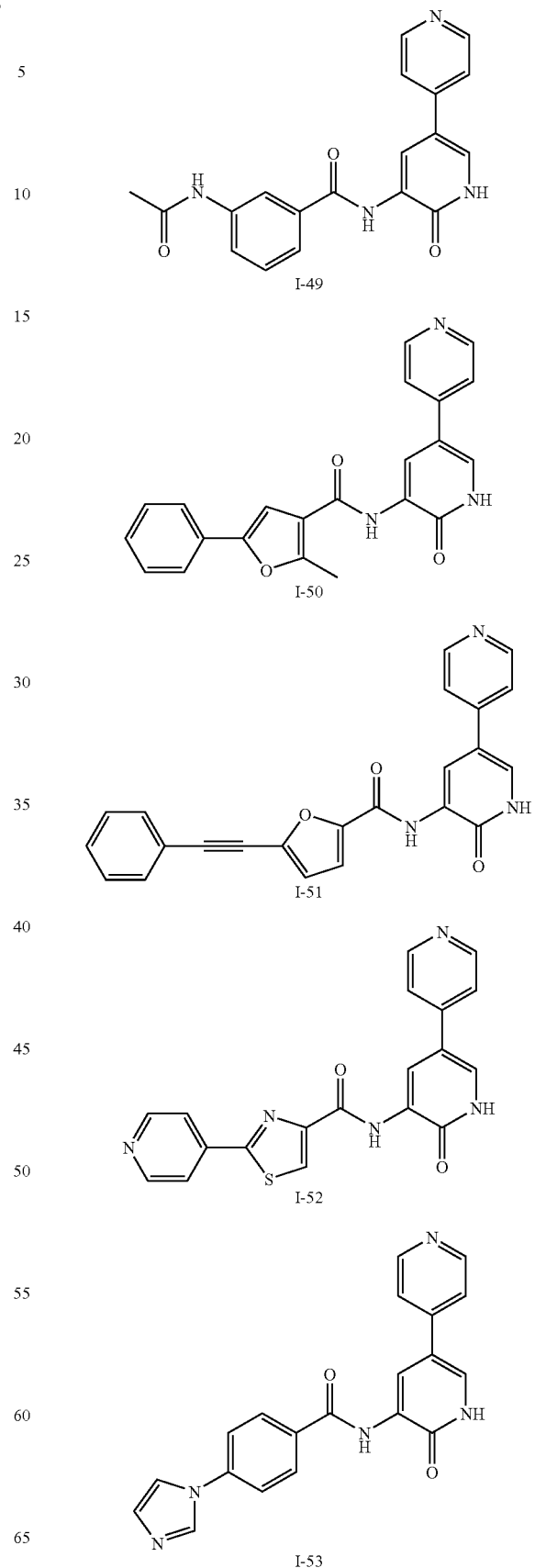

TABLE I-continued
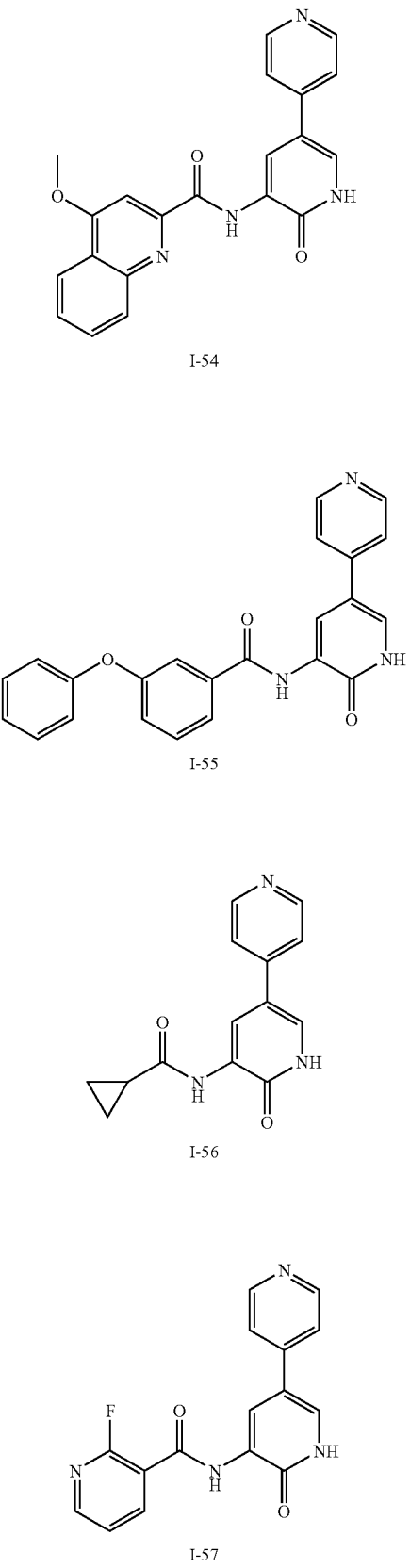
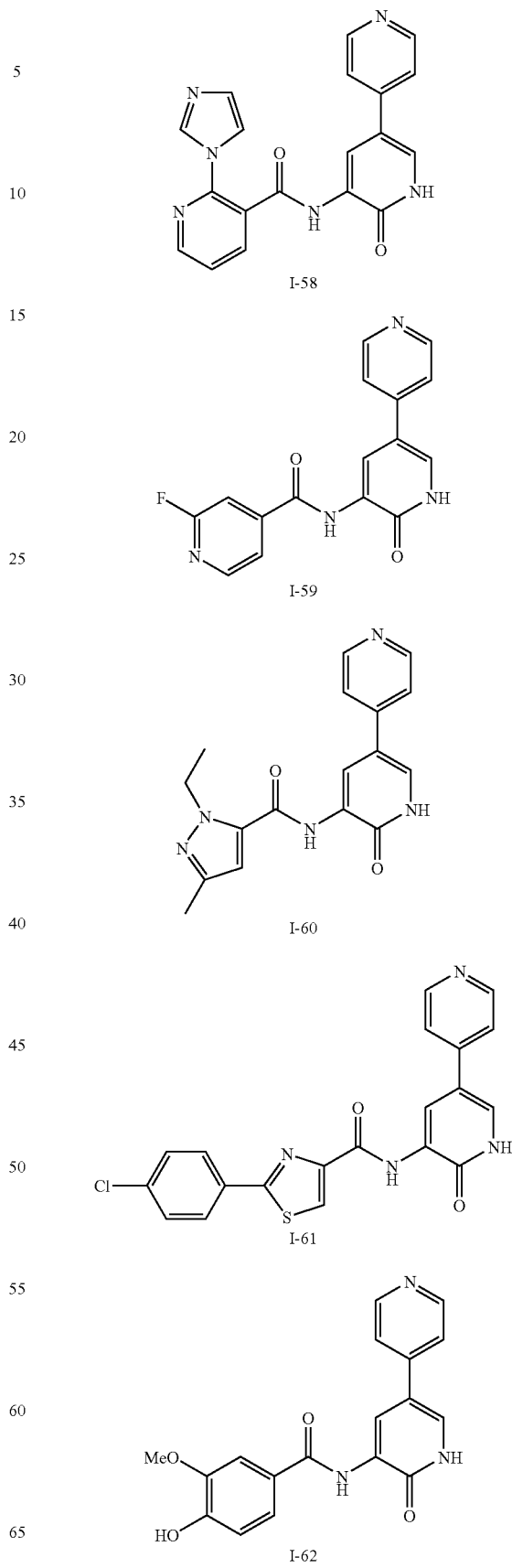

TABLE I-continued
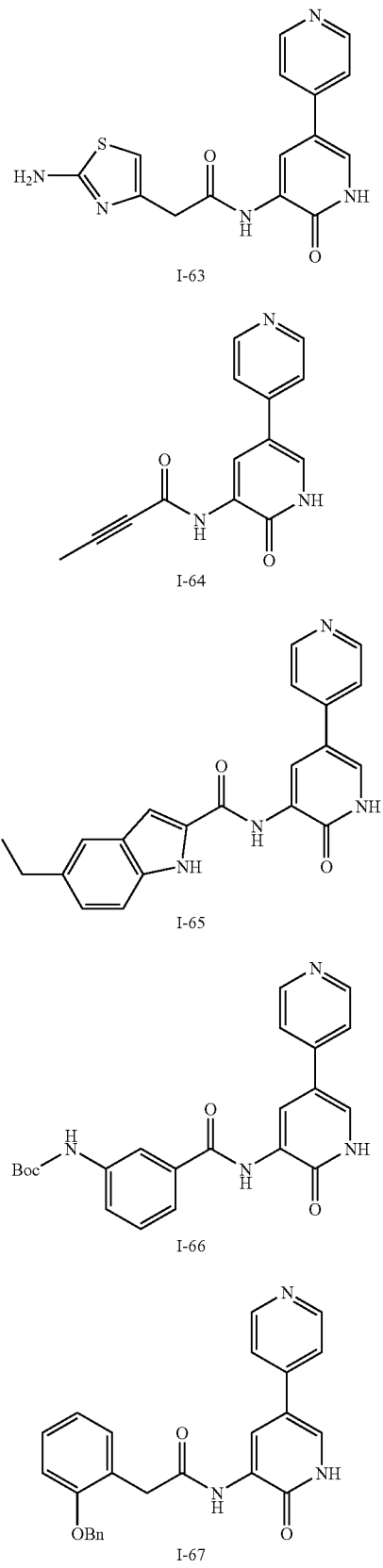
I-63
I-64
I-65
I-66
I-67
TABLE I-continued
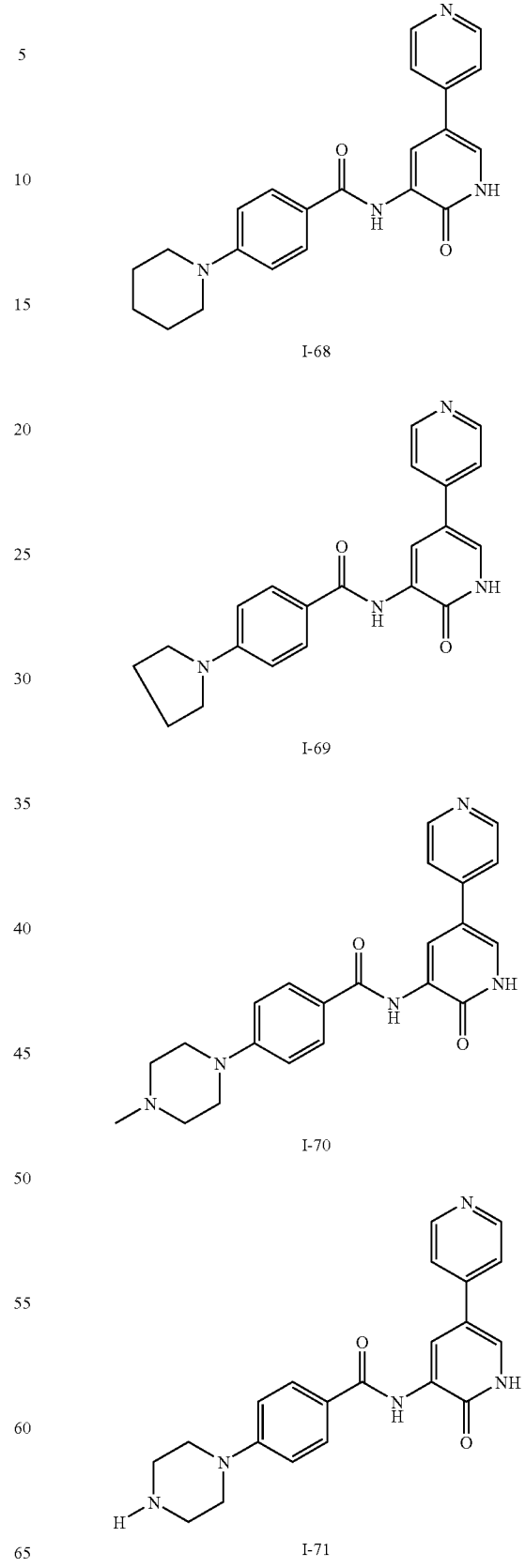
I-68
I-69
I-70
I-71

TABLE I-continued
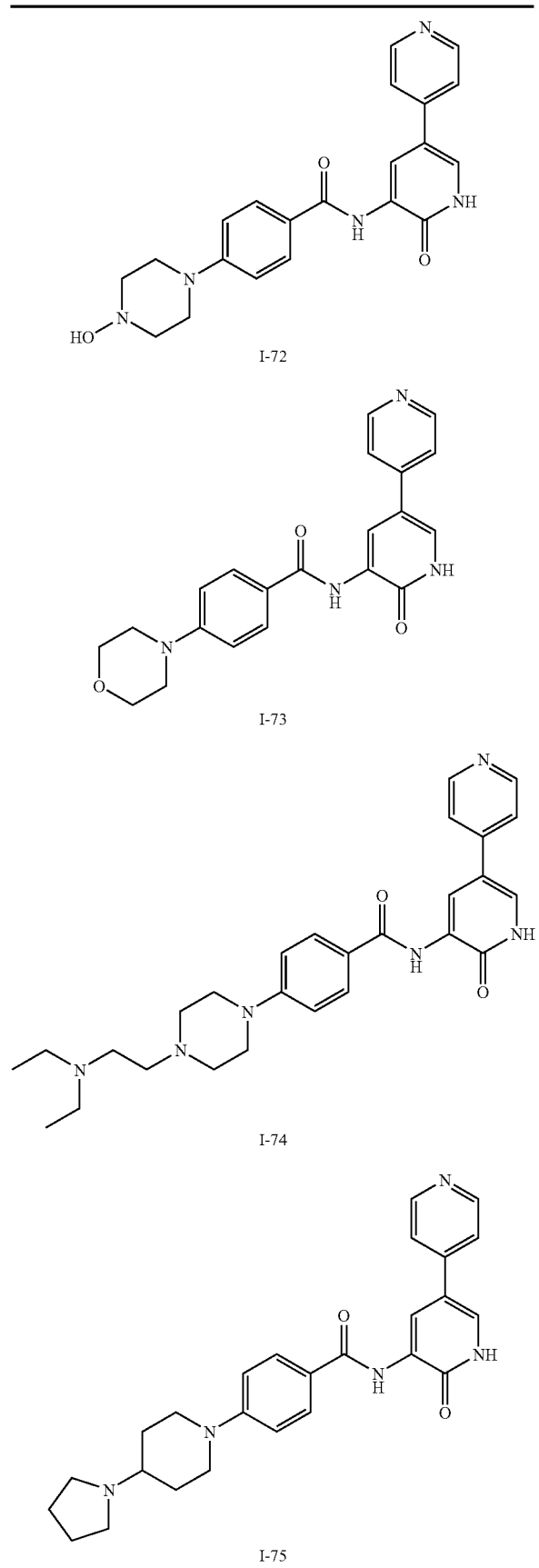
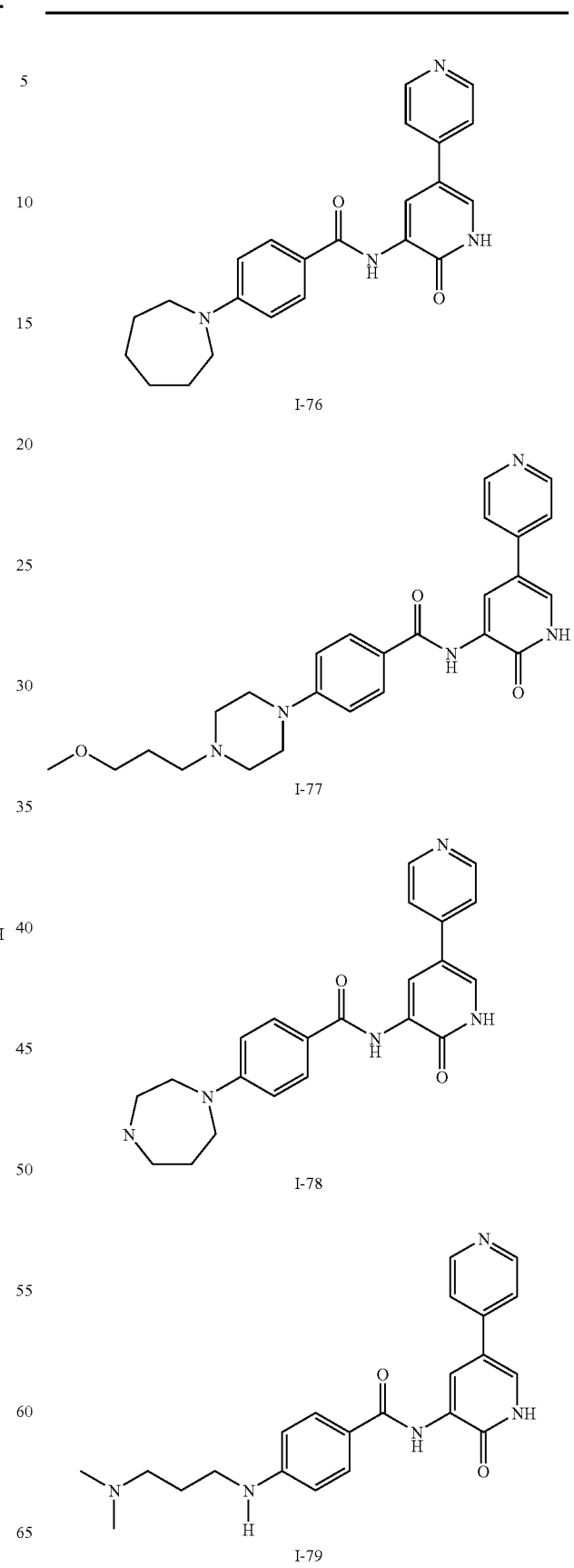

TABLE I-continued
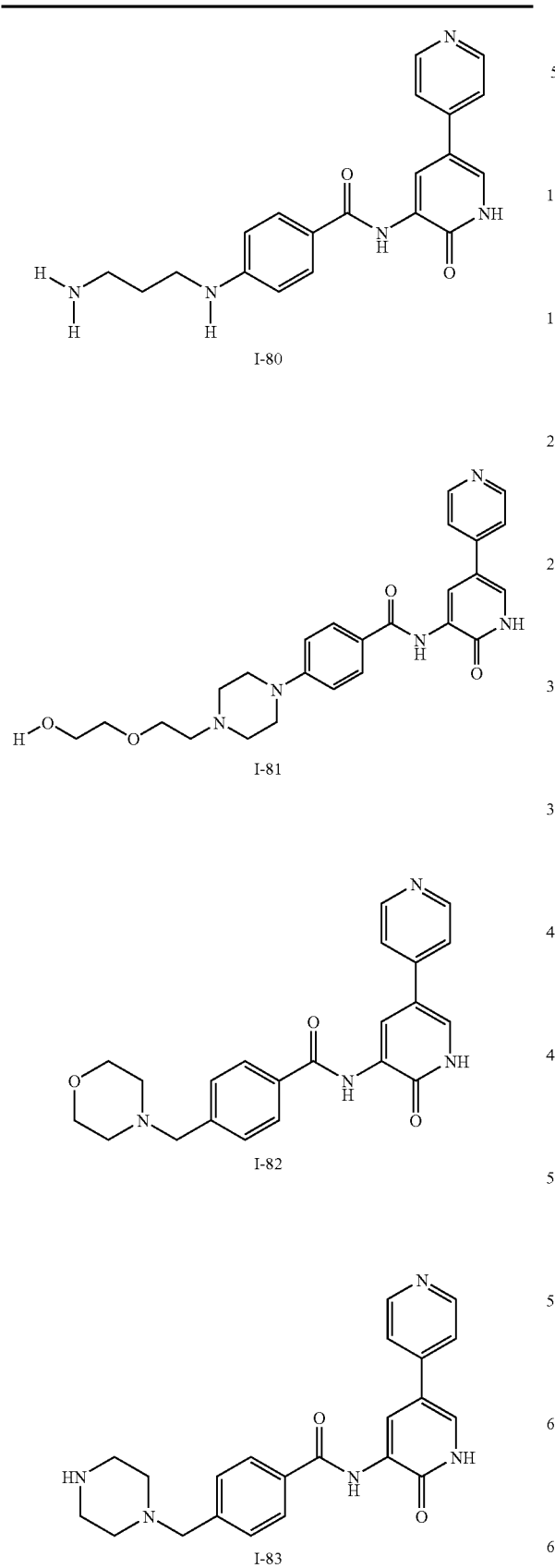
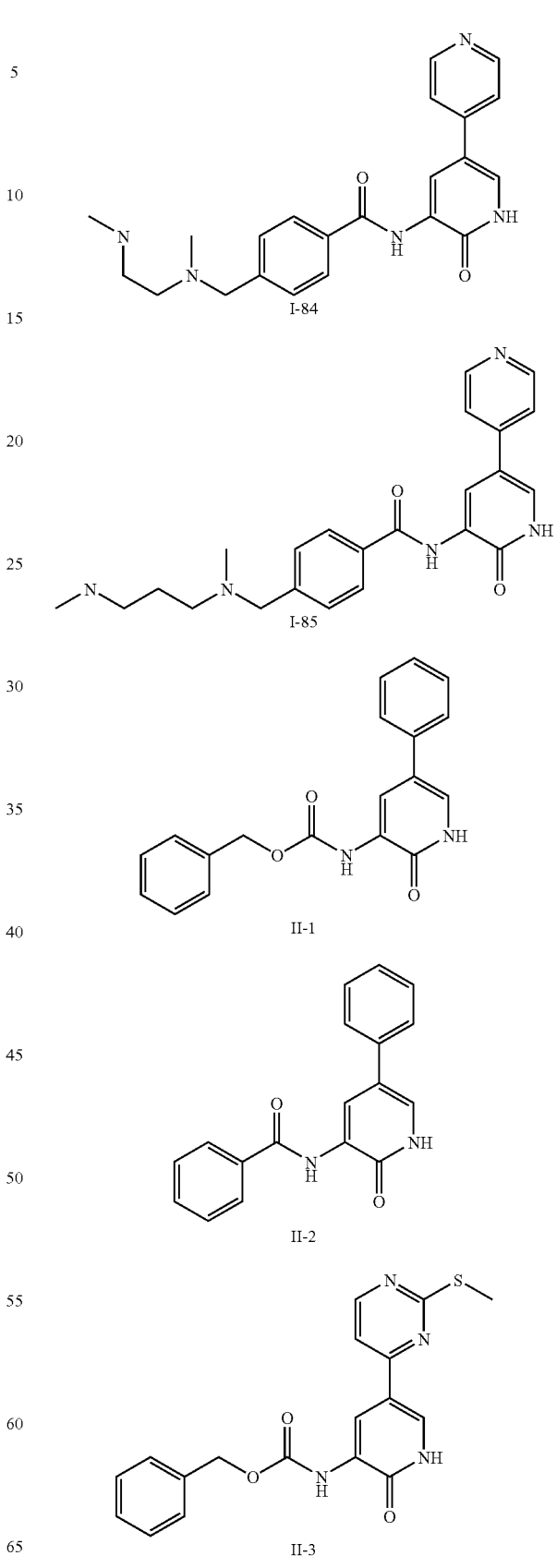

TABLE I-continued
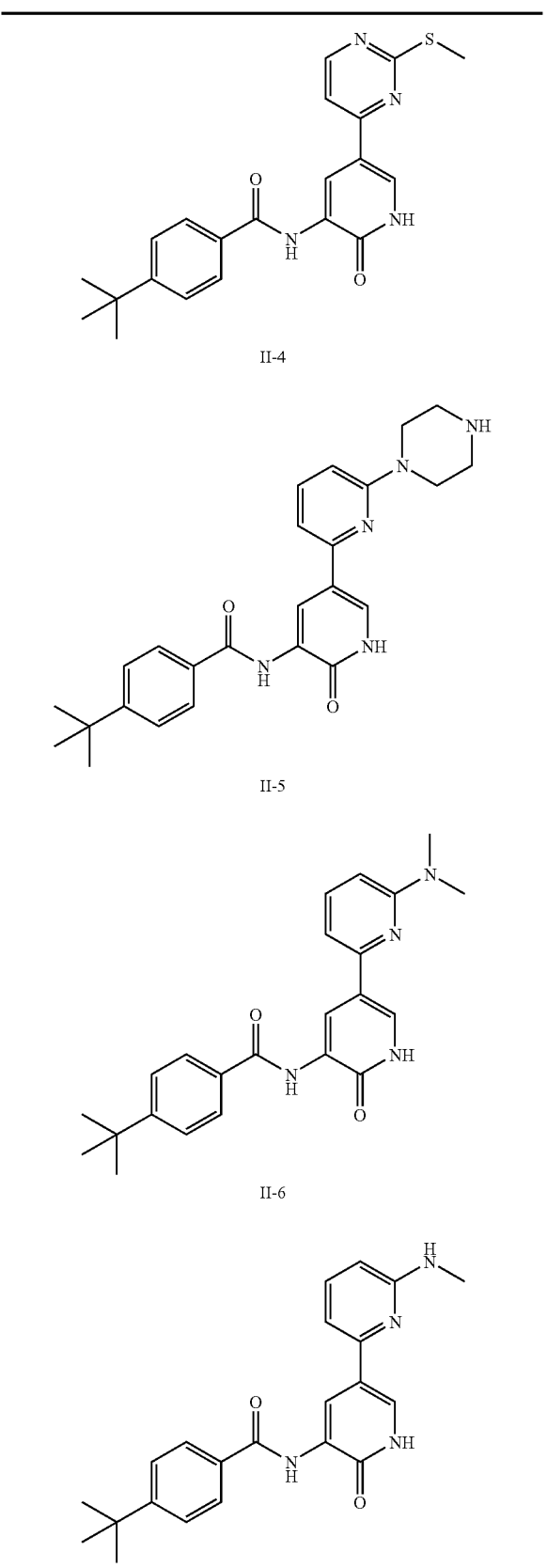
II-4
II-5
II-6
II-7
TABLE I-continued
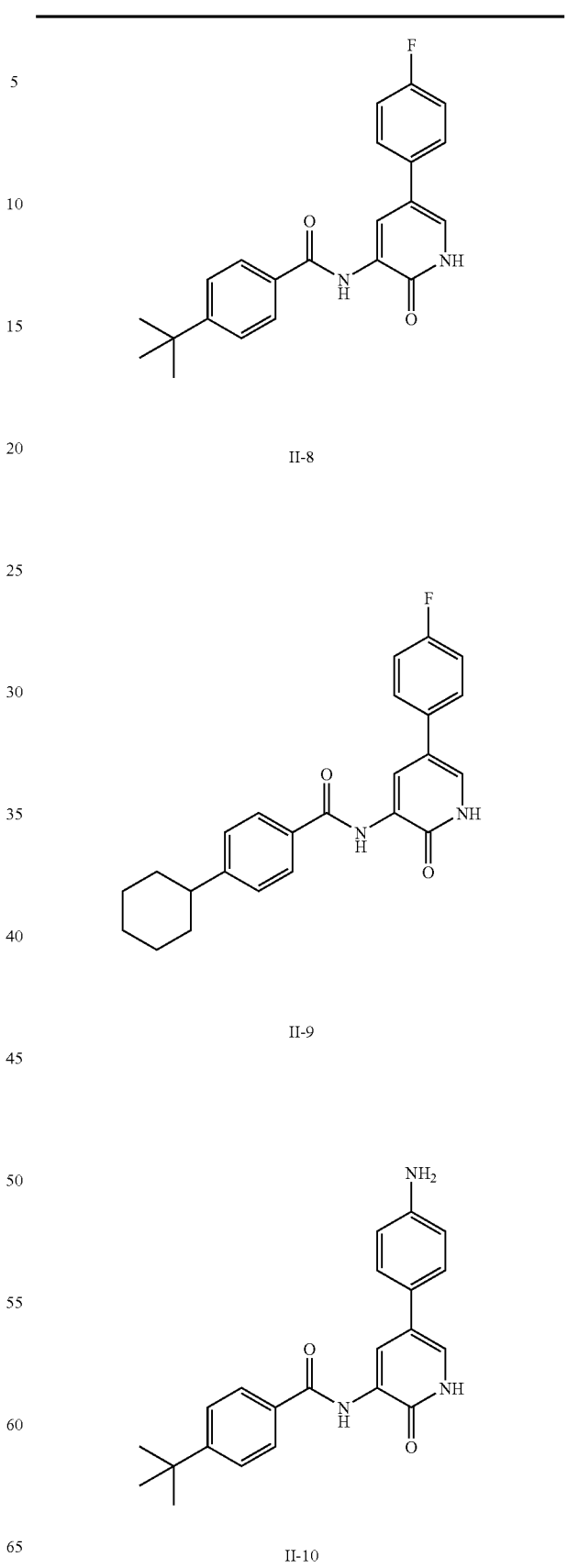
II-8
II-9
II-10

TABLE I-continued
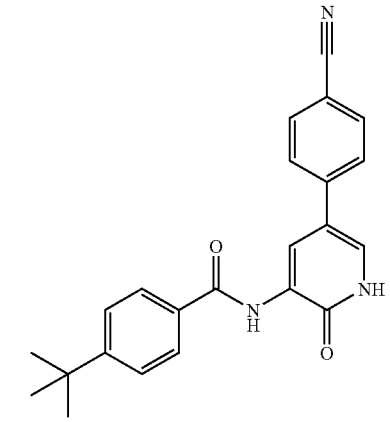
II-11
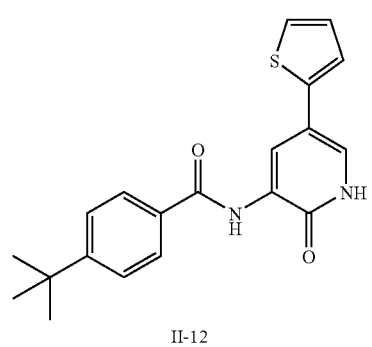
II-12
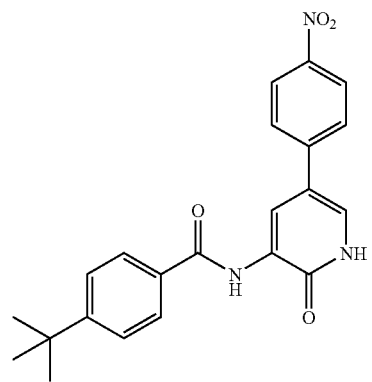
II-13
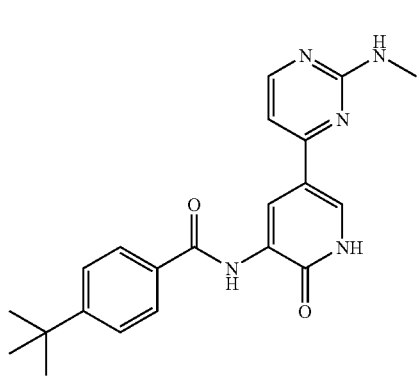
II-14
TABLE I-continued
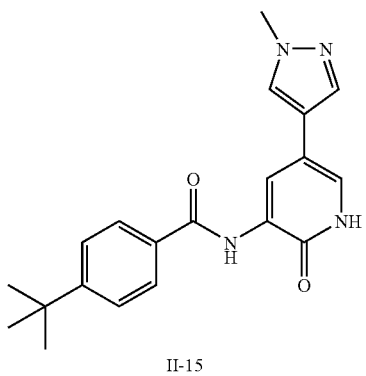
II-15
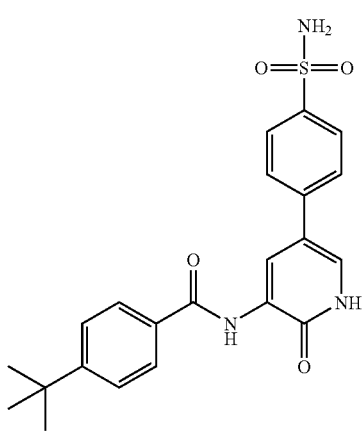
II-16
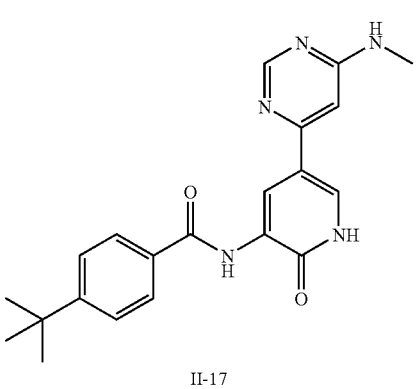
II-17
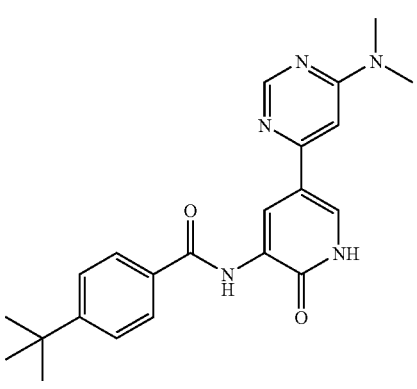
II-18

TABLE I-continued
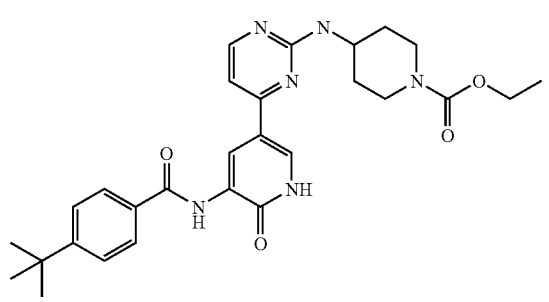
II-19
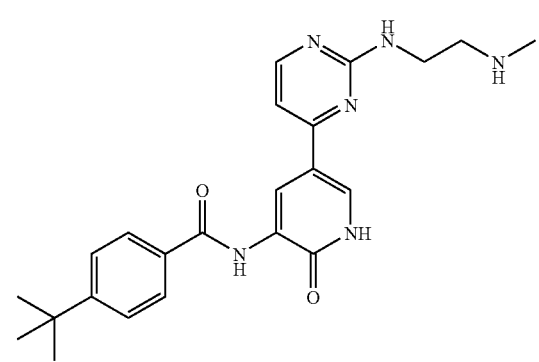
II-20
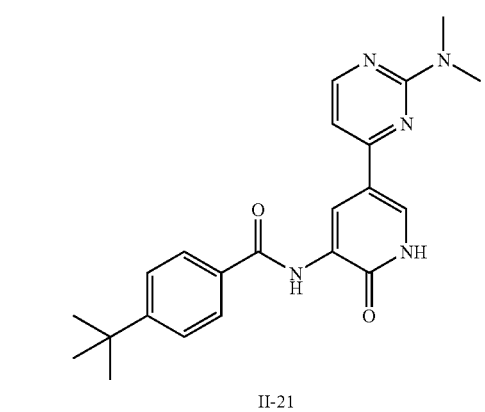
II-21
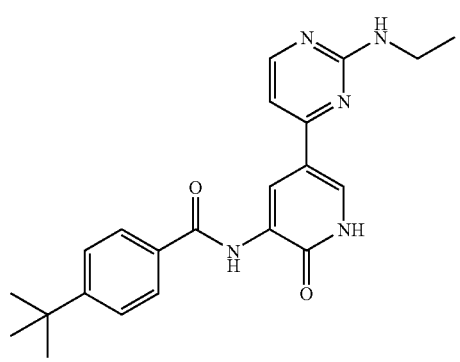
II-22
TABLE I-continued
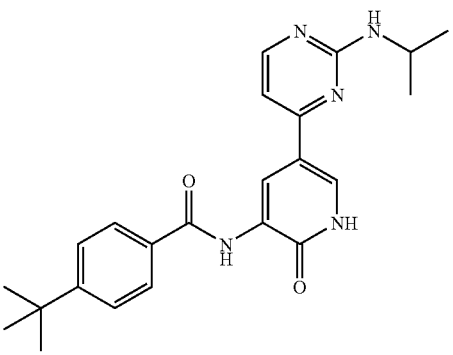
II-23
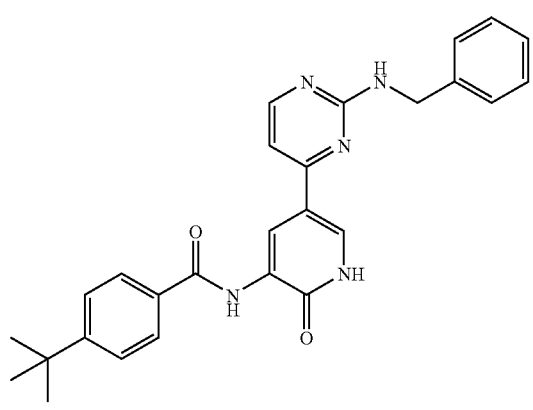
II-24
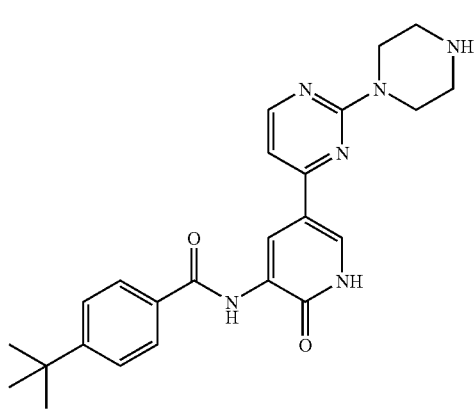
II-25
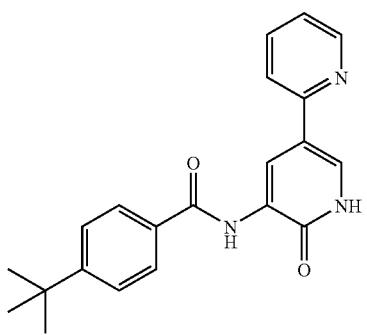
II-26

TABLE I-continued
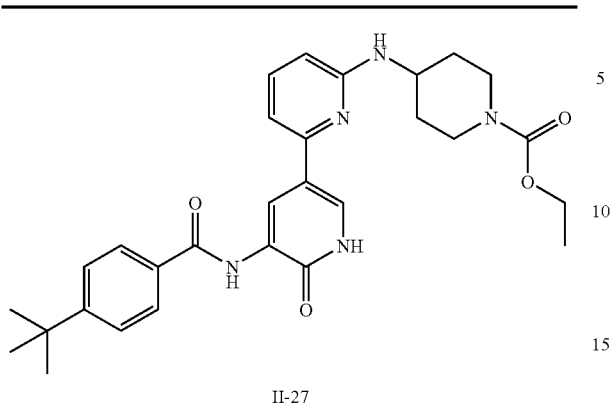
II-27
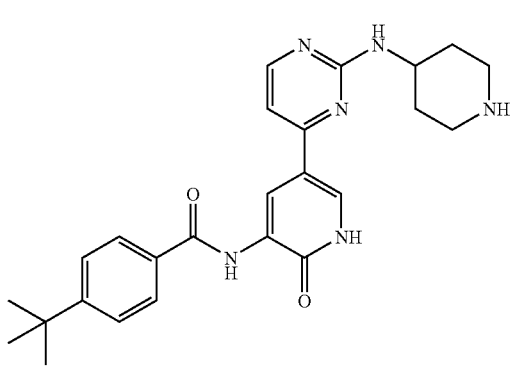
II-28
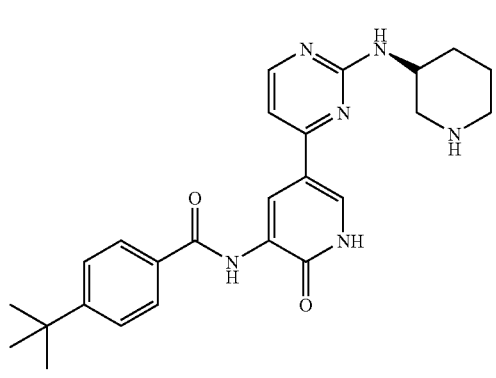
II-29
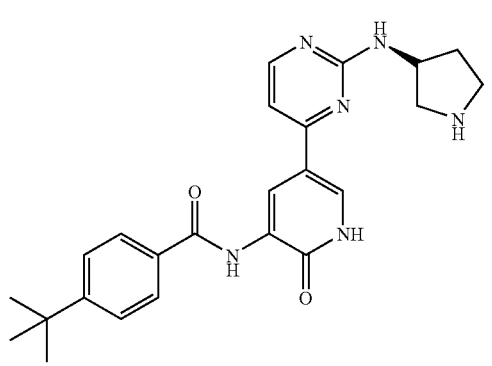
II-30
TABLE I-continued
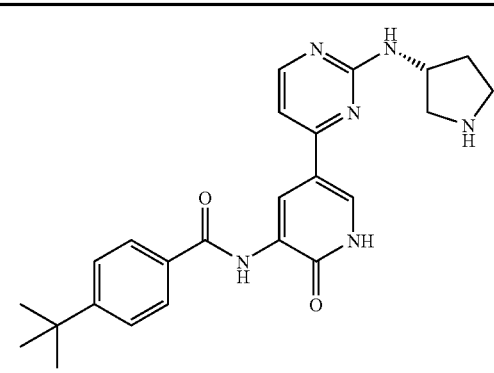
II-31
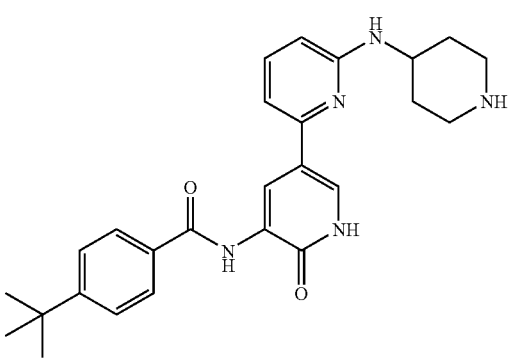
II-32
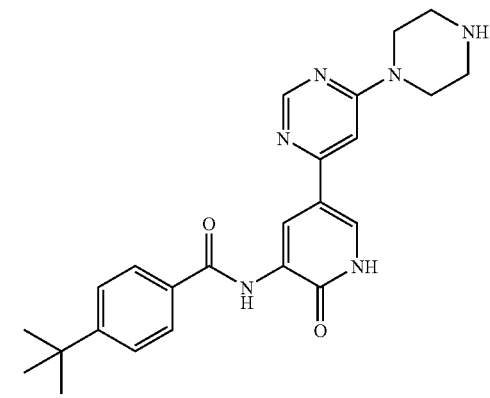
II-33
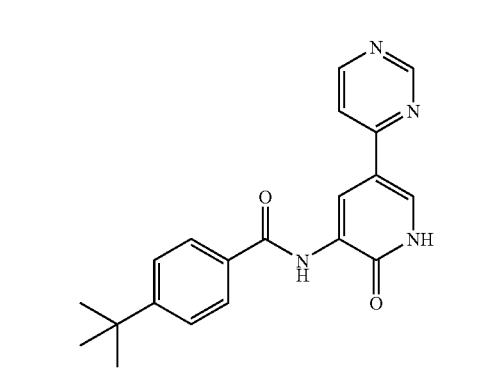
II-34

TABLE I-continued
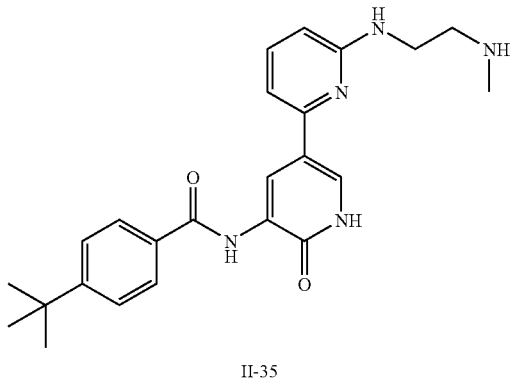
II-35
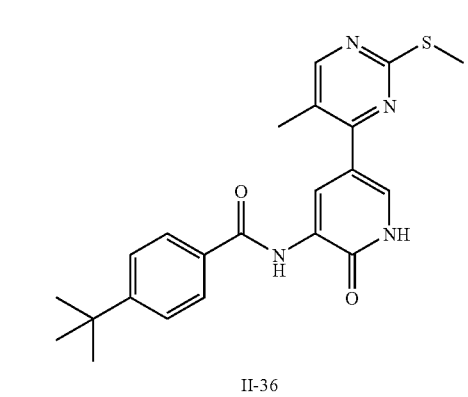
II-36
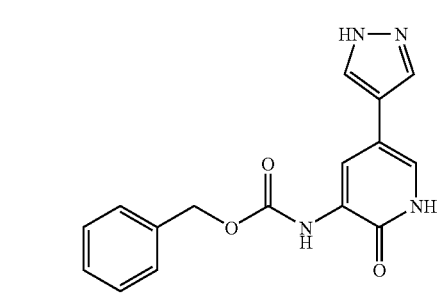
II-37
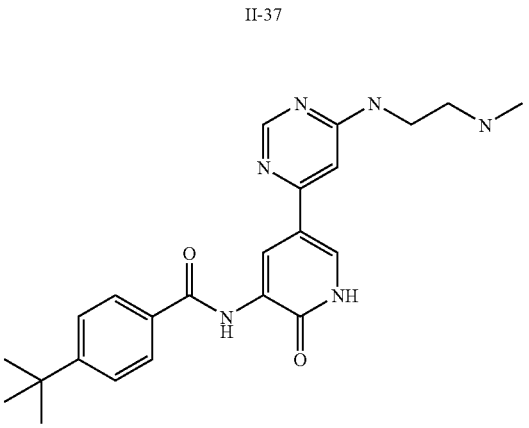
II-38
TABLE I-continued
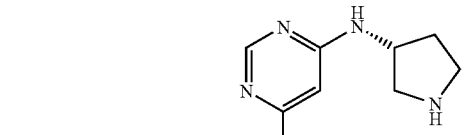
II-39
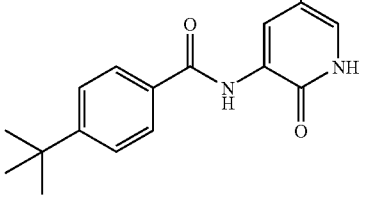
II-40
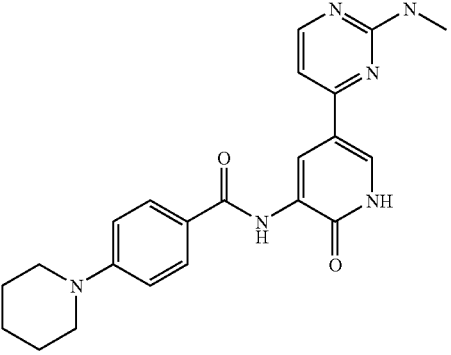
II-41
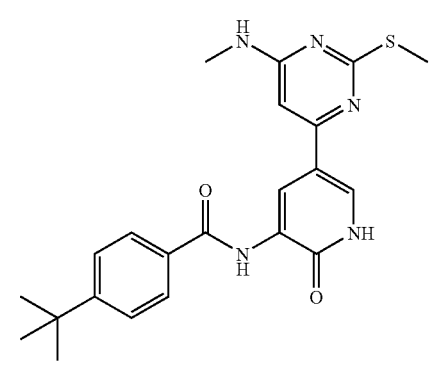
II-42

TABLE I-continued
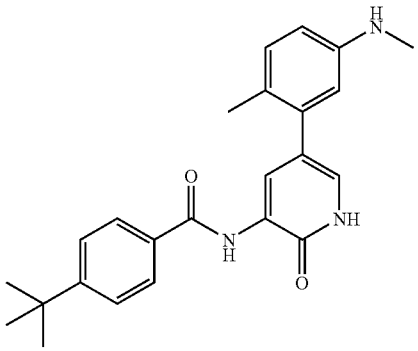
II-43
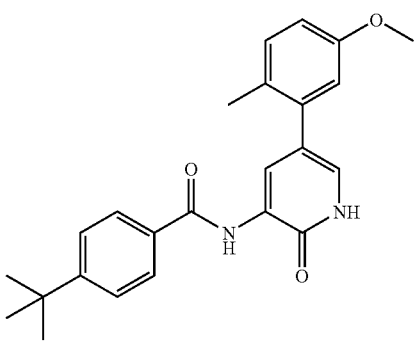
II-44
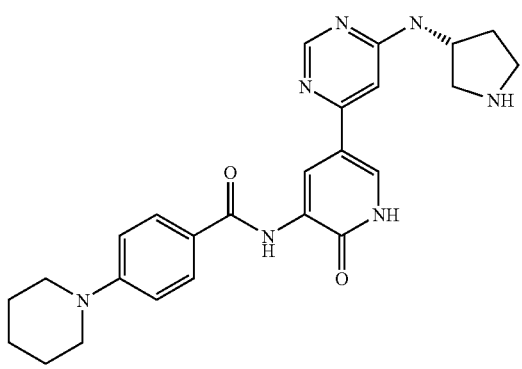
II-45
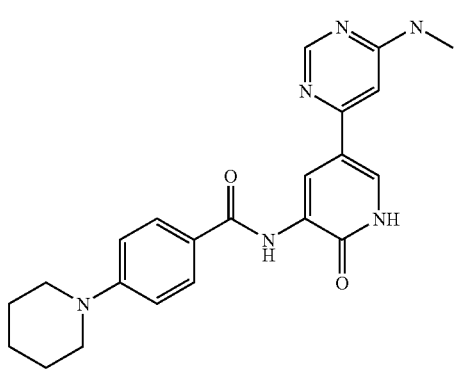
II-46
TABLE I-continued
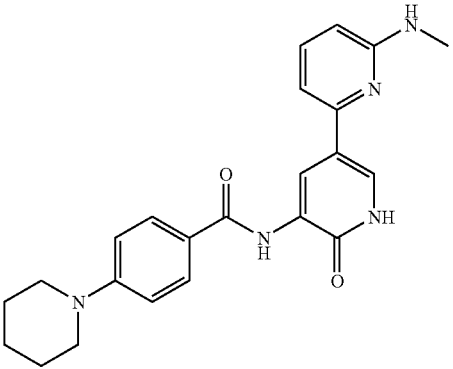
II-47
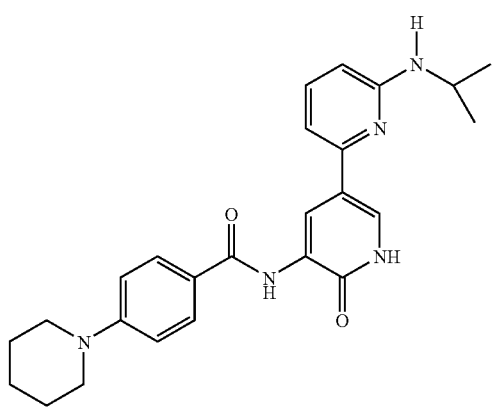
II-48
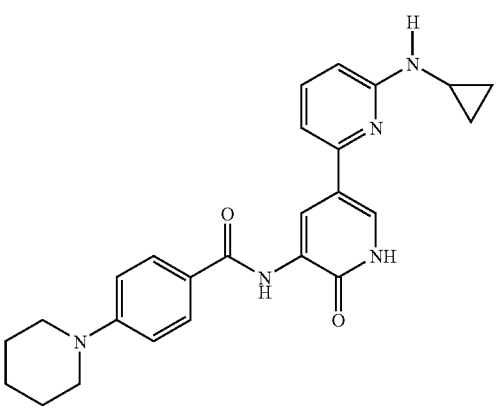
II-49

TABLE I-continued
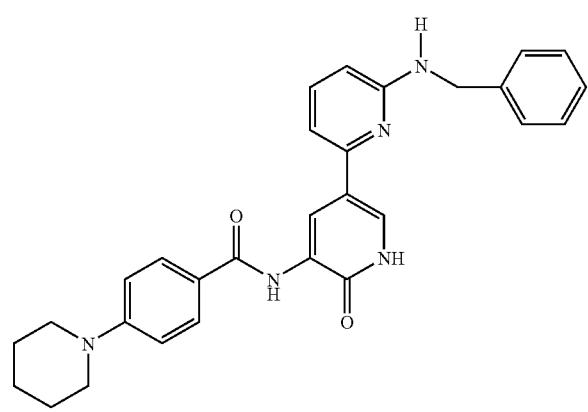
II-50
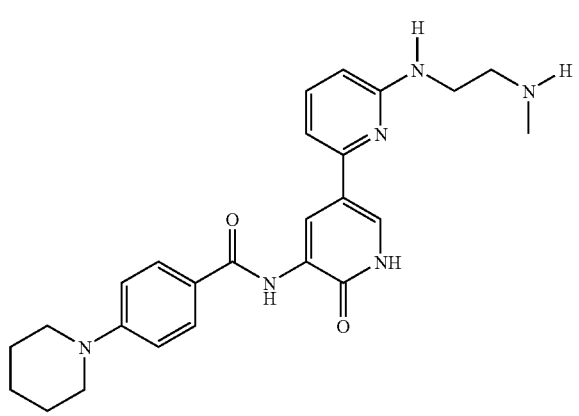
II-51
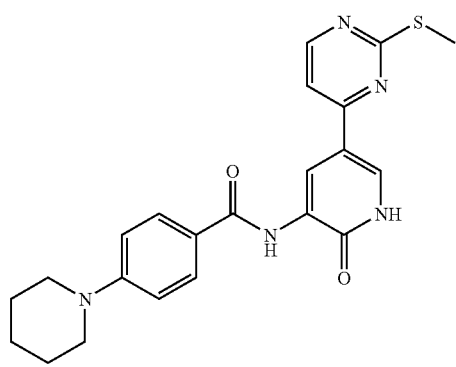
II-52
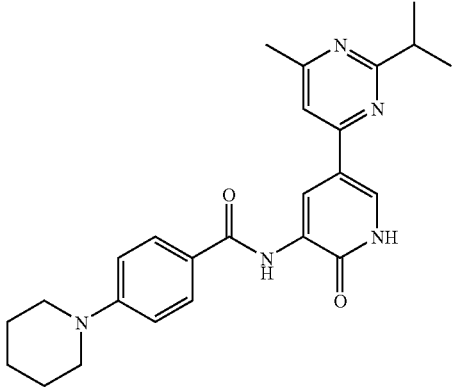
II-53
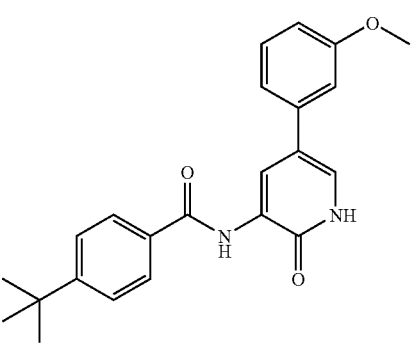
II-54
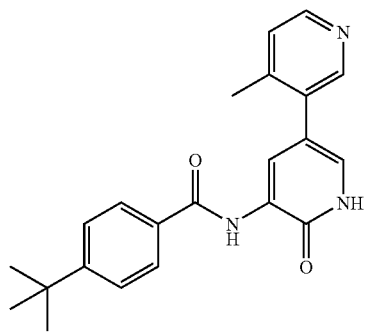
II-55
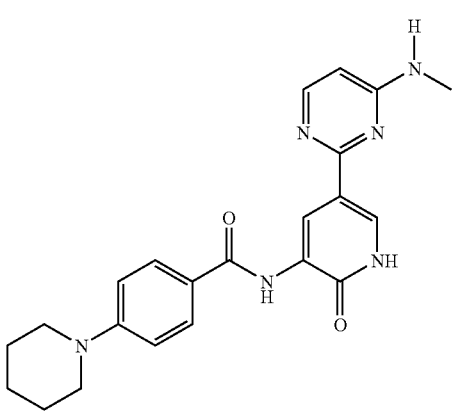
II-56

TABLE I-continued
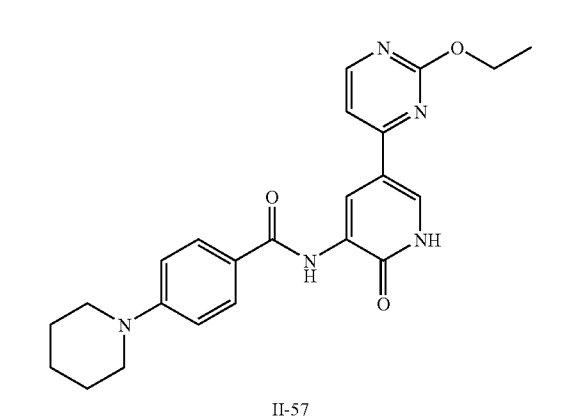
II-57
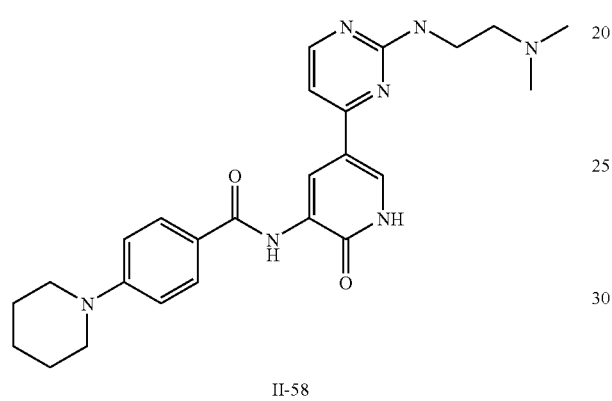
II-58
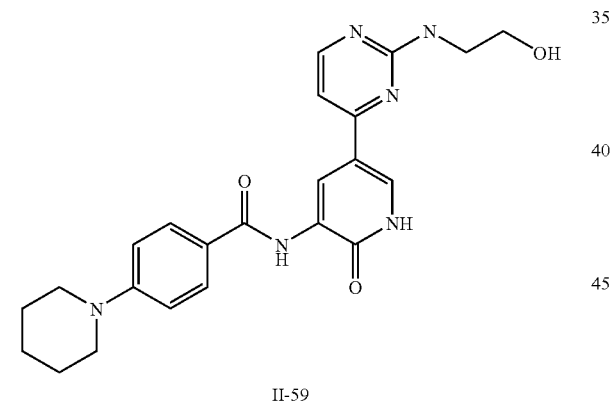
II-59
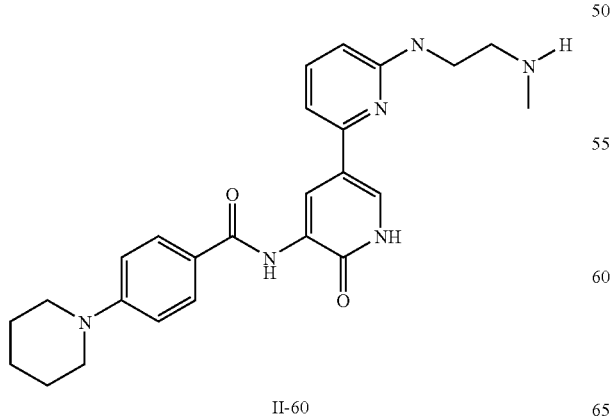
II-60
TABLE I-continued
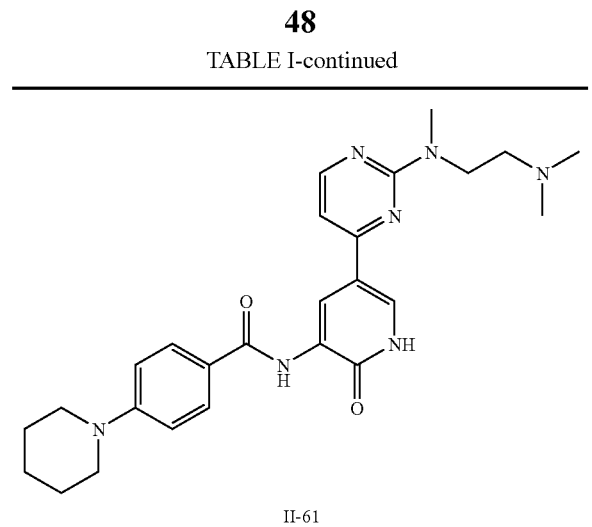
II-61
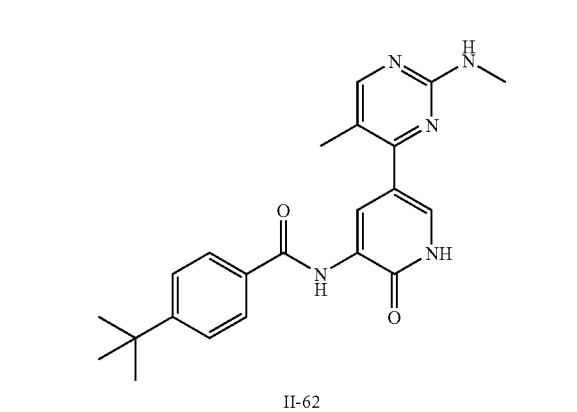
II-62
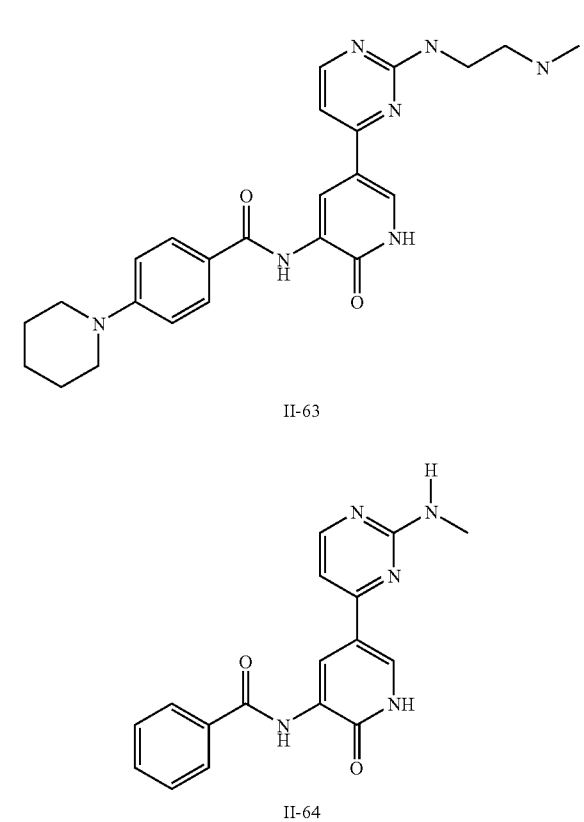
II-63
II-64

TABLE I-continued
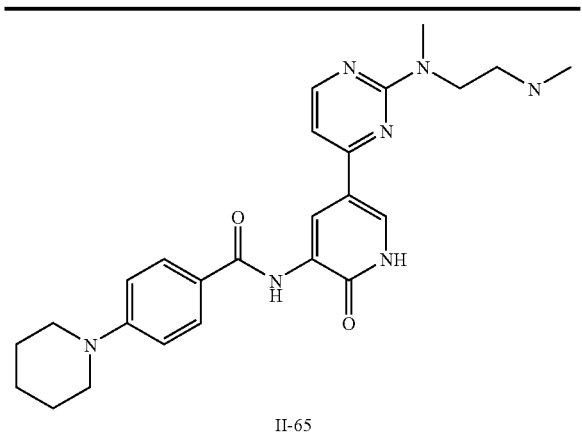
II-65
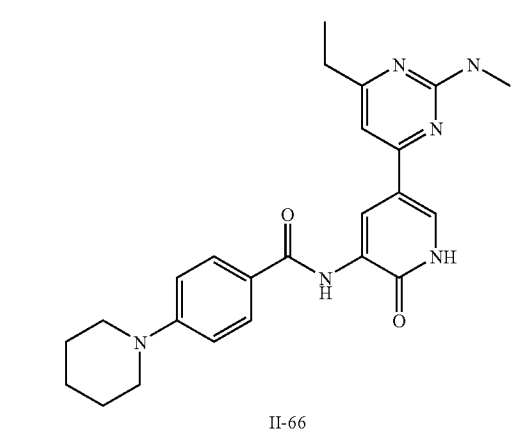
II-66
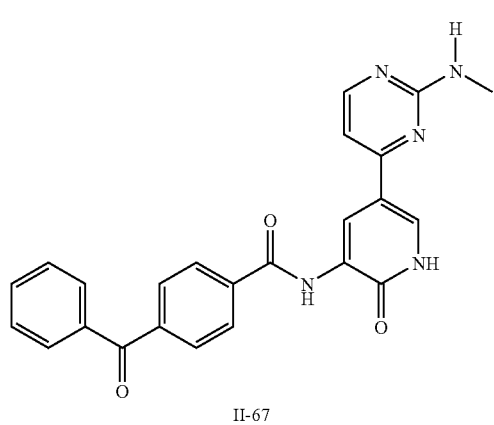
II-67
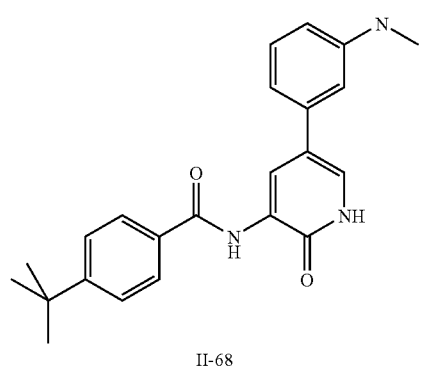
II-68
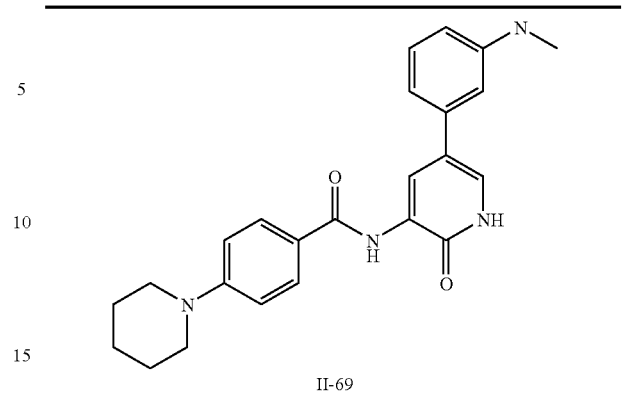
II-69
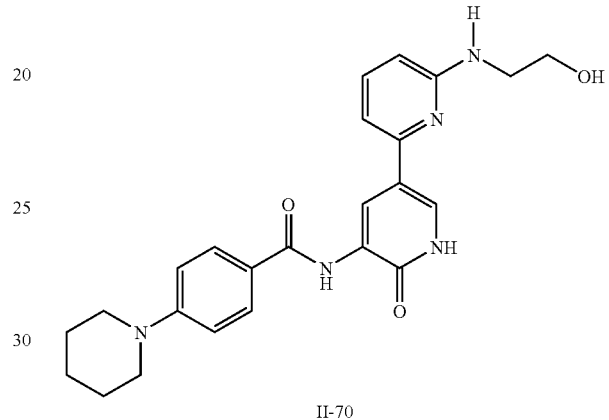
II-70
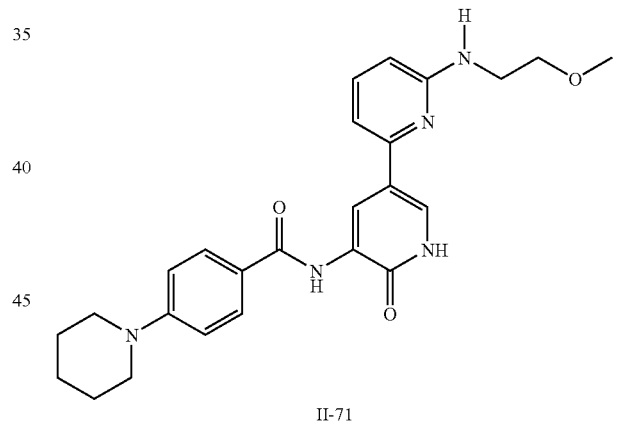
II-71
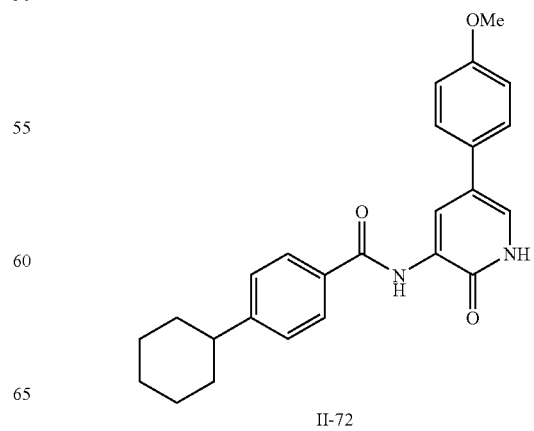
II-72

TABLE I-continued
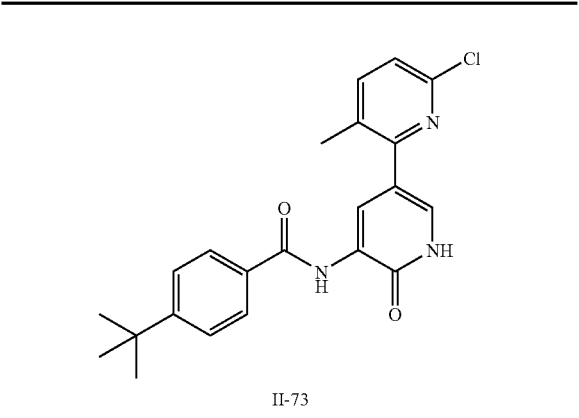
II-73
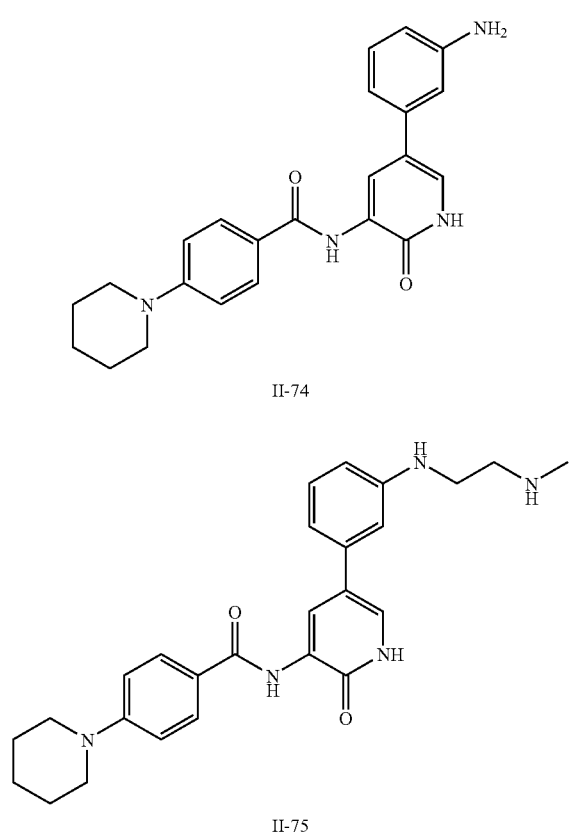
II-74
II-75
II-76
TABLE I-continued
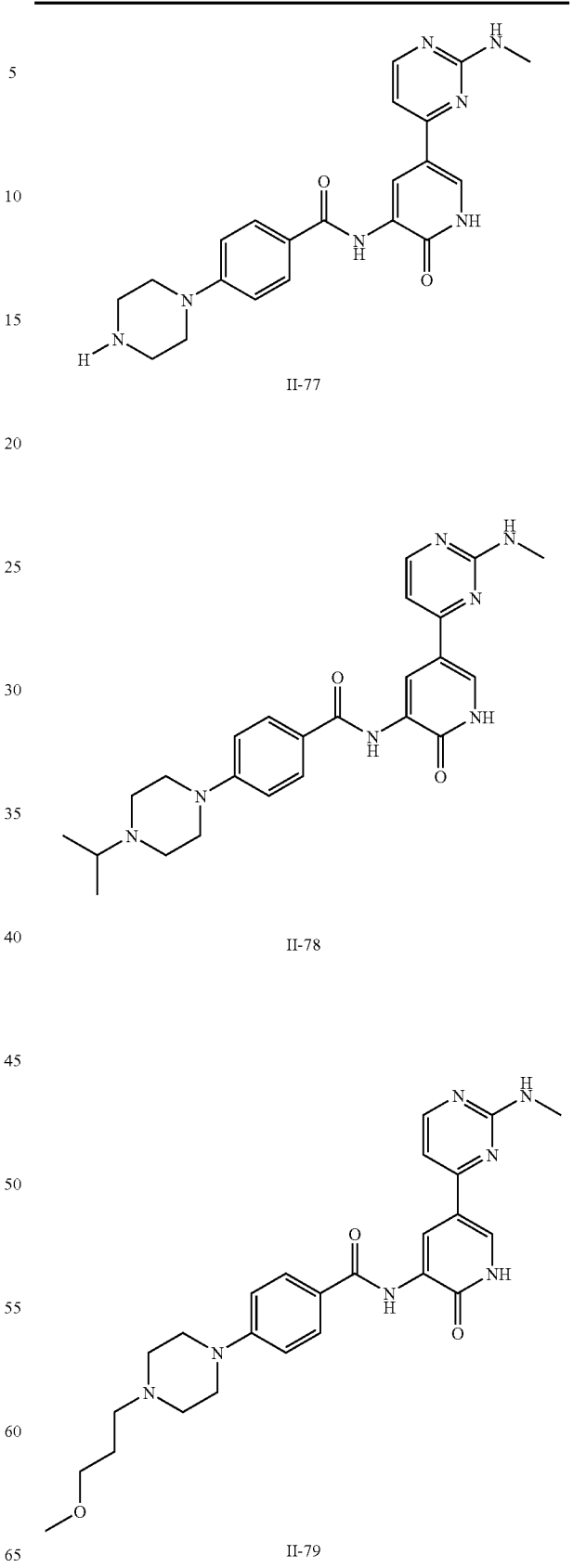
II-77
II-78
II-79

TABLE I-continued
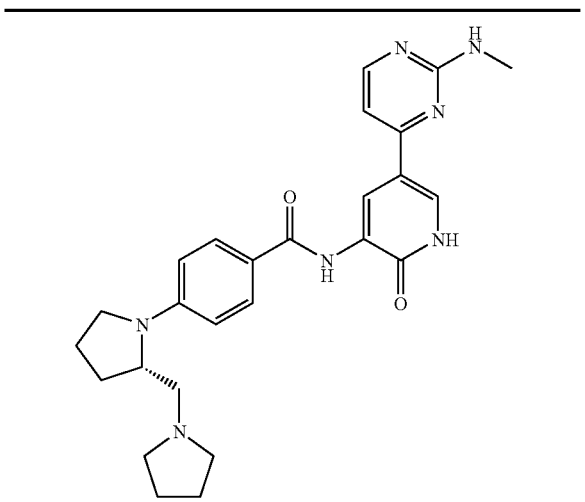
II-80
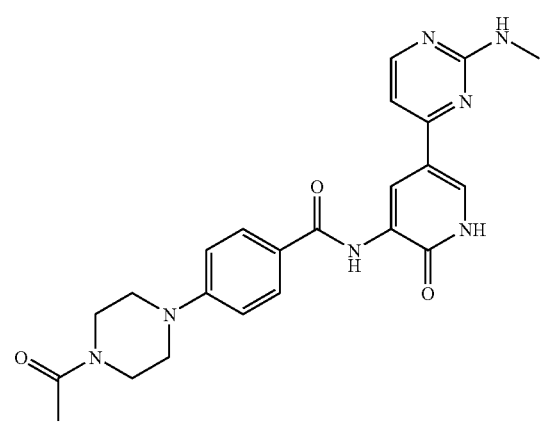
II-81
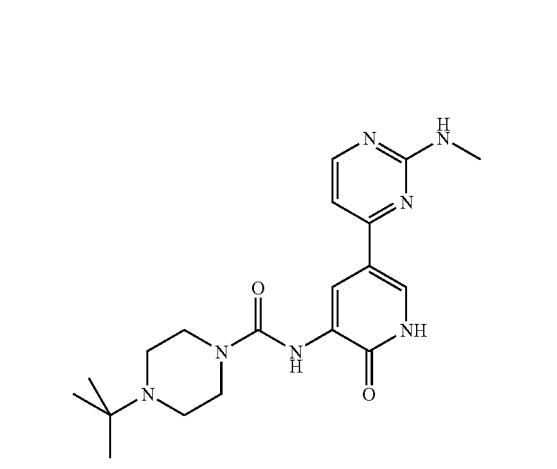
II-82
TABLE I-continued
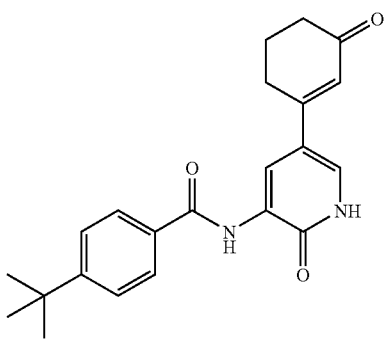
II-83
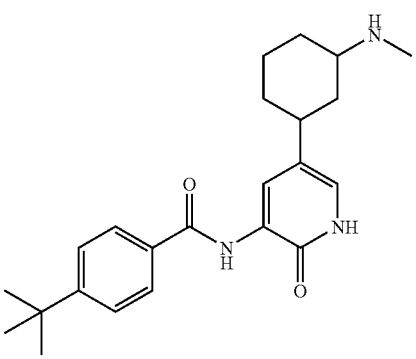
II-84
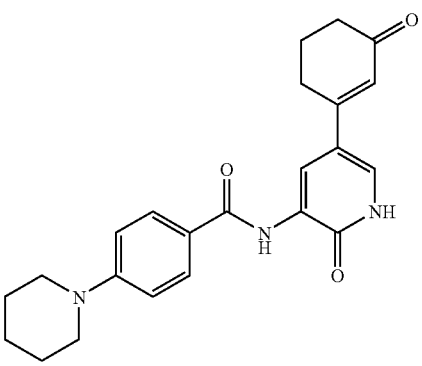
II-85
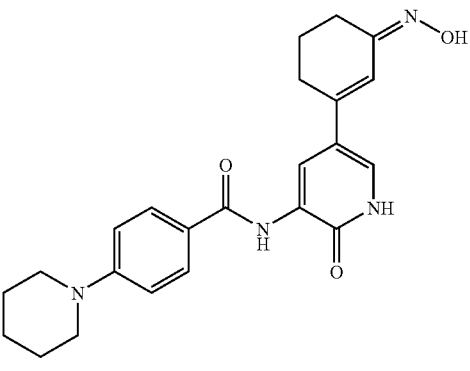
II-86

TABLE I-continued
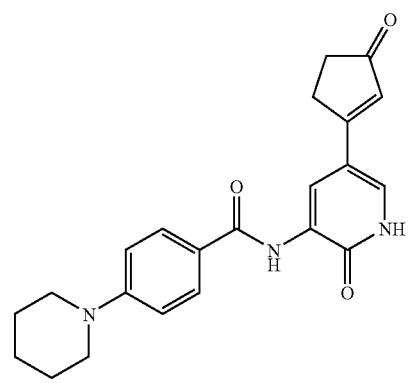
II-87
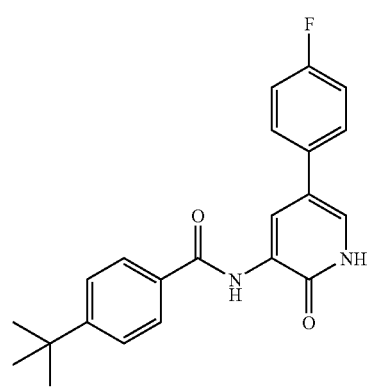
II-88
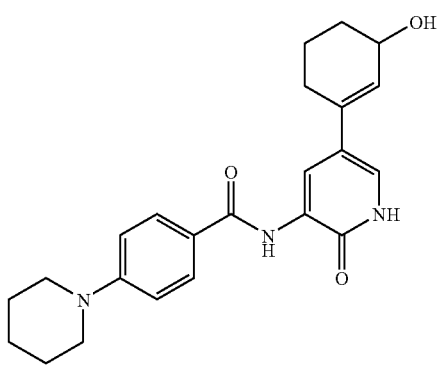
II-89
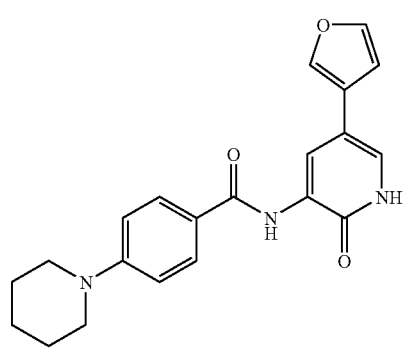
II-90
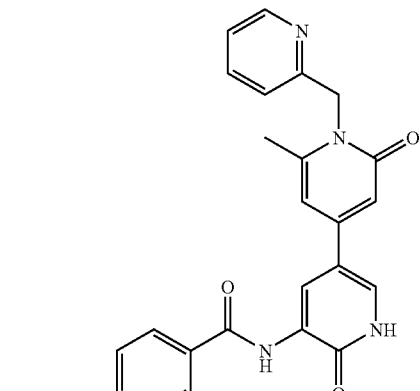
II-91
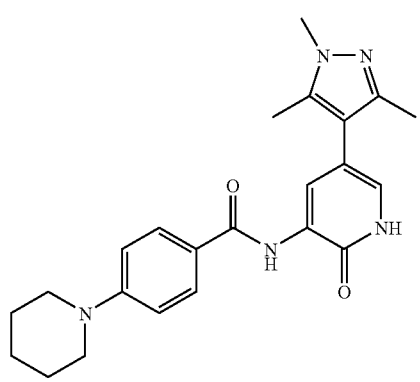
II-92
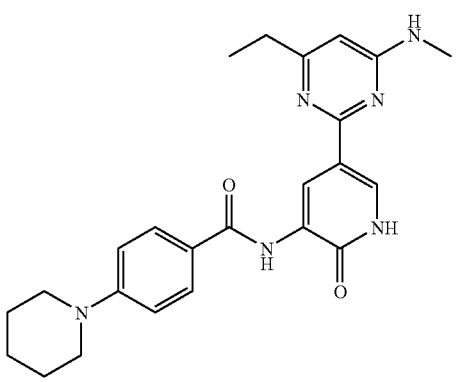
II-93

TABLE I-continued
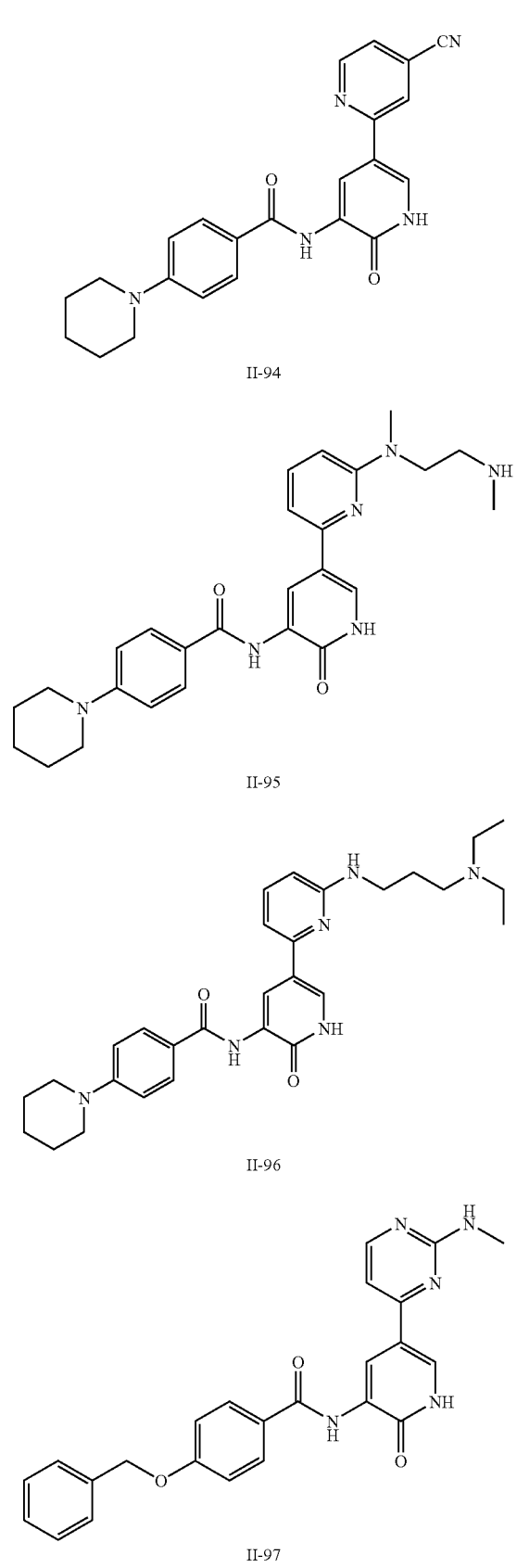
II-94, II-95, II-96, II-97, II-98, II-99, II-100, II-101

TABLE I-continued
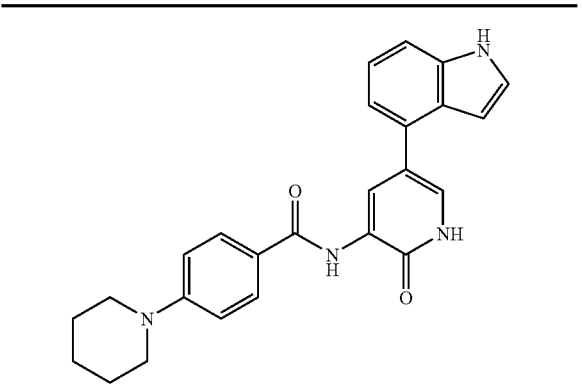
II-102
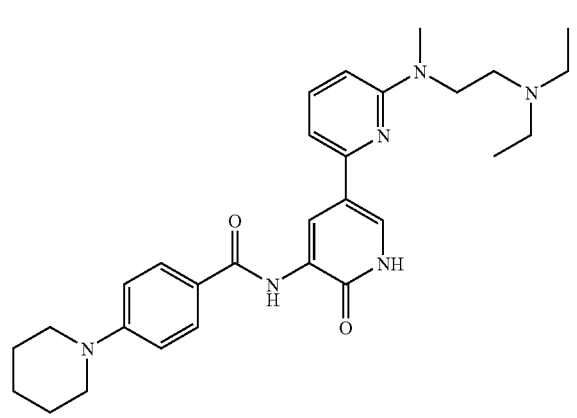
II-103
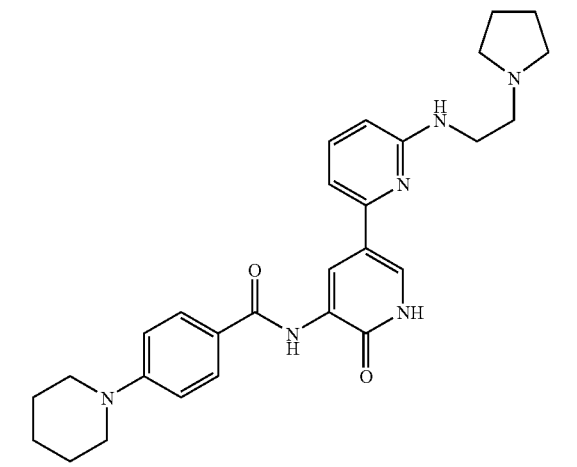
II-104
TABLE I-continued
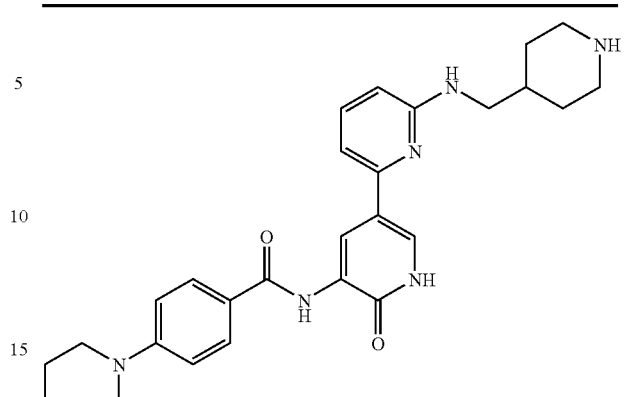
II-105
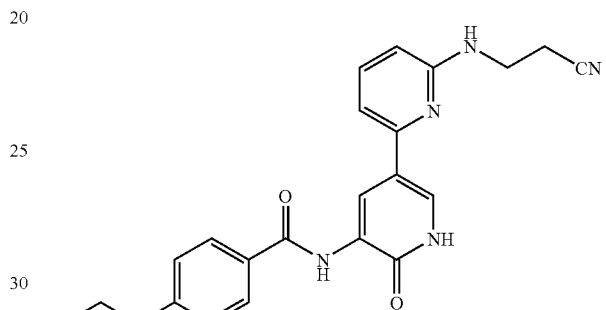
II-106
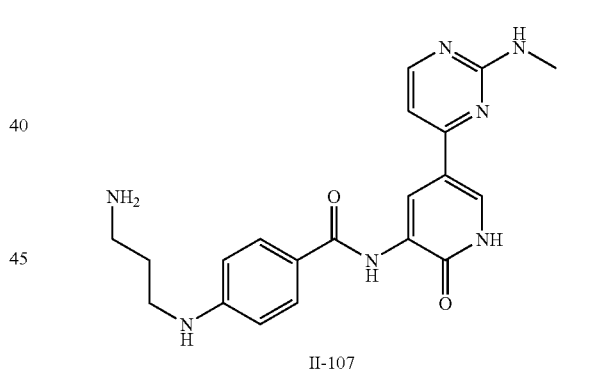
II-107
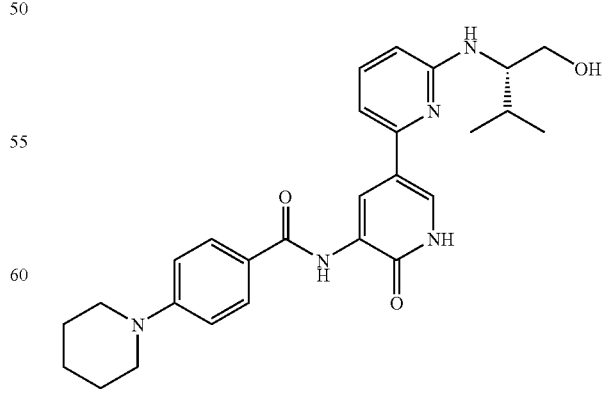
II-108

TABLE I-continued
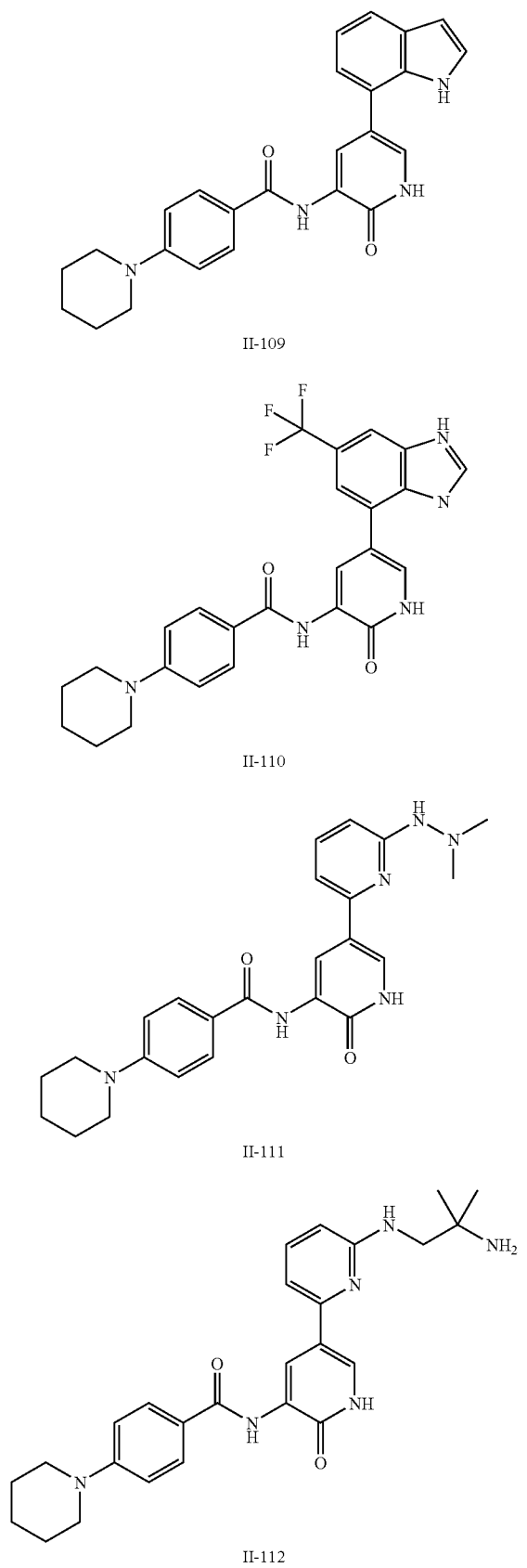
II-109
II-110
II-111
II-112
TABLE I-continued
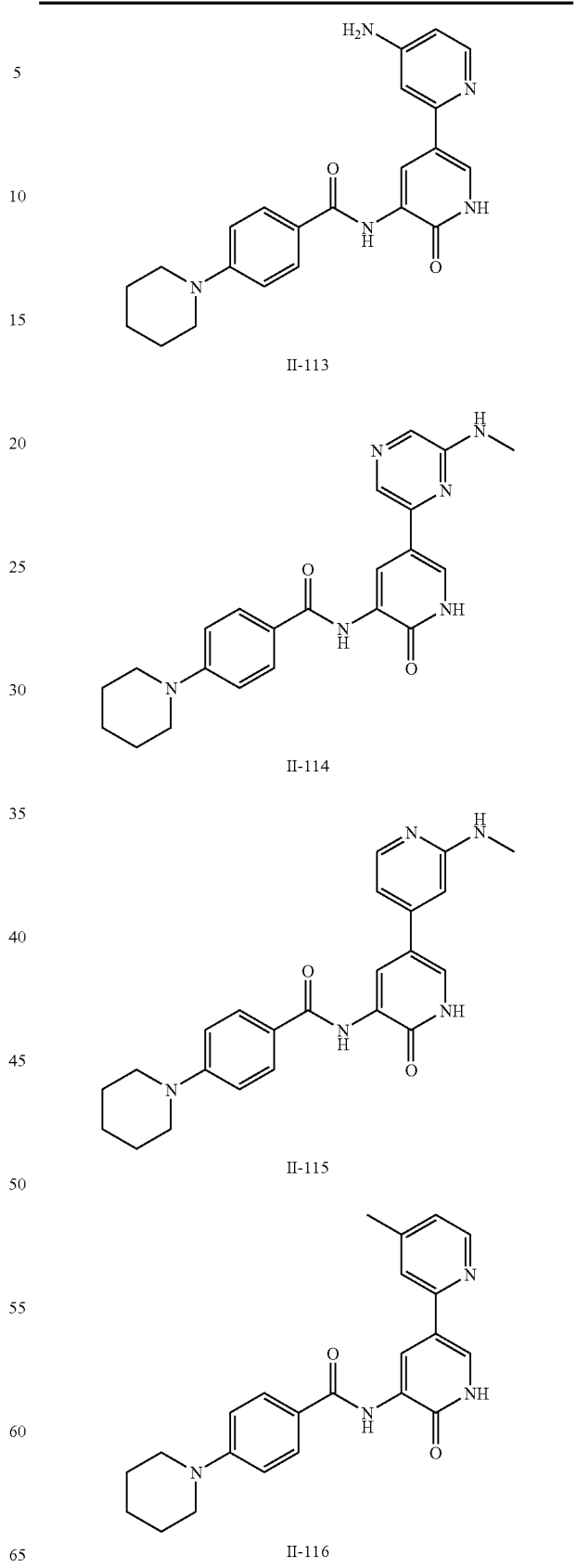
II-113
II-114
II-115
II-116

TABLE I-continued
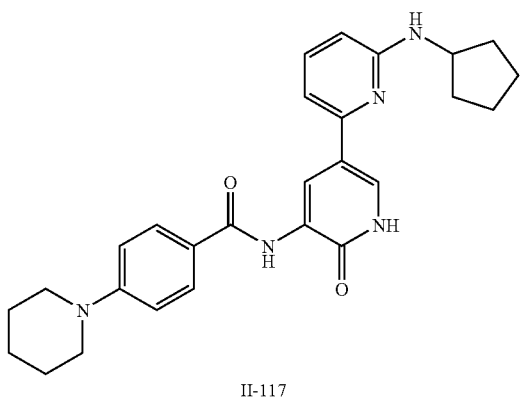
II-117
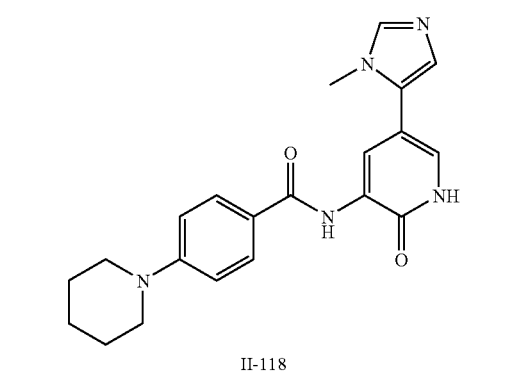
II-118
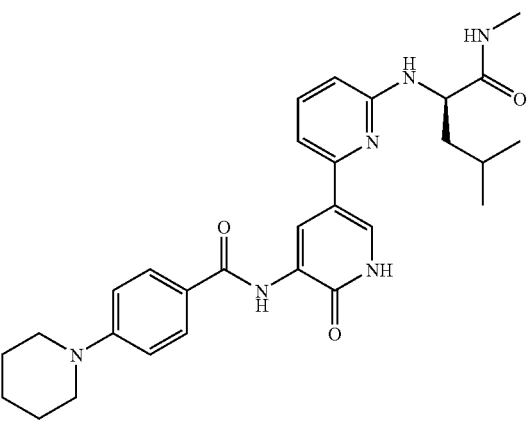
II-119
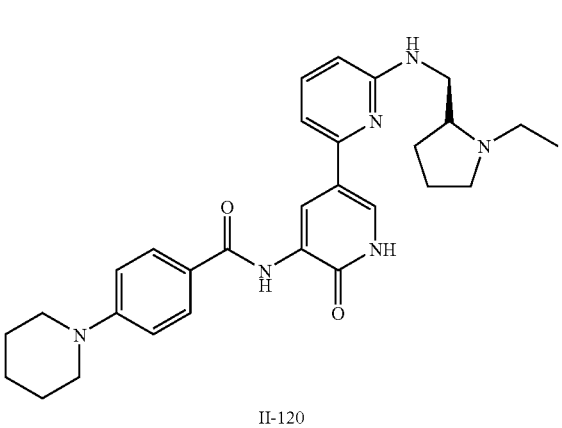
II-120
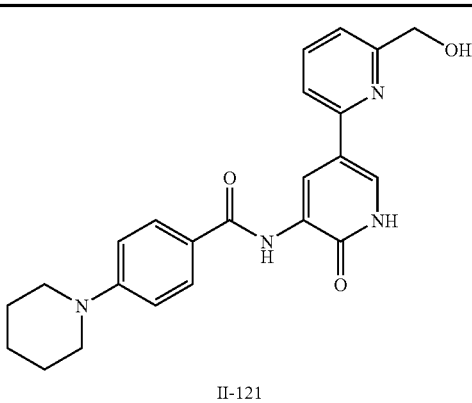
II-121
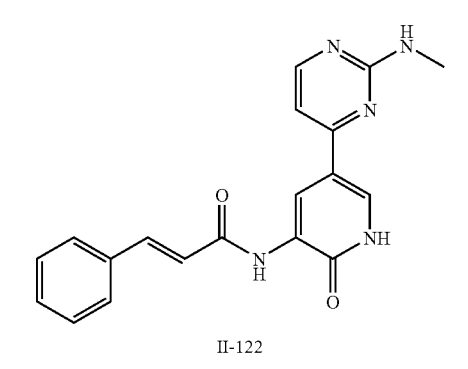
II-122
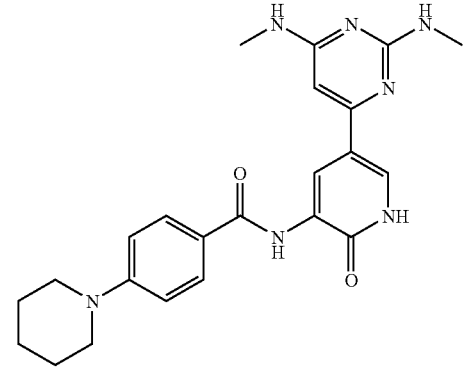
II-123
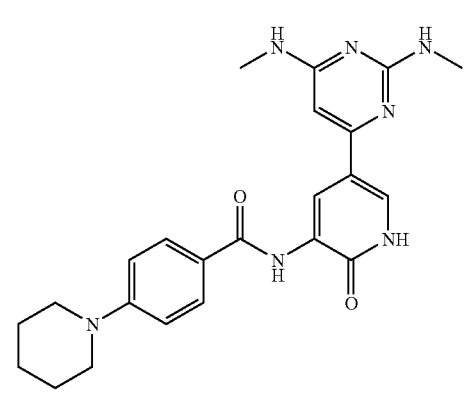
II-124

TABLE I-continued
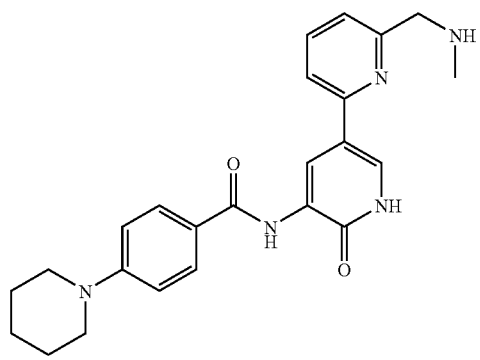
II-125
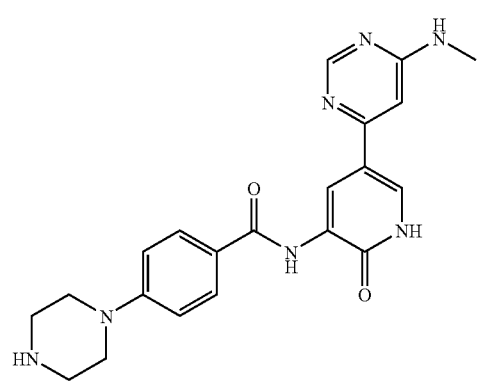
II-126
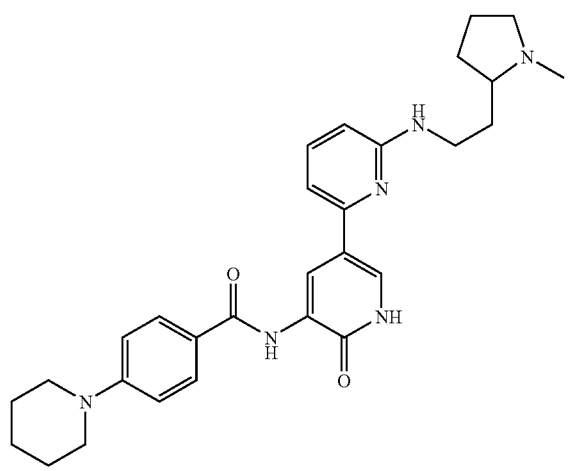
II-127
TABLE I-continued
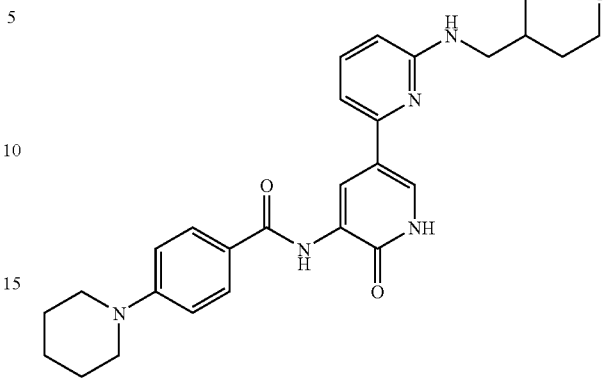
II-128
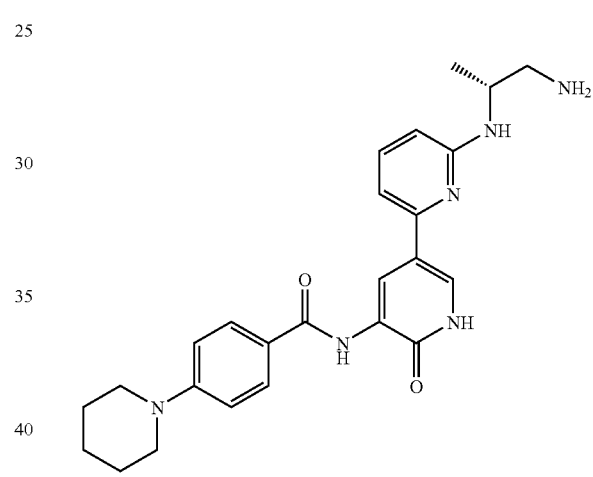
II-129
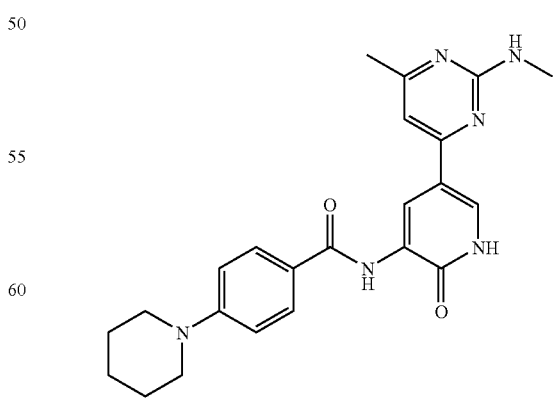
II-130

TABLE I-continued
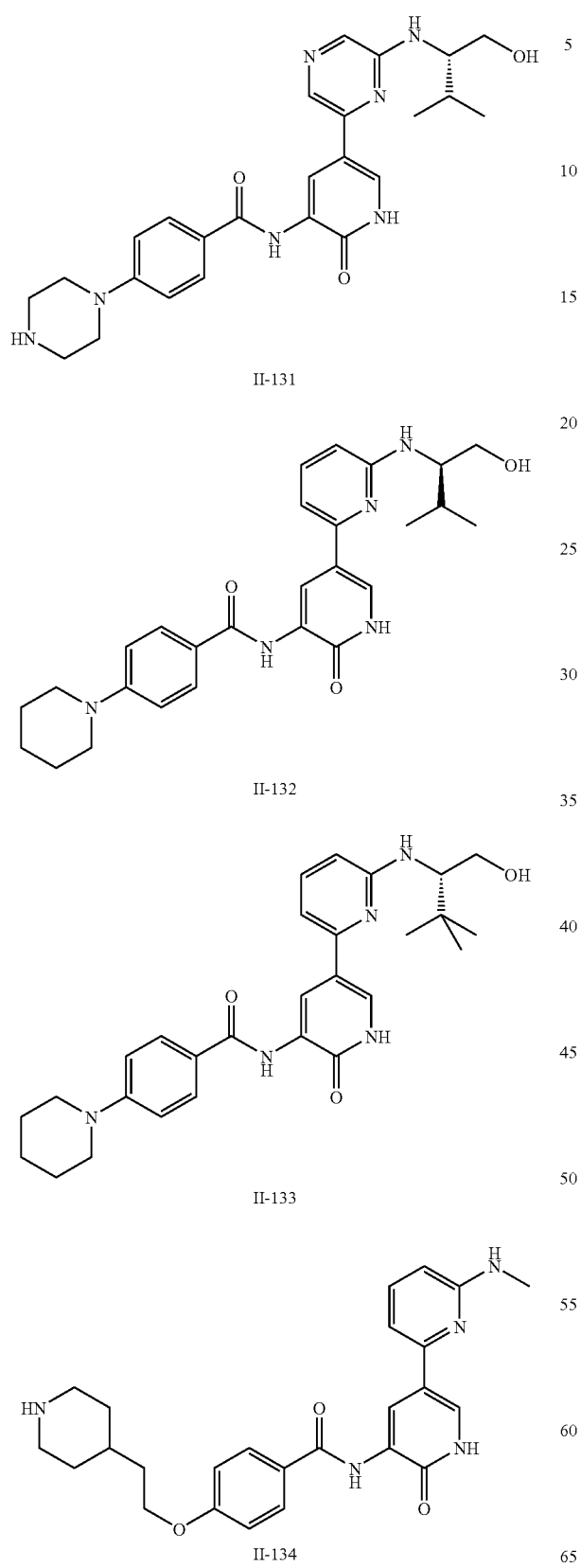
II-131
II-132
II-133
II-134
TABLE I-continued
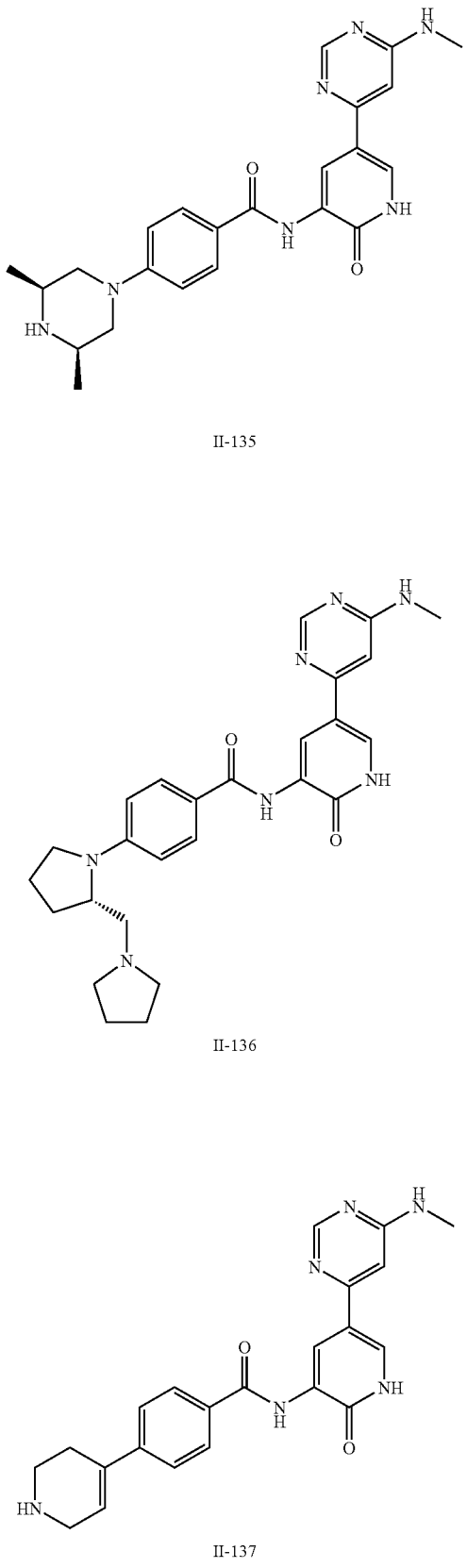
II-135
II-136
II-137

TABLE I-continued
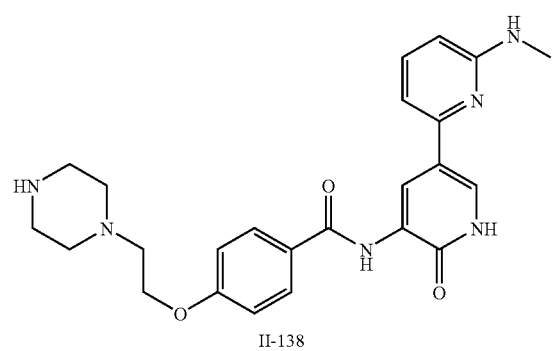
II-138
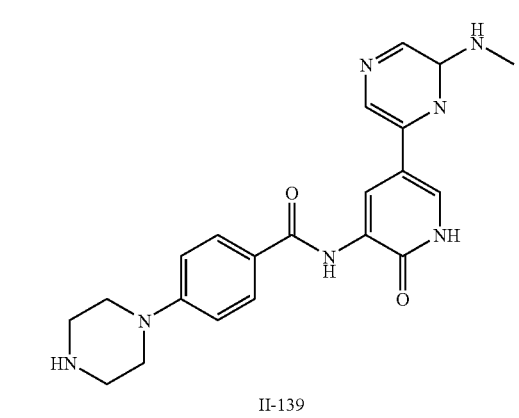
II-139
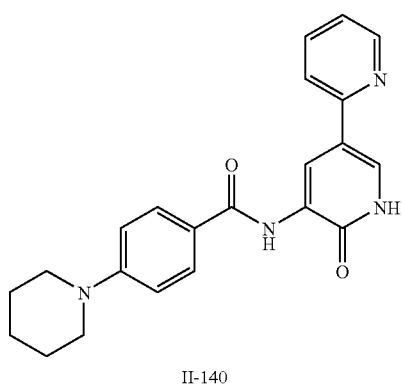
II-140
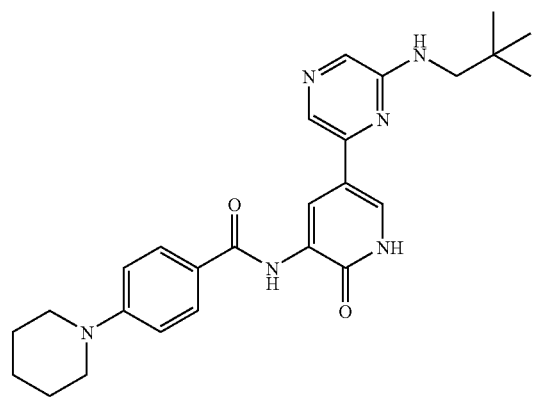
II-141
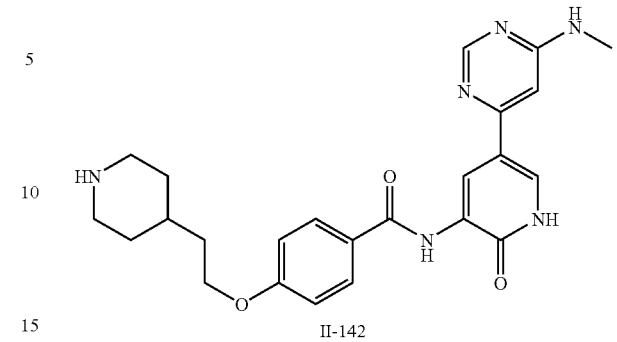
II-142
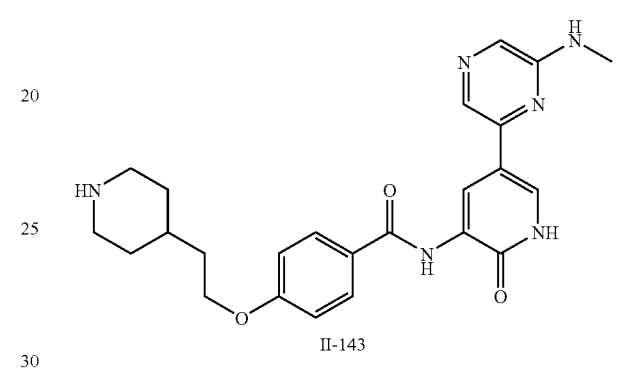
II-143
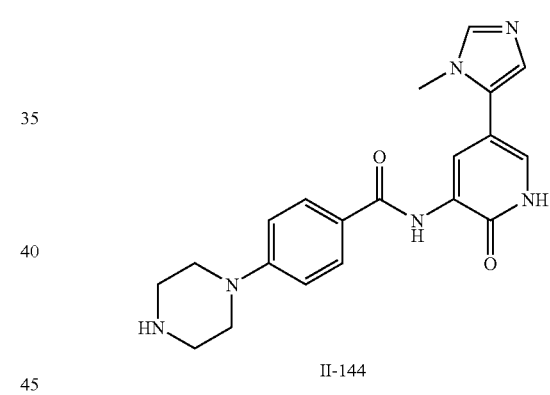
II-144
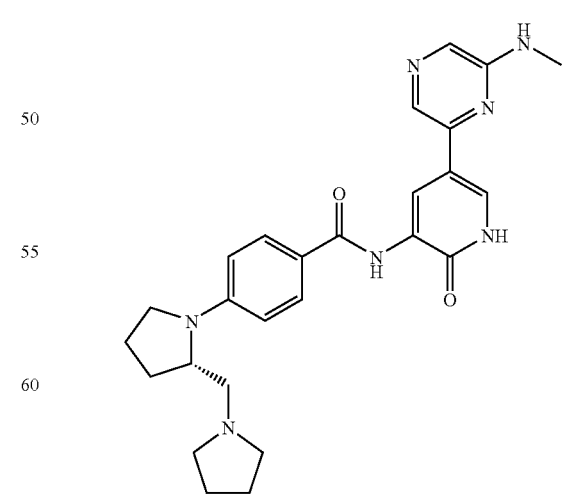
II-145

TABLE I-continued
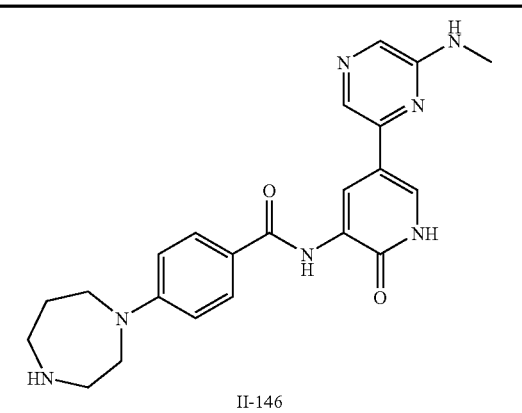
II-146
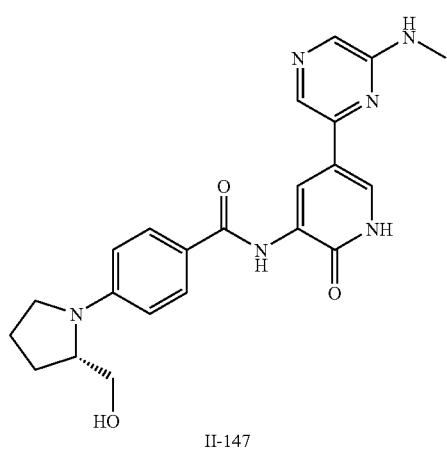
II-147
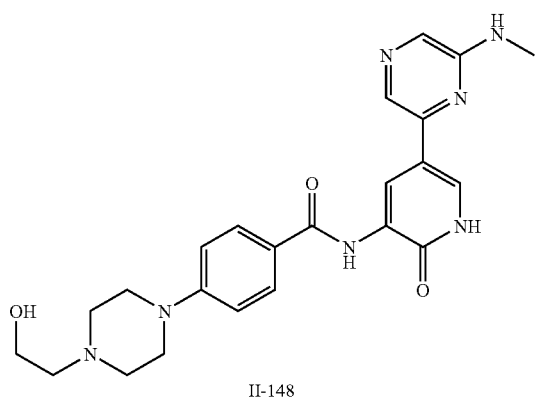
II-148
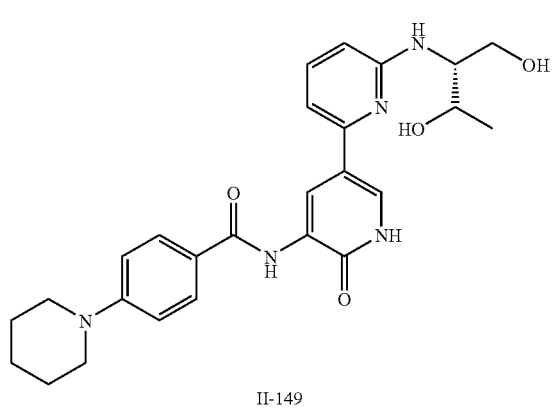
II-149
TABLE I-continued
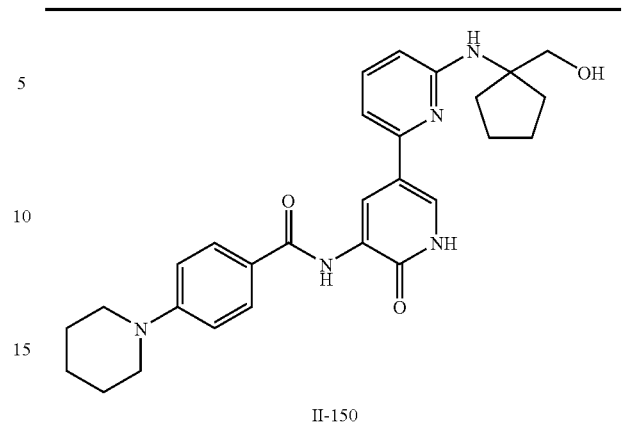
II-150
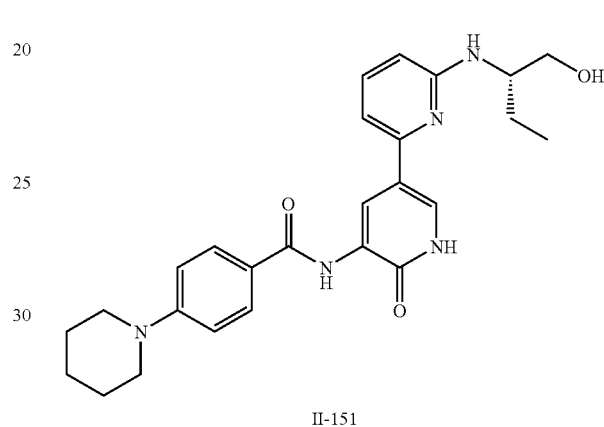
II-151
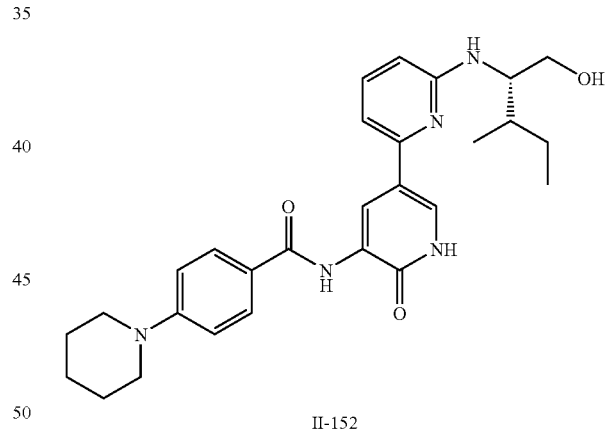
II-152
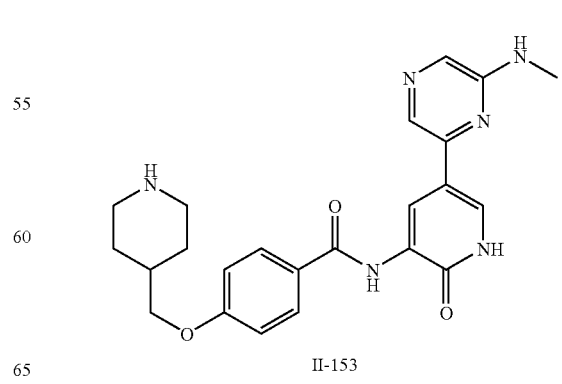
II-153

TABLE I-continued
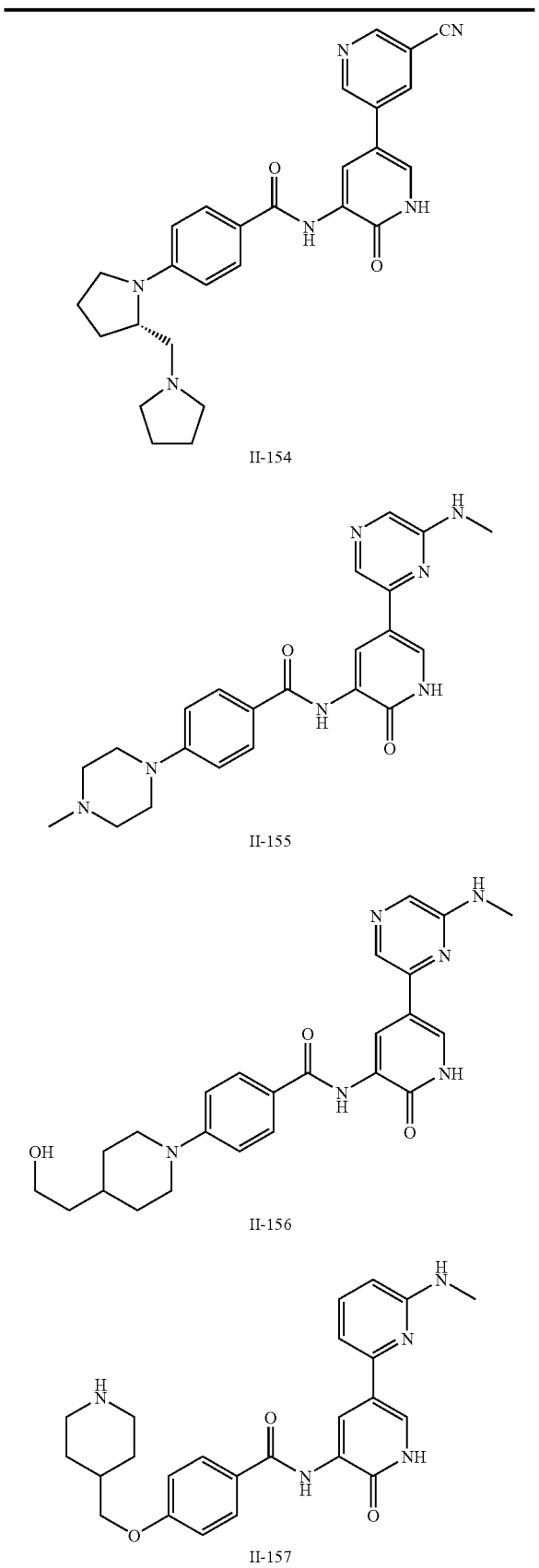
II-154
II-155
II-156
II-157
TABLE I-continued
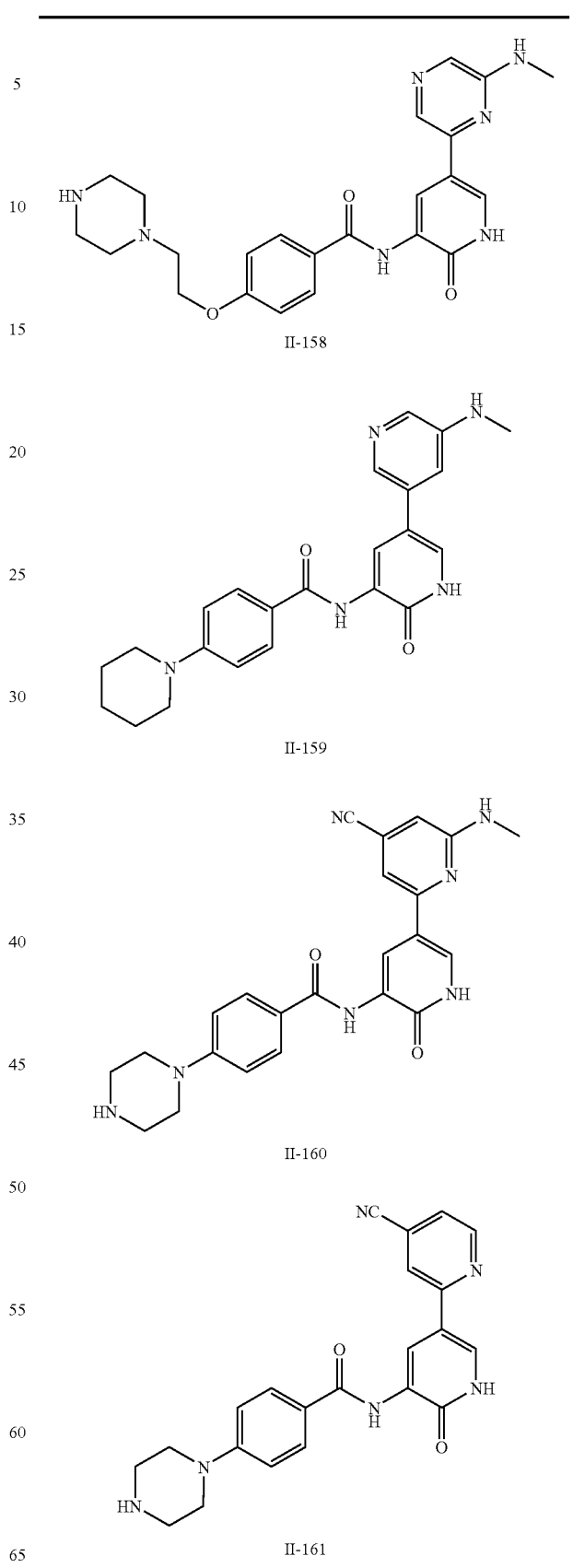
II-158
II-159
II-160
II-161

TABLE I-continued
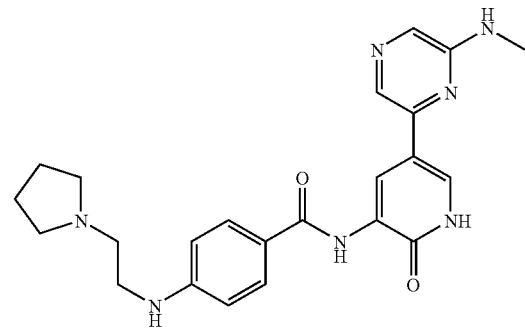
II-162
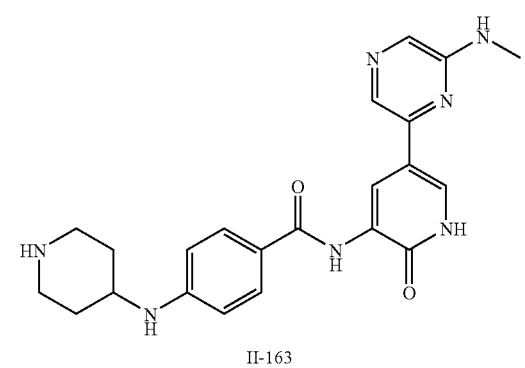
II-163
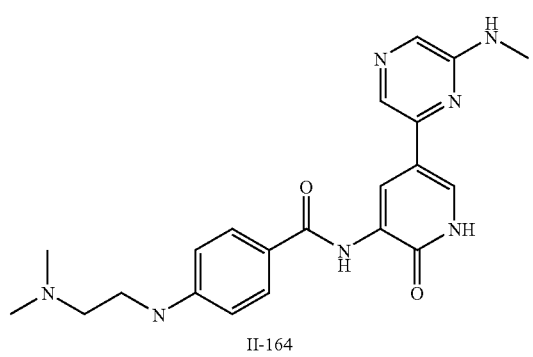
II-164
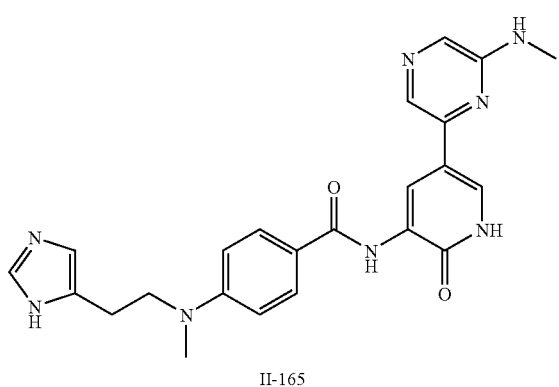
II-165
TABLE I-continued
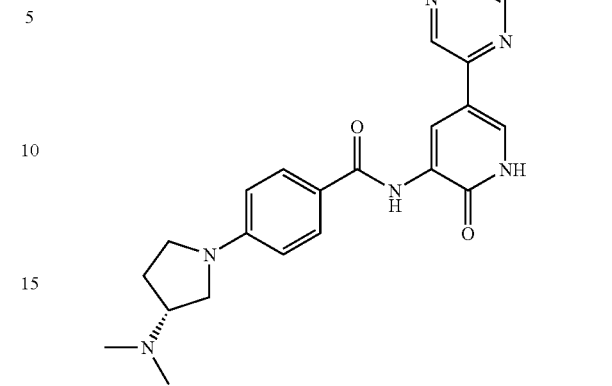
II-166
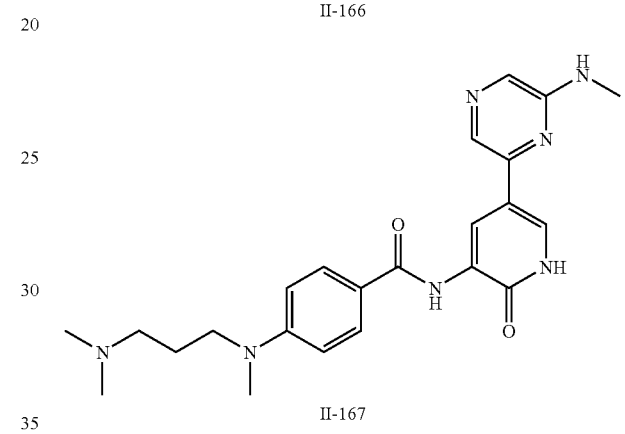
II-167
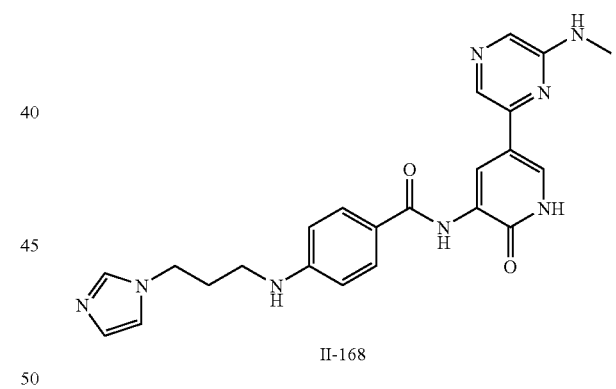
II-168
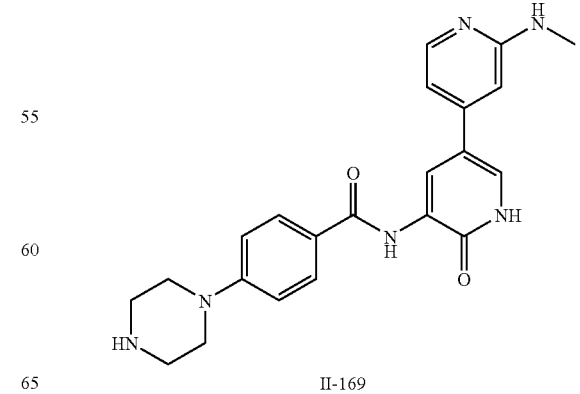
II-169

TABLE I-continued
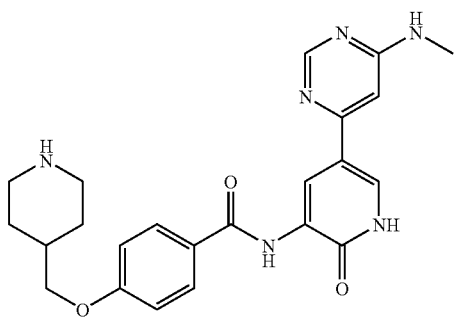
II-170
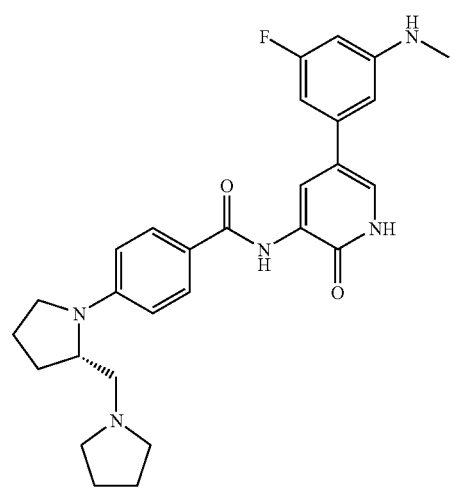
II-171
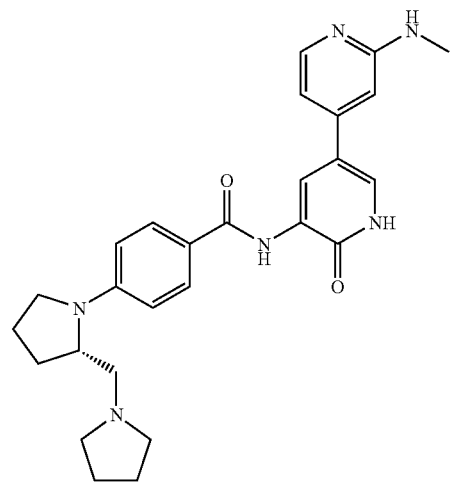
II-172
TABLE I-continued
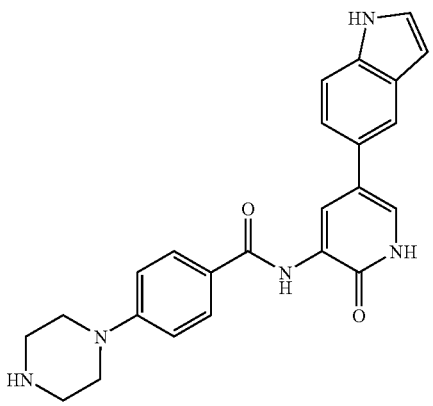
II-173
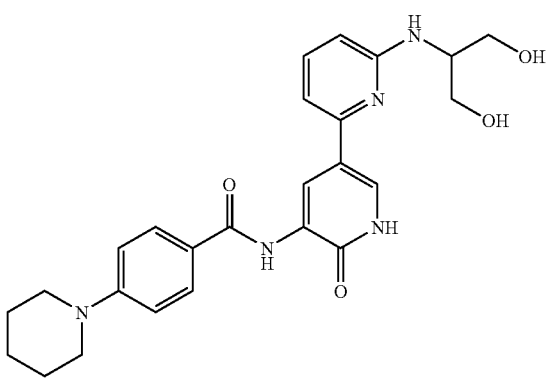
II-174
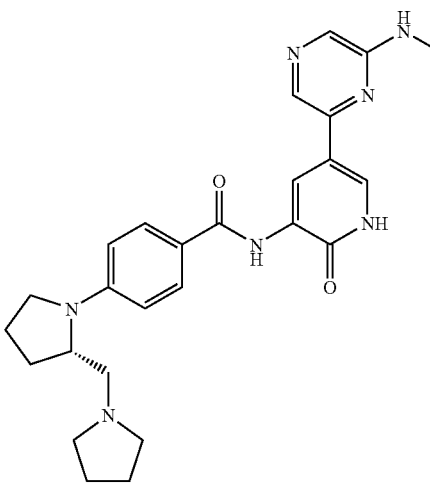
II-175

TABLE I-continued
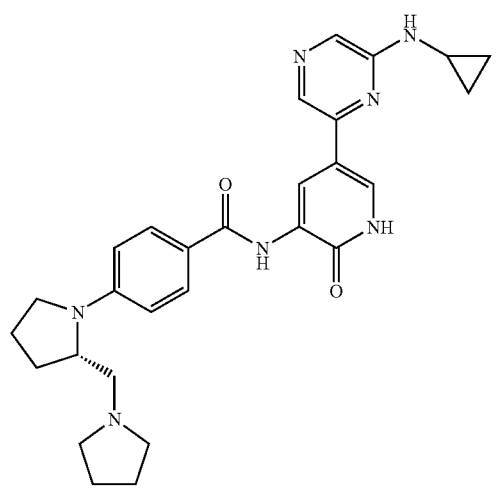
II-176
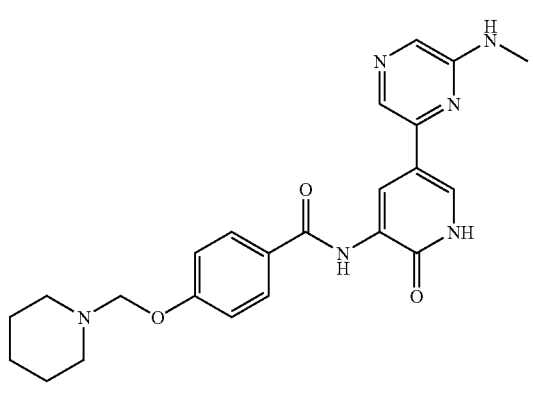
II-177
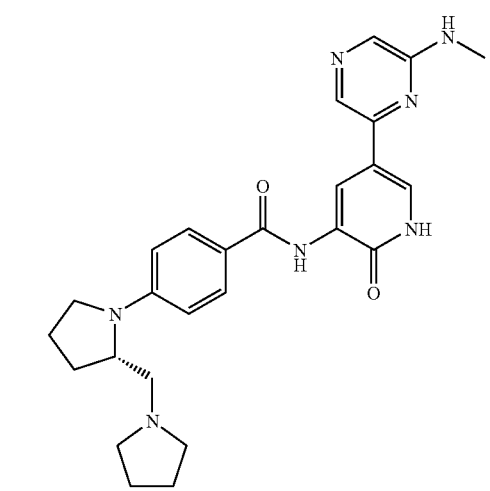
II-178
TABLE I-continued
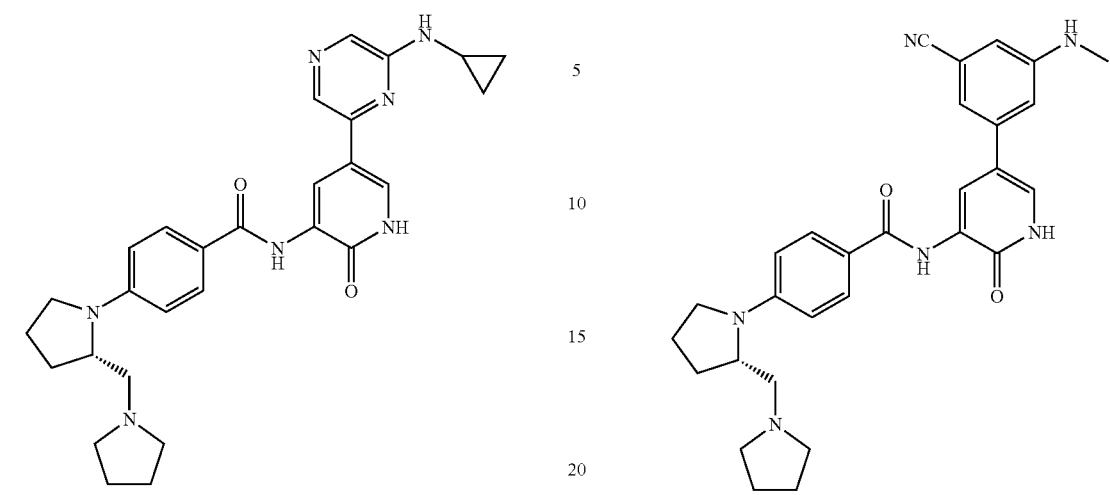
II-179
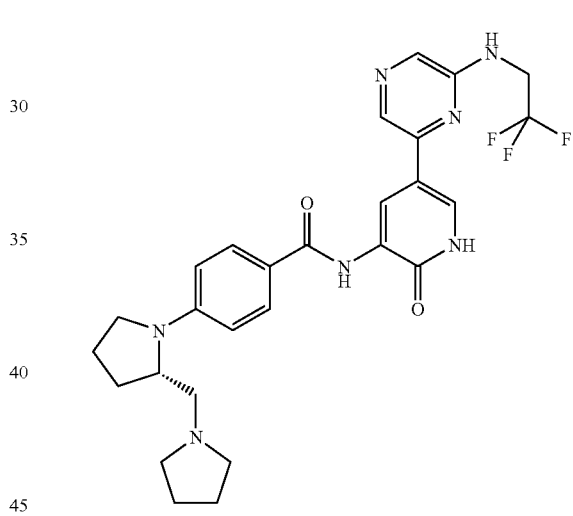
II-180
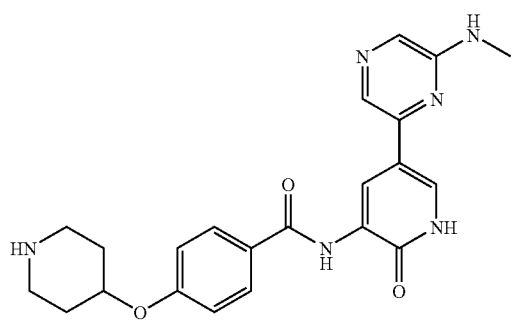
II-181

TABLE I-continued
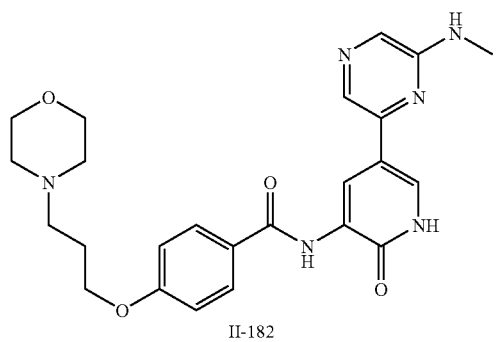
II-182
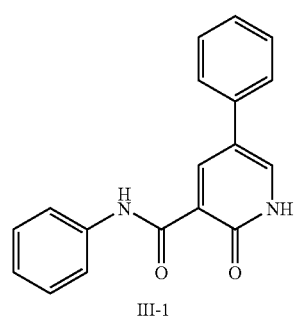
III-1
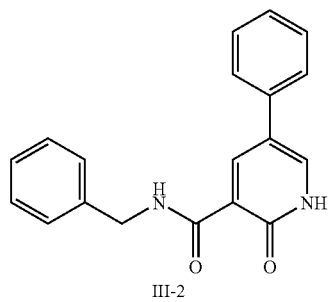
III-2
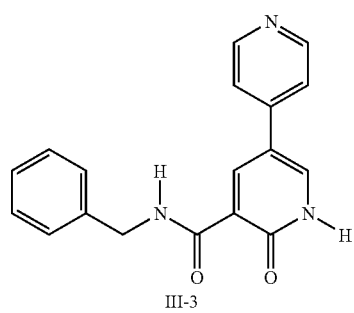
III-3
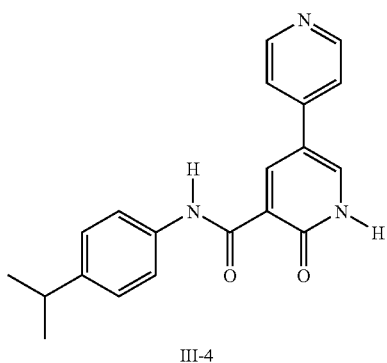
III-4
TABLE I-continued
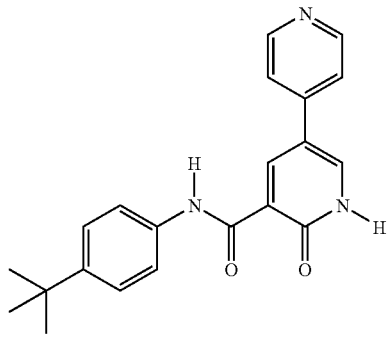
III-5
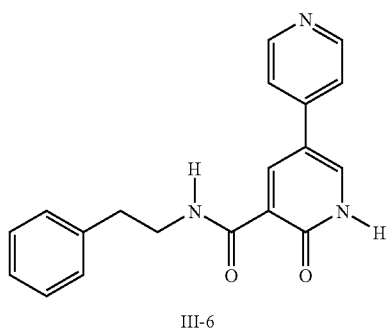
III-6
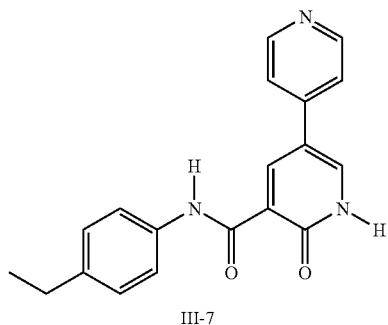
III-7
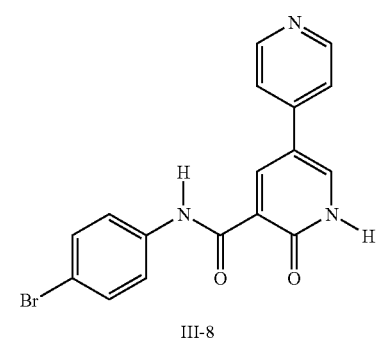
III-8

TABLE I-continued
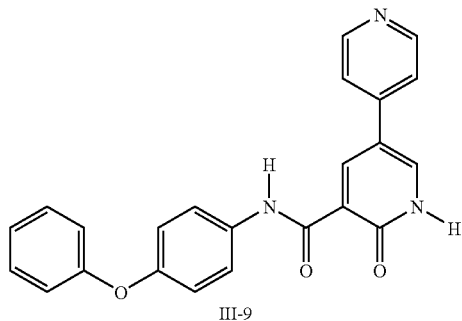
III-9
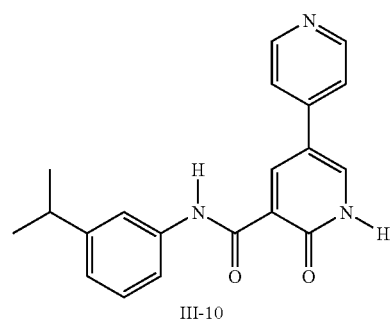
III-10
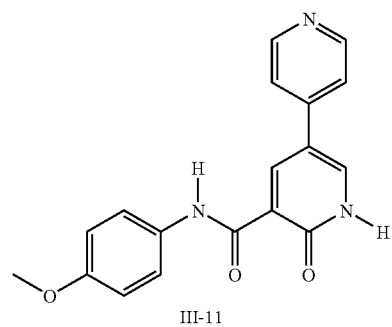
III-11
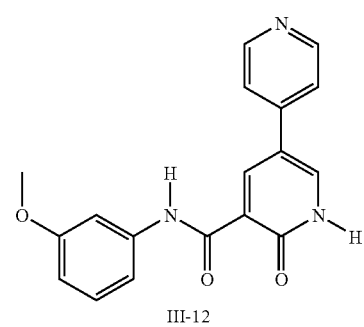
III-12
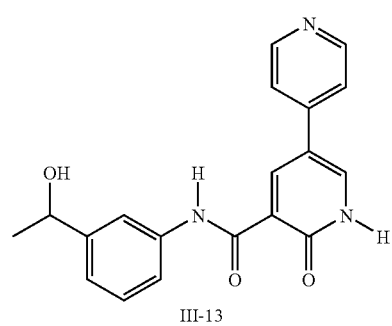
III-13
TABLE I-continued
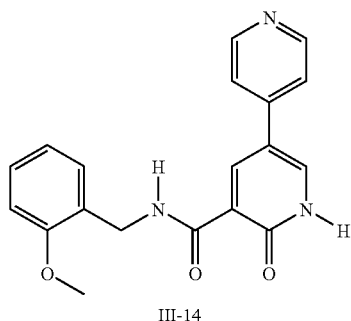
III-14
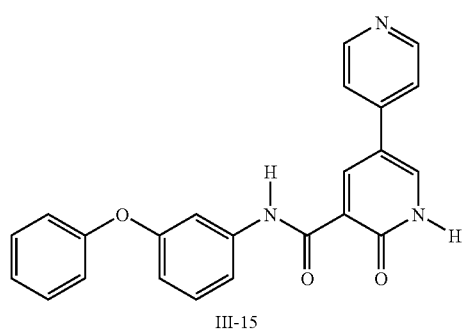
III-15
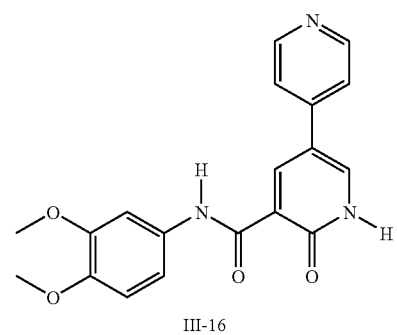
III-16
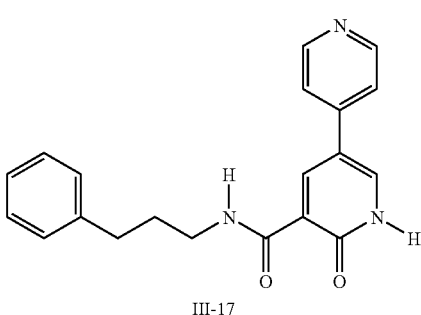
III-17

TABLE I-continued
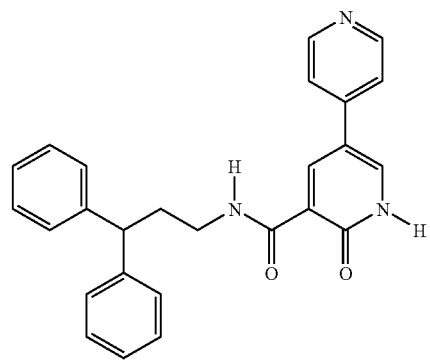
III-18
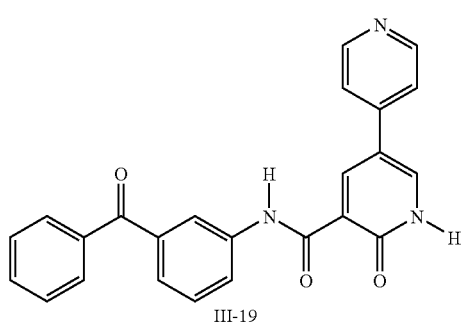
III-19
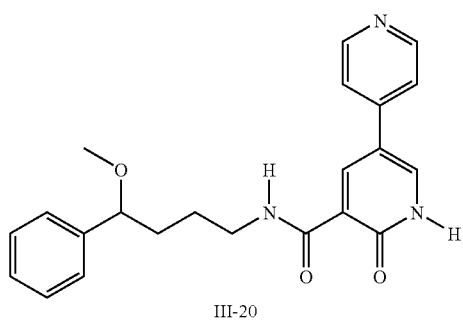
III-20
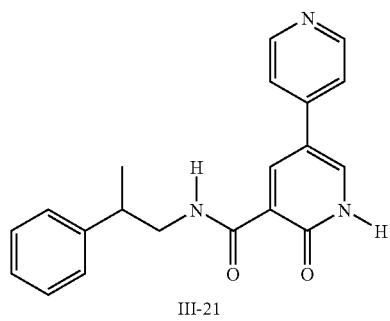
III-21
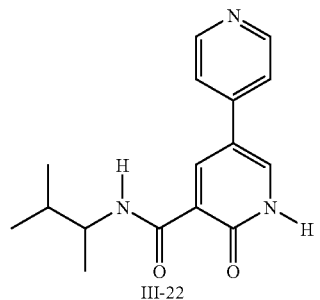
III-22
TABLE I-continued
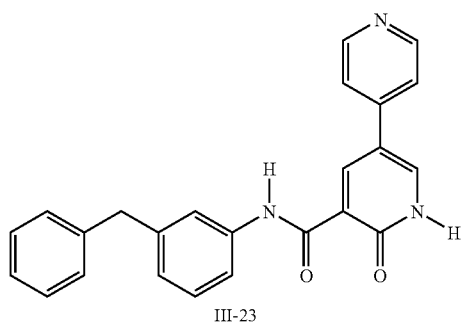
III-23
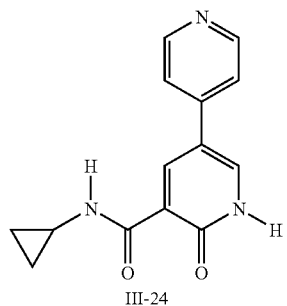
III-24
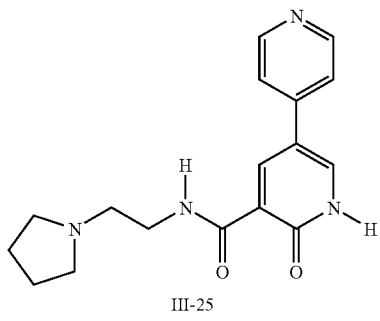
III-25
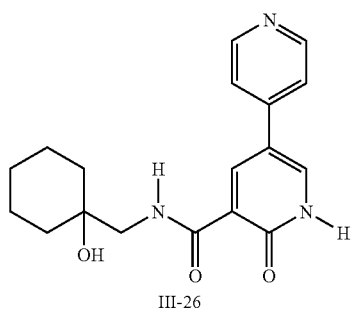
III-26
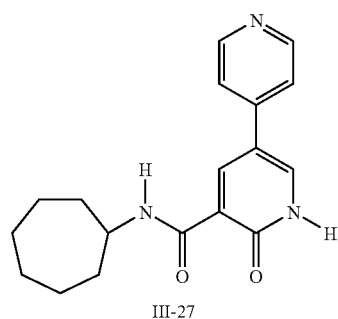
III-27

TABLE I-continued
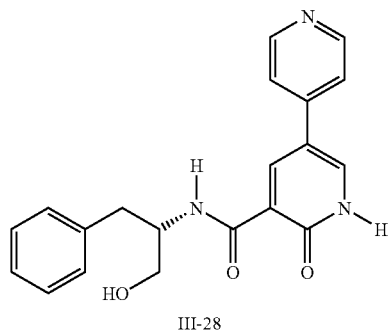
III-28
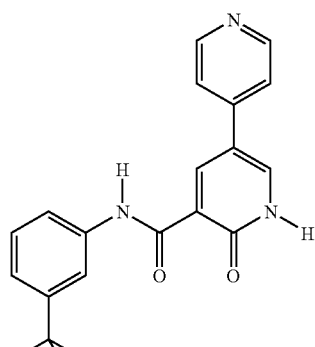
III-29
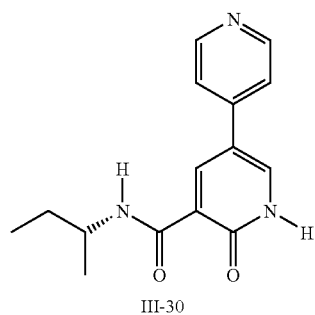
III-30
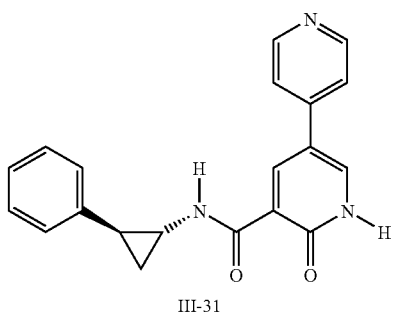
III-31
TABLE I-continued
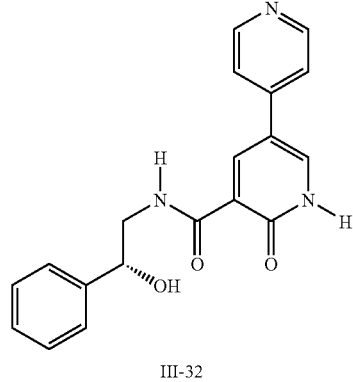
III-32
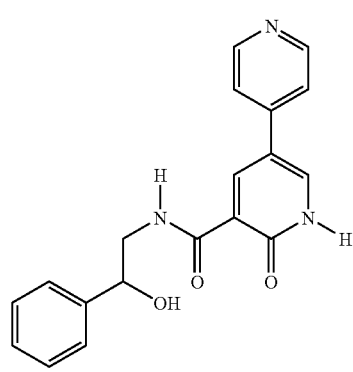
III-33
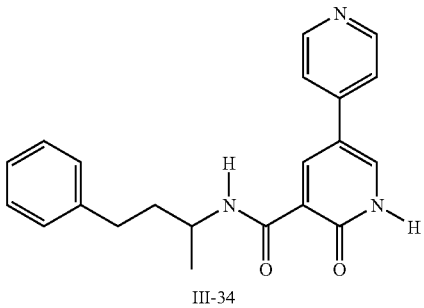
III-34
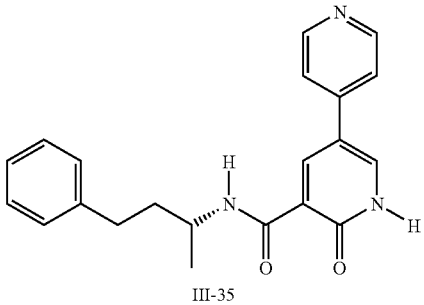
III-35

TABLE I-continued
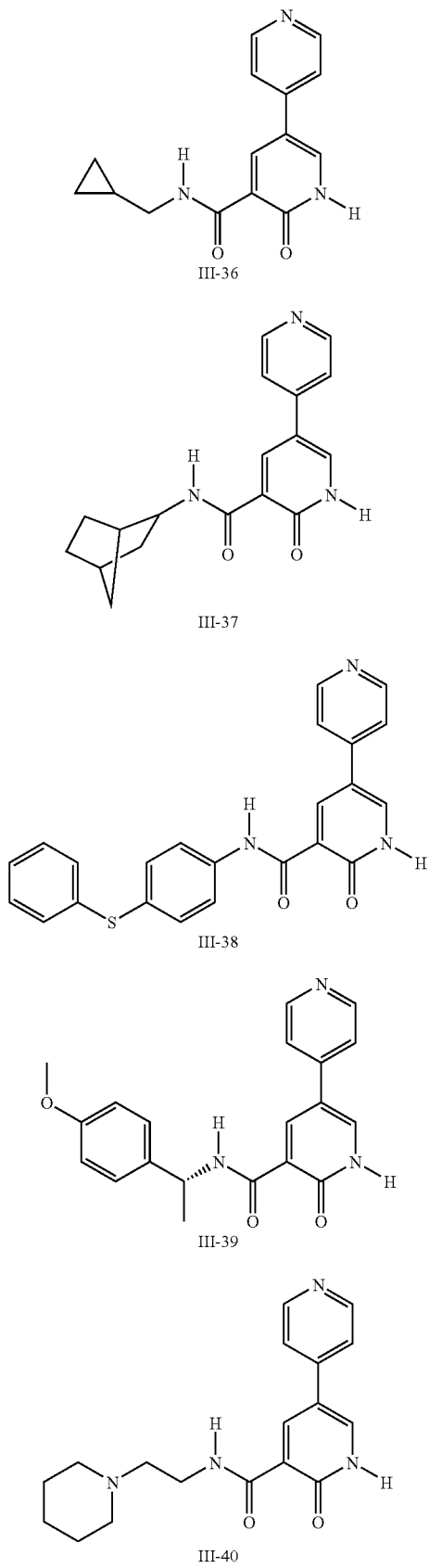
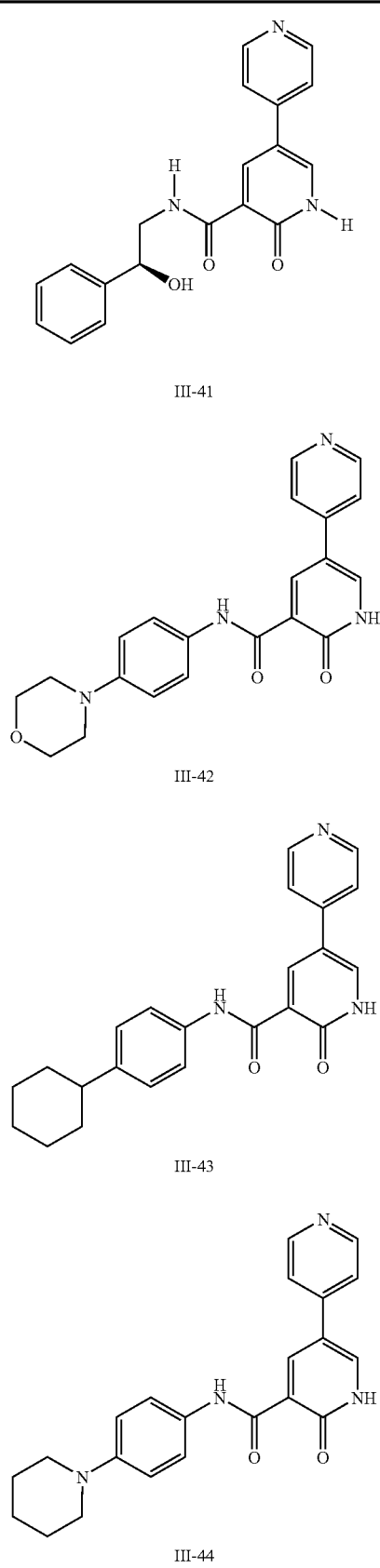

TABLE I-continued
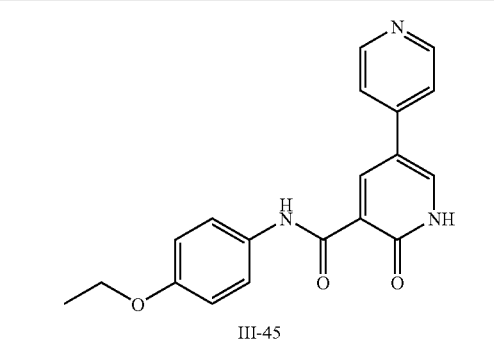
III-45
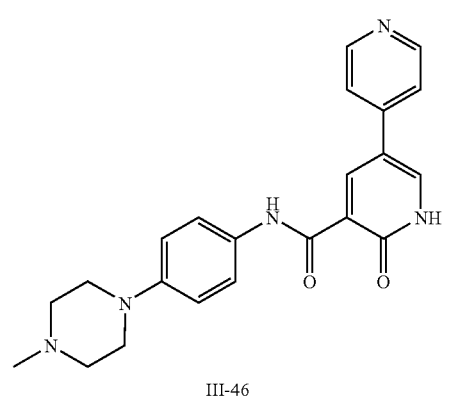
III-46
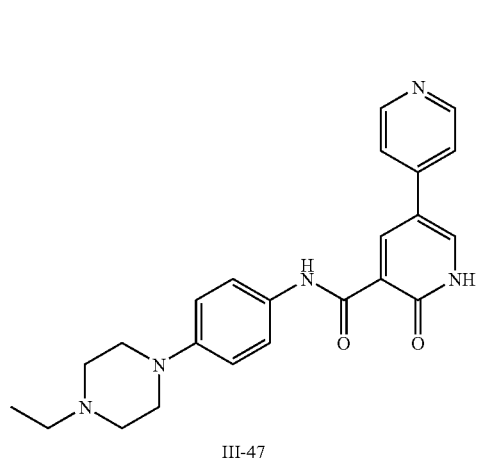
III-47
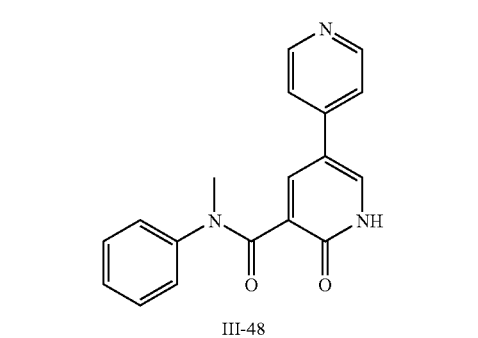
III-48
TABLE I-continued
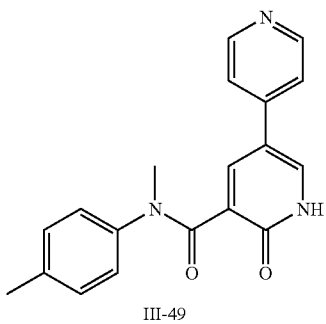
III-49
III-50
III-51
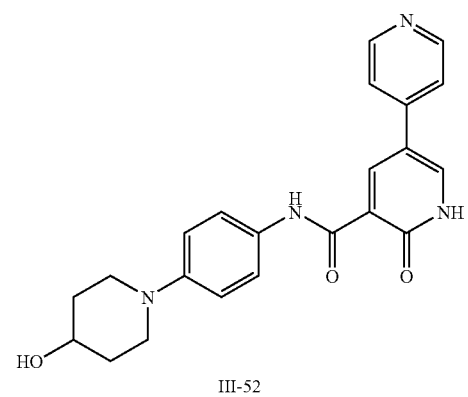
III-52

TABLE I-continued

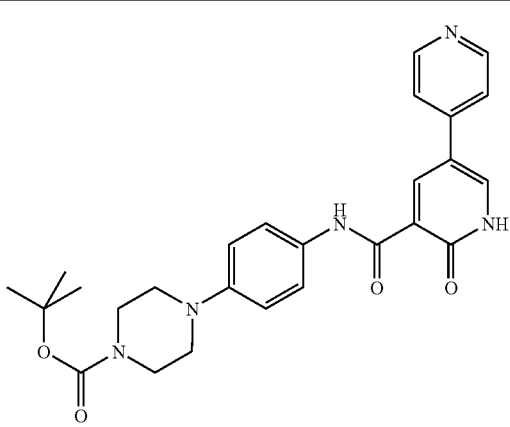

III-53

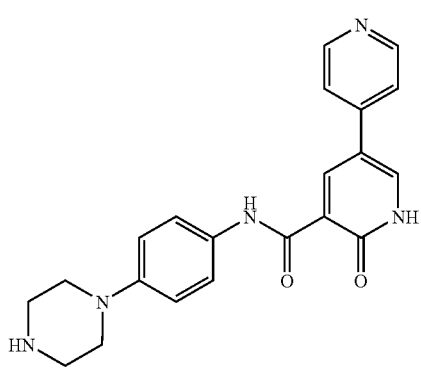

III-54

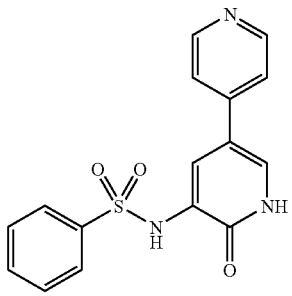

IV-1

The compounds of this invention may be prepared in general by methods known to those skilled in the art for analogous compounds, as illustrated by the general scheme below, and the preparative examples that follow.

Scheme I

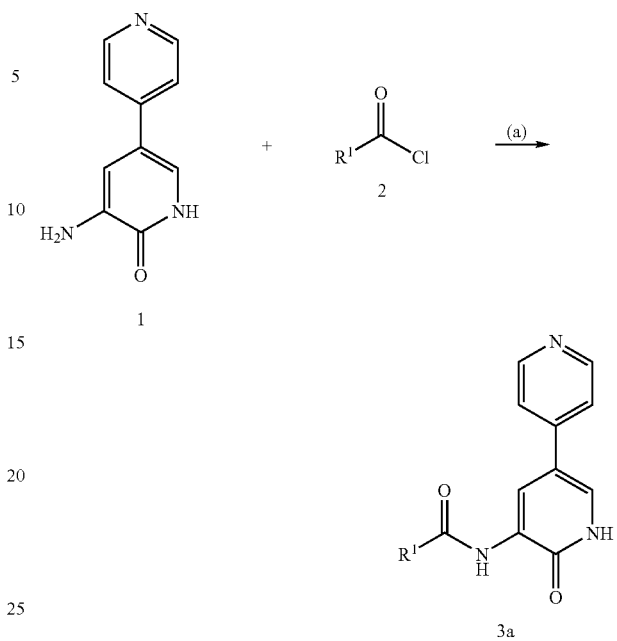

Reagents and conditions: (a) Pyridine, RT, 16 hours.

Scheme I above shows a general synthetic route that is used for preparing the compounds 3a of this invention when $R^1$ is as described herein. Compounds of formula 3a may be prepared by reaction of amrinone 1 with an acid chloride in pyridine according to step (a) of Scheme I. The reaction is amenable to a variety of acid chlorides.

Compounds I-1 to I-67 and I-82 to I-85 were prepared according to the general methods described in Scheme I.

Scheme II

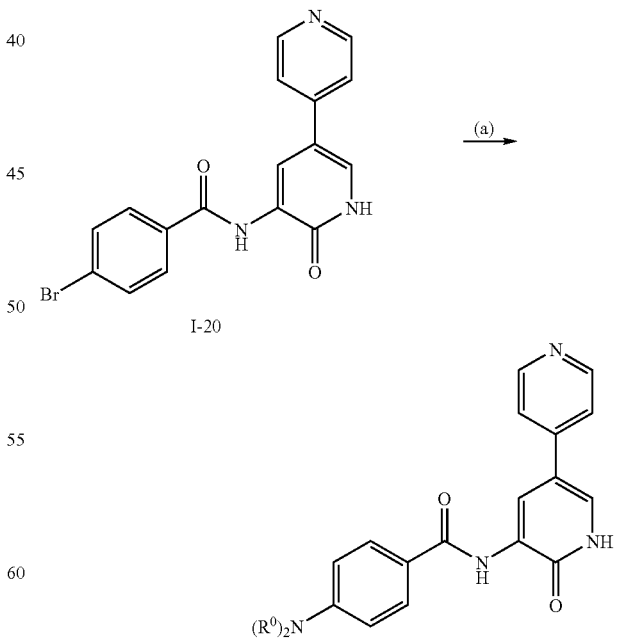

Reagents and conditions: (a) NMP, xs $(R^0)_2NH$, 160° C., 2 hours, μwawe.

Scheme II above shows a general synthetic route that is used for preparing the compounds 3b of this invention when R⁰ is as described herein. Compounds of formula 3b may be prepared by reaction of 1-20 with an excess of amine in NMP according to step (a) of Scheme II. The reaction is amenable to a variety of amines.

Compounds I-68 to I-81 were prepared according to the general methods described in Scheme II.

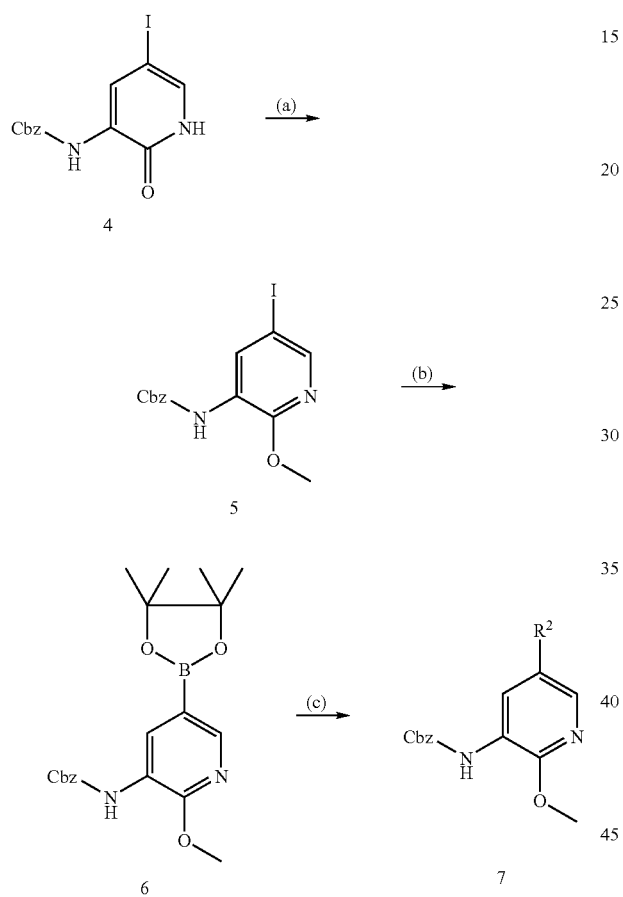

Scheme III

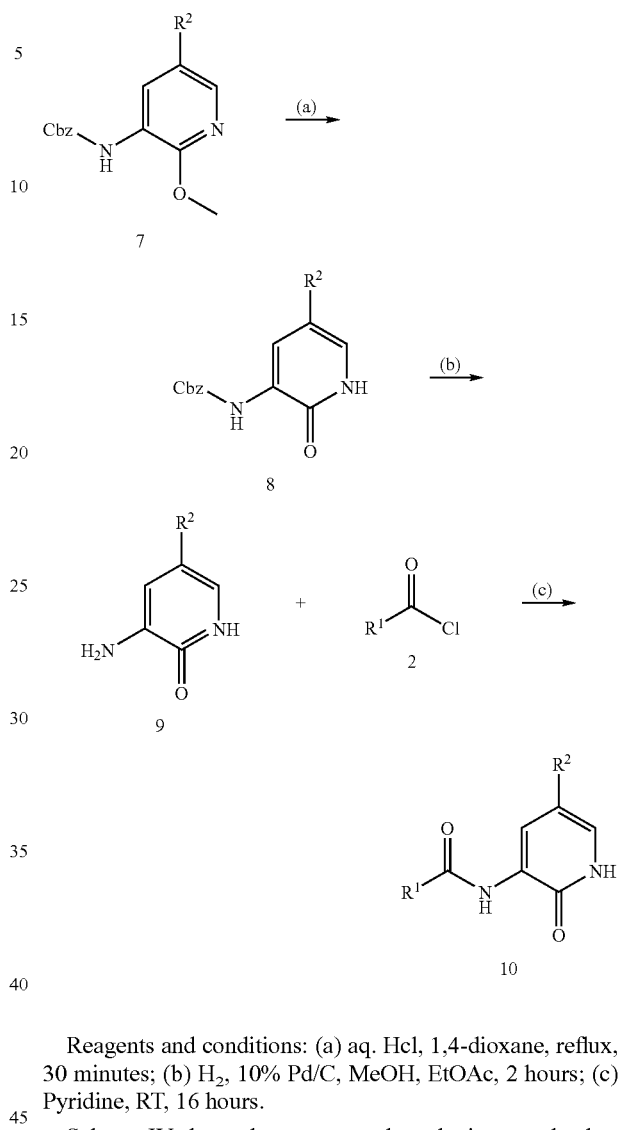

Scheme IV

Reagents and conditions: (a) MeI, Ag$_2$CO$_3$, CHCl$_3$, RT, 48 hours; (b) bis(pinacolato)diboron, Pd(Oac)$_2$, KOAc, DMF, 85° C., 3 hours; (c) R$^2$-Hal, Pd(Pph$_3$)$_4$, aq. Na$_2$CO$_3$, toluene, EtOH, reflux, 4 hours.

Scheme III above shows a general synthetic route that is used for preparing the compounds 7 of this invention when R$^2$ is as described herein. Starting material 4, which may be prepared by methods described by Warner, et al, *J. Med. Chem.* 1994, 37, 3090, is methylated according to step (a) of Scheme II. Compound of formula 6 is formed by reaction of the iodide 5 with bis(pinacolato)diboron in presence of palladium as a catalyst. The formation of derivatives 7 is achieved by treating the boronic ester derivatives 6 with a halide R$^2$-Hal in the presence of palladium as a catalyst by using the Suzuki coupling methods that are well known in the art. The reaction is amenable to a variety of substituted halides R$^2$-Hal.

Reagents and conditions: (a) aq. Hcl, 1,4-dioxane, reflux, 30 minutes; (b) H$_2$, 10% Pd/C, MeOH, EtOAc, 2 hours; (c) Pyridine, RT, 16 hours.

Scheme IV above shows a general synthetic route that has been used for preparing compounds 10 of this invention when R$^1$ and R$^2$ are as described herein. Demethylation of 7 in acidic conditions leads to the formation of 8, which is deprotected according to step (b). Finally, compounds of formula 10 may be prepared by reaction of derivatives 9 with an acid chloride 2 in pyridine. The reaction is amenable to a variety of acid chlorides 2.

Scheme V

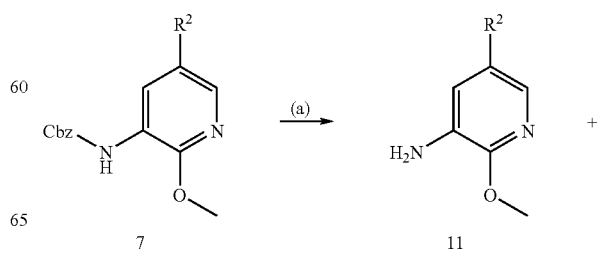

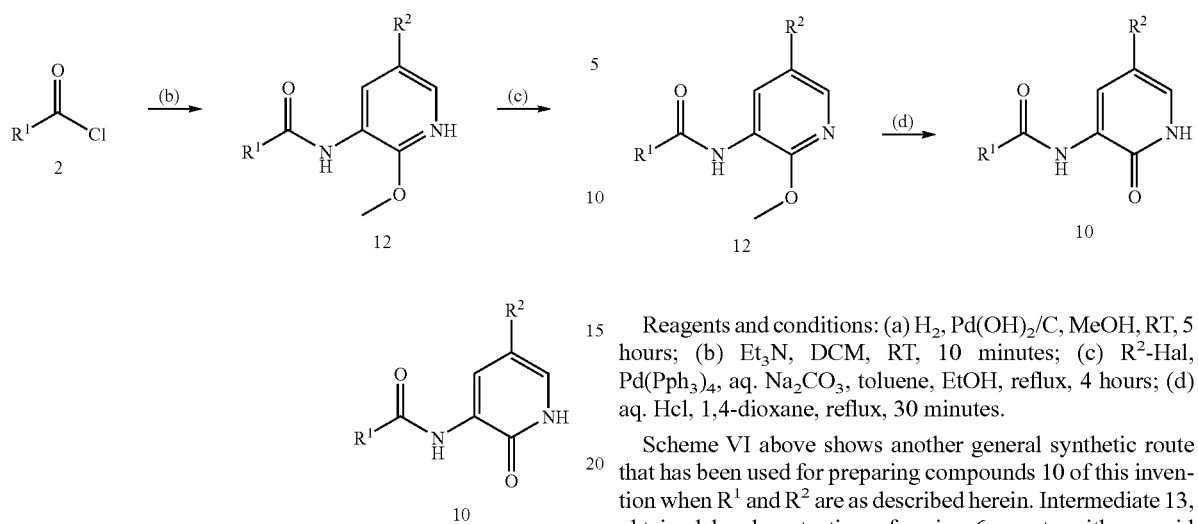

Reagents and conditions: (a) H₂, 10% Pd/C, MeOH, EtOAc, 2 hours; (b) Pyridine, RT, 16 hours; (c) aq. Hcl, 1,4-dioxane, reflux, 30 minutes.

Scheme V above shows another general synthetic route that has been used for preparing compounds 10 of this invention when $R^1$ and $R^2$ are as described herein. Intermediates 11, obtained by deprotection of amines 7, react with an acid chloride 2 in pyridine. The reaction is amenable to a variety of acid chlorides 2. After demethylation of intermediates 12 in acidic medium, pyridones 10 are obtained.

Reagents and conditions: (a) H₂, Pd(OH)₂/C, MeOH, RT, 5 hours; (b) Et₃N, DCM, RT, 10 minutes; (c) R²-Hal, Pd(Pph₃)₄, aq. Na₂CO₃, toluene, EtOH, reflux, 4 hours; (d) aq. Hcl, 1,4-dioxane, reflux, 30 minutes.

Scheme VI above shows another general synthetic route that has been used for preparing compounds 10 of this invention when $R^1$ and $R^2$ are as described herein. Intermediate 13, obtained by deprotection of amine 6, reacts with an acid chloride 2 to form compounds of formula 14. The reaction is amenable to a variety of acid chlorides 2. The formation of derivatives 12 is achieved by treating the boronic ester derivatives 14 with a halide R²-Hal in the presence of palladium as a catalyst by using the Suzuki coupling methods that are well known in the art. The reaction is amenable to a variety of substituted halides R²-Hal. After demethylation of intermediates 12 in acidic medium, pyridones 10 are obtained.

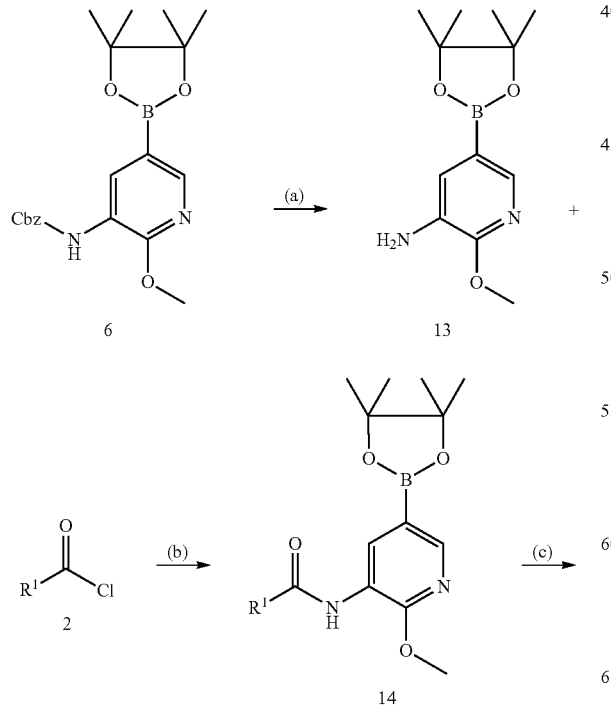

Scheme VI

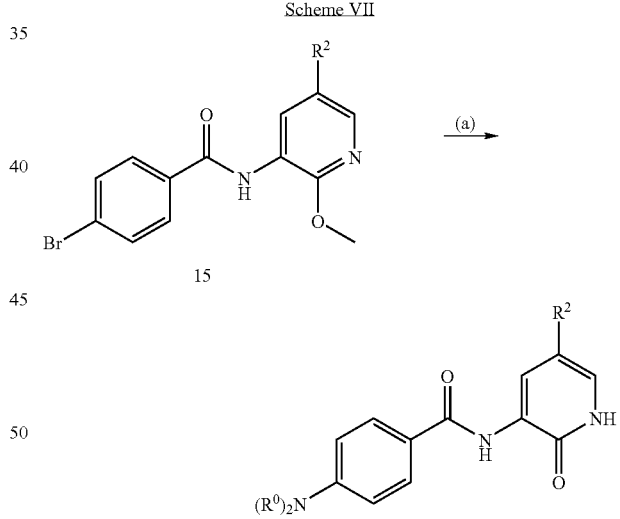

Scheme VII

Reagents and conditions: (a) (a) NMP, xs (R⁰)₂NH, 160° C., 2 hours, µwawe.

Scheme VII above shows a general synthetic route that is used for preparing the compounds 16 of this invention when $R^2$ and $R^0$ are as described herein. Compounds of formula 16 may be prepared by reaction of 15 with an excess of amine in NMP according to step (a) of Scheme VII. The reaction is amenable to a variety of amines.

Compounds II-1 to II-182 were prepared according to the general methods described in Schemes III, IV, V, VI and VII.

Scheme VIII

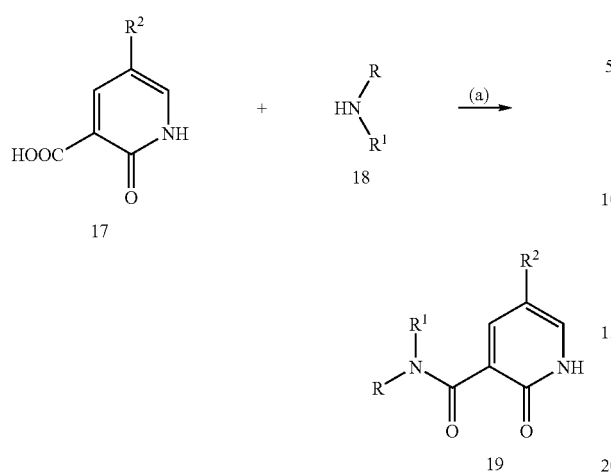

Reagents and conditions: (a) HOBt, DMAP, EDC, THF, RT, 16 hours.

Scheme VIII above shows a general synthetic route that has been used for preparing compounds 19 of this invention when R, $R^1$ and $R^2$ are as described herein. Starting material 17 may be prepared by methods substantially similar to those described in the literature by Church et al *J. Org. Chem.* 1995, 60, 3750. Compounds of formula 19 are prepared according to step (a) of scheme VIII.

Compounds III-1 to III-54 were prepared according to the general method described in Schemes VIII.

Scheme IX

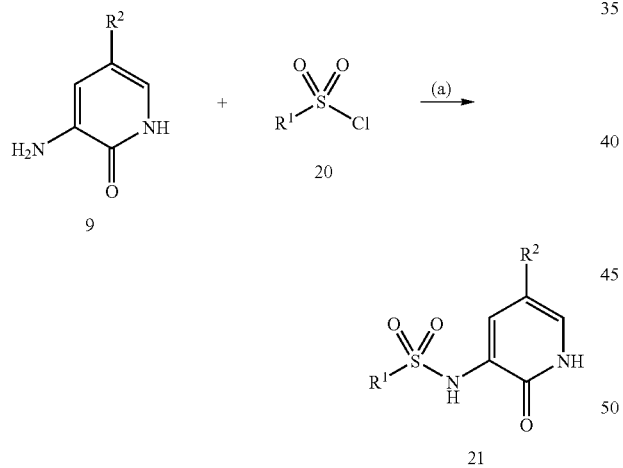

Reagents and conditions: (a) Pyridine, 0° C., 2 hours.

Scheme IX above shows a general synthetic route that is used for preparing the compounds 21 of this invention when $R^1$ and $R^2$ are as described herein. Compounds of formula 21 may be prepared by reaction of derivatives 9 with a sulfonyl chloride 20 in pyridine. The reaction is amenable to a variety of sulfonyl chlorides 20.

Compound IV-1 was prepared according to the general method described in Scheme IX.

This invention also provides compounds that can be used as intermediates to synthesize compounds of this invention. Additionally, this invention provides processes for using these intermediate compounds to prepare compounds of this invention.

Specifically, a compound 22 can be used as an intermediate compound in a process for preparing a compound 23. Compound 23 can then be carried on to a compound of formula I.

Scheme X

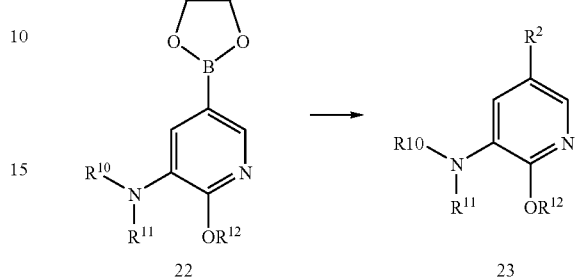

wherein:
$R^{10}$ is an amino protective group;
$R^{11}$ is H or $C_{1-6}$ alkyl or $R^{10}$ and $R^{11}$ together with the nitrogen atom to which they are bound form an amine protective group;
$R^{12}$ is a hydroxyl protecting group; and
$R^2$ is as defined herein.

In one embodiment, compound 22 is reacted with an appropriate compound comprising $R^2$ under appropriate reaction conditions to form compound 23. An example of an appropriate compound comprising $R^2$ is $R^2$—X, wherein X is an appropriate leaving group, such as a halo group. Appropriate reaction conditions are coupling conditions that allow bond formation between a boronic ester (or boronic acid) and $R^2$—X. Appropriate leaving groups and appropriate coupling conditions are known to skilled practitioners (see, e.g., March, supra).

Compound 23 can be prepared by treating the boronic ester derivative 22 with a halide $R^2$-Hal in the presence of palladium as a catalyst by using coupling methods that are well known in the art, e.g., by using Suzuki coupling.

Scheme XI depicts an example of using Suzuki coupling conditions in a method of this invention. In Scheme XI, $R^{10}$ is a Cbz group, $R^{11}$ is hydrogen, and $R^{12}$ is a methyl group. Nevertheless, it should be understood that the reaction depicted in Scheme XI could be employed with compound 22 in the place of compound 6 and compound 23 in the place of 7.

Scheme XI

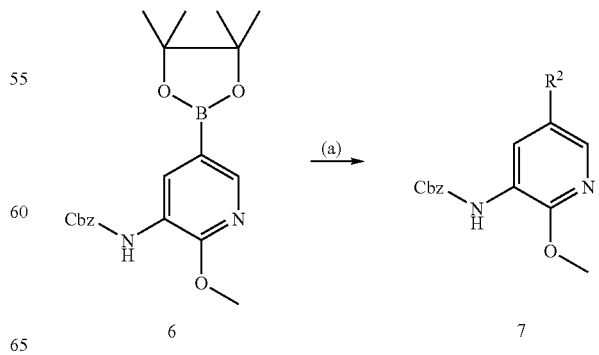

(a) $R^2$-Hal, Pd(Pph$_3$)$_4$, aq. Na$_2$CO$_3$, toluene, EtOH, reflux.

Compound 23 can be also prepared by treating the boronic ester derivative 22 with a nitrogen containing saturated, partially unsaturated, or fully unsaturated monocyclic or bicyclic ring (as described in the $R^2$ definition) by reacting through a nitrogen atom in the ring, in the presence of copper as a catalyst, e.g., by using coupling methods that are well known in the art (see, Chemick et al. *J. Org. Chem.* 2005, 1486) to provide 23 (wherein $R^2$ is a 3-8-membered saturated, partially unsaturated, or fully unsaturated monocyclic ring having at least one nitrogen heteroatom; or an 8-12 membered saturated, partially unsaturated, or fully unsaturated bicyclic ring system having having at least one nitrogen heteroatom and $R^2$ being optionally substituted with $J^R$). Scheme XII depicts an example of cooper mediated coupling conditions in a method of this invention. In Scheme XII, $R^{10}$ is a Cbz group, $R^{11}$ is hydrogen, and $R^{12}$ is a methyl group. Nevertheless, it should be understood that the reaction depicted in Scheme XII could be employed with compound 22 in the place of compound 6 and compound 23 in the place of 7.

Scheme XII

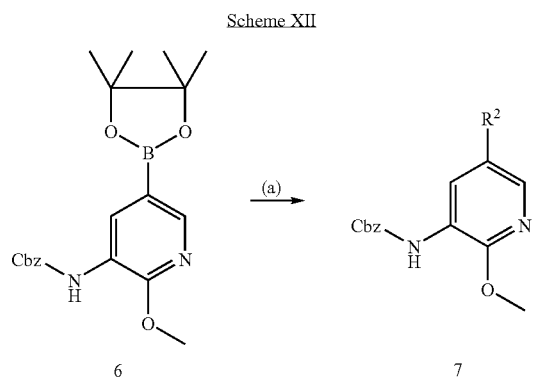

(a) Cu $(OAc)_2$, $Et_3N$, $O_2$, $CH_2Cl_2$, r.t., 20 h.

In a process of this invention, compound 23 (and related compounds, such as compound 7) is converted to a compound of formula I by methods known to skilled practitioners including, but not limited to, those disclosed herein. In certain embodiments, the hydroxyl protective group in compound 23 is removed and then the amino protective group is removed. The resulting amine is reacted with an appropriate $R^1$ containing intermediate to provide the compound of formula I. For specific examples of this embodiment, see Scheme IV and Scheme IX. In Scheme IV, $R^{10}$ is a Cbz group, $R^{11}$ is hydrogen, and $R^{12}$ is a methyl group. Nevertheless, it should be understood that the reaction depicted in Scheme IV could be employed with compound 23 in the place of compound 7.

In another embodiment, the amino protective group in compound 23 is removed and then the resulting amine is reacted with an appropriate $R^1$ containing intermediate to provide a compound X. A compound of formula I is provided by removing the hydroxyl protective group from compound X. For a specific example of this embodiment, see Scheme V. In Scheme V, $R^{10}$ is a Cbz group, $R^{11}$ is hydrogen, and $R^{12}$ is a methyl group. Nevertheless, it should be understood that the reaction depicted in Scheme V could be employed with compound X in the place of compound 11 and compound XX in the place of compound 12.

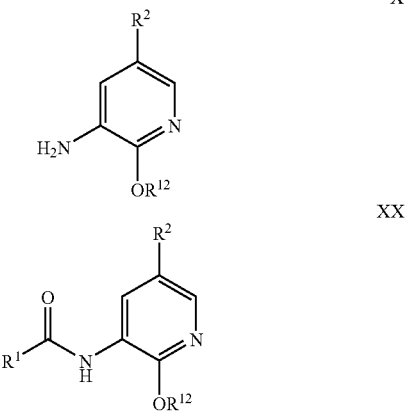

In embodiments wherein $X^1$ is —NR—, the amino protective group $R^{11}$ may be a group $R^1$—$X^2$—. As would be recognized, in such embodiments, it would not be necessary to remove the amino protective group and replace it with an $R^1$ containing group. Accordingly, to obtain a compound of formula I, compound 23 would be reacted under conditions suitable to remove the hydroxyl protective group (thus providing the compound of formula I). In embodiments where the $R^1C(=O)$— group is incompatible with the boronic ester formation, the boronic ester could be formed with $R^{10}$ being Cbz and then the Cbz group could be replaced with an $R^1$ containing group after formation of the boronic ester. For a specific example of this embodiment, see Scheme VI. In Scheme VI, $R^{10}$ (in compound 14) is $R^1C(=O)$—, $R^{11}$ is hydrogen, and $R^{12}$ is a methyl group. Nevertheless, it should be understood that the reaction depicted in Scheme VI could be employed with compound 22 in the place of compound 6.

Alternatively, $R^{10}$ in 23 may be converted to $R^1$—$X^2$—. That is, a functional group in $R^{10}$ could be converted to the desired $R^1$ containing group. Then, the hydroxyl protective group would be removed to provide the compound of formula I. For specific examples of this embodiment, see Scheme II and Scheme VII.

Compound 22 may be prepared by methods known to skilled practitioners including, but not limited to, methods disclosed herein. In one embodiment, an iodo compound 24 is reacted under conditions to form the boronic ester 22 (Scheme XIII). For a specific example of such conditions, see Scheme III. In Scheme III, $R^{10}$ is a Cbz group, $R^{11}$ is hydrogen, and $R^{12}$ is a methyl group. Nevertheless, it should be understood that the reaction depicted in Scheme XII could be employed with compound 22 in the place of compound 6 and compound 23 in the place of 7.

Scheme XIII

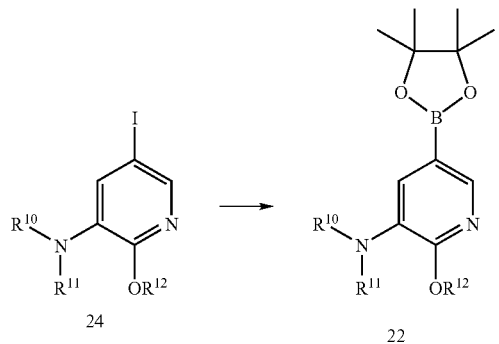

It should be understood that instead of using a boronic ester 22 in a process of this invention, the corresponding boronic acid, could be used (Scheme XIV). The boronic acid could be used as a starting material or generated in situ. Compound 25 may be prepared by known methods including, but not limited to, conversion of boronic ester 22 to boronic acid 25.

Scheme XIV

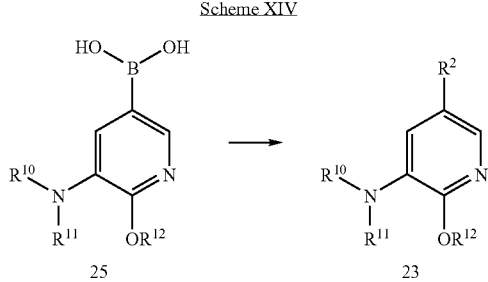

The protective groups protect the amino and hydroxyl functional groups from reacting under conditions for converting the boronic ester or acid to the $R^2$ group. Many amino protective groups and hydroxyl protective groups are known to skilled practitioners. Examples of such protective groups may be found in T. W. Greene and P. G. M. Wutz, "Protective Groups in Organic Synthesis", $3^{rd}$ Edition, John Wiley & Sons, Inc. (1999) and earlier editions of this book and J. W. F. McOmie, "Protective Groups in Organic Synthesis", Plenum Press (1973).

In certain embodiments, $R^{10}$ is —C(O)$R^{13}$ or —C(O)O$R^{13}$, wherein:
$R^{13}$ is:
  unsubstituted $C_{1-6}$ alkyl,
  $C_{1-6}$ alkyl substituted with C6-C10 aryl, or
  C6-C10 aryl, wherein each C6-C10 aryl is optionally substituted with halo, —CN, —NO$_2$, —N($R^{14}$)$_2$, unsubstituted $C_{1-6}$ alkyl, or —CF$_3$; and
$R^{14}$ is H or unsubstituted $C_{1-6}$ alkyl.
Preferably, $R^{10}$ is Cbz (carbobenzyloxy) or Boc (t-butoxycarbonyl).
In certain embodiments, $R^{11}$ is hydrogen.
In certain embodiments, $R^{12}$ is $C_{1-6}$ alkyl. Preferably, $R^{12}$ is methyl or ethyl.
In a preferred embodiment, $R^{10}$ is Cbz (carbobenzyloxy) or Boc (t-butoxycarbonyl); $R^{11}$ is hydrogen; and $R^{12}$ methyl.

Although certain exemplary embodiments are depicted and described above and herein, it will be appreciated that a compounds of the invention can be prepared according to the methods described generally above using appropriate starting materials by methods generally available to one of ordinary skill in the art.

As disclosed herein, the present invention provides compounds that are inhibitors of protein kinases, and thus the present compounds are useful for the treatment of diseases, disorders, and conditions including, but not limited to an autoimmune, inflammatory, proliferative, or hyperproliferative disease or an immunologically-mediated disease. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents. Such additional therapeutic agents include, but are not limited to an agent for the treatment of an autoimmune, inflammatory, proliferative, hyperproliferative disease, or an immunologically-mediated disease including rejection of transplanted organs or tissues and Acquired Immunodeficiency Syndrome (AIDS).

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a Tec family (e.g., Tec, Btk, Itk/Emt/Tsk, Bmx, Txk/Rlk) protein kinases kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In certain embodiments, the composition comprises an effective amount of the compound of claim 1, and a pharmaceutically acceptable carrier, adjuvant, or vehicle. In a specific embodiment, the compound is present in an amount to detectably inhibit a Tec family (e.g., Tec, Btk, Itk/Emt/Tsk, Bmx, Txk/Rlk) protein kinase.

This invention also provides a pharmaceutical composition made by combining a compound of this invention and a pharmaceutically acceptable carrier, adjuvant, or vehicle and a process for making a pharmaceutical composition comprising combining a compound of this invention and a pharmaceutically acceptable carrier, adjuvant, or vehicle.

In yet another aspect, a method for the treatment or lessening the severity of a Tec family (e.g., Tec, Btk, Itk/Emt/Tsk, Bmx, Txk/Rlk)-mediated diseases is provided comprising administering an effective amount of a compound, or a pharmaceutically acceptable composition comprising a compound to a subject in need thereof. The methods may employ a compound of Formula I or any of the other compounds of this invention:

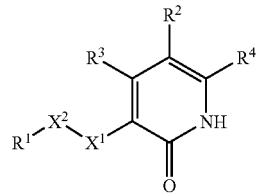

Formula I or a pharmaceutically accepted salt thereof, wherein each $R^3$ and $R^4$ is independently H, halogen or $C_{1-4}$ aliphatic optionally substituted with halogen, $C_{1-2}$ aliphatic, $OCH_3$, $NO_2$, $NH_2$, CN, $NHCH_3$, $SCH_3$, or $N(CH)_2$.

$R^2$ is a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; $R^2$ is optionally substituted with $J^R$;

each $X^1$ and $X^2$ is independently —C(O)—, —NR—, or —SO$_2$— wherein one of $X^1$ or $X^2$ is —NR— and the other of $X^1$ or $X^2$ is —C(O)— or —SO$_2$—;

R is H, unsubstituted $C_{1-6}$ aliphatic;

$R^1$ is -T-Q;

T is a bond or $C_{1-6}$ aliphatic, wherein up to three methylene units of the chain are optionally and independently replaced by G or G' wherein G is —NR$^5$—, —O—, —S—, —SO—, SO$_2$—, —CS—, or —CO—; G' is cyclopropyl, C≡C, or C═C; T is optionally substituted with $J^T$;

Q is independently hydrogen, a $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; Q is optionally substituted with $J^Q$; and $R^5$ is optionally substituted R, $C_{6-10}$ aryl, $C_{3-10}$ cycloaliphatic, 5-14 membered heteroaryl, or 5-14 membered heterocyclyl; or two $R^5$ groups, together with the atom(s) to which they are attached, form an optionally substituted 3-7 membered monocyclic or 8-14 membered bicyclic ring;

wherein the optional substituents $J^R$, $J^T$, and $J^Q$ are defined herein.

In certain embodiments of the present invention an "effective amount" of the compound or pharmaceutically acceptable composition is that amount effective for a Tec family (e.g., Tec, Btk, Itk/Emt/Tsk, Bmx, Txk/Rlk)-mediated disease. The compounds and compositions, according to the method of the present invention, may be administered using any amount and any route of administration effective for treating or lessening the severity of a Tec family (e.g., Tec, Btk, Itk/Emt/Tsk, Bmx, Txk/Rlk)-mediated disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and I) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of Tec family (e.g., Tec, Btk, Itk/Emt/Tsk, Bmx, Txk/Rlk) kinase, and thus, without wishing to be bound by any particular theory, the compounds and compositions are particularly useful for treating or lessening the severity of a disease, condition, or disorder where activation of one or more of a Tec family (e.g., Tec, Btk, Itk/Emt/Tsk, Bmx, Txk/Rlk) kinase is implicated in the disease, condition, or disorder. When activation of Tec family (e.g., Tec, Btk, Itk/Emt/Tsk, Bmx, Txk/Rlk) is implicated in a particular disease, condition, or disorder, the disease, condition, or disorder may also be referred to as a "Tec family (e.g., Tec, Btk, Itk/Emt/Tsk, Bmx, Txk/Rlk)-mediated disease" or disease symptom. Accordingly, in another aspect, the present invention provides a method for treating or lessening the severity of a disease, condition, or disorder where activation or one or more of Tec family (e.g., Tec, Btk, Itk/Emt/Tsk, Bmx, Txk/Rlk) is implicated in the disease state.

Also without wishing to be bound by any particular theory, the compounds and compositions of this invention are particularly useful for treating or lessening the severity of a disease, condition, or disorder where activation of Itk kinase is implicated in the disease, condition, or disorder and are particularly useful for inhibiting Itk selectively over Btk and Rlk (see, Examples 14-16 and 18).

The activity of a compound utilized in this invention as an inhibitor of a Tec family (e.g., Tec, Btk, Itk/Emt/Tsk, Bmx, Txk/Rlk) kinase may be assayed in vitro, in vivo or in a cell line. In vitro assays include assays that determine inhibition of either the phosphorylation activity or ATPase activity of activated Tec family (e.g., Tec, Btk, Itk/Emt/Tsk, Bmx, Txk/Rlk) kinase. Alternate in vitro assays quantitate the ability of the inhibitor to bind to a Tec family (e.g., Tec, Btk, Itk/Emt/Tsk, Bmx, Txk/Rlk) kinase. Inhibitor binding may be measured by radiolabelling the inhibitor prior to binding, isolating the inhibitor/Tec family (e.g., Tec, Btk, Itk/Emt/Tsk, Bmx, Txk/Rlk), complex and determining the amount of radiolabel bound. Alternatively, inhibitor binding may be determined by running a competition experiment where new inhibitors are incubated with a Tec family (e.g., Tec, Btk, Itk/Emt/Tsk, Bmx, Txk/Rlk) kinase bound to known radioligands.

The term "measurably inhibit", as used herein means a measurable change in a Tec family (e.g., Tec, Btk, Itk/Emt/Tsk, Bmx, Txk/Rlk) kinase activity between a sample comprising said composition and a Tec family (e.g., Tec, Btk, Itk/Emt/Tsk, Bmx, Txk/Rlk) kinase and an equivalent sample comprising a Tec family (e.g., Tec, Btk, Itk/Emt/Tsk, Bmx, Txk/Rlk) kinase in the absence of said composition.

The term "Tec family tyrosine kinases-mediated condition", as used herein means any disease or other deleterious condition in which Tec family kinases are known to play a role. Such conditions include, without limitation, autoimmune, inflammatory, proliferative, and hyperproliferative diseases and immunologically mediated diseases including rejection of transplanted organs or tissues and Acquired Immunodeficiency Syndrome (AIDS).

For example, Tec family tyrosine kinases-mediated conditions include diseases of the respiratory tract including, without limitation, reversible obstructive airways diseases including asthma, such as bronchial, allergic, intrinsic, extrinsic and dust asthma, particularly chronic or inveterate asthma (e.g., late asthma airways hyper-responsiveness) and bronchitis. Additionally, Tec family tyrosine kinases diseases include, without limitation, those conditions by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofulous rhinitis, seasonal rhinitis including rhinitis nervosa (hay fever) and vasomotor rhinitis, sarcoidosis, farmer's lung and related diseases, fibroid lung and idiopathic interstitial pneumonia.

Tec family tyrosine kinases-mediated conditions also include diseases of the bone and joints including, without limitation, (pannus formation in) rheumatoid arthritis, seronegative spondyloarthropathis (including ankylosing spondylitis, psoriatic arthritis and Reiter's disease), Behcet's disease, Sjogren's syndrome, and systemic sclerosis.

Tec family kinases-mediated conditions also include diseases and disorders of the skin, including, without limitation, psoriasis, systemic sclerosis, atopical dermatitis, contact dermatitis and other eczematous dermatitis, seborrhoetic dermatitis, Lichen planus, Pemphigus, bullous Pemphigus, epidermolysis bullosa, urticaria, angiodermas, vasculitides, erythemas, cutaneous eosinophilias, uveitis, Alopecia, areata and vernal conjunctivitis.

Tec family tyrosine kinases-mediated conditions also include diseases and disorders of the gastrointestinal tract, including, without limitation, Coeliac disease, proctitis, eosinophilic gastro-enteritis, mastocytosis, pancreatitis, Crohn's disease, ulcerative colitis, food-related allergies which have effects remote from the gut, e.g., migraine, rhinitis and eczema.

Tec family tyrosine kinases-mediated conditions also include those diseases and disorders of other tissues and systemic disease, including, without limitation, multiple sclerosis, atherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas), artherosclerosis, and systemic lupus erythematosus.

Tec family tyrosine kinases-mediated conditions also include allograft rejection including, without limitation, acute and chronic allograft rejection following for example transplantation of kidney, heart, liver, lung, bone marrow, skin and cornea; and chronic graft versus host disease.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

Additional therapeutic agents that may be used in the methods of this invention include, but are not limited to, agents for the treatment of an autoimmune, inflammatory, proliferative, hyperproliferative disease, or an immunologically-mediated disease including rejection of transplanted organs or tissues and Acquired Immunodeficiency Syndrome (AIDS), wherein the additional therapeutic agent is appropriate for the disease being treated; and the additional therapeutic agent is administered together with said composition as a single dosage form or separately from said composition as part of a multiple dosage form.

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting Tec family (e.g., Tec, Btk, Itk/Emt/Tsk, Bmx, Txk/Rlk) activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Tec family (e.g., Tec, Btk, Itk/Emt/Tsk, Bmx, Txk/Rlk) kinase activity in a biological sample is useful for a variety of purposes that are known to one of skill in the art. Examples of such purposes include, but are not limited to, blood transfusion, organ-transplantation, biological specimen storage, and biological assays.

EXAMPLES

As used herein, the term "Rt(min)" refers to the HPLC retention time, in minutes, associated with the compound. Unless otherwise indicated, the HPLC method utilized to obtain the reported retention time is as follows:
Column: Ace 5 C8, 15 cm×4.6 mm id
Gradient: 0-100% acetonitrile+methanol (50:50) (20 mM Tris phosphate at pH 7.0)
Flow rate: 1.5 ml/min
Detection: 225 nm

Example 1

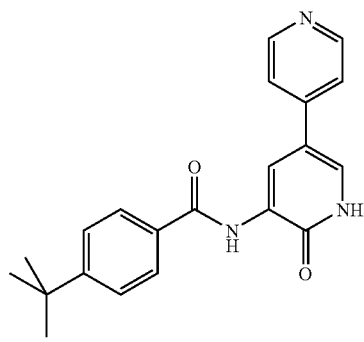

4-tert-Butyl-N-(6-oxo-1,6-dihydro-[3,4']bipyridinyl-5-yl)-benzamide I-11

Amrinone (200 mg, 1.07 mmol) was suspended in pyridine (5 mL) and 4-tert-butylbenzoyl chloride (209 μL, 1.07 mmol) was added. The reaction mixture was stirred overnight at room temperature. The solid was filtered and rinsed with MeOH to give the title compound as a pink solid (33 mg, 9% yield). MS (ES+) m/e=348. $^1$H NMR (DMSO-$d_6$) δH 1.43 (9H, s), 7.57-7.62 (4H, m), 7.81 (1H, s), 7.88 (2H, d), 8.59 (2H, d), 8.78 (1H, d), 9.32 (1H, s), 12.61 (1H, s).

Example 2

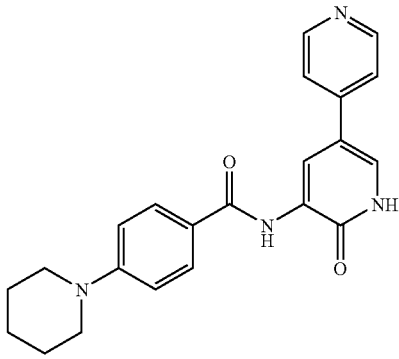

N-(1,2-dihydro-2-oxo-5-(pyridin-4-yl)pyridin-3-yl)-4-(piperidin-1-yl)benzamide I-68

4-Bromo-N-(1,2-dihydro-2-oxo-5-(pyridin-4-yl)pyridin-3-yl)benzamide (30 mg, 0.081 mmol) I-20 was placed in a microwave tube equipped with a stirrer bar. NMP (0.75 mL) was added, followed by piperidine (1.5 mL). The reaction vessel was heated at 160° C. for 2 hours in a microwave. After cooling, the solvent and excess piperidine were removed in vacuo. The crude compound was recrystallized from methanol to give the title compound as a white solid (13 mg, 43% yield).). MS (ES+) m/e=375. $^1$H NMR (DMSO-$d_6$) δH 1.54-1.65 (6H, m), 3.30-3.38 (4H, m), 7.02 (2H, d), 7.61 (2H, d) 7.72-7.80 (1H, m), 7.78 (2H, d), 8.59 (2H, d), 8.77 (1H, d), 9.13 (1H, s), 12.58 (1H, bs).

A variety of other compounds of Formula I have been prepared by methods substantially similar to those described herein. The characterization data for these compounds is summarized in Table I-A below and includes HPLC, LC/MS (observed) and $^1$H NMR data.

$^1$H NMR data is summarized in Table I-A below wherein $^1$H NMR data was obtained at 400 Mhz in deuterated DMSO, unless otherwise indicated, and was found to be consistent with structure. Compound numbers correspond to the compound numbers listed in Table 1.

TABLE I-A

Characterization Data for Selected Compounds of Formula I

| Compound No I- | M+1(obs) | Rt(min) | $^1$H-NMR |
|---|---|---|---|
| 1 | 292 | 7.5 | (CDCl$_3$) 7.02-7.65(6H, m), 7.95-7.99(2H, m), 8.69-8.70(2H, m), 9.11(1H, br s), 9.16(1H, br s), 11.43(1H, br s) |
| 2 | 322 | 7.7 | 3.85(3H, s), 7.10(2H, d), 7.61(2H, d), 7.80(1H, s), 7.93(2H, d), 8.58(2H, d), 8.75(1H, m), 9.28(1H, s), 12.60(1H, s) |
| 3 | 306 | 7.5 | 3.85(2H, s), 7.19-7.34(5H, m), 7.52(2H, d), 7.70(1H, s), 8.54(1H, d), 8.72(1H, s), 9.58(1H, s), 12.45(1H, s) |
| 4 | 298 | 8.1 | 1.25-1.40(5H, m), 1.64(1H, br d), 1.72(2H, br d), 1.80(2H, br d), |

TABLE I-A-continued

Characterization Data for Selected Compounds of Formula I

| Compound No I- | M+1(obs) | Rt(min) | ¹H-NMR |
|---|---|---|---|
| | | | 2.60-2.67(1H, m), 7.55(2H, d), 7.71(1H, s), 8.55(2H, d), 8.72(1H, s), 9.18(1H, s), 12.40(1H, br s) |
| 5 | 340 | 8.2 | 4.86(2H, s), 7.58-7.65(4H, m), 7.83(1H, s), 7.97(2H, m), 8.59(2H, m), 8.76(1H, s), 9.44(1H, s), 12.63(1H, br s) |
| 6 | 320 | 8.7 | 1.22(3H, t), 2.70(2H, q), 7.41(2H, d), 7.61(2H, d), 7.81(1H, d), 7.87(2H, d), 8.58(2H, d), 8.77(1H, d), 9.33(1H, s), 12.62(1H, br s) |
| 7 | 342 | 8.7 | 7.62-7.69(4H, m), 7.84(1H, s), 8.02(2H, t), 8.10(1H, d), 8.16(1H, d), 8.59-8.62(3H, m), 8.82(1H, s), 9.59(1H, s), 12.65(1H, s) |
| 8 | 306 | 8.0 | 2.40(3H, s), 7.37(2H, d), 7.86(2H, d), 8.01(2H, d), 8.09(1H, s), 8.75(2H, d), 8.83(1H, d), 9.39(1H, s), 12.88(1H, s) |
| 9 | 317 | 7.4 | 7.62(2H, d), 7.87(1H, s), 8.04(2H, d), 8.11(2H, d), 8.59(2H, d), 8.72(1H, s), 9.72(1H, s), 12.63(1H, s) |
| 10 | 334 | 9.2 | 0.91(3H, t), 1.62(2H, m), 2.64(2H, t), 7.38(2H, d), 7.61(2H, d), 7.81(1H, s), 7.87(2H, d), 8.59(2H, d), 8.77(1H, d), 9.33(1H, s), 12.61(1H, s) |
| 12 | 368 | 9.3 | 7.44(1H, t), 7.53(2H, t), 7.63(2H, d), 7.77(2H, d), 7.84(1H, d), 7.88(2H, d), 8.05(2H, d), 8.60(2H, d), 8.79(1H, d), 9.47(1H, d), 12.64(1H, br s) |
| 13 | 306 | 8.2 | 2.41(3H, s), 7.44-7.48(2H, m), 7.74-7.78(2H, m), 8.21-8.25(3H, m), 8.82-8.86(3H, m), 9.41(1H, s), 13.02(1H, s) |
| 14 | 336 | 8.3 | 1.37(3H, t), 4.12(2H, q), 7.19(1H, d), 7.44-7.51(3H, m), 7.61(2H, d), 7.83(1H, d), 8.59(2H, d), 8.74(1H, d), 9.37(1H, s), 12.61(1H, s) |
| 15 | 374 | 8.6 | 7.60-7.84(3H, m), 8.05-8.26(5H, m), 8.76-8.84(3H, m), 9.73(1H, s), 13.00(1H, s) |
| 16 | 376 | 9.0 | 7.66(1H, d), 7.72(1H, t), 7.93(1H, s), 8.02(1H, d), 8.20(2H, d), 8.26(1H, s), 8.81-8.83(3H, m), 9.78(1H, s), 12.99(1H, s) |
| 17 | 390 | 8.8 | 4.00(3H, s), 7.43(1H, d), 8.14-8.28(5H, m), 8.74-8.82(3H, m), 9.75(1H, s), 12.93(1H, br s) |
| 18 | 376 | 9.0 | 7.55-7.57(2H, m), 8.09-8.11(2H, m), 8.18-8.19(2H, m), 8.23(1H, m), 8.81-8.83(3H, m), 9.66(1H, s), 12.97(1H, s) |
| 19 | 320 | 8.0 | 2.79-2.92(4H, m), 7.18(1H, m), 7.28-7.30(4H, m), 8.13-8.14(3H, m), 8.75-8.79(2H, m), 8.87(1H, s), 9.64(1H, s), 12.82(1H, s) |
| 20 | 372 | 8.6 | 7.61(2H, dd), 7.77(2H, d), 7.84(1H, d), 7.90(2H, d), 8.58(2H, dd), 8.73(1H, d), 9.52(1H, s), 12.61(1H, br s) |
| 21 | 350 | 8.7 | 1.30(6H, s), 4.75(1H, s), 7.07(2H, d), 7.91(2H, d), 8.20-8.21(3H, m), 8.82-8.86(3H, m), 9.32(1H, s), 12.98(1H, s) |
| 22 | 384 | 9.3 | 7.11-7.15(4H, m), 7.25(1H, m), 7.45-7.49(2H, m), 7.94-8.02(4H, m), 8.09(1H, s), 8.70-8.82(2H, m), 8.82(1H, m), 9.40(1H, s), 12.86(1H, s) |
| 23 | 332 | 8.5 | 1.31(1H, m), 1.48(1H, m), 2.37(1H, m), 2.79(1H, m), 7.16-7.22(3H, m), 7.28-7.32(2H, m), 8.12-8.14(3H, m), 8.80(2H, d), 8.87(1H, m), 9.99(1H, s), 12.81(1H, s) |
| 24 | 374 | 10.3 | 1.27(1H, m), 1.40-1.49(4H, m), 1.72(1H, m), 1.80-1.82(4H, m), 2.60(1H, m), 7.41-7.44(3H, m), 7.86-7.92(6H, |

TABLE I-A-continued

Characterization Data for Selected Compounds of Formula I

| Compound No I- | M+1(obs) | Rt(min) | ¹H-NMR |
|---|---|---|---|
| | | | m), 8.79(1H, s), 9.33(1H, s), 12.70(1H, s) |
| 25 | 326 | 7.7 | 7.40-7.67(6H, m), 7.83(1H, s), 8.59(2H, d), 8.80(1H, d), 9.67(1H, s), 12.6(1H, s) |
| 26 | 293 | 6.1 | 7.58-7.63(3H, m), 7.86(1H, s), 8.31(1H, d), 8.59(2H, d), 8.74(1H, d), 8.78(1H, d), 9.10(1H, s), 9.74(1H, s), 12.6(1H, s) |
| 27 | 326 | 8.4 | 7.61-7.65(4H, m), 7.84(1H, d), 7.98(2H, d), 8.58(2H, d), 8.73(1H, d), 9.52(1H, s), 12.62(1H, bs) |
| 28 | 426 | 6.7 | 2.93(3H, s), 3.17(3H, s), 7.62(2H, d), 7.77(1H, d), 7.85(2H, d), 7.93(2H, d), 8.27(1H, s), 8.59(2H, d), 8.75(1H, d), 9.60(1H, s), 12.61(1H, bs) |
| 29 | 293 | 7.4 | 7.62(2H, d), 7.74(1H, m), 7.83(1H, m), 8.13(1H, m), 8.20(1H, m), 8.60(2H, d), 8.78(1H, d), 8.92(1H, d), 10.76(1H, s), 12.68(1H, s) |
| 30 | 327 | 7.1 | 7.61(2H, dd), 7.70(1H, d), 7.86(1H, d), 8.34(1H, dd), 8.58(2H, d), 8.71(1H, d), 8.93(1H, d), 9.87(1H, s), 12.60(1H, br s) |
| 31 | 327 | — | 7.35(1H, m), 7.70(2H, m), 7.80(2H, m), 8.00(1H, s), 8.68(2H, m), 8.90(1H, s), 9.80(1H, m) |
| 32 | 327 | — | 7.55(2H, m), 7.70(1H, m), 7.90(2H, br s), 8.05(1H, br s), 8.70(2H, m), 8.90(1H, s), 9.80(1H, m) |
| 33 | 327 | — | 7.55(1H, m), 7.65(2H, m), 7.90(2H, m), 8.09(1H, s), 8.74(3H, m), 9.7(1H, s) |
| 34 | 297 | — | 7.23(1H, m), 7.90(1H, s), 8.05(1H, s), 8.20(3H, m), 8.75(1H, s), 8.80(2H, m), 9.57(1H, s) |
| 35 | 281 | — | 6.75(1H, m), 7.35(1H, m), 7.90(2H, m), 8.05(2H, m), 8.70(2H, m), 8.75(1H, s), 9.23(1H, s) |
| 36 | 377 | — | 7.65(1H, m), 8.15(2H, m), 8.20(1H, m), 8.80(2H, m), 8.85(1H, s), 10.00(1H, s) |
| 37 | 316 | — | 7.75(2H, m), 7.60(2H, s), 7.76(1H, m), 7.85(1H, s), 8.10(1H, m), 8.25(1H, m), 8.41(1H, s), 8.58(2H, m), 8.75(1H, s), 9.85(1H, s) |
| 38 | 369 | — | (CD₃OD) 3.20(3H, s), 7.20(1H, s), 7.70(1H, s), 8.20-8.40(6H, m), 8.70(2H, d), 8.80(1H, d) |
| 39 | 310 | — | 7.40(2H, m), 8.10(2H, m), 8.20(3H, m), 8.80(3H, m), 9.60(1H, s) |
| 40 | 372 | 8.6 | 7.54(1H, t), 7.58-7.65(2H, m), 7.80-7.88(2H, m), 794(1H, d), 8.13(1H, s), 8.57-8.63(2H, m), 8.73(1H, s), 9.62(1H, s) |
| 41 | 335 | — | — |
| 42 | 359 | — | — |
| 43 | 360 | — | 7.80(1H, m), 8.00(1H, m), 3.18(2H, m), 8.25(3H, m), 8.80(3H, m), 9.85(1H, s) |
| 44 | 309 | — | 7.42(2H, m), 7.55(2H, m), 7.65(1H, m), 7.80(1H, s), 8.00(1H, m), 8.60(2H, m), 8.90(1H, s), 9.70(1H, m) |
| 45 | 335 | 8.0 | 3.02(6H, s), 6.80(2H, d), 7.60(2H, dd), 7.75-7.80(3H, m), 8.58(2H, d), 8.77(1H, d), 9.11(1H, s), 12.57(1H, br s) |
| 46 | 398 | — | (CDCl₃) 5.20(2H, s), 7.10(3H, d), 7.50(5H, m), 8.00(3H, m), 8.70(2H, d), 9.10(2H, d) |
| 47 | 307 | — | 6.70(2H, d), 7.40(2H, d), 7.60(2H, m), 8.00(1H, s), 8.40(2H, d), 8.50(1H, s), 9.50(1H, s), |

TABLE I-A-continued

Characterization Data for Selected Compounds of Formula I

| Compound No I- | M+1(obs) | Rt(min) | ¹H-NMR |
|---|---|---|---|
| 48 | 348 | — | 2.10(3H, s), 7.60(2H, d), 7.70(3H, m), 7.90(2H, d), 8.60(2H, d), 8.80(1H, s), 9.30(1H, s), 10.30(1H, s) |
| 49 | 348 | — | 2.10(3H, s), 7.50(1H, m), 7.60(3H, s), 7.80(1H, s), 7.90(2H, d), 8.20(1H, s), 8.60(2H, d), 8.80(1H, s), 9.30(1H, s), 10.20(1H, s) |
| 50 | 372 | — | 9.00(1H, s), 8.70(1H, s), 8.60(2H, d), 7.80(2H, d), 7.75(2H, d), 7.60(2H, d), 7.40-7.50(3H, m), 7.30(1H, t), 2.70(3H, s) |
| 51 | 382 | — | 7.10(1H, d), 7.45(2H, d), 7.50(3H, m), 7.60(2H, m), 7.70(2H, d), 7.80(1H, d), 8.60(2H, d), 8.70(1H, d), 9.30(1H, s) |
| 52 | 376 | — | — |
| 53 | 358 | — | — |
| 54 | 373 | — | — |
| 55 | — | — | — |
| 56 | 256 | — | 0.80(4H, m), 2.20(1H, m), 7.90(2H, m), 7.95(1H, s), 8.70(2H, m), 8.78(1H, s), 9.75(1H, s) |
| 57 | 311 | — | 7.55(1H, m), 7.90(2H, m), 8.10(1H, m), 8.40(2H, m), 8.70(2H, m), 9.90(1H, s), 10.0(1H, s) |
| 58 | 359 | — | 7.43(1H, m), 7.65(1H, m), 7.85(3H, m), 8.05(1H, m), 8.25(1H, m), 8.70(4H, m), 8.95(1H, br s), 10.20(1H, s) |
| 59 | 311 | — | 7.65(1H, s), 7.80(1H, m), 7.92(2H, m), 8.10(1H, br s), 8.45(1H, m), 8.75(3H, m), 9.90(1H, s) |
| 60 | 324 | — | 1.35(3H, t), 2.20(3H, s), 4.45(2H, q), 6.80(1H, s), 7.95(2H, m), 8.05(1H, br s), 8.70(3H, m), 9.20(1H, s) |
| 61 | 409 | — | — |
| 62 | — | — | 3.90(3H, s), 6.90(1H, d), 7.40(2H, d), 7.50(1H, s), 7.90(2H, d), 8.00(1H, s), 8.70(2H, d), 8.80(1H, s), 9.20(1H, s), 9.80(1H, s) |
| 63 | 327 | — | 2.60(2H, s), 6.70(1H, s), 8.00(1H, s), 8.10(2H, d), 8.60(1H, s), 8.80(2H, d) |
| 64 | 254 | — | 3.00(3H, s), 7.80(1H, s), 7.95(1H, s), 8.00(2H, d), 8.50(1H, s), 8.70(2H, d) |
| 65 | 359 | — | 1.30(3H, t), 2.80(2H, q), 6.80(1H, s), 7.10(1H, m), 7.40(2H, d), 7.50(1H, s), 7.60(2H, d), 7.80(1H, m), 8.60(2H, d), 11.40(1H, s) |
| 66 | 407 | — | 1.50(9H, s), 7.40(1H, m), 7.50(1H, d), 7.60(2H, d), 7.70(1H, m), 7.80(1H, s), 8.10(1H, s), 8.60(2H, d), 8.80(1H, s), 9.30(1H, s), 9.60(1H, s) |
| 67 | 412 | — | 3.80(2H, s), 5.20(2H, s), 6.90(1H, m), 7.10(1H, d), 7.20-7.30(5H, m), 7.40(2H, d), 7.50(2H, d), 7.70(1H, s), 8.60(2H, d), 8.70(1H, s), 9.25(1H, s) |
| 69 | 361 | 8.8 | 1.96-2.00(4H, m), 3.29-3.35(4H, m), 6.63(2H, d), 7.60(2H, d), 7.75-7.79(3H, m), 8.58(2H, d), 8.77(1H, d), 9.08(1H, s), 12.45(1H, br s) |
| 70 | 390 | 7.4 | 2.23(3H, s), 2.43-2.48(4H, m), 3.28-3.34(4H, m), 7.05(2H, d), 7.60(2H, d), 7.76-7.84(3H, m), 8.58(2H, d), 8.77(1H, d), 9.16(1H, s), 12.58(1H, br s) |
| 71 | 376 | 6.3 | 2.81-2.86(4H, m), 3.20-3.26(4H, m), 7.02(2H, d), 7.60(2H, d), 7.75-7.82(3H, m), 8.58(2H, d), 8.77(1H, d), 9.14(1H, s) |
| 72 | 391 | 7.1 | 1.38-1.48(2H, m), 1.76-1.84(2H, m), 3.00-3.07(2H, m), 3.66-3.76(3H, m), 4.73(1H, bs), 7.03(2H, d), 7.54(2H, d), 7.75(2H, d), 7.85(1H, d), 8.52(2H, d), 8.68(1H, d), 9.28(1H, br s) |

TABLE I-A-continued

Characterization Data for Selected Compounds of Formula I

| Compound No I- | M+1(obs) | Rt(min) | $^1$H-NMR |
|---|---|---|---|
| 73 | 377 | 7.5 | 3.25-3.29(4H, m), 3.72-3.77(4H, m), 7.06(2H, d), 7.60(2H, dd), 7.78(1H, d), 7.82(2H, d), 8.58(2H, dd), 8.76(1H, d), 9.18(1H, s), 12.56(1H, br s) |
| 74 | 476 | 7.0 | 0.95(6H, t), 2.39-2.56(12H, m), 3.26-3.39(4H, m), 7.03(2H, d), 7.60(2H, d), 7.75-7.82(3H, m), 8.58(2H, d), 8.77(1H, d), 9.15(1H, s) |
| 75 | 444 | 6.8 | 1.47-1.59(2H, m), 1.63-1.86(4H, m), 1.92-2.06(2H, m), 2.89(2H, t), 3.26-3.39(5H, m), 3.82-3.98(2H, m), 7.06(2H, d), 7.60(2H, d), 7.76-7.82(3H, m), 8.59(2H, d), 8.77(1H, d), 9.15(1H, s), 12.58(1H, br s) |
| 76 | 389 | 9.5 | 1.44-1.49(4H, m), 1.70-1.77(4H, m), 3.50-3.56(4H, m), 6.79(2H, d), 7.59(2H, d), 7.73-7.77(3H, m), 8.57(2H, d), 8.76(1H, d), 9.08(1H, s) |
| 77 | 449 | 7.8 | 1.69(2H, quintet), 2.36(2H, t), 3.22(3H, s), 3.27-3.38(10H, m), 7.04(2H, d), 7.60(2H, d), 7.76-7.82(3H, m), 8.58(2H, d), 8.76(1H, d), 9.16(1H, s), 12.42(1H, v br s) |
| 78 | 390 | 6.4 | 1.74-1.81(2H, m), 2.62(2H, t), 2.85(2H, t), 3.29-3.37(2H, m), 3.53(2H, t), 3.61(2H, t), 6.81(2H, d), 7.59(2H, d), 7.72-7.76(3H, m), 8.58(2H, d), 8.77(1H, d), 9.07(1H, s) |
| 79 | 392 | 6.5 | 1.68(2H, m), 2.14(6H, s), 2.29(2H, t), 3.09(2H, dt), 6.41-6.48(1H, m), 6.63(2H, d), 7.50-7.54(2H, m), 7.66(2H, d), 7.82-7.86(1H, m), 8.46-8.51(2H, m), 8.63-8.68(1H, m), 9.21(1H, br s) |
| 80 | 364 | 6.0 | 1.63(2H, m), 2.65(2H, t), 3.13(2H, dt), 6.50(1H, t), 6.65(2H, d), 7.58(2H, d), 7.68(2H, d), 7.76(1H, d), 8.57(2H, d), 8.75(1H, d), 9.05(1H, s) |
| 81 | 464 | 7.0 | 2.50-2.58(6H, m), 3.25-3.29(4H, m), 3.42(2H, t), 3.46-3.52(2H, m), 3.56(2H, t), 4.62(1H, br s), 7.04(2H, d), 7.60(2H, d), 7.77-7.82(3H, m), 8.58(2H, d), 8.76(1H, d), 9.17(1H, s) |
| 82 | 391 | 7.4 | 3.19(4H, m), 3.5-4.0(masked protons), 4.43(2H, s), 7.67-7.71(2H, m), 7.97(2H, m), 8.04-8.10(3H, m), 8.74-8.82(3H, m), 9.51(1H, s), 12.87(1H, br s) |
| 83 | 390 | 6.4 | (DMSO+D$_2$O) 3.00(4H, m), 3.22(4H, m), 4.03(2H, s), 7.58(2H, d), 7.96(2H, d), 8.09-8.12(3H, m), 8.69(2H, d), 8.79(1H, s) |
| 84 | 392 | 6.7 | (D$_2$O) 2.68(3H, s), 2.77(3H, s), 3.43-3.51(4H, m), 4.41(2H, s), 7.58(2H, d), 7.90(2H, d), 8.04(1H, m), 8.09(2H, m), 8.60(2H, m), 8.70(1H, m) |
| 85 | 406 | 6.7 | (D$_2$O) 2.08(2H, m), 2.60(3H, s), 2.73(3H, s), 2.98(2H, m), 3.19(2H, m), 4.35(2H, m), 7.55(2H, m), 7.88(2H, m), 8.01-8.10(3H, m), 8.59-8.69(3H, m) |

Example 3

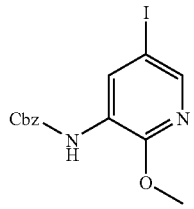

(5-Iodo-2-methoxy-pyridin-3-yl)-carbamic acid benzyl ester (5-Iodo-2-oxo-1,2-dihydro-pyridin-3-yl)-carbamic acid benzyl ester (3.68 g, 9.94 mmol) was dissolved in chloroform (50 mL) at room temperature under nitrogen in the dark (foil wrapped). Silver carbonate (3.70 g, 13.2 mmol) was added followed by iodomethane (6.2 mL, 99.4 mmol). The reaction mixture was allowed to stir at room temperature for 48 hours. The silver salts were removed by filtration through a pad of celite, washing with more chloroform and the filtrate concentrated in vacuo. The residue was purified by column chromatography to give the title compound as a white solid (3.14 g, 82% yield). MS (ES$^+$) m/e=385. $^1$H NMR (CDCl$_3$) δH 3.97 (3H, s), 5.23 (2H, s), 7.15 (1H, br s), 7.35-7.47 (5H, m), 8.00 (1H, s), 8.64 (1H, br s).

Example 4

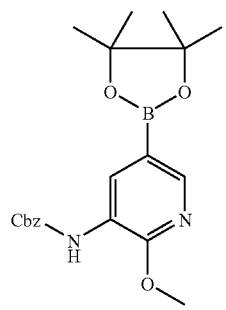

[2-Methoxy-5-(4,4,5,5-tetramethyl-[1,3,2]dioxaborolan-2-yl)-pyridin-3-yl]-carbamic acid benzyl ester (5-Iodo-2-methoxy-pyridin-3-yl)-carbamic acid benzyl ester (1 g, 2.6 mmol), bis(pinacolato)diboron (727 mg, 2.86 mmol), KOAc (766 mg, 7.81 mmol) and Pd(Oac)$_2$ (18 mg, 3 mol %) were suspended in anhydrous DMF (20 mL). This was degassed by slowly bubbling nitrogen through the system for 30 minutes and then heated to 85° C. for 3 hours. The reaction was cooled to room temperature and diluted with water. The reaction mixture was extracted with EtOAc (×3), dried over MgSO$_4$, filtered and concentrated in vacuo. Purification by column chromatography gave the title compound as a white solid (501 mg, 50% yield). MS (ES$^+$) m/e=385. $^1$H NMR (DMSO-d$_6$) δH 1.34 (12H, s), 4.03 (3H, s), 5.24 (2H, s), 7.15 (1H, br s), 7.34-7.46 (5H, m), 8.21 (1H, s), 8.63 (1H, br s).

Example 5

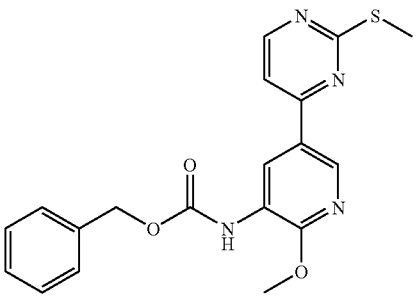

[2-Methoxy-5-(2-methylsulfanyl-pyrimidin-4-yl)-pyridin-3-yl]-carbamic acid benzyl ester

[2-Methoxy-5-(4,4,5,5-tetramethyl-[1,3,2]dioxaborolan-2-yl)-pyridin-3-yl]-carbamic acid benzyl ester (377 mg, 0.98 mmol), 4-chloro-2-thiomethylpyrimidine (171 μL, 1.47 mmol) and Pd(Pph$_3$)$_4$ (113 mg, 10 mol %) were dissolved in toluene (15 mL) and EtOH (3 mL). Na$_2$CO$_3$ (717 mg, 6.77 mmol) in water (6 mL) was added and the reaction mixture was heated to reflux for 4 hours. After cooling down to room temperature, the reaction mixture was diluted with water and extracted with EtOAc (×3). The combined organic extracts were dried over MgSO$_4$, filtered and concentrated in vacuo. The residue was absorbed onto silica and purified by column chromatography to give the title compound as an off-white solid (261 mg, 70% yield). MS (ES$^+$) m/e=383. $^1$H NMR (DMSO-d$_6$) δH 2.67 (3H, s), 4.09 (3H, s), 5.27 (2H, s), 7.30-7.47 (7H, m), 8.54 (1H, d), 8.67 (1H, s), 9.01 (1H, br s).

Example 6

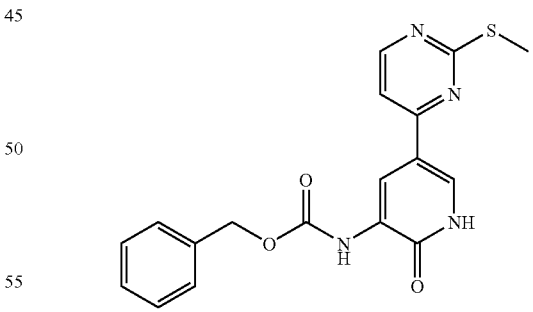

[5-(2-Methylsulfanyl-pyrimidin-4-yl)-2-oxo-1,2-dihydro-pyridin-3-yl]-carbamic acid benzyl ester II-3

[2-Methoxy-5-(2-methylsulfanyl-pyrimidin-4-yl)-pyridin-3-yl]-acid benzyl ester (20 mg, 0.05 mmol) was dissolved in 1,4-dioxane (1 mL) and water (300 μL). Concentrated HCl (100 μL) was added and the reaction mixture was heated to reflux for 30 minutes. The reaction mixture was cooled down to room temperature and water was added. The obtained precipitate was isolated by filtration and dried under vacuum to give the title compound as a yellow solid (12.9 mg, 67% yield). MS (ES⁺) m/e=369. ¹H NMR (DMSO-d₆) δH 2.56 (3H, s), 5.20 (2H, s), 7.38-7.46 (5H, m), 7.60 (1H, d), 8.10 (1H, br d), 8.56 (1H, d), 8.61 (1H, s), 8.69 (1H, s), 12.52 (1H, br d).

Example 7

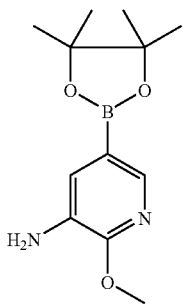

2-Methoxy-5-(4,4,5,5-tetramethyl-[1,3,2]dioxaborolan-2-yl)-pyridin-3-ylamine

[2-Methoxy-5-(4,4,5,5-tetramethyl-[1,3,2]dioxaborolan-2-yl)-pyridin-3-yl]-carbamic acid benzyl ester (506 mg, 1.32 mmol) was dissolved in methanol (10 mL). Pd(OH)₂ on carbon (51 mg, 10 mol %) was added and the reaction was degassed with nitrogen. The nitrogen atmosphere was replaced by hydrogen and the reaction mixture was stirred at room temperature for 5 hours. The palladium residue was removed by filtration through a path of Celite, rinsing with more methanol. The filtrate was concentrated in vacuo to give the title compound as an off-white solid (319 mg, 97% yield). MS (ES⁺) m/e=251. ¹H NMR (DMSO-d₆) δH 1.27 (12H, s), 3.88 (3H, s), 4.89 (2H, br s), 7.13 (1H, s), 7.64 (1H, s).

Example 8

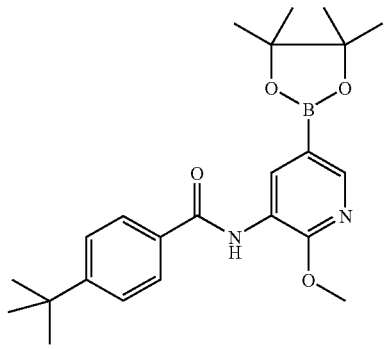

4-tert-Butyl-N-[2-Methoxy-5-(4,4,5,5-tetramethyl-[1,3,2]dioxaborolan-2-yl)-pyridin-3-yl]-benzamide

[2-Methoxy-5-(4,4,5,5-tetramethyl-[1,3,2]dioxaborolan-2-yl)-pyridin-3-ylamine (319 mg, 1.28 mmol) was dissolved in dichloromethane (5 mL). Triethylamine (117 µL, 1.40 mmol) and 4-tert-butylbenzoyl chloride (274 µL, 1.40 mmol) were added and the reaction was stirred at room temperature for 10 minutes. The crude mixture was absorbed onto silica and purified by column chromatography to give the title compound as an off-white solid (274 mg, 52% yield). MS (ES⁺) m/e=411. ¹H NMR (CDCl₃) δH 1.36 (12H, s), 1.39 (9H, s), 4.10 (3H, s), 7.55 (2H, d), 7.86 (2H, d), 8.28 (1H, s), 8.36 (1H, br s), 9.07 (1H, s).

Example 9

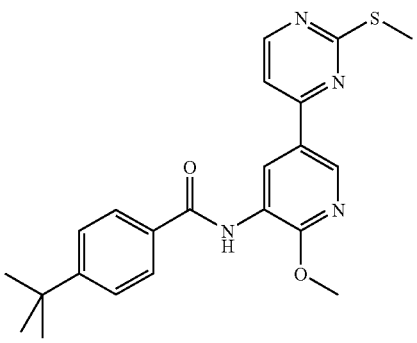

4-tert-Butyl-N-[2-methoxy-5-(2-methylsulfanyl-pyrimidin-4-yl)-pyridin-3-yl]-benzamide 4-tert-Butyl-N-[2-Methoxy-5-(4,4,5,5-tetramethyl-[1,3,2]dioxaborolan-2-yl)-pyridin-3-yl]-benzamide (274 mg, 0.67 mmol), 4-chloro-2-thiomethylpyrimidine (116 µL, 1.00 mmol) and Pd(Pph₃)₄ (77 mg, 10 mol %) were dissolved in toluene (10 mL) and EtOH (2 mL). Na₂CO₃ (488 mg, 4.61 mmol) in water (4 mL) was added and the reaction mixture was heated to reflux for 2 hours. After cooling down to room temperature, the reaction mixture was diluted with water and extracted with EtOAc (×3). The combined organic extracts were dried over MgSO₄, filtered and concentrated in vacuo. The residue was absorbed onto silica and purified by column chromatography to give the title compound as a yellow solid (120 mg, 44% yield). MS (ES⁺) m/e=409. ¹H NMR (CDCl₃) δH 1.40 (9H, s), 2.69 (3H, s), 4.17 (3H, s), 7.41 (1H, d), 7.57 (2H, d), 8.45 (1H, br s), 8.56 (1H, d), 8.76 (1H, d), 9.46 (1H, d).

Example 10

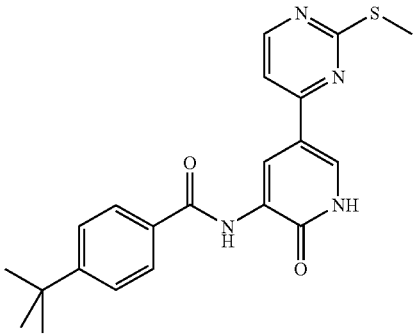

4-tert-Butyl-N-[5-(2-methylsulfanyl-pyrimidin-4-yl)-2-oxo-1,2-dihydro-pyridin-3-yl]-benzamide II-4

4-tert-Butyl-N-[2-methoxy-5-(2-methylsulfanyl-pyrimidin-4-yl)-pyridin-3-yl]-benzamide (120 mg, 0.29 mmol) was dissolved in 1,4-dioxane (6 mL) and water (1.2 mL). Concentrated Hcl (600 μL) was added and the reaction mixture was heated to reflux for 30 minutes. The reaction mixture was cooled down to room temperature and water was added. The obtained precipitate was isolated by filtration and dried under vacuum. The crude solid was purified by flash chromatography to give the title compound as a fawn solid (29 mg, 25% yield). MS (ES$^+$) m/e=395. $^1$H NMR (DMSO-d$_6$) δH 1.33 (9H, s), 2.58 (3H, s), 7.59 (2H, d), 7.64 (1H, d), 7.88 (2H, d), 8.21 (1H, s), 8.58 (1H, d), 9.11 (1H, s), 9.30 (1H, s), 12.72 (1H, br s).

Example 11

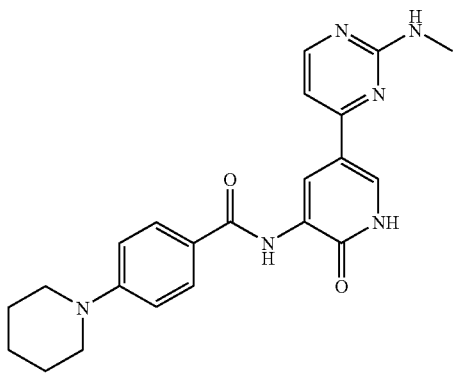

N-(1,2-dihydro-5-(2-(methylamino)pyrimidin-4-yl)-2-oxopyridin-3-yl)-4-(piperidin-1-yl)benzamide II-40

4-Bromo-N-(2-methoxy-5-(2-(methylamino)pyrimidin-4-yl)pyridin-3-yl)benzamide (50 mg, 0.121 mmol) was placed in a microwave tube equipped with a stirrer bar. NMP (1.5 mL) was added, followed by piperidine (1.5 mL). The reaction vessel was heated at 160° C. for 2 hours in a microwave. After cooling, the solvent and excess piperidine were removed in vacuo. The crude compound was recrystallized from methanol to give the title compound as a white solid (22 mg, 45% yield).). MS (ES$^+$) m/e=405. $^1$H NMR (DMSO-d$_6$) δH 1.54-1.61 (6H, m), 2.85 (3H, br s), 3.28-3.36 (4H, m), 6.95-7.12 (4H, m), 7.77 (2H, d), 8.00 (1H, s), 8.27 (1H, d), 9.02 (1H, br s), 9.09 (1H, s), 12.53 (1H, br s).

A variety of other compounds of Formula II have been prepared by methods substantially similar to those described herein. The characterization data for these compounds is summarized in Table II-A below and includes HPLC, LC/MS (observed) and $^1$H NMR data.

$^1$H NMR data is summarized in Table II-A below wherein $^1$H NMR data was obtained at 400 Mhz in deuterated DMSO, unless otherwise indicated, and was found to be consistent with structure. Compound numbers correspond to the compound numbers listed in Table 1.

TABLE II-A

Characterization Data for Selected Compounds of Formula I

| Compound No II- | M+1(obs) | Rt(min) | $^1$H-NMR |
|---|---|---|---|
| 1 | 321 | 9.5 | 5.26(2H, s), 7.28-7.51(11H, m), 7.85(1H, s), 8.56(1H, s), 12.49(1H br s) |
| 2 | 291 | 8.9 | 7.33-7.62(9H, m), 7.95(2H, m), 8.71(1H, s), 9.36(1H, s), 12.34(1H, br s) |
| 3 | | | See, Example 6 |
| 4 | | | See, Example 10 |
| 5 | 432 | 9.8 | 1.38(9H, s), 3.80-4.14(8H, br m), 6.85(1H, d), 7.16(1H, d), 7.54(2H, d), 7.60(1H, t), 7.88(2H, d), 7.94(1H, br s), 8.94(2H, br s), 9.01(1H, s), 9.28(1H, s), 12.47(1H, br d) |
| 6 | 391 | 10.4 | 1.33(9H, s), 3.11(6H, s), 6.62(1H, br d), 7.00(1H, d), 7.58(3H, d), 7.88(3H, d), 9.05(1H, br s), 9.27(1H, br s), 12.45(1H, br s) |
| 7 | 377 | 9.8 | 1.33(9H, s), 2.91(3H, s), 6.94(1H, br d), 7.36-7.46(1H, m), 7.53-7.69(3H, m), 7.88(3H, d), 8.90(1H, br s), 9.36(1H, br s), 12.56(1H, br s) |
| 8 | 365 | — | (CDCl$_3$) 1.25(9H, s), 7.05(2H, m), 7.25(1H, s), 7.45(2H, d), 7.50(2H, d), 7.85(2H, d), 8.95(1H, s), 9.05(1H br, s) |
| 9 | 391 | — | (MeOH-d$_4$) 1.35(1H, m), 1.47(4H, m), 1.80(1H, m), 1.90(4H, m), 2.62(1H, m), 7.15(2H, m), 7.40(3H, m), 7.55(2H, m), 7.90(2H, d), 8.85(1H, s) |
| 10 | 362 | — | 1.31(9H, s), 6.80(2H, m), 7.30(3H, m), 7.55(3H, m), 7.85(2H, m), 6.65(1H, m), 9.30(1H, br s) |
| 11 | 372 | — | 1.33(9H, s), 7.58(2H, m), 7.75(2H, m), 7.80(1H, d), 7.85(4H, m), 8.70(1H, s), 9.40(1H, br s) |

TABLE II-A-continued

Characterization Data for Selected Compounds of Formula I

| Compound No II- | M+1(obs) | Rt(min) | $^1$H-NMR |
|---|---|---|---|
| 12 | 353 | — | 1.33(9H, s), 7.05(2H, m), 7.18(1H, m), 7.30(1H, m), 7.55(2H, m), 7.60(1H, s), 7.83(2H, m), 8.50(1H, m), 9.45(1H, br s) |
| 13 | 392 | — | 1.30(9H, s), 7.55(3H, m), 7.80(1H, br s), 7.90(4H, m), 8.30(2H, m), 8.80(1H, s), 9.30(1H, s) |
| 14 | 378 | 9.5 | 1.33(9H, s), 2.91(3H, br s), 7.14(1H, br s), 7.59(2H, d), 7.88(2H, d), 8.17(1H, br s), 8.29(1H, d), 9.07(1H, br s), 9.30(1H, s), 12.70(1H, br s) |
| 15 | 351 | — | 1.33(9H, s), 3.85(3H, s), 7.40(1H, s), 7.60(2H, d), 7.65(1H, s), 7.85(2H, d), 8.00(1H, s), 8.50(1H, s), 9.30(1H, br s) |
| 16 | 426 | — | 1.32(9H, s), 7.33(1H, s), 7.57(2H, d), 7.65(1H, m), 7.78(2H, d), 7.90(4H, m), 8.75(1H, s), 9.30(1H, s) |
| 17 | 378 | 9.2 | (80° C.) 3.01(3H, s), 6.90(1H, s), 7.60(2H, d), 7.88(2H, d), 8.04(1H, d), 8.34(1H, s), 8.81(1H, s), 9.22(1H, s), 12.58(1H, br s) |
| 18 | 392 | 9.6 | 1.32(9H, s), 3.30(6H, s), 7.16(1H, s), 7.59(2H, d), 7.90(2H, d), 8.18(1H, d), 8.73(1H, s), 8.80(1H, s), 9.40(1H, s), 12.99(1H, br s) |
| 19 | 520 | 10.1 | 1.19(3H, t), 1.32(9H, s), 1.46(2H, m), 1.96(2H, m), 2.85-3.10(2H, m), 3.92-4.10(6H, m), 7.33(1H, br s), 7.58(2H, d), 7.88(2H, d), 8.32(3H, m), 9.06-9.16(1H, m), 9.29(1H, s), 12.87(1H, s) |
| 20 | 421 | 9.4 | 1.32(9H, s), 2.62(3H, m), 3.19(2H, m), 3.74(2H, m), 7.32(1H, br s), 7.59(2H, d), 7.89(2H, d), 8.17(1H, vbr s), 8.37(1H, br s), 8.87(2H, vbr s), 9.08(1H, s), 9.33(1H, s), 12.87(1H, br s) |
| 21 | 392 | 10.0 | 1.33(9H, s), 3.23(6H, s), 7.16(1H, br s), 7.58(2H, d), 7.88(2H, d), 8.19(1H, br s), 8.34(1H, d), 9.12(1H, s), 9.29(1H, s), 12.70(1H, br s) |
| 22 | 392 | 9.8 | 1.21(3H, t), 1.32(9H, s), 3.50(3H, br m), 7.31(1H, br d), 7.58(2H, d), 7.88(2H, d), 8.30(1H, s), 8.31(1H, br s), 9.08(1H, s), 9.31(1H, s), 12.86(1H, br s) |
| 23 | 406 | 10.1 | 1.24(6H, d), 1.33(9H, s), 4.12(2H, br m), 7.24(1H, br s), 7.58(2H, d), 7.88(2H, d), 8.26(1H, br s), 8.29(1H, d), 9.06(1H, s), 9.31(1H, s), 12.82(1H, br s) |
| 24 | 454 | 10.3 | 1.32(9H, s), 4.66(2H, br s), 7.22-7.35(4H, m), 7.49(1H, br s), 7.59(2H, d), 7.89(2H, d), 8.28(1H, br s), 8.32(1H, br s), 9.10(1H, br s), 9.31(1H, s), 12.84(1H, br s) |
| 25 | 433 | 9.7 | 1.33(9H, s), 3.22(4H, br m), 4.04(4H, br m), 7.19(1H, d), 7.59(2H, d), 7.88(2H, d), 8.14(1H, br d), 8.43(1H, d), 8.93(1H, br s), 9.04(1H, s), 9.31(1H, s), 12.71(1H, br d) |
| 26 | 348 | 9.6 | 7.45(1H, t), 7.58(2H, d), 7.85(2H, d), 7.94-8.04(3H, m), 8.65(1H, d), 9.04(1H, s), 9.31(1H, s). |
| 27 | 519 | 10.4 | 1.20(3H, t), 1.32(9H, s), 1.96-2.05(2H, m), 2.95-3.12(2H, m), 3.30-3.36(2H, m), 3.90-4.06(5H, m+q), 6.37(1H, d), 6.52-6.58(1H, m), 6.85(1H, d), 7.40(1H, t), 7.57(2H, d), 7.76-7.84(1H, m), 7.84(1H, d), 9.07(1H, s), 9.20(1H, s). |
| 28 | 448 | 9.5 | 1.32(9H, s), 1.76-7.82(2H, m), 2.07-2.20(2H, m), 3.07(2H, br m), 3.33-3.39(2H, m), 4.10(1H, m), 7.29(1H, br s), 7.49(2H, d), 7.88(2H, d), |

TABLE II-A-continued

Characterization Data for Selected Compounds of Formula I

| Compound No II- | M+1(obs) | Rt(min) | $^1$H-NMR |
|---|---|---|---|
| 29 | 448 | 9.5 | 8.27(1H, br s), 8.34(1H, s), 9.01-9.23(1H, br m), 12.82(1H, br s) 1.32(9H, s), 1.61-2.07(4H, m), 2.82-2.99(2H, br m), 3.19(1H, m), 3.39(1H, m), 4.21(1H, m), 7.23(1H, br s), 7.59(2H, d), 7.89(2H, d), 8.08-8.28(2H, br m), 8.35(1H, s), 9.06(1H, s), 12.79(1H, br s) |
| 30 | 433 | 9.5 | 1.32(9H, s), 2.07(1H, m), 2.25(1H, m), 3.28(2H, m), 3.37(1H, m), 3.47(1H, m), 4.55(1H, m), 7.25(1H, s), 7.59(2H, d), 7.88(2H, d), 8.16(1H, s), 8.35(1H, d), 9.08(1H, s), 9.14-9.26(1H, br m), 12.76(1H, br s) |
| 31 | 433 | 9.5 | 1.32(9H, s), 2.09(1H, m), 2.27(1H, m), 3.27(2H, m), 3.39(1H, m), 3.45(1H, m), 4.49(1H, m), 7.28(1H, s), 7.61(2H, d), 7.88(2H, d), 8.19(1H, s), 8.36(1H, d), 9.12(1H, s), 9.14-9.35(1H, br m), 12.80(1H, br s) |
| 32 | 447 | 9.8 | 1.22-1.30(2H, m), 1.33(9H, s), 1.86-1.95(2H, m), 2.51-2.60(2H, m), 2.91-2.97(2H, m), 3.75-3.85(1H, m), 6.35(1H, d), 6.47(1H, d), 6.83(1H, d), 7.36(1H, t), 7.59(2H, d), 7.80(1H, s), 7.85(2H, d), 9.02(1H, s), 9.22(1H, s). |
| 33 | 433 | 9.5 | 1.32(9H, s), 3.23(4H, s), 4.05(4H, s), 7.36(1H, s), 7.59(2H, d), 7.89(2H, d), 8.22(1H, s), 8.71(1H, s), 8.96(1H, s), 9.35(1H, s), 9.38(1H, br s), 12.86(1H, br s) |
| 34 | 349 | 9.4 | 1.32(9H, s), 7.59(2H, d), 7.88(2H, d), 7.98(1H, d), 8.22(1H, s), 8.76(1H, d), 9.17(2H, d), 9.30(1H, s), 12.71(1H, br s) |
| 35 | 420 | 9.1 | 1.35(9H, s), 2.65(3H, s), 3.16-3.25(2H, m), 3.63-3.70(2H, m), 7.03(1H, d), 7.60(2H, d), 7.90(2H, d), 8.80-8.95(2H, m), 9.00(1H, s), 9.32(1H, s) |
| 36 | 409 | 10.1 | 1.33(9H, s), 2.37(3H, s), 2.55(3H, s), 7.55(2H, d), 7.69(1H, s), 7.85(2H, d), 8.48(1H, s), 8.78(1H, s), 9.25(1H, s). |
| 37 | 311 | — | 5.17(2H, s), 7.35(7H, m), 7.85(2H, br s), 8.10(1H, s), 8.37(1H, br s) |
| 38 | 421 | 8.7 | 1.32(9H, s), 2.58-2.60(3H, m), 3.13-3.15(2H, m), 3.75-3.76(2H, m), 6.94(1H, br s), 7.59(2H, d), 7.89(2H, d), 8.11(1H, br s), 8.69(1H, s), 8.84(1H, s), 8.93(2H, br s), 9.36(1H, s), 12.85(1H, br s) |
| 39 | 433 | 8.7 | 1.32(9H, s), 1.99(1H, m), 2.38(1H, m), 3.16(1H, m), 3.30(1H, m), 3.37(1H, m), 3.52(1H, m), 4.64(1H, m), 6.93(1H, s), 7.61(2H, d), 7.88(2H, d), 8.09(1H, br s), 8.69(1H, s), 8.85(1H, s), 9.33(2H, br s), 9.36(1H, s), 12.82(1H, br s) |
| 41 | 424 | 10.1 | 1.31(9H, s), 2.83(3H, s), 6.49(1H, s), 7.46-7.61(3H, m), 7.81-7.98(3H, m), 8.90(1H, br s), 9.27(1H, s), 12.48(1H, br s) |
| 42 | 376 | 9.7 | 1.31(9H, s), 2.11(3H, s), 4.95(2H, s), 6.41-6.51(2H, m), 6.89(1H, m), 7.05(1H, s)), 7.58(2H, m) 7.85(2H, m), 8.32(1H, s), 9.25(1H) |
| 43 | 390 | 10.2 | 1.36(9H, s), 2.15(3H, s), 2.67(3H, m), 5.55(1H, m), 6.36-6.51(2H, m), 6.97(1H, m), 7.08(1H, s)), 7.58(2H, m) 7.85(2H, m), 8.35(1H, s), 9.25(1H) |
| 44 | 391 | 10.5 | 1.31(9H, s), 2.22(3H, s), 3.75(3H, s), 6.78-6.89(2H, m), 7.18-7.22(2H, m, 7.58(2H, m), 7.85(2H, m), 8.35(1H, s), 9.29(1H) |
| 45 | 460 | 8.6 | 1.55-1.65(6H, m), 1.94(1H, m), 2.24(1H, m), 3.11(1H, m), 3.27-3.29(2H, |

TABLE II-A-continued

Characterization Data for Selected Compounds of Formula I

| Compound No II- | M+1(obs) | Rt(min) | $^1$H-NMR |
|---|---|---|---|
| | | | m), 3.29-3.35(4H, m), 3.44(1H, m), 4.53(1H, m), 6.82(1H, s), 7.02(2H, d), 7.77(2H, d), 7.86-7.94(2H, m), 8.50(1H, s), 8.96-8.99(2H, m), 9.10(1H, s), 12.51(1H, br s) |
| 46 | 405 | 8.9 | 1.50-1.60(6H, m), 2.84(3H, br s), 3.31-3.34(4H, m), 6.75(1H, s), 7.02(2H, d), 7.39(1H, br s), 7.77(2H, d), 7.92(1H, br s), 8.42(1H, br s), 8.95(1H, s), 9.09(1H, s), 12.44(1H, br s) |
| 47 | 404 | 9.5 | 1.55-1.65(6H, m), 3.30-3.37(4H, m), 2.83(3H, s), 6.33(1H, d), 6.48-6.59(1H, br s), 6.84(1H, d), 7.00(2H, d), 7.43(1H, t), 7.72-7.80(3H, m), 9.00(1H, s), 9.06(1H, s). |
| 48 | 432 | 10.1 | 1.21(6H, d), 1.55-1.63(6H, m), 3.30-3.38(4H, m), 3.99-4.09(1H, m), 6.33(1H, d), 6.38(1H, d), 6.76(1H, d), 6.99(2H, d), 7.36(1H, t), 7.72-7.78(3H, m), 8.93(1H, s), 9.05(1H, s). |
| 49 | 430 | 10.1 | 0.40-0.46(2H, m), 0.67-0.75(2H, m), 1.55-1.64(6H, m), 2.49-2.57(1H, m), 3.30-3.38(4H, m), 6.50(1H, d), 6.80(1H, s), 6.91(1H, d), 7.00(1H, d), 7.49(1H, t), 7.71-7.79(3H, m), 8.97(1H, s), 9.05(1H, s). |
| 50 | 480 | 10.3 | 1.55-1.64(6H, m), 3.30-3.38(4H, m), 4.53(2H, d), 6.37(1H, d), 7.83(1H, d), 7.00(2H, d), 7.15-7.22(2H, m), 7.25-7.33(2H, m), 7.35-7.44(3H, m), 7.70-7.77(3H, m), 8.96(1H, s), 9.05(1H, s) |
| 51 | 447 | 8.7 | 1.53-1.64(6H, m), 2.30(3H, s), 2.63-2.70(2H, m), 3.30-3.44(6H, m), 6.35(1H, d), 6.45-6.52(1H, m), 6.80(1H, d), 7.00(2H, d), 7.38(1H, t), 7.70-7.78(3H, m), 8.95(1H, s), 9.05(1H, s). |
| 52 | 422 | 9.8 | 1.59(6H, br s), 2.54(3H, s), 3.23(4H, br s), 7.01(2H, d), 7.36(1H, br s), 7.71(2H, d), 8.33(1H, br s), 8.39(1H, br s), 8.84(1H, br s), 9.39(1H, br s) |
| 53 | 432 | 10.2 | 1.30(6H, d), 1.60(6H, br s), 2.46(4H, br s), 3.10(1H, m), 3.31(3H, s), 7.02(2H, d), 7.60(1H, s), 7.77(2H, d), 8.10(1H, br d), 9.11(2H, br s d), 12.61(1H, br d) |
| 54 | 377 | 10.3 | 1.34(9H, s), 3.85(3H, s), 6.91(1H, m), 7.10-7.16(2H, m), 7.36(1H, m), 7.58(3H, m), 7.89(2H, m), 8.71(1H, s), 9.30(1H) |
| 55 | 362 | 9.7 | 1.31(9H, s), 2.55(3H, s), 7.41(1H, s), 7.56(2H, m), 7.89(3H, m), 8.40(1H, s), 8.70-8.78(2H, m), 9.35(1H) |
| 56 | 405 | 9.1 | 1.62(6H, m), 2.90(3H, m), 6.34(1H, d), 7.04(2H, d), 7.38(1H, br m), 7.75(2H, d), 8.09(2H, m), 9.08(1H, s), 9.22(1H, s), 12.35(1H, s) |
| 57 | 420 | 9.7 | 1.79(3H, t), 2.01(6H, br s), 3.70(4H, br s), 4.82(2H, m), 7.43(2H, d), 7.96(1H, m), 8.19(2H, d), 8.56(1H, br s), 8.96(1H, m), 9.50(2H, d), 13.06(1H, br s) |
| 58 | 462 | 9.4 | 1.53(6H, m), 2.77(6H, m), 4.20-4.50(6H, m), 4.60-4.80(2H, m), 7.05(2H, m), 7.35(1H, m), 7.73(1H, m), 7.99(1H, m), 8.27(1H, m), 9.05(2H, m), 9.32(1H, br s), 9.93(1H, br s), 12.91(1H, br s) |
| 59 | 435 | 8.6 | 1.55-1.65(6H, m), 3.33-3.40(6H, m), 3.54(2H, m), 4.58(1H, br s), 6.90-7.02(4H, m), 7.76(2H, d), 7.98(1H, s), 8.26(1H, s), 8.99(1H, s), 9.08(1H, s), 12.50(1H, br s) |
| 60 | 448 | 8.9 | 1.50-1.65(6H, m), 2.34(3H, s), 2.77-2.90(2H, m), 3.24-3.40(4H, m), 4.30-4.40(2H, m), 6.60(1H, m), |

TABLE II-A-continued

Characterization Data for Selected Compounds of Formula I

| Compound No II- | M+1(obs) | Rt(min) | ¹H-NMR |
|---|---|---|---|
| | | | 6.93-7.05(2H, m), 7.26-7.35(1H, m), 7.64-7.80(3H, m), 7.89(1H, s), 8.97(1H, s), 9.10(1H, s). |
| 61 | 476 | 9.7 | 1.56(6H, m), 2.46(3H, masked signal), 2.85(6H, m), 3.20-3.60(6H, m), 3.97(2H, m), 6.98-7.11(2H, m), 7.73(2H, br s), 8.04(1H, br s), 8.34(1H, br s), 9.07(2H, br s), 9.26(1H, br s), 12.6((br s) |
| 62 | 392 | 9.6 | 1.30(9H, s), 2.20(3H, s), 2.80(3H, d), 6.91(1H, br d), 7.55-7.61(3H, m), 7.85(2H, d), 8.16(1H, s), 8.75(1H, s), 9.26(1H, s) |
| 63 | 448 | 8.7 | 1.60(6H, m), 2.62(3H, s), 3.16(2H, m), 3.33(4H, m), 3.62(2H, m), 7.01(1H, d), 7.10(1H, d), 7.16(1H, t), 7.77(2H, d), 8.04(1H, m), 8.33(1H, d), 8.58(2H, m), 9.06-9.09(2H, m), 12.6(1H, d) |
| 64 | 322 | 7.6 | 2.82-2.89(3H, m), 6.99(1H, d), 7.11(1H, d), 7.53-7.67(3H, m), 7.94(2H, d), 8.05(1H, s), 8.27(1H, d), 9.04(1H, s), 9.35(1H, s), 12.58(1H, d). |
| 65 | 462 | 9.1 | 1.59(6H, m), 2.32(3H, s), 2.67(3H, s), 3.18(2H, m), 3.35-3.60(4H, m), 3.78(2H, m), 7.00-7.10(3H, m), 7.76(2H, d), 8.03(1H, d), 8.33(1H, d), 9.07(2H, m) |
| 66 | 433 | 9.8 | 1.21(3H, t), 1.59(6H, m), 2.54(2H, m), 2.85(3H, s), 3.39(4H, br m), 6.82(1H, s), 7.01(2H, d), 7.75(2H, d), 8.09(1H, s), 8.95(1H, s) |
| 67 | 426 | 8.8 | 2.86(3H, br ss), 7.01(1H, d), 7.12(1H, d), 7.60(2H, dd), 7.66-7.76(1H, m), 7.79(2H, d), 7.88(2H, d), 8.06-8.12(3H, m), 8.28(1H, d), 9.05(1H, s), 9.55(1H, s), 12.60(1H, s) |
| 68 | 376 | 10.0 | 1.35(9H, s), 2.86(3H, s), 6.95(1H, m), 7.18(2H, m), 7.39(1H, m), 7.54(1H, s), 7.61(2H, d), 7.92(2H, d), 8.72(1H, s), 9.31(1H, s) |
| 69 | 403 | 9.7 | 1.58(6H, s), 2.71(3H, s), 3.36(4H, m), 6.45(1H, m), 6.65-6.72(2H, m), 6.98(2H, d), 7.11(1H, t), 7.37(1H, s), 7.75(2H, d), 8.67(1H, s) |
| 70 | 434 | 9.0 | 1.53-1.62(6H, m), 3.30-3.42(4+2H, 2xm), 3.51-3.60(2H, m), 4.72(1H, t), 6.38(1H, d), 6.53(1H, t), 6.80(1H, d), 6.99(2H, d), 7.37(1H, t), 7.72-7.78(3H, m), 8.92(1H, s), 9.06(1H, s). |
| 71 | 448 | 9.6 | 1.54-1.65(6H, m), 3.27(3H, s), 3.30-3.37(4H, m), 4.46-4.55(4H, m), 6.2(1H, d), 6.63(1H, t), 6.85(1H, d), 7.01(2H, d), 7.41(1H, t), 7.72-7.82(3H, m), 8.99(1H, s), 9.06(1H, s) |
| 72 | 403 | — | (CDCl₃) 1.7-1.2(6H, m), 1.85(4H, m), 2.55(1H, m), 3.80(3H, s), 6.90(2H, d), 7.15(2H, m), 7.30(2H, d), 7.40(2H, d), 7.85(2H, d), 8.95(1H, br s), 9.05(1H, br s) |
| 73 | 396 | 10.2 | 1.3(9H, s), 2.3(3H, s), 7.3(1H, d), 7.4(1H, s), 7.6(2H, d), 7.8(1H, d), 7.9(2H, d), 8.6(1H, s) |
| 74 | 389 | 9.1 | 1.6(6H, s), 3.4(4H, m), 7.0(2H, br m), 7.2(1H, br m), 7.4-7.6(4H, m), 7.8(2H, d), 8.7(1H, s) |
| 75 | 446 | 9.1 | 1.6(6H, s), 2.6(3H, s), 3.1(2H, m), 3.3(4H, m), 3.4(2H, m), 6.6(1H, m), 6.8(2H, m), 7.0(2H, m), 7.2(1H, t), 7.4(1H, s), 7.8(2H, d), 8.6(1H, s), 9.1(1H, s) |
| 76 | 449 | 8.6 | 1.59(6H, br s), 2.49(5H, br s), 3.33(4H, br s), 4.53(2H, br s), 7.00(2H, br d), 7.63(1H, br s), 7.75(2H, br s), 8.17(1H, br s), 8.57(1H, br s), 9.08(2H, br d) |

TABLE II-A-continued

Characterization Data for Selected Compounds of Formula I

| Compound No II- | M+1(obs) | Rt(min) | $^1$H-NMR |
|---|---|---|---|
| 77 | 406 | 6.3 | 2.85(3H, s), 3.17-3.20(4H, m), 3.44-3.50(4H, m), 6.97(1H, d), 7.05-7.12(3H, m), 7.85(2H, d), 8.01(1H, s), 8.27(1H, d), 9.02(1H, bs), 9.15(1H, s). |
| 78 | 448 | 7.7 | 1.01(6H, d), 2.53-2.59(4H, m), 2.66-2.69(1H, m), 2.85(3H, bs), 3.26-3.36(4H, m), 6.97(1H, d), 7.03(2H, d), 7.09(1H, d), 7.78(2H, d), 8.00(1H, s), 8.27(1H, d), 9.03(1H, s), 9.10(1H, s), 12.51(1H, br s). |
| 79 | 478 | 7.8 | 1.63-1.75(2H, m), 2.30-2.41(2H, m), 2.82-2.90(4H, m), 3.22(3H, s), 3.28-3.39(6H, m), 6.94-7.12(4H, m), 7.79(2H, d), 8.00(1H, s), 8.27(1H, d), 9.03(1H, s), 9.11(1H, s), 12.53(1H, d). |
| 80 | 474 | 7.9 | 1.66-1.73(4H, m), 1.89-2.09(4H, m), 2.31-2.54(4H, m), 2.57-2.68(2H, m), 2.88(3H, bs), 3.11-3.19(1H, m), 3.39-3.48(1H, m), 3.91-3.99(1H, m), 6.66(2H, d), 6.97(1H, d), 7.10(1H, d), 7.77(2H, d), 7.99(1H, s), 8.27(1H, d), 9.03(2H, s), 12.49(1H, bs). |
| 81 | 448 | 7.1 | 2.05(3H, s), 2.85(3H, s), 3.28-3.40(4H, m), 3.56-3.61(4H, m), 6.97(1H, d), 7.02-7.11(3H, m), 7.81(2H, d), 8.01(1H, s), 8.26(1H, d), 9.02(1H, s), 9.12(1H, s), 12.52(1H, br s). |
| 82 | 386 | 6.5 | 1.02(9H, s), 2.82(3H, s), 3.35-3.39(8H, m), 6.90(1H, m), 7.05(1H, m), 7.86(2H, m), 8.24(1H, m), 8.68(1H, m), 12.38(1H, br s) |
| 83 | 379 | — | 1.31(9H, s), 2.05(2H, m), 2.35(2H, m), 2.72(2H, m), 6.17(1H, s), 7.55(2H, m), 7.60(1H, m), 7.88(2H, m), 8.65(1H, s), 9.25(1H, br s) |
| 84 | 382 | — | — |
| 85 | 392 | — | (CDCl$_3$) 1.70-1.50(6H, m), 2.05(2H, m), 2.40(2H, m), 2.60(2H, m), 3.25(4H, m), 6.35(1H, s), 6.90(2H, m), 7.30(1H, s), 7.80(2H, m), 8.90(2H, d) |
| 86 | 407 | — | 1.60(6H, s), 1.80(4H, m), 2.45(4H, m), 3.35(4H, m), 6.35(1H, s), 7.00(2H, m), 7.25(1H, m), 7.75(2H, m), 8.70(1H, s), 9.10(1H, s) |
| 87 | 378 | — | (CDCl$_3$) 1.50-1.70(6H, m), 2.50(2H, m), 2.90(2H, m), 3.30(4H, m), 6.43(s, 1H), 6.85(2H, m), 7.35(1H, s), 7.80(2H, m), 8.90(2H, d) |
| 88 | 365 | — | (CDCl$_3$) 1.25(9H, s), 7.05(2H, m), 7.25(1H, s), 7.45(2H, d), 7.50(2H, d), 7.85(2H, d), 8.95(1H, s), 9.05(1H, br s) |
| 89 | 394 | — | 1.60(8H, m), 1.85(3H, m), 2.20(2H, m), 3.25(4H, m), 4.30(1H, br s), 6.05(1H, s), 6.85(2H, m), 7.00(1H, s), 7.75(2H, m), 8.80(1H, m), 8.90(1H, m) |
| 90 | 364. | — | — |
| 91 | 496 | — | — |
| 92 | 406 | — | — |
| 93 | 433 | 9.6 | 1.21(3H, t), 1.60(6H, m), 2.54(2H, q), 2.87(3H, s), 3.3(4 masked protons), 6.17(1H, s), 7.02(2H, d), 7.77(2H, d), 8.07(1H, s), 9.21(1H, s) |
| 94 | 400 | 9.5 | 1.60(6H, m), 3.3(4 masked protons), 7.02(2H, d), 7.70(1H, d), 7.77(2H, d), 8.09(1H, d), 8.39(1H, s), 8.84(1H, d), 9.13(1H, d) |
| 95 | 461 | 9.4 | 1.52-1.62(6H, m), 2.30(3H, s), 2.70(2H, t), 3.05(3H, s), 3.24-3.36(4H, m), 3.61(2H, t), 6.51(1H, d), 6.90(1H, d), 6.97(2H, d), 7.47(1H, t), 7.70(2H, d), 7.85(1H, s), 9.03(1H, s), 9.05(1H, s) |

TABLE II-A-continued

Characterization Data for Selected Compounds of Formula I

| Compound No II- | M+1(obs) | Rt(min) | $^1$H-NMR |
|---|---|---|---|
| 96 | 503 | 9.3 | 0.93(6H, t), 1.55-1.60(6H, m), 1.62-1.71(2H, m), 2.38-2.54(6H, m), 3.25-3.37(6H, m), 6.32(1H, d), 6.57-6.63(1H, m), 6.80(1H, d), 7.00(2H, d), 7.37(1H, t), 7.71-7.80(3H, m), 8.95(1H, s), 9.03(1H, s) |
| 97 | 428 | 9.2 | 2.88(3H, br s), 5.21(2H, s), 7.09(1H, d), 7.17(2H, d), 7.30-7.48(5H, m), 7.92(2H, d), 8.12(1H, br s), 8.28(1H, d), 9.03(1H, br s), 9.25(1H, s), 12.65(1H, br s) |
| 98 | 412 | 9.4 | 2.85(3H, br s), 4.04(2H, s), 6.97(1H, d), 7.09(1H, d), 7.16-7.34(5H, m), 7.42(2H, d), 7.86(2H, d), 8.04(1H, s), 8.25(1H, d), 9.02(1H, br s), 9.28(1H, br s) |
| 99 | 400 | 9.2 | 1.59(6H, m), 3.3(4 masked protons), 7.02(2H, d), 7.76-7.78(3H, m), 8.54(1H, s), 8.70(1H, d), 8.94(1H, s), 9.07(1H, d) |
| 100 | 377 | 6.1 | 2.77(4H, t), 3.57(4H, t), 6.88(1H, d), 7.60(2H, d), 7.78(1H, d), 8.00(1H, dd), 8.57(2H, d), 8.68(1H, d), 8.73(1H, d) |
| 101 | 475 | 9.1 | 1.56-1.63(6H, m), 1.82(3H, s), 3.22-3.29(2H, m), 3.30-3.37(6H, m), 6.36(1H, d), 6.63(1H, t), 6.99(2H, d), 7.41(1H, t), 7.73(2H, d), 7.81(1H, s), 7.95(1H, t), 9.00(1H, s), 9.07(1H, s) |
| 102 | 413 | 9.5 | 1.60(6H, br s), 3.34(4H, br s), 6.60(1H, d), 7.03(3H, t), 7.08(1H, t), 7.14(1H, d), 7.16(1H, d), 7.36(1H, d), 7.77(2H, d), 8.79(1H, d) |
| 103 | 503 | 9.7 | 0.91(6H, m), 1.59(6H, m), 2.40-2.60(6H, m), 3.04(3H, s), 3.30-3.45(4H, m), 3.65(2H, m), 6.48(1H, m), 6.91(1H, m), 7.01(2H, d), 7.44(1H, m), 7.75-7.781(3H, m), 9.03(2H, d), 12.30(1H, br s) |
| 104 | 487 | 9.7 | 1.60(6H, m), 1.87-1.91(2H, m), 2.02(2H, m), 3.15(2H, m), 3.28-3.30(4H, m), 3.43-3.46(2H, m), 3.53-3.56(4H, m), 6.45(1H, d), 6.91(1H, br s), 6.97-7.10(2H, m), 7.49(1H, m), 7.75-7.81(3H, m), 9.07-9.12(2H, m), 9.51(1H, br s), 12.35(1H, m) |
| 105 | 487 | 9.2 | 1.29-1.38(2H, m), 1.60(6H, m), 1.91-2.03(4H, m), 2.90-2.93(2H, m), 3.24-3.25(2H, m), 3.30-3.34(5H, m), 6.43(1H, d), 6.901(1H, d), 6.97-7.03(2H, m), 7.44(1H, m), 7.75-7.78(3H, m), 8.15(1H, d), 8.49(1H, d), 9.06-9.08(2H, m). 12.48(1H, br s) |
| 106 | 443 | 9.3 | 1.60(6H, m), 2.84-2.87(2H, m), 3.30-3.50(4H, m), 3.56-3.60(2H, m), 6.45(1H, d), 6.92(1H, d), 7.01-7.05(3H, m), 7.48(1H, m), 7.76(2H, m), 7.81(1H, d), 9.00(1H, d), 9.07(1H, s), 12.30(1H, s) |
| 107 | 394 | 6.0 | 1.78-1.86(2H, m), 2.65-2.70(2H, m), 2.85-2.91(3H, m), 3.18(1.4H, t), 3.30(0.6H, t), 6.67(2H, d), 7.06(1H, d), 7.72(2H, d), 8.03-8.09(1H, m), 8.28(1H, d), 9.01(1H, s), 9.02-9.06(1H, m) |
| 108 | 476 | 9.6 | 0.85-0.95(6H, m), 1.51-1.62(6H, m), 1.65-1.77(1H, m), 2.82-2.90(1H, m), 3.24-3.35(4H, m), 4.06-4.15(1H, m), 4.25-4.33(1H, m), 6.68(1H, d), 7.00(2H, d), 7.31(1H, d), 7.66-7.76(3H, m), 7.87(1H, s), 9.02(1H, s), 9.06(1H, s) |
| 109 | 413 | 10.0 | 1.60(6H, br s), 3.25(4H, br s), 6.52(1H, d), 7.01-7.10(4H, m), 7.36(2H, d), 7.64(1H, d), 7.75(2H, d), 8.65(1H, d) |

TABLE II-A-continued

Characterization Data for Selected Compounds of Formula I

| Compound No II- | M+1(obs) | Rt(min) | ¹H-NMR |
|---|---|---|---|
| 110 | 482 | 9.9 | 1.60(6H, br s), 3.35(4H, br s), 7.02(2H, d), 7.50(1H, s), 7.78(2H, d), 7.83(1H, s), 8.41(1H, s), 8.47(1H, br s), 9.01(1H, br s) |
| 111 | 433 | 9.9 | 1.65-1.77(6H, m), 2.65(6H, s), 3.40-3.50(4H, m), 6.84(1H, d), 7.06(1H, d), 7.14(2H, d), 7.36(1H, s), 7.66(1H, t), 7.85-7.90(3H, m), 9.07(1H, s), 9.18(1H, s) |
| 112 | 461 | 9.1 | 1.07(6H, s), 1.53-1.62(6H, m), 3.23-3.37(6H, 2xm), 6.43(1H, d), 6.47(1H, t), 6.80(1H, d), 6.99(2H, d), 7.37(1H, t), 7.72(2H, d), 7.76(1H, s), 8.98 91H, s), 9.04(1H, s) |
| 113 | 390 | 8.6 | 1.60(6H, br s), 3.34(4H, br s), 6.08(1H, br d), 6.38(1H, d), 6.84(1H, s), 7.02(2H, d), 7.72-7.77(3H, m), 8.01(1H, d), 8.95(1H, s) |
| 114 | 405 | 9.1 | 1.60(6H, m), 2.87(3H, s), 3.3(4 masked protons), 7.02(2H, d), 7.76(2H, d), 7.78(1H, s), 7.90(1H, d), 8.08(1H, s), 8.98(1H, d) |
| 115 | 404 | 9.2 | 1.60(6H, s), 2.47(3H, s), 3.34(4H, s), 6.57(1H, s), 6.68(1H, d), 7.02(2H, d), 7.59(1H, s), 7.75(2H, d), 7.97(1H, d), 8.66(1H, s) |
| 116 | 389 | 9.7 | 1.60(6H, s), 2.37(3H, s), 3.35(4H, s), 7.02(2H, d), 7.12(1H, d), 7.66(1H, s), 7.76(2H, d), 7.89(1H, d), 8.85(1H, d), 9.12(1H, s) |
| 117 | 458 | 10.5 | 1.46-1.54(2H, m), 1.57-1.60(8H, m), 1.68-1.70(2H, m), 1.96-2.02(2H, m), 3.35(4H, m), 4.15(1H, m), 6.37(1H, m), 6.56(1H, m), 6.82(1H, d), 7.02(2H, d), 7.41(1H, m), 7.75-7.80(3H, m), 8.98(1H, s), 9.07(1H, s), 12.3(1H, s) |
| 118 | 378 | 8.6 | 1.60(6H, s), 3.35(4H, s), 3.64(3H, s), 7.01(3H, m), 7.28(1H, s), 7.75(3H, m), 8.38(1H, d) |
| 119 | 517 | 10.0 | 0.86(3H, d), 0.94(3H, d), 1.45-1.55(2H, m), 1.52-1.64(6H, m), 1.65-1.75(1H, m), 2.57(3H, d), 3.32-3.42(4H, m), 4.29-4.38(1H, m), 6.45(1H, d), 6.65-6.74(1H, m), 6.81(1H, d), 7.00(2H, d), 7.40(1H, t), 7.72-.82(4H, m), 8.89(1H, s), 9.08(1H, s) |
| 120 | 501 | 9.7 | 0.95-1.10(3H, m), 1.53-1.75(9H, m), 1.78-2.65(4H, m), 2.85-3.18(3H, m), 3.30-3.37(4H, m), 3.55-3.68(1H, m), 6.38(1H, d), 6.5-6.85(1H, m), 7.00(2H, d), 7.37(1H, t), 7.69-7.78(3H, m), 8.93(1H, s), 9.04(1H, s) |
| 121 | 405 | 8.9 | 1.60(6H, s), 3.34(4H, s), 4.60(2H, s), 7.02(2H, d), 7.34(1H, d), 7.63(1H, d), 7.76(2H, d), 7.82(1H, t), 7.93(1H, d), 9.02(1H, s) |
| 122 | 348 | 8.3 | 2.87(3H, br s), 6.98(1H, d), 7.35-7.47(4H, m), 7.57(1H, d), 7.65(2H, d), 8.02(1H, s), 8.27(1H, d), 9.20(1H, br s), 9.62(1H, s) |
| 123 | 434 | 9.3 | 1.60(6H, m), 2.80(6H, 2s), 3.3(4 masked protons), 6.05(1H, s), 6.41(1H, br s), 6.89(1H, br s), 7.02(2H, d), 7.77(2H, d), 7.85(1H, s), 8.88(1H, s) |
| 124 | 432 | 9.2 | 1.54-1.63(6H, m), 2.85(3H, s), 3.25-3.40(4H, m), 7.00(2H, d), 7.70-7.82(4H, m), 7.91(1H, t), 8.40(1H, s), 8.89(1H, s) |
| 125 | 418 | 8.9 | 1.60(6H, s), 2.38(3H, s), 3.35(4H, s), 3.86(2H, s), 7.02(2H, d), 7.32(1H, d), 7.66(1H, d), 7.79(2H, d), 7.82(1H, t), 7.96(1H, d), 9.06(1H, d) |
| 126 | 406 | 6.2 | 2.78-2.86(7H, m), 3.19-3.24(4H, m), 6.73(1H, s), 7.02(2H, d), 7.34(1H, br |

TABLE II-A-continued

Characterization Data for Selected Compounds of Formula I

| Compound No II- | M+1(obs) | Rt(min) | ¹H-NMR |
|---|---|---|---|
| | | | s), 7.77(2H, d), 7.98(1H, br s), 8.41(1H, s), 8.92(1H, br s), 9.16(1H, s) |
| 127 | 501 | 10.1 | 1.55-1.60(10H, m), 1.70(3H, s), 1.99(2H, m), 2.32(4H, m), 3.15(1H, m), 3.34(4H, m), 6.35(1H, d), 6.63(1H, s), 6.84(1H, d), 7.02(2H, d), 7.40(1H, m), 7.76-7.78(3H, m), 8.99(1H, s), 9.08(1H, s), 12.30(1H, s) |
| 128 | 488 | 9.9 | 1.19-1.28(2H, m), 1.60(6H, m), 1.67-1.70(4H, m), 1.88-1.91(2H, m), 3.23-3.37(5H, m), 3.86-3.88(2H, m), 6.48(1H, s), 6.88(1H, m), 7.03(2H, d), 7.49(1H, m), 7.60-7.80(4H, m), 8.96(1H, s), 9.09(1H, s), 12.40(1H, s) |
| 129 | 447 | 9.1 | 1.16(3H, d), 1.53-1.63(6H, m), 2.55-2.73(2H, m), 3.25-3.40(4H, m), 3.85-3.96(1H, m), 6.35(1H, d), 6.82(1H, d), 7.01(2H, d), 7.39(1H, t), 7.70-7.80(3H, m), 8.97(1H, s) |
| 130 | 419 | 9.4 | — |
| 131 | 478 | 7.3 | — |
| 132 | 476 | 9.8 | 0.93-0.98(6H, m), 1.60(6H, m), 1.78(1H, m), 2.94(1H, m), 3.34(4H, m), 4.18(1H, m), 4.36(1H, m), 6.70(1H, d), 7.02(2H, d), 7.36(1H, d), 7.73-7.89(3H, m), 7.90(1H, s), 9.04(1H, s), 9.09(1H, s) |
| 133 | 490 | 10.1 | 0.96-0.99(9H, m), 1.60(6H, m), 2.96(1H, m), 3.32-3.34(4H, m), 4.13(1H, m), 4.64(1H, m), 6.75(1H, m), 7.02(2H, d), 7.38(1H, d), 7.71-7.78(3H, m), 7.90(1H, d), 9.06-9.08(2H, m) |
| 134 | 448 | 7.7 | 1.10(2H, m), 1.48-1.78(5H, m), 2.40-2.47(2H, m), 2.85(3H, m), 2.89(2H, m), 4.10(2H, m), 6.31(1H, m), 6.52(NH), 6.85(1H, m), 7.09(2H, m), 7.42(1H, t), 7.81-7.91(3H, m), 9.00(1H, s), 9.12(1H, s) |
| 135 | 434 | 6.3 | 1.28(6H, d), 2.76(2H, t), 2.93(3H, s), 3.34-3.52(2H, m), 4.08(2H, d), 6.85(1H, s), 7.15(2H, d), 7.85(2H, d), 7.94(1H, br s), 8.59(1H, br s), 8.85(1H, br s), 9.21(1H, s), 12.69(1H, br s) |
| 136 | 474 | 7.6 | 1.84-2.20(8H, m), 2.93(3H, s), 3.06-3.52(6H, m), 3.57-3.68(1H, m), 3.78-3.86(1H, m), 4.18-4.28(1H, m), 6.77(2H, d), 6.84(1H, br s), 7.83(2H, d), 7.93(1H, br s), 8.58(1H, br s), 8.87(1H, br s), 9.11(1H, s) |
| 137 | 403 | 6.2 | 2.34-2.39(2H, m), 2.84(3H, s), 2.92(2H, t), 3.30-3.42(2H, m), 6.40(1H, s), 6.74(1H, s), 7.60(2H, d), 7.89(2H, d), 7.96-8.08(1H, m), 8.41(1H, s), 8.92(1H, br s), 9.38(1H, s) |
| 138 | 449 | 7.4 | 2.38-2.42(4H, m), 2.67(6H, m), 2.81(3H, m), 4.14(2H, m), 6.35(1H, m), 6.51(NH), 6.89(1H, m), 7.10(2H, m), 7.45(1H, t), 7.85-7.92(3H, m), 8.98(1H, s), 9.11(1H, s) |
| 139 | 406 | 6.5 | (MeOD) 3.02(3H, s), 3.37(4H, t), 3.60(4H, t), 7.16(2H, d), 7.78(1H, s), 7.95(2H, d), 7.97(1H, d), 8.05(1H, s), 9.21(1H, d) |
| 140 | 375 | 9.3 | 1.55-1.62(6H, m), 3.25-3.40(4H, m), 6.98(2H, d), 7.16-7.22(1H, m), 7.71-7.80(4H, m), 7.95(1H, s), 8.54-8.57(1H, m), 9.00(1H, s) |
| 141 | 462 | 9.0 | 1.1(6H, m), 1.6(6H, s), 3.2-3.4(6H, m), 7.0(3H, m), 7.7-7.8(2H, m), 7.8-7.9(2H, m), 8.0-8.1(1H, s), 9.0(1H, m), 9.1(1H, s) |
| 142 | 449 | 6.8 | 1.21-1.36(2H, m), 1.72(3H, m), 1.83(2H, m), 2.71-2.85(5H, m), 3.10(2H, m), 4.11(2H, m), 6.75(1H, s), 7.10(2H, m), 7.39(NH), 7.91(2H, m), 8.45(1H, s), 8.95(1H, br s), 9.22(1H, s) |

TABLE II-A-continued

Characterization Data for Selected Compounds of Formula I

| Compound No II- | M+1(obs) | Rt(min) | ¹H-NMR |
|---|---|---|---|
| 143 | 449 | 7.2 | 1.18-1.30(2H, m), 1.69-1.85(5H, m), 2.68(2H, m), 2.86(3H, m), 3.11(2H, m), 4.13(2H, m), 7.09(2H, m), 7.12(NH), 7.80(1H, m), 7.90(3H, m), 8.10(1H, m), 9.00(1H, s), 9.21(1H, s) |
| 144 | 379 | 5.8 | 2.81-2.82(4H, m), 3.19-3.21(4H, m), 3.61(3H, s), 6.89(1H, s), 7.02(2H, d), 7.33(1H, s), 7.64(1H, s), 7.75(2H, d), 8.31(1H, s), 9.26(1H, s) |
| 145 | 474 | 8.0 | — |
| 146 | 420 | 6.7 | 1.74-1.82(2H, m), 2.63(2H, t), 2.82-2.90(5H, m), 3.53(2H, t), 3.61(2H, t), 6.81(2H, d), 7.08-7.16(1H, m), 7.73(2H, d), 7.80(1H, s), 7.86(1H, d), 8.09(1H, s), 9.00(1H, d) |
| 147 | 421 | 7.6 | 1.85-2.08(4H, m), 2.88(3H, d), 3.09-3.18(1H, m), 3.20-3.28(1H, m), 3.40-3.52(2H, m), 3.78-3.84(1H, m), 6.70(2H, d), 7.07-7.15(1H, m), 7.76(2H, d), 7.80(1H, s), 7.87(1H, d), 8.09(1H, s), 9.00(1H, d) |
| 148 | 450 | 6.7 | 2.44(2H, t), 2.55(4H, m), 2.88(3H, d), 3.26-3.37(4H, m), 3.54(2H, t), 7.04(2H, d), 7.08-7.14(1H, m), 7.78(2H, d), 7.80(1H, s), 7.88(1H, d), 8.10(1H, s), 9.00(1H, d), 9.12(1H, s), 12.42(1H, br s) |
| 149 | 478 | 9.1 | 1.04-1.13(3H, m), 1.50-1.62(6H, m), 3.78-3.85(1H, m), 3.63-3.83(1H, m), 4.10-4.34(2H, 2xm), 6.54-6.61(1H, m), 7.01(2H, d), 7.21(1H, t), 7.66(1H, t), 7.71(2H, d), 8.01+8.11(1H, 2xs), 8.90(1H, s) |
| 150 | 488 | 9.8 | 1.37-1.43(2H, m), 1.50-1.66(12H, m), 1.70-1.80(2H, m), 3.22-3.36(4H, m), 4.18(2H, s), 6.60(1H, d), 7.01(2H, d), 7.20(1H, d), 7.65(1H, t), 7.73(2H, d), 8.02(1H, s), 8.85(1H s) |
| 151 | 462 | 9.6 | 0.96(3H, t), 1.30-1.40(1H, m), 1.55-1.60(6H, m), 2.95-3.02(1H, m), 3.30-3.36(4H, m), 4.10-4.27(2H, m), 6.70(1H, d), 7.01(2H, d), 7.32(1H, d), 7.70-7.78(4H, m), 7.86(1H, s), 9.01(1H, s) |
| 152 | 490 | 10.1 | 0.86(3H, t), 0.95(3H, d), 1.13-1.25(1H, m), 1.47-1.60(8H, m), 2.95-3.01(1H, m), 3.30-3.40(4H, m), 4.10-4.20(1H, m), 3.38-3.45(1H, m), 6.70(1H, d), 7.00(2H, d), 7.33(1H, d), 7.70-7.85(3H, m), 7.90(1H, s), 9.05(1H, s) |
| 153 | 435 | 7.0 | 1.41-1.52(2H, m), 1.96(2H, m), 2.13(1H, m), 2.89(3H, m), 3.01(4H, m), 3.97(2H, m), 7.09(2H, m), 7.11(1H, s), 7.81(1H, s), 7.94(3H, m), 8.16(1H, s), 9.00(1H, s), 9.24(1H, s) |
| 154 | 469 | 8.2 | 1.65-1.75(4H, m), 1.94-2.09(4H, m), 2.41-2.51(4H, m), 2.61-2.62(2H, m), 3.16(1H, m), 3.42(1H, m), 3.93(1H, m), 6.67(2H, d), 7.72(2H, d), 7.88(1H, d), 8.35(1H, m), 8.54(1H, d), 8.76(1H, d), 8.97(1H, d), 9.42,(1H, d) |
| 155 | 420 | 7.5 | 2.35-2.52(4H, m), 2.62-2.86(3H, m), 2.87(3H, s), 3.28-3.48(4H, m), 7.07(2H, d), 7.80(1H, s), 7.82(2H, d), 7.89(1H, d), 8.10(1H, s), 9.00(1H, d), 9.14(1H, s), 12.45(1H, d) |
| 156 | 449 | 7.8 | 1.12-1.24(2H, m), 1.38(2H, q), 1.56-1.69(1H, m), 1.74(2H, d), 2.80(2H, t), 2.87(3H, s), 3.46(2H, t), 3.91(2H, d), 7.02(2H, d), 7.08-7.14(1H, m), 7.76(2H, d), 7.80(1H, s), 7.88(1H, d), 8.09(1H, s), 9.00(1H, d) |
| 157 | 434 | 7.7 | 1.15-1.26(2H, m), 1.75(2H, m), 1.78(1H, m), 2.85(3H, m), 2.98(2H, m), 3.40(2H, m), 3.89(2H, m), 6.32(1H, |

TABLE II-A-continued

Characterization Data for Selected Compounds of Formula I

| Compound No II- | M+1(obs) | Rt(min) | ¹H-NMR |
|---|---|---|---|
| | | | m), 6.55(NH), 6.89(1H, m), 7.09(2H, m), 7.42(1H, m), 7.85(1H, s), 7.91(2H, m), 9.00(1H, s), 9.21(1H, s) |
| 158 | 450 | 6.8 | 2.45(4H, m). 2.71(2H, m), 2.81(4H, m), 2.89(3H, m), 4.18(2H, m), 7.08-7.12(3H, m), 7.80(1H, s). 7.91(3H, m), 8.10(1H, s), 8.97(1H, s), 9.25(1H, s) |
| 159 | 404 | 9.0 | 1.55-1.63(6H, m), 2.72(3H, s), 3.25-3.40(4H, m), 6.97(1H, s), 7.01(2H, d), 7.51(1H, s), 7.75(2H, d), 7.86(1H, s), 7.95(1H, s), 8.51(1H, s) |
| 160 | 430 | 79 | 2.8-3.0(7H, m), 3.1(4H, m), 6.7(1H, s), 7.0(2H, m), 7.1-7.2(1H, m), 7.2-7.3(1H, s), 7.7-7.8(2H, m), 7.9(1H, m), 9.0(1H, m), 9.1(1H, s) |
| 161 | 401 | 7.2 | 2.8-2.9(4H, m), 3.2-3.3(4H, m), 7.0(2H, m), 7.7(1H, m), 7.8(2H, m), 8.0-8.1(1H, m), 8.4(1H, s), 8.8(1H, m), 9.1(2H, m) |
| 162 | 434 | 6.7 | 1.84-1.94(2H, m), 1.98-2.07(2H, m), 2.88(3H, s), 3.02-3.10(2H, m), 3.30-3.42(2H, m), 3.48-3.54(2H, m), 3.56-3.64(2H, m), 6.75(2H, d), 7.76(2H, d), 7.81(1H, s), 7.88(1H, d), 8.10(1H, s), 9.00(1H, d) |
| 163 | 420 | 6.4 | 1.47-1.58(2H, m), 1.90-1.98(2H, m), 2.88(3H, s), 2.90-3.00(2H, m), 3.24-3.40(1H, m), 3.95-4.02(2H, m), 7.08(2H, d), 7.81(2H, d), 7.82(1H, s), 7.90(1H, d), 8.11(1H, s), 9.02(1H, d) |
| 164 | 422 | 7.6 | 2.87(6H, s), 2.88(3H, s), 3.03(3H, s), 3.24-3.30(2H, m), 3.75-3.81(2H, m), 6.90(2H, d), 7.81(1H, s), 7.82(2H, d), 7.89(1H, d), 8.10(1H, s), 9.00(1H, d) |
| 165 | 431 | 6.8 | 2.87(3H, s), 2.92(2H, t), 3.43(2H, t), 6.70(2H, d), 7.50(1H, s), 7.72(2H, d), 7.81(1H, s), 7.87(1H, d), 8.09(1H, s), 8.97-9.01(2H, m), 9.03(1H, s), 12.43(1H, d) |
| 166 | 434 | 7.9 | 2.14-2.26(2H, m), 2.88(6H, s), 2.90(3H, s), 3.30-3.64(3H, m), 3.72-3.78(1H, m), 3.98-4.08(1H, m), 6.73(2H, d), 7.81(1H, s), 7.84(2H, d), 7.89(1H, d), 8.10(1H, s), 9.01(1H, d) |
| 167 | 436 | 7.4 | 1.86-1.96(2H, m), 2.78(6H, s), 2.88(3H, s), 3.01(3H, s), 3.07-3.14(2H, m), 3.49(2H, t), 6.84(2H, d), 7.79(2H, d), 7.81(1H, s), 7.88(1H, d), 8.10(1H, s), 9.00(1H, d) |
| 168 | 445 | 7.1 | 2.04(2H, quintet), 2.87(3H, s), 3.06(2H, t), 4.14(2H, t), 6.64(2H, d), 7.15(1H, s), 7.40(1H, s), 7.71(2H, d), 7.81(1H, s), 7.86(1H, d), 8.09(2H, s), 9.00(1H, d), 9.02(1H, s) |
| 169 | 405 | 6.9 | 2.79-2.84(7H, m), 3.16-3.24(4H, m), 6.41(1H, m), 6.54(1H, s), 6.66(1H, d), 7.02-7.03(2H, m), 7.74(2H, d), 7.91(1H, d), 8.56(1H, d), 9.39(1H, d) |
| 170 | 435 | 6.5 | 1.51(2H, m), 1.88(2H, m), 2.09(1H, m), 2.78-2.86(5H, m), 3.21(2H, m), 3.95(2H, m), 6.78(1H, s), 7.11(2H, m). 7.45(1H, br s), 7.93(2H, m), 8.45(1H, s), 8.96(1H, s), 9.23(1H, s) |
| 171 | 490 | 9.2 | 1.68-1.75(4H, m), 1.90-2.12(4H, m), 2.35-2.65(6H, m), 2.70(3H, s), 3.10-3.20(1H, m), 3.40-3.50(1H, m), 3.90-3.99(1H, m), 6.27(1H, d), 6.45-6.55(2H, m), 6.70(2H, d), 7.43-7.61(2H, m), 7.75(2H, d), 8.68(1H, s) |
| 172 | 473 | 7.9 | 1.70-1.80(4H, m), 1.98-2.07(4H, m), 2.401-2.49(2H, m), 2.61-2.62(2H, m), 2.80(3H, s), 3.16-3.17(2H, m), |

TABLE II-A-continued

Characterization Data for Selected Compounds of Formula I

| Compound No II- | M+1(obs) | Rt(min) | ¹H-NMR |
|---|---|---|---|
| | | | 3.42-3.44(2H, m), 3.95(1H, m), 6.52(1H, d), 6.58(1H, s), 6.66-6.70(3H, m), 7.62(1H, d), 7.76(2H, d), 7.97(1H, d), 8.67(1H, d), 9.16(1H, s) |
| 173 | 416 | 6.3 | 3.00-3.05(4H, m), 3.29-3.39(4H, m), 6.69(1H, d), 7.08(2H, d), 7.84(2H, d), 7.86-7.90(1H, m), 7.96(1H, d), 8.75(1H, s), 9.14-9.18(2H, m), 12.08(1H, br s) |
| 174 | 464 | 8.8 | 1.55-1.70(6H, m), 3.30-3.53(4+2H, m), 4.13-4.25(2H, m), 4.62-4.72(1H, m), 6.71(1H, d), 7.03(2H, d), 7.33(1H, d), 7.70-7.80(3H, m), 7.88(1H, s), 9.00(1H, s), 9.07(1H, s) |
| 175 | 488 | 8.4 | 1.21(3H, t), 1.71(4H, br s), 1.91-2.07(4H, m), 2.33-2.40(1H, m), 2.61-2.68(4H, m), 3.12-3.19(1H, m), 3.35(3H, s), 3.38-3.46(1H, m), 3.93-3.97(1H, m), 6.67(2H, d), 7.11-7.14(1H, m), 7.76(1H, s), 7.78(2H, d), 7.85(1H, d), 8.07(1H, s), 8.97(1H, d) |
| 176 | 500 | 8.6 | 0.41(2H, br s), 0.78(2H, br d), 1.71(3H, br s), 1.81-2.19(7H, br m), 2.65(2H, br s), 3.16(1H, br s), 3.36(3H, s), 3.45(1H, br s), 3.87-3.97(1H, m), 6.68(2H, br d), 7.78(2H, br s), 7.88(1H, s), 7.92(1H, s), 8.21(1H, s), 9.00(1H, s), 9.06(1H, s) |
| 177 | 463 | 7.1 | 1.41-1.58(6H, br m), 1.91(2H, br m), 2.38(4H, m) 2.90(3H, m), 3.35(4H, m), 4.11(2H, m), 7.07-7.15(NH and 2H, m), 7.82(1H, s). 7.96(3H, m), 8.13(1H, s), 9.01(1H, s), 9.27(1H, s) |
| 178 | 473 | 7.5 | 1.91(4H, m), 2.04(4H, m), 2.50-2.51(2H, m), 2.76(3H, s), 3.15-3.22(2H, m), 3.45-3.49(2H, m), 3.65(1H, m), 3.80(1H, m), 4.24(1H, m), 6.06(1H, m), 6.78(2H, d), 6.97(1H, m), 7.50(1H, m), 7.81(2H, d), 7.93(1H, m), 7.97(1H, m), 8.67(1H, m), 9.12(1H, s), 10.02(1H, br s) |
| 179 | 497 | 9.0 | 1.65-1.75(4H, m), 1.85-2.05(6H, m), 2.50-2.60(3H, m), 2.75(3H, d), 3.08-3.19(1H, m), 3.35-3.45(2H, m), 3.85-3.92(1H, m), 6.27-6..34(1H, m), 6.63(2H, d), 6.75(1H, s), 6.94(1H, s), 7.09(1H, s), 7.48(1H, s), 7.75(2H, d), 8.63(1H, s), 9.04(1H, s) |
| 180 | 542 | 8.8 | 1.71(4H, br s), 1.94-2.19(4H, m), 2.38-2.51(4H, m), 2.61-2.68(2H, m), 3.16-3.18(1H, m), 3.44-3.47(1H, m), 3.92-3.95(1H, m), 4.20-4.32(2H, m), 6.67(2H, d), 7.71(1H, br t), 7.76(2H, d), 7.83(1H, s), 7.98(1H, s), 8.21(1H, s), 8.92(1H, s), 9.15 91H, s) |
| 181 | 421 | 6.6 | 1.45(2H, m), 1.98(2H, m), 2.61(2H, m) 2.95(3H, m), 3.00(2H, m), 4.55(2H, m), 7.10-7.15(NH and 2H, m), 7.86(1H, s). 7.95(3H, m), 8.15(1H, s), 9.02(1H, s), 9.28(1H, s) |
| 182 | 465 | 7.7 | 1.95(2H, m), 2.39(4H, m), 2.89(3H, m) 3.35(2H, m), 3.59(4H, m), 4.12(2H, m), 7.08-7.14(3H, m), 7.80(1H, s). 7.89(3H, m), 8.10(1H, s), 8.99(1H, s), 9.24(1H, s) |

Example 12

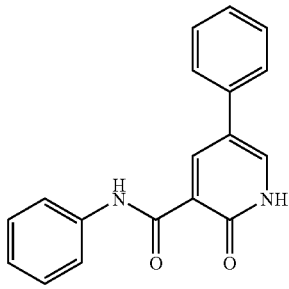

2-Oxo-5-phenyl-1,2-dihydro-pyridine-3-carboxylic acid phenylamide III-1

To a solution of 2-Oxo-5-phenyl-1,2-dihydro-pyridine-3-carboxylic acid (44 g, 0.20 mmol) in tetrahydrofuran (5 mL) were successively added aniline (20 μL, 0.23 mmol), hydroxybenzotriazole (30 mg, 0.23 mmol), dimethylaminopyridine (27 mg, 0.23 mmol) and EDC (43 mg, 0.23 mmol). The reaction mixture was stirred at room temperature for 16 hours. The solvent was removed in vacuo and the residue was purified by silica gel chromatography eluting with DCM containing 10% of MeOH to afford the title compound as a white solid (20 mg, 34% yield). MS (ES$^+$) 291. δH (DMSO-d$_6$) 7.2 (3H, m), 7.9 (1H, t), 8.5 (1H, d), 8.6 (2H, m), 9.3 (1H, s).

A variety of other compounds of Formula III have been prepared by methods substantially similar to those described herein Example 12. The characterization data for these compounds is summarized in Table III-A below and includes HPLC, LC/MS (observed) and $^1$H NMR data.

$^1$H NMR data is summarized in Table III-A below wherein $^1$H NMR data was obtained at 400 Mhz in deuterated DMSO, unless otherwise indicated, and was found to be consistent with structure. Compound numbers correspond to the compound numbers listed in Table 1.

TABLE III-A

Characterization Data for Selected Compounds of Formula III

| Compound No III- | M+1(obs) | Rt(min) | $^1$H-NMR |
|---|---|---|---|
| 2 | 305 | 8.6 | 4.56(2H, d), 7.28(1H, m), 7.34-7.37(5H, m), 7.46(2H, t), 7.62(2H, d), 8.06(1H, s), 8.66(1H, d), 10.20(1H, br t), 12.86(1H, br s). |
| 3 | 306 | 7.4 | 4.51(2H, d), 7.20-7.40(5H, m), 7.60(2H, d), 8.40(1H, m), 8.50-8.70(3H, m), 11.10(1H, br s). |
| 4 | 334 | 9.2 | 1H NMR(DMSO) 1.19-1.25(6H, m), 2.80-2.92(1H, m), 7.19-7.29(2H, m), 7.58-7.66(2H, m), 7.70-7.76(2H, m), 8.35-8.40(1H, m), 8.58-8.65(2H, m), 8.78-8.83(1H, m), 12.08(1H, br s), 13.22(1H, br s). |
| 5 | 348 | 9.6 | 1.29(9H, s), 7.39(2H, d), 7.63(2H, d), 7.73(2H, d), 8.39(1H, d), 8.61(2H, d), 8.81(1H, d), 12.10(1H, br s), 13.24(1H, br s). |
| 6 | 320 | 7.6 | 2.84(2H, t), 3.58(2H, q), 7.18-7.34(5H, m), 7.65-7.69(2H, m), 8.29(1H, d), 8.57-8.61(2H, m), 8.70(1H, d), 9.78(1H, br t), 13.0(1H, br s). |
| 7 | 320 | 8.8 | 1.18(3H, t), 2.59(2H, q), 7.21(2H, d), 7.62(2H, d), 7.73(2H, d), 8.39(1H, d), 8.61(2H, d), 8.80(1H, d), 12.10(1H, br s), 13.20(1H, br s). |
| 8 | 371 | 8.9 | 7.57(2H, d), 7.68-7.75(4H, m), 8.41(1H, d), 8.61(2H, d), 8.81(1H, d), 12.20(1H, s), 13.30(1H, br s). |
| 9 | 384 | 9.3 | 6.96-7.18(5H, m), 7.32-7.46(2H, m), 7.62-7.81(4H, m), 8.35-8.45(1H, m), 8.56-8.66(2H, m), 8.77-8.84(1H, m), 12.19(1H, br s). |
| 10 | 334 | 9.2 | 1.22(6H, d), 2.83-2.96(1H, m), 6.98-7.04(1H, m), 7.24-7.33(1H, m), 7.51-7.61(2H, m), 7.68-7.78(2H, m), 8.35-8.40(1H, m), 8.59-8.64(2H, m), 8.78-8.84(1H, m), 12.02(1H, br s). |
| 11 | 322 | — | (300 Mhz) 3.75(3H, s), 6.95(2H, d), 7.64(2H, d), 7.72(21H, d), 8.36(1H, d), 8.61(2H, d), 8.80(1H, d), 11.92(1H, s) |
| 12 | 322 | — | (300 Mhz) 3.77(3H, s), 6.7(1H, d), 7.16(1H, d), 7.27(1H, t), 7.47(1H, s), 7.72(2H, d), 8.39(1H, s), 8.60(2H, d), 8.79(1H, d), 12.20(1H, s), 13.0(1H, br s) |
| 13 | 336 | — | (300 Mhz) 1.33(3H, d), 4.7(1H, q), 5.2(1H, br s), 7.13(1H, d), 7.36(1H, |

TABLE III-A-continued

Characterization Data for Selected Compounds of Formula III

| Compound No III- | M+1(obs) | Rt(min) | ¹H-NMR |
|---|---|---|---|
| | | | t), 7.62(1H, d), 7.64(1H, s), 7.71(2H, d), 8.40(1H, d), 8.61(2H, d), 8.80(1H, d), 12.23(1H, s), 13.2(1H, br s) |
| 14 | 336 | — | (300 Mhz) 3.85(3H, s), 4.50(2H, d), 6.91(1H, t), 7.02(1H, d), 7.30-7.22(2H, m), 7.67(2H, dd), 8.29(1H, d), 8.59(2H, d), 8.71(1H, d), 10.09(1H, t) |
| 15 | 384 | — | (300 Mhz) 6.83-6.79(1H, m), 7.08-7.05(2H, m), 7.28-7.18(2H, m), 7.47-7.39(3H, m), 7.59(1H, t), 7.70(2H, dd), 8.33(1H, d), 8.60(2H, dd), 8.78(1H, d), 12.11(1H, br s), 13.24(1H, br s) |
| 16 | 352 | — | (300 Mhz) 3.76(3H, s), 3.79(3H, s), 6.95(1H, d), 7.20(1H, dd), 7.45(1H, d), 7.72(2H, dd), 8.37(1H, d), 8.61(2H, d), 8.81(1H, d), 11.95(1H, br s) |
| 17 | 334 | — | (300 Mhz) 1.84(2H, quint.), 2.64(2H, t), 3.34(2H, q), 7.31-7.15(5H, m), 7.94(2H, d), 8.39(1H, d), 8.68(2H, d), 8.78(1H, d), 9.70(1H, t), 13.16(1H, br s) |
| 18 | 410 | — | (300 Mhz) 2.31(2H, q), 3.25(2H, t), 4.03(1H, t), 7.17(2H, t), 7.35-7.28(8H, m), 7.67(2H, dd), 8.28(1H, d), 8.58(2H, dd), 8.67(1H, d), 9.77(1H, t), 12.90(1H, br s) |
| 19 | 396 | — | (300 Mhz) 7.48(1H, d), 7.79-7.55(8H, m), 7.89(1H, d), 8.23(1H, s), 8.40(1H, d), 8.60(2H, d), 8.80(1H, d), 12.40(1H, br s), 13.0(1H, br s) |
| 20 | 350 | — | (300 Mhz) 2.82(2H, q), 3.53(2H, q), 3.79(3H, s), 6.87(1H, t), 6.96(1H, d), 7.23-7.16(2H, m), 7.67(2H, d), 8.27(1H, d), 8.59(2H, d), 8.69(1H, d), 9.70(1H, t), 12.90(1H, br s) |
| 21 | 334 | — | (300 Mhz) 1.25(3H, d), 3.0(1H, sext.), 3.55-3.49(2H, m), 7.34-7.18(5H, m), 7.66(2H, d), 8.26(1H, d), 8.58(2H, d), 8.68(1H, d), 9.74(1H, t), 12.86(1H, br s) |
| 22 | 286 | — | (300 Mhz) 0.92-0.88(6H, m), 1.10(3H, d), 1.76(1H, sext.), 3.90(1H, sext.), 7.67(2H, d), 8.27(1H, d), 8.59(2H, d), 8.70(1H, d), 9.73(1H, d), 12.94(1H, br s) |
| 23 | 382 | — | (300 Mhz) 3.95(2H, s), 7.0(1H, d), 7.32-7.19(5H, m), 7.56(1H, s), 7.58(2H, d), 7.71(2H, d), 8.38(1H, d), 8.61(2H, d), 8.79(1H, d), 12.10(1H, br s), 13.20(1H, br s) |
| 24 | 256 | — | (300 Mhz) 0.55-0.49(2H, m), 0.79-0.70(2H, m), 2.90-2.84(1H, m), 7.67(2H, dd), 8.27(1H, d), 8.59(2H, d), 8.68(1H, d), 9.68(1H, s), 12.98(1H, br s) |
| 25 | 313 | — | (300 Mhz) 9.79(1H, s), 8.70(1H, d), 8.59(2H, d), 8.28(1H, d), 7.67(2H, d), 3.48(2H, t), 2.79-2.69(6H, m), 1.80-1.60(4H, m) |
| 26 | 328 | — | (300 Mhz) 1.58-1.24(10H, m), 3.30(2H, s), 4.39(1H, s), 7.68(2H, d), 8.28(1H, d), 8.59(2H, dd), 8.71(1H, d), 9.84(1H, t), 12.89(1H, br s) |
| 27 | 312 | — | (300 Mhz) 1.57-1.43(10H, m), 1.91-1.85(2H, m), 4.04-3.99(1H, m), 7.66(2H, dd), 8.28(1H, d), 8.59(2H, dd), 8.68(1H, d), 9.82(1H, d), 12.40(1H, br s) |
| 28 | 350 | — | (300 Mhz) 2.79(1H, dd), 2.94(1H, dd), 3.45-3.32(2H, m), 4.17(1H, d), 4.95(1H, br s), 7.26-7.19(5H, m), 7.66(2H, dd), 8.28(1H, d), 8.58(2H, |

TABLE III-A-continued

Characterization Data for Selected Compounds of Formula III

| Compound No III- | M+1(obs) | Rt(min) | ¹H-NMR |
|---|---|---|---|
| | | | d), 8.68(1H, d), 9.82(1H, d), 12.20(1H, br s) |
| 29 | 348 | — | (300 Mhz) 1.24(9H, s), 7.17(1H, d), 7.30(1H, t), 7.53(1H, d), 7.73(2H, d), 7.74(1H, s), 8.38(1H, d), 8.61(2H, d), 8.82(1H, d), 12.07(1H, br s), 13.19(1H, br s) |
| 30 | 272 | — | (300 Mhz) 0.82(3H, t), 1.10(3H, d), 1.52-1.40(2H, m), 3.89-3.83(1H, m), 7.65(2H, d), 8.30(1H, d), 8.57(2H, d), 8.65(1H, d), 9.91(1H, d) |
| 31 | 332 | — | (300 Mhz) 1.30-1.25(2H, m), 2.11-2.05(1H, m), 3.05-2.99(1H, m), 7.33-7.17(5H, m), 7.67(2H, dd), 8.30(1H, d), 8.59(2H, dd), 8.69(1H, d), 9.91(1H, d), 13.01(1H, br s) |
| 32 | 336 | — | (300 Mhz) 3.44(1H, dd), 3.66(1H, dd), 4.76(1H, dd), 5.63(1H, br s), 7.41-7.22(5H, m), 7.63(2H, d), 8.32(1H, d), 8.55(2H, d), 8.62(1H, d), 10.29(1H, s), 12.80(1H, br s) |
| 33 | 336 | — | (300 Mhz) 3.45(1H, dd), 3.66(1H, dd), 4.76(1H, dd), 5.62(1H, br s), 7.41-7.22(5H, m), 7.65(2H, d), 8.30(1H, d), 8.57(2H, d), 8.65(1H, d), 10.12(1H, s), 12.80(1H, br s) |
| 34 | 348 | — | (300 Mhz) 1.20(3H, d), 1.84-1.77(2H, m), 2.66-2.61(2H, m), 4.03-3.98(1H, m), 7.30-7.16(5H, m), 7.67(2H, dd), 8.29(1H, d), 8.58(2H, dd), 8.70(1H, d), 9.76(1H, d), 12.8(1H, br s) |
| 35 | 348 | — | (300 Mhz) 1.20(3H, d), 1.84-1.77(2H, m), 2.66-2.60(2H, m), 4.05-3.96(1H, m), 7.30-7.14(5H, m), 7.68(2H, dd), 8.30(1H, d), 8.59(2H, d), 8.71(1H, d), 9.70(1H, d), 13.0(1H, br s) |
| 36 | 270 | — | (300 Mhz) 0.23-0.18(2H, m), 0.48-0.42(2H, m), 1.04-0.95(2H, m), 3.19(2H, d), 7.67(2H, dd), 8.28(1H, d), 8.59(2H, dd), 8.70(1H, d), 9.79(1H, t), 12.96(1H, br s) |
| 37 | 310 | — | (300 Mhz) 1.51-1.10(7H, m), 1.80-1.74(1H, m), 2.29-2.19(2H, m), 3.81-3.70(1H, m), 7.66(2H, d), 8.27(1H, d), 8.59(2H, d), 8.67(1H, d), 9.75(1H, d) |
| 38 | 400 | — | (300 Mhz) 7.43-7.24(7H, m), 7.79-7.71(4H, m), 8.40(1H, d), 8.61(2H, d), 8.80(1H, d), 12.24(1H, s), 13.25(1H, br s) |
| 39 | 350 | — | (300 Mhz) 1.46(3H, d), 3.74(3H, s), 5.10(1H, quint.), 6.91(2H, d), 7.30(2H, d), 7.67(2H, d), 8.27(1H, d), 8.59(2H, d), 8.70(1H, d), 10.10(1H, d) |
| 40 | 327 | — | (300 Mhz) 1.52-1.24(6H, m), 2.47-2.40(6H, m), 3.43(2H, t), 7.68(2H, d), 8.30(1H, d), 8.59(2H, dd), 8.70(1H, d), 9.81(1H, t) |
| 41 | 336 | — | (300 Mhz) 3.41-3.34(1H, m), 3.72-3.61(1H, m), 4.72-4.70(1H, dd), 5.63(1H, d), 7.41-7.22(5H, m), 7.65(2H, d), 8.30(1H, d), 8.57(2H, d), 8.65(1H, d), 10.11(1H, br s) |
| 42 | 377 | 7.2 | 3.04-3.14(4H, m), 3.70-3.79(4H, m), 6.98(2H, d), 7.59(2H, d), 7.71(2H, d), 8.37(1H, d), 8.61(2H, d), 11.91(1H, br s), 13.20(1H, br s) |
| 43 | 374 | 7.2 | 1.10-1.90(10H, m), 2.40-2.56(1H, m), 7.22(2H, d), 7.62(2H, d), 7.72(2H, d), 8.39(1H, d), 8.61(2H, d), 8.80(1H, d), 12.10(1H, br s) |
| 44 | 375 | 8.8 | 1.48-1.68(6H, m), 3.05-3.15(4H, m), 6.93(2H, d), 7.56(2H, d), 7.72(2H, d), 8.36(1H, d), 8.61(2H, d), 8.80(1H, d), 11.90(1H, s), 13.20(1H, br s) |

TABLE III-A-continued

Characterization Data for Selected Compounds of Formula III

| Compound No III- | M+1(obs) | Rt(min) | $^1$H-NMR |
|---|---|---|---|
| 45 | 336 | 8.1 | 1.31(3H, t), 4.01(2H, q), 6.94(2H, d), 7.62(2H, d), 7.72(2H, d), 8.39(1H, d), 8.61(2H, d), 8.80(1H, d), 11.99, 13.25(1H, 2br s) |
| 46 | 390 | 7.1 | 2.23(3H, s), 2.43-2.50(4H, m), 3.08-3.14(4H, m), 6.95(2H, d), 7.59(2H, d), 7.72(2H, d), 8.37(1H, d), 8.61(2H, d), 8.80(1H, d), 11.92(0.5H, s) |
| 47 | 404 | 7.1 | 1.03(3H, t), 2.38(2H, q), 2.45-2.54(4H, m), 3.06-3.14(4H, m), 6.95(2H, d), 7.58(2H, d), 7.72(2H, d), 8.38(1H, d), 8.61(2H, d), 8.80(1H, d), 12.00(0.4H, s) |
| 48 | 306 | 6.3 | 3.39(3H, s), 7.10-7.39(5H, m), 7.46-7.60(2H, m), 7.80-8.02(2H, m), 8.48-8.56(2H, m), 12.10(0.1H, br s) |
| 49 | 320 | 6.9 | 2.20(3H, s), 3.30(3H, s), 7.00-7.20(4H, m), 7.50-7.62(2H, m), 7.85-8.02(2H, m), 8.49-8.60(2H, m), 12.10(0.2H, br s) |
| 50 | 320 | 8.8 | 1.20(3H, t), 2.61(2H, q), 6.98(1H, br d), 7.25-7.32(1H, m), 7.51-7.60(2H, m), 7.72(2H, d), 8.39(1H, d), 8.61(2H, d), 8.81(1H, d), 12.02(1H, s), 13.26(0.8H, br s) |
| 51 | 306 | 8.3 | 2.31(3H, s), 6.94(1H, d), 7.23-7.29(1H, m), 7.48-7.59(2H, m), 7.72(2H, d), 8.39(1H, d), 8.61(2H, d), 8.81(1H, d), 12.02(0.5H, s) |
| 52 | 391 | 6.7 | 1.40-1.57(2H, m), 1.76-1.87(2H, m), 2.75-2.86(2H, m), 3.43-3.68(3H, m), 4.70(1H, d), 6.95(2H, d), 7.56(2H, d), 7.73(2H, d), 8.37(1H, d), 8.61(2H, d), 8.80(1H, d), 11.90(1H, s), 13.20(0.6H, br s) |
| 53 | 476 | 9.1 | 1.42(9H, s), 3.02-3.10(4H, m), 3.41-3.50(4H, m), 6.98(2H, d), 7.60(2H, d), 7.71(2H, d), 8.38(1H, d), 8.61(2H, d), 8.80(1H, d 11.93(0.6H, s) |
| 54 | 376 | 6.2 | 2.81-2.97(4H, m), 3.00-3.12(4H, m), 6.89-6.99(2H, m), 7.52-7.62(2H, m), 7.65-7.75(2H, m), 8.38(1H, br s), 8.55-8.62(2H, m), 8.75(1H, br s), 12.15(0.6H, br s) |

Example 13

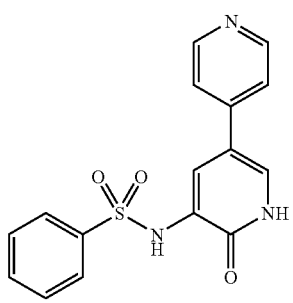

N-(6-Oxo-1,6-dihydro-[3,4']bipyridinyl-5-yl)-benzenesulfonamide-IV-1

Amrinone (100 mg, 0.53 mmol) was suspended in pyridine (2 mL) and benzenesulfonyl chloride (75 µL, 0.59 mmol) was added dropwise at 0° C. The reaction mixture was stirred for 2 hours. The pyridine was removed in vacuo. MeOH was added to the crude mixture and the solid was filtered and rinsed with more MeOH to give the title compound as a light yellow solid (100 mg, 57% yield). MS (ES$^+$) m/e=328. $^1$H NMR (DMSO-d$_6$) δH 7.51 (2H, dd), 7.54-7.58 (2H, m), 7.61-7.65 (1H, m), 7.75 (2H, dd), 7.90 (2H, dd), 8.56 (2H, dd), 9.78 (1H, br s), 12.33 (1H, br s).

Example 14

ITK Inhibition Assay

Compounds were screened for their ability to inhibit Itk using a radioactive-phosphate incorporation assay. Assays were carried out in a mixture of 100 mM HEPES (pH 7.5), 10 mM MgCl2, 25 mM NaCl, 0.01% BSA and 1 mM DTT. Final substrate concentrations were 15 µM [γ-33P]ATP (400 mCi 33P ATP/mmol ATP, Amersham Pharmacia Biotech/Sigma Chemicals) and 2 µM peptide (SAM68 protein D332-443). Assays were carried out at 25° C. in the presence of 30 nM Itk. An assay stock buffer solution was prepared containing all of the reagents listed above, with the exception of ATP and the test compound of interest. 50 µL of the stock solution was placed in a 96 well plate followed by addition of 1.5 µL of DMSO stock containing serial dilutions of the test compound (typically starting from a final concentration of 15 µM with 2-fold serial dilutions) in duplicate (final DMSO concentration 1.5%). The plate was pre-incubated for 10 minutes at 25° C. and the reaction initiated by addition of 50 µL [γ-33P]ATP (final concentration 15 µM).

The reaction was stopped after 10 minutes by the addition of 50 µL of a TCA/ATP mixture (20% TCA, 0.4 mM ATP). A Unifilter GF/C 96 well plate (Perkin Elmer Life Sciences, Cat no. 6005174) was pretreated with 50 µL Milli Q water prior to the addition of the entire reaction mixture (150 µL). The plate was washed with 200 µL Milli Q water followed by 200 mL of a TCA/ATP mixture (5% TCA, 1 mM ATP). This wash cycle was repeated a further 2 times. After drying, 30 µL Optiphase 'SuperMix' liquid scintillation cocktail (Perkin Elmer) was added to the well prior to scintillation counting (1450 Microbeta Liquid Scintillation Counter, Wallac).

IC50 data were calculated from non-linear regression analysis of the initial rate data using the Prism software package (GraphPad Prism version 3.0cx for Macintosh, GraphPad Software, San Diego Calif., USA).

Assays were carried out in a mixture of 20 mM MOPS (pH 7.0), 10 nM MgCl2, 0.1% BSA and 1 mM DTT. Final substrate concentrations in the assay were 7.5 µM [γ-33P]ATP (400 mCi 33P ATP/mmol ATP, Amersham Pharmacia Biotech/Sigma Chemicals) and 3 µM peptide (SAM68 protein D332-443). Assays were carried out at 25° C. in the presence of 50 nM Itk. An assay stock buffer solution was prepared containing all of the reagents listed above, with the exception of ATP and the test compound of interest. 50 µL of the stock solution was placed in a 96 well plate followed by addition of 2 µL of DMSO stock containing serial dilutions of the test compound (typically starting from a final concentration of 50 µM with 2-fold serial dilutions) in duplicate (final DMSO concentration 2%). The plate was pre-incubated for 10 minutes at 25° C. and the reaction initiated by addition of 50 µL [γ-33P]ATP (final concentration 7.5 µM).

The reaction was stopped after 10 minutes by the addition of 100 mL 0.2M phosphoric acid+0.01% TWEEN 20. A multiscreen phosphocellulose filter 96-well plate (Millipore, Cat no. MAPHN0B50) was pretreated with 10 µL 0.2M phosphoric acid+0.01% TWEEN 20 prior to the addition of 170 mL of the stopped assay mixture. The plate was washed with 4×200 µL 0.2M phosphoric acid+0.01% TWEEN 20. After drying, 30 µL Optiphase 'SuperMix' liquid scintillation cocktail (Perkin Elmer) was added to the well prior to scintillation counting (1450 Microbeta Liquid Scintillation Counter, Wallac).

Ki(app) data were calculated from non-linear regression analysis of the initial rate data using the Prism software package (GraphPad Prism version 3.0cx for Macintosh, GraphPad Software, San Diego Calif., USA).

In general, compounds of the invention are effective for the inhibition of ITK. Preferred compounds showed Ki below 0.1 µM in the radioactive incorporation assay (I-68, I-71, I-74, I-77, I-81, II-14, II-17, II-20, II-22, II-23, II-28, II-29, II-30, II-31, II-35, II-40, II-46, II-51, II-58, II-63, II-64, II-65, II-66, II-77, II-78, II-79, II-80, II-81, II-97, II-107, II-112, II-114, II-115, II-126, II-129, II-130, II-131, II-134, II-135, II-136, II-138, II-139, II-142, II-143, II-145, II-146, II-147, II-148, II-153, II-155, II-156, II-157, II-158, II-159, II-160, II-162, II-163, II-164, II-165, II-166, II-167, II-168, II-169, II-170, II-171, II-172, II-177, II-178, II-179, II-181, II-182, III-42, III-44, III-46, III-47, III-52, III-54). Preferred compounds showed Ki between 0.1 µM and 1 µM in the radioactive incorporation assay (I-5, I-10, I-11, I-20, I-21, I-22, I-27, I-45, I-46, I-47, I-69, I-72, I-73, I-75, I-82, I-83, I-84, I-85, II-4, II-7, II-15, II-21, II-32, II-34, II-38, II-39, II-41, II-43, II-45, II-47, II-52, II-56, II-57, II-59, II-60, II-61, II-62, II-69, II-70, II-71, II-75, II-76, II-83, II-85, II-87, II-95, II-98, II-99, II-100, II-101, II-104, II-105, II-108, II-120, II-121, II-123, II-124, II-132, II-133, II-137, II-140, II-144, II-149, II-150, II-151, II-152, II-154, II-161, II-174, II-175, II-176, III-4, III-5, III-7, III-8, III-11, III-16, III-43, III-45).

Example 15

ITK Inhibition Assay (UV)

Compounds were screened for their ability to inhibit Itk using a standard coupled enzyme assay (Fox et al., Protein Sci., (1998) 7, 2249).

Assays were carried out in a mixture of 20 mM MOPS (pH 7.0), 10 mM MgCl2, 0.1% BSA, 1 mM DTT, 2.5 mM phosphoenolpyruvate, 300 µM NADH, 30 µg/ml pyruvate kinase and 10 µg/ml lactate dehydrogenase. Final substrate concentrations in the assay were 100 µM ATP (Sigma Chemicals) and 3 µM peptide (Biotinylated SAM68 D332-443). Assays were carried out at 25° C. and in the presence of 100 nM Itk.

An assay stock buffer solution was prepared containing all of the reagents listed above, with the exception of ATP and the test compound of interest. 60 µl of the stock solution was placed in a 96 well plate followed by addition of 2 µl of DMSO stock containing serial dilutions of the test compound (typically starting from a final concentration of 15 µM). The plate was preincubated for 10 minutes at 25° C. and the reaction initiated by addition of 5 µl of ATP. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

In general, compounds of the invention are effective for the inhibition of ITK. Preferred compounds showed Ki below 0.1 µM in the coupled enzyme assay (I-70, I-76, I-78, I-79, I-80). Preferred compounds showed Ki between 0.1 µM and 1 µM in the coupled enzyme assay (I-5, I-10, I-11, I-69, I-82, I-83, I-84, II-4, II-7, II-41).

Example 16

BTK Inhibition Assay

Compounds were screened for their ability to inhibit Btk using a radioactive-phosphate incorporation assay at Vertex Pharmaceuticals. Assays were carried out in a mixture of 20 mM MOPS (pH 7.0), 10 mM MgCl2, 0.1% BSA and 1 mM DTT. Final substrate concentrations in the assay were 50 µM [γ-33P]ATP (200 mCi 33P ATP/mmol ATP, Amersham Pharmacia Biotech, Amersham, UK/Sigma Chemicals) and 2 µM peptide (SAM68 D332-443). Assays were carried out at 25° C. and in the presence of 25 nM Btk. An assay stock buffer solution was prepared containing all of the reagents listed above, with the exception of the peptide and the test compound of interest. 75 µL of the stock solution was placed in a 96 well plate followed by addition of 2 µL of DMSO stock containing serial dilutions of the test compound (typically starting from a final concentration of 15 µM) in duplicate (final DMSO concentration 2%). The plate was preincubated for 15 minutes at 25° C. and the reaction initiated by addition of 25 µL peptide (final concentration 2 µM). Background counts were determined by the addition of 100 mL 0.2M phosphoric acid+0.01% TWEEN to control wells containing assay stock buffer and DMSO prior to initiation with peptide.

The reaction was stopped after 10 minutes by the addition of 100 mL 0.2M phosphoric acid+0.01% TWEEN. A multiscreen phosphocellulose filter 96-well plate (Millipore, Cat no. MAPHN0B50) was pretreated with 100 µL 0.2M phosphoric acid+0.01% TWEEN 20 prior to the addition of 170 mL of the stopped assay mixture. The plate was washed with 4×200 µL 0.2M phosphoric acid+0.01% TWEEN 20. After drying, 30 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis using the Prism software package (GraphPad Prism version 3.0cx for Macintosh, GraphPad Software, San Diego Calif., USA).

In general, compounds of the invention, including compounds in Table 1, are effective for the inhibition of Btk. Preferred compounds showed Ki above 0.5 µM in the radioactive incorporation assay (II-43, II-61, II-114, II-149). Preferred compounds showed Ki below 0.5 µM in the radioactive incorporation assay (II-51, II-58, II-61, II-63, II-77, II-78, II-80, II-112).

Example 17

BTK Inhibition Assay (AlphaScreen™)

Compounds were screened for their ability to inhibit Btk using an AlphaScreen™ phosphotyrosine assay at Vertex Pharmaceuticals. Assays were carried out in a mixture of 20 mM MOPS (pH 7.0), 10 mM MgCl2, 0.1% BSA and 1 mM DTT. Final substrate concentrations in the assay were 50 µM ATP (Sigma Chemicals) and 2 µM peptide (Biotinylated SAM68 D332-443). Assays were carried out at 25° C. and in the presence of 25 nM Btk. An assay stock buffer solution was prepared containing all of the reagents listed above, with the exception of peptide and the test compound of interest. 37.5 µL of the stock solution was placed in each well of a 96 well plate followed by 1 µL of DMSO containing serial dilutions of the test compound (typically starting from a final concentration of 15 µM) in duplicate (final DMSO concentration 2%). The plate was preincubated for 15 minutes at 25° C. and the reaction initiated by addition of 12.5 µL peptide (final concentration 2 µM). Background counts were determined by the addition of 5 µL 500 mM EDTA to control wells containing assay stock buffer and DMSO prior to initiation with Biotin-SAM68.

The reaction was stopped after 30 minutes by diluting the reaction 225-fold into MOPS buffer (20 mM MOPS (pH 7.0), 1 mM DTT, 10 mM MgCl2, 0.1% BSA) containing 50 mM EDTA to bring the final concentration of peptide to 9 nM.

AlphaScreen™ reagents were prepared according to the manufacturers instructions (AlphaScreen™ phosphotyrosine (P-Tyr-100) assay kit, PerkinElmer catalogue number 6760620C). Under subdued lighting, 20 µL of AlphaScreen™ reagents were placed in each well of a white half area 96 well plate (Corning Inc.—COSTAR 3693) with 30 µL of the stopped, diluted kinase reactions. Plates were incubated in the dark for 60 minutes prior to reading on a Fusion Alpha plate reader (PerkinElmer).

After removing mean background values for all of the data points, Ki(app) data were calculated from non-linear regression analysis using the Prism software package (GraphPad Prism version 3.0cx for Macintosh, GraphPad Software, San Diego Calif., USA).

Example 18

RLK Inhibition Assay

Compounds were screened for their ability to inhibit Rlk using a standard coupled enzyme assay (Fox et al., *Protein Sci.*, (1998) 7, 2249). Assays were carried out in a mixture of 20 mM MOPS (pH 7.0), 10 mM MgCl2, 0.1% BSA and 1 mM DTT. Final substrate concentrations in the assay were 100 µM ATP (Sigma Chemicals) and 10 µM peptide (Poly Glu:Tyr 4:1). Assays were carried out at 30° C. and in the presence of 40 nM Rlk. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of ATP and the test compound of interest. 60 µl of the stock solution was placed in a 96 well plate followed by addition of 2 µl of DMSO stock containing serial dilutions of the test compound (typically starting from a final concentration of 7.5 µM). The plate was preincubated for 10 minutes at 30° C. and the reaction initiated by addition of 5 µl of ATP. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

In general, compounds of the invention are effective for the inhibition of RLK. Preferred compounds showed Ki above 1 µM in the coupled enzyme assay (I-5, I-11, I-71, I-74, II-7, II-15, II-17, II-38, II-41, II-46, II-47, II-65, II-75, II-83, II-85, II-87, II-114, II-115, II-143, II-148, II-149, II-159, II-160, II-163, II-164, II-166, II-168, II-171, II-178, II-179, III-4, III-5). Preferred compounds showed Ki below 1 µM in the coupled enzyme assay (II-14, II-28, II-29, II-30, II-31, II-35, II-40, II-77, II-78, II-79, II-80, II-81, II-112).

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I:

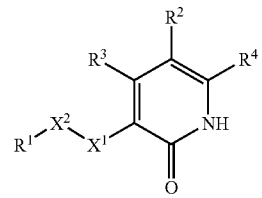

Formula I or a pharmaceutically accepted salt thereof, wherein
each $R^3$ and $R^4$ is H
$R^2$ is a pyridine ring; $R^2$ is optionally substituted with $J^R$;
each $X^1$ and $X^2$ is independently —C(O)— or NR—, wherein one of $X^1$ or $X^2$ is —NR— and the other of $X^1$ or $X^2$ is —C(O)—;
R is H, unsubstituted $C_{1-6}$ aliphatic;
$R^1$ is -T-Q;

T is a bond or $C_{1-3}$aliphatic, wherein up to one methylene unit of the chain is optionally and independently replaced by G or G' wherein G is —$NR^5$—, —O—, or —S—; G' is cyclopropyl, C≡C, or C═C; and T is optionally substituted with OH, $C_{1-6}$aliphatic, or phenyl;

each $J^Q$ is selected from halogen, $C_{1-6}$ alkyl, CN, $C_{1-4}$-haloalkyl, —$OR^o$, —$N(R^o)_2$, $SCHF_2$, unsubstituted phenyl, benzyl, a 5-7 membered heterocyclyl having 1-2 heteroatoms selected from oxygen or nitrogen, the 5-7 membered heterocyclyl is optionally substituted with pyrrolidinyl or with a $C_{1-6}$alkyl wherein up to three methylene units of the $C_{1-6}$alkyl are optionally and independently replaced by, —$NR^o$—, —O—, or —S—; $C_{3-6}$cycloaliphatic, $C_{1-6}$alkyl-(5-6 membered heterocyclyl having 1-2 heteroatoms selected from oxygen or nitrogen), 5-6 membered heteroaryl having 1-2 nitrogen atoms, CO(phenyl), —$SO_2R^o$, —$SO_2N(R^o)_2$, or $C_{1-6}$alkyl wherein up to three methylene units are optionally and independently replaced by, —$NR^o$—, —O—, —S—, $SO_2$—, or —CO—, in a chemically stable arrangement; each $J^Q$ is optionally and independently substituted with $R^o$;

Q is a phenyl ring; Q is optionally substituted with $J^Q$;

$R^5$ is optionally substituted R, $C_{6-10}$ aryl, $C_{3-10}$ cycloaliphatic, 5-14 membered heteroaryl, or 5-14 membered heterocyclyl; or two $R^5$ groups, together with the atom(s) to which they are attached, form an optionally substituted 3-7 membered monocyclic or 8-14 membered bicyclic ring;

$J^R$ is CN, oxo, halo, 5-8 membered heterocyclyl having 1-2 heteroatoms selected from oxygen or nitrogen, —$NR(C_{1-4}$alkyl)$OR^o$, —NH(5-6 membered heterocyclyl having 1-2 nitrogen atoms), —$(C_{1-6}$alkyl)-$OR^o$, or a $C_{1-6}$alkyl chain wherein up to three methylene units of the chain are independently replaced by, —$NR^o$—, —O—, or —CO— in a chemically stable arrangement; each $J^R$ is independently and optionally substituted with $R^o$;

each $R^o$ is independently selected from hydrogen, $CO_2(C_{1-4}$aliphatic)halo$C_{1-4}$aliphatic, optionally substituted $C_{1-6}$ aliphatic wherein up to 2 methylene units are optionally replaced by O, N, or S, 5-6 membered heterocyclyl optionally substituted with $C_{1-3}$alkyl; unsubstituted phenyl, unsubstituted —$CH_2$(Ph), unsubstituted —$CH_2$(5-7 membered heterocyclyl); or, notwithstanding the definition above, two independent occurrences of $R^o$, on the same substituent, taken together with the atom to which each $R^o$ group is bound, form an optionally substituted 3-6 membered saturated, partially unsaturated, or fully unsaturated monocyclic or bicyclic ring having 0-3 heteroatoms independently selected from nitrogen, oxygen, or sulfur;

optional substituents on the aliphatic group of $R^o$ or on the ring formed by 2 $R^o$ groups are selected from $NH_2$, $NH(C_{1-4}$aliphatic), $N(C_{1-4}$aliphatic$)_2$, halogen, $C_{1-4}$aliphatic, OH, $O(C_{1-4}$aliphatic), $NO_2$, CN, $CO_2H$, $CO_2(C_{1-4}$aliphatic), O(halo$C_{1-4}$ aliphatic), and halo$C_{1-4}$aliphatic, wherein each of the foregoing $C_{1-4}$aliphatic groups of $R^o$ is unsubstituted; provided that when $R^2$ is 4-pyridyl, $R^3$ and $R^4$ are H, $X^1$ is —NR—, R is H, and $X^2$ is —C(O)—, then when T is —$CH_2$—, Q is not 3-OH-phenyl, 4-OH-phenyl, 3-$NO_2$-phenyl.

2. The compound according to claim 1, wherein T is $C_{1-3}$aliphatic optionally interrupted with zero or one G groups wherein G is selected from O, $NR^5$, and S.

3. The compound according to claim 1, wherein T is —$C_{1-2}$aliphatic-G- wherein G is O or $NR^5$, and G is bound to Q in a chemically stable arrangement.

4. The compound according to claim 1, wherein T is $C_{1-3}$aliphatic optionally interrupted with zero G groups.

5. The compound according to claim 1, wherein T is $C_{1-3}$aliphatic optionally interrupted with zero or one G' groups.

6. The compound according to claim 1, wherein T is —$CH_2$—.

7. The compound according to claim 1, wherein T is a bond.

8. The compound according to claim 1 wherein $R^2$ is 2-pyridinyl optionally substituted with up to five $J^R$ groups.

9. The compound according to claim 1 wherein $R^2$ is 3-pyridinyl optionally substituted with up to five $J^R$ groups.

10. The compound according to claim 1 wherein $R^2$ is 4-pyridinyl optionally substituted with up to five $J^R$ groups.

11. The compound according to claim 1, wherein each $J^R$ is selected from $C_{1-6}$alkyl, —$OR^o$, —$N(R^o)_2$, CN, 5-8 membered heterocyclyl having 1-2 heteroatoms selected from oxygen or nitrogen, —$(C_{1-6}$alkyl)-$OR^o$, —C(O)$OR^o$, —$NR^o$-$COR^o$, —$COR^o$, —$CON(R^o)_2$, or $C_{1-6}$alkyl wherein up to three methylene units of the chain are independently replaced by, —$NR^o$—, —O—, or —CO— in a chemically stable arrangement; each $J^R$ is independently and optionally substituted with $R^o$.

12. The compound according to claim 11, wherein each $J^R$ is independently and optionally substituted with $R^o$ and is selected from —$OR^o$, —$N(R^o)_2$, or —$(C_{1-6}$alkyl)-$OR^o$.

13. The compound according to claim 11, wherein each $J^R$ is independently selected from optionally substituted 5-8 membered heterocyclyl having 1-2 heteroatoms selected from oxygen or nitrogen, optionally substituted)-$NR(C_{1-4}$alkyl)$N(R^o)_2$, optionally substituted —$NR(C_{1-4}$alkyl)$OR^o$, —$N(R^o)_2$, or optionally substituted —NH(5-6 membered heterocyclyl having 1-2 nitrogen atoms).

14. The compound according to claim 13, wherein each $J^R$ is independently selected from optionally substituted —NH (5-6 membered heterocyclyl having 1-2 nitrogen atoms).

15. The compound according to claim 14 wherein the 5-6 membered heterocyclyl of the —NH(5-6 membered heterocyclyl having 1-2 nitrogen atoms) is selected from pyrrolidine, piperidine, or piperazine.

16. The compound according to claim 14, wherein $X^1$ is C(O) and $X_2$ is NR.

17. The compound according to claim 14, wherein $X^1$ is NR and $X_2$ is C(O).

18. The compound according to claim 16 or 17, wherein Q is substituted with up to 3 $J^Q$ groups wherein each $J^Q$ is selected from CN, $C_{1-6}$ alkyl, $C_{1-4}$haloalkyl, —$OR^o$, —$N(R^o)_2$, $SCHF_2$, phenyl, benzyl, $C_{3-6}$cycloaliphatic, a 5-7 membered heterocyclyl having 1-2 heteroatoms selected from oxygen or nitrogen, the 5-7 membered heterocyclyl is optionally substituted with pyrrolidinyl or with a $C_{1-6}$alkyl wherein up to three methylene units of the $C_{1-6}$alkyl are optionally and independently replaced by, —$NR^o$—, —O—, or —S—; $C_{1-6}$alkyl-(5-6 membered heterocyclyl), —$NR^o$-$COR^o$, —$COR^o$, —$SO_2R^o$, —$SO_2N(R^o)_2$, or $C_{1-6}$alkyl wherein up to three methylene units are optionally and independently replaced by, —$NR^o$—, —O—, —S—, $SO_2$—, or —CO—, in a chemically stable arrangement; each $J^Q$ is optionally and independently substituted with $R^o$.

19. The compound according to claim 16 or claim 17, wherein each $J^Q$ is —$SO_2N(R^o)_2$, —$SO_2R^o$, phenyl, —O-Ph, —O—$CH_2$Ph, 5-6 membered heteroaryl having 1-2 nitrogen atoms, a 5-7 membered heterocyclyl having 1-2 heteroatoms selected from oxygen or nitrogen, the 5-7 membered heterocyclyl is optionally substituted with pyrrolidinyl or with a $C_{1-6}$alkyl wherein up to three methylene units of the $C_{1-6}$alkyl are optionally and independently replaced by, —$NR^o$—, —O—, or —S—; or $C_{3-6}$cycloaliphatic.

20. The compound according to claim 18, wherein each $J^Q$ is CN, $C_{1-6}$alkyl, —$CF_3$, —$OCF_3$, —$OR^o$, —$N(R^o)_2$, —$SR^o$, —$CH_2$-halogen, $SCHF_2$, —$(C_{1-6}$alkyl$)$-$N(R^o)_2$, phenyl, 5-6 membered heteroaryl having 1-2 nitrogen atoms, —$NR^o$-$COR^o$, or —$COR^o$.

21. The compound according to claim 18, wherein $R^o$ is selected from methyl, ethyl, n-propyl, isopropyl, cyclopropyl, sec-butyl, n-butyl, t-butyl, halogen, —$CH_2$-pyrrolidine, $COCH_3$, —$(C_{1-4}$alkyl$)_{0-1}$-$O(C_{1-4}$alkyl$)$, —$(C_{1-4}$alkyl$)_{0-1}$-$O$ $(C_{1-4}$alkyl$)OH$, —$(C_{1-4}$alkyl$)_{0-1}$-$NH(C_{1-4}$alkyl$)$, —$(C_{1-4}$alkyl$)_{0-1}$-$N(C_{1-4}$alkyl$)_2$, or —$(C_{1-4}$alkyl$)_{0-1}$-$NH_2$.

22. The compound of claim 1, where the compound is selected from the following:

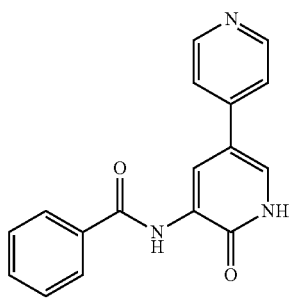

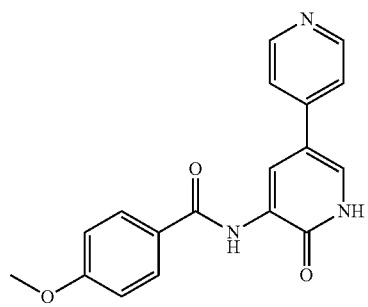

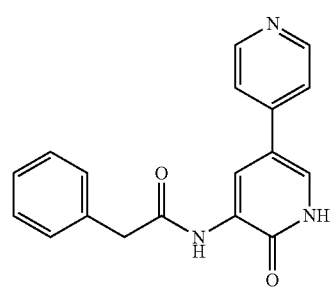

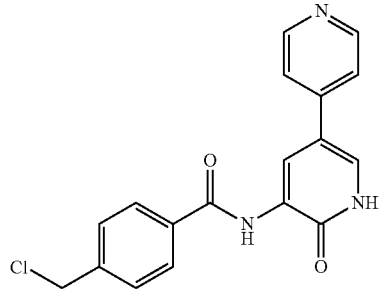

-continued

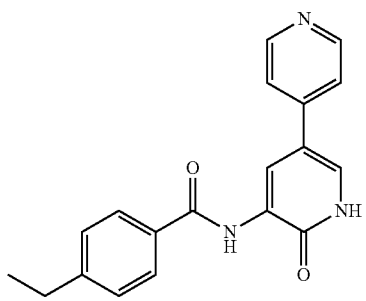

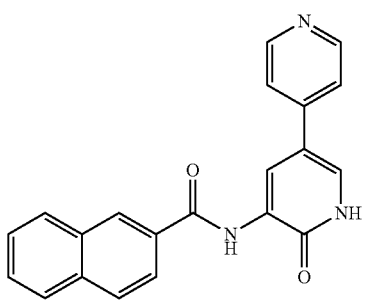

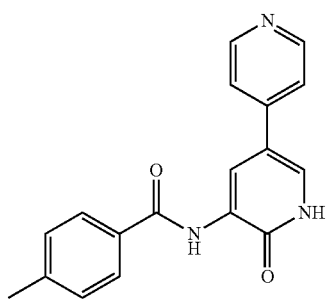

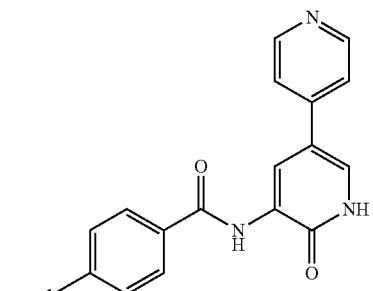

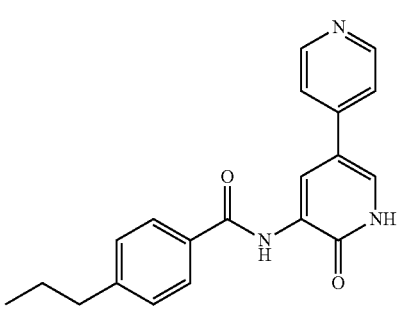

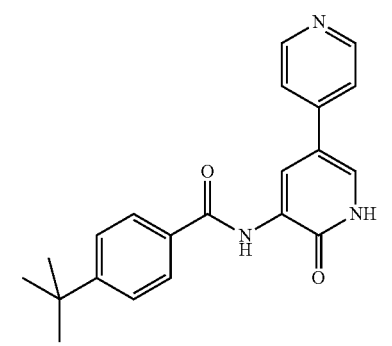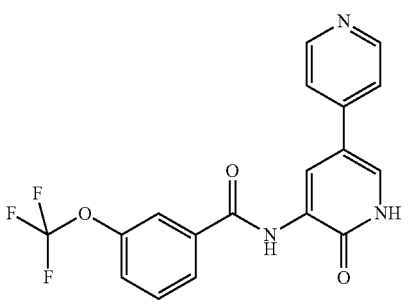

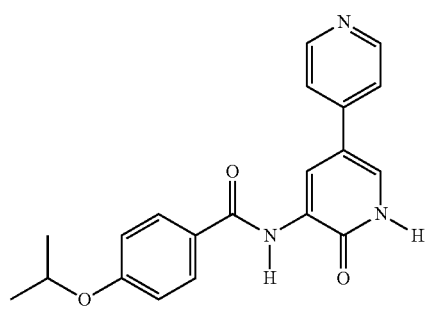
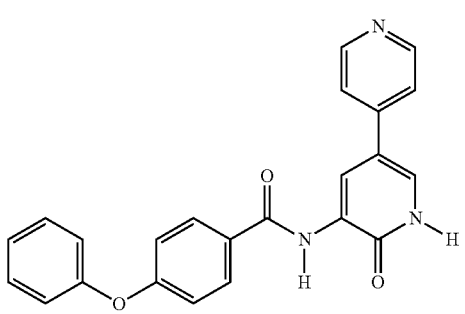
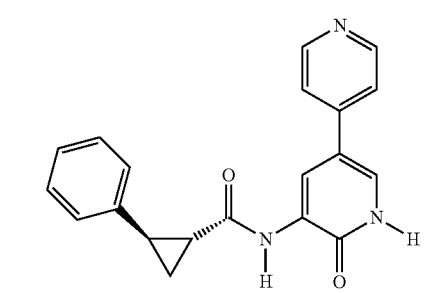
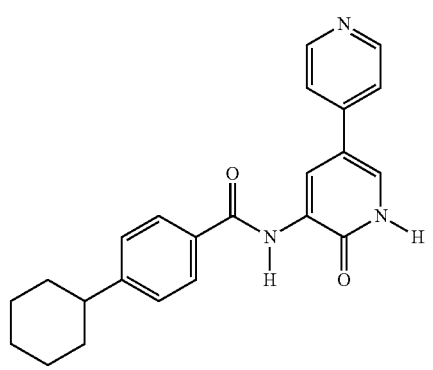
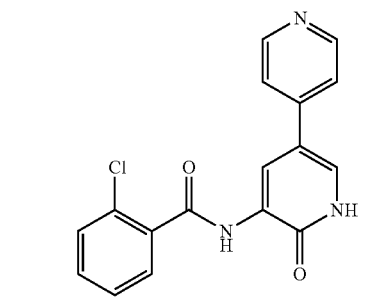
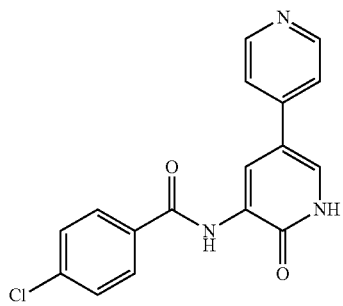
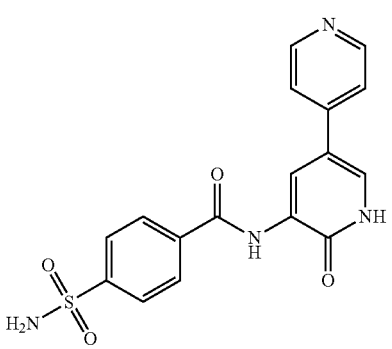
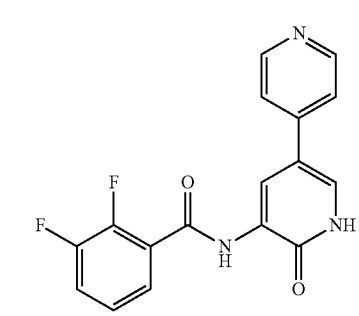
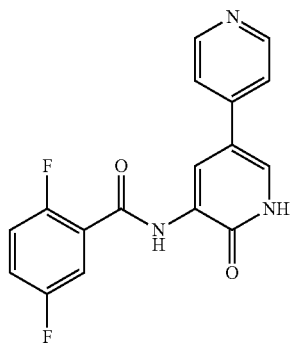
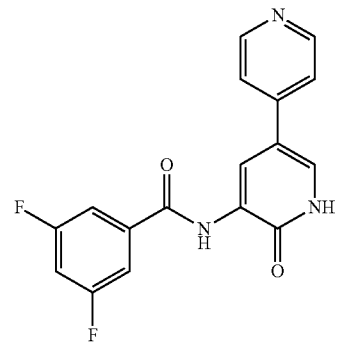

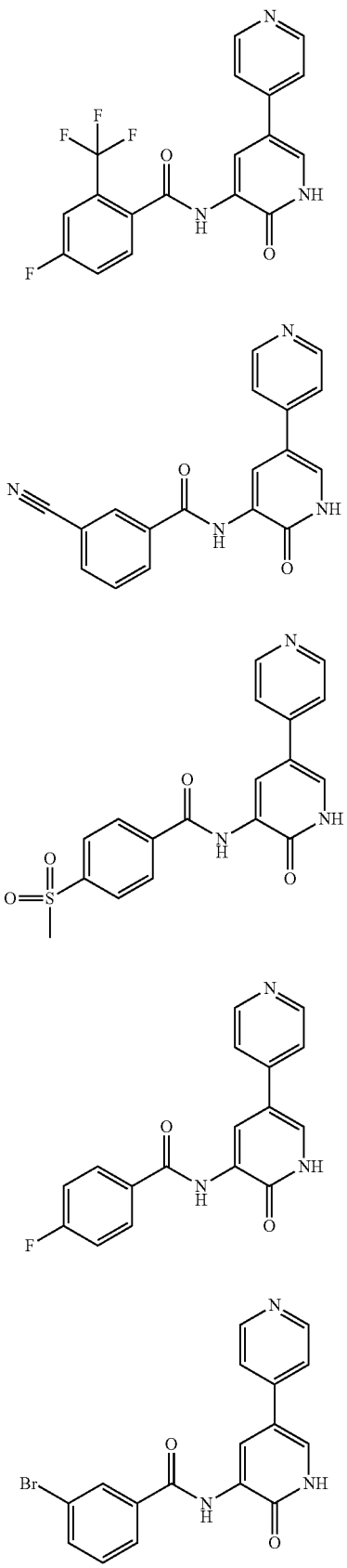
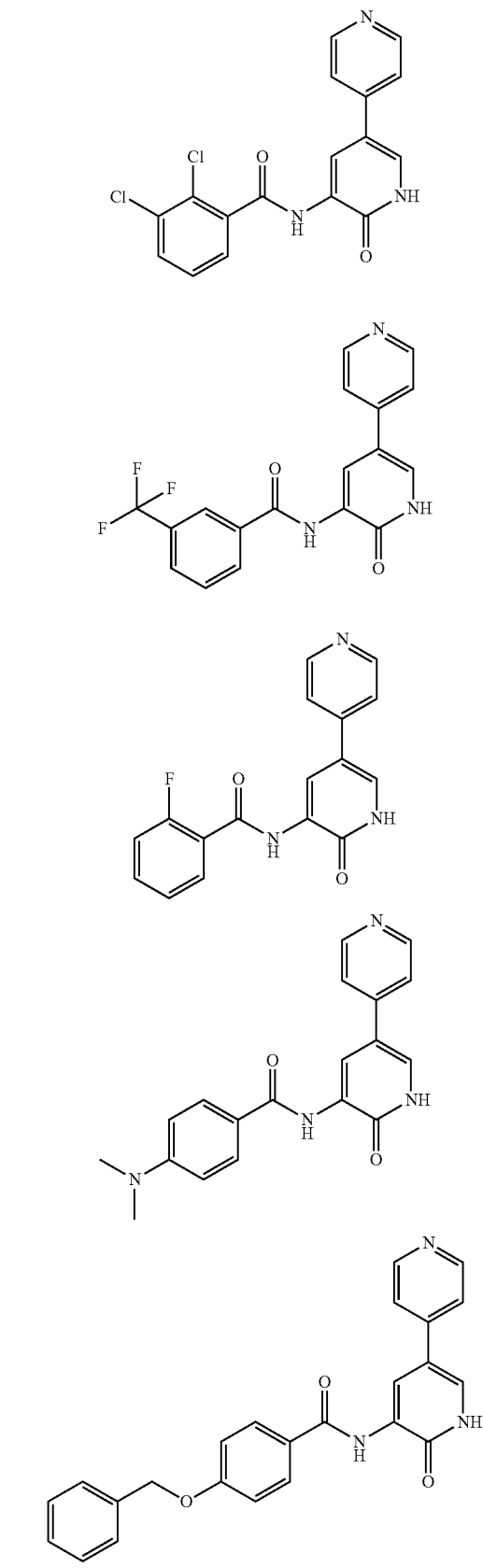

-continued
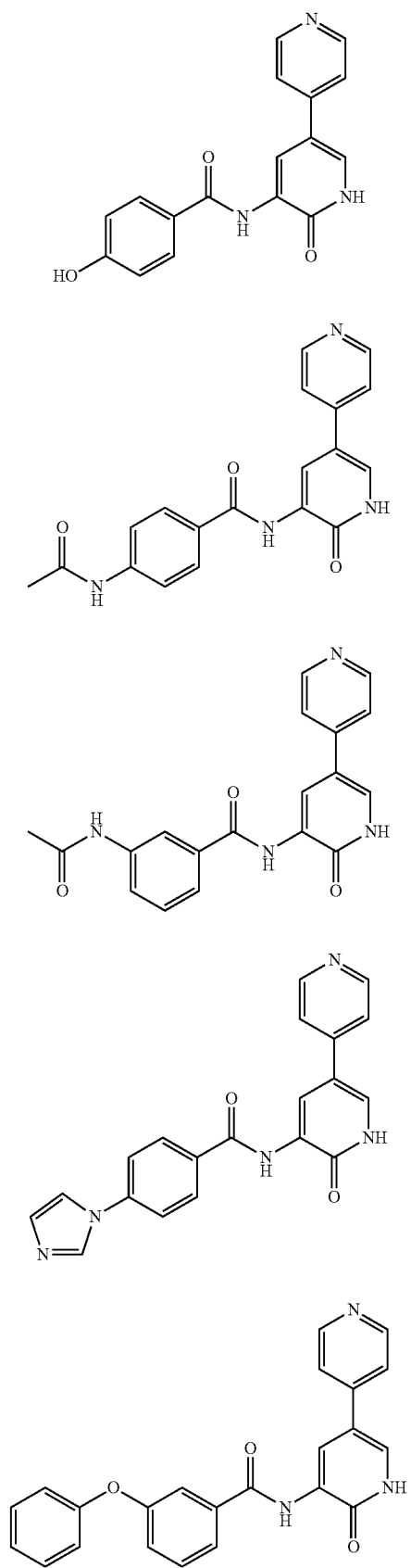
-continued
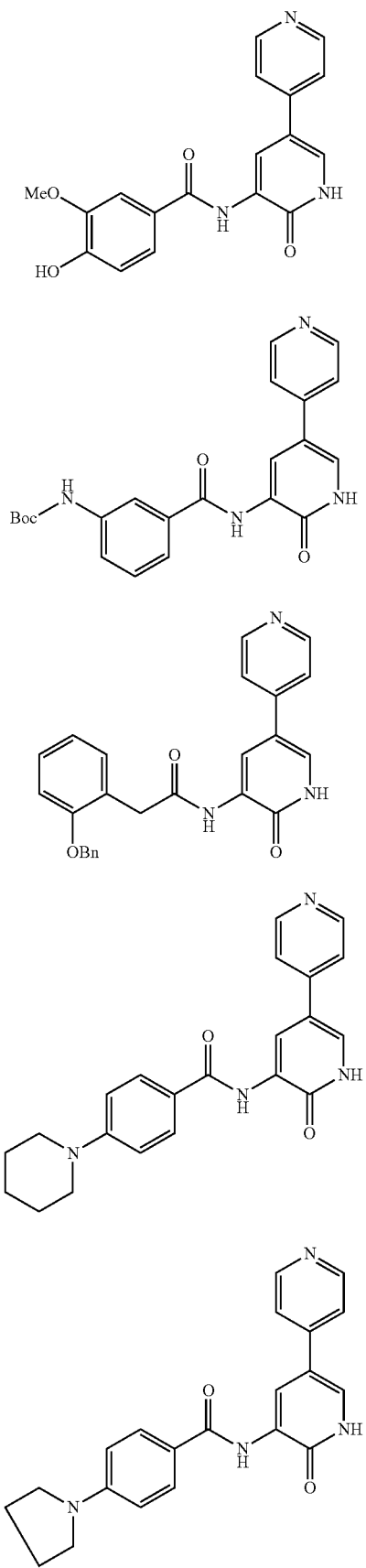

175
-continued
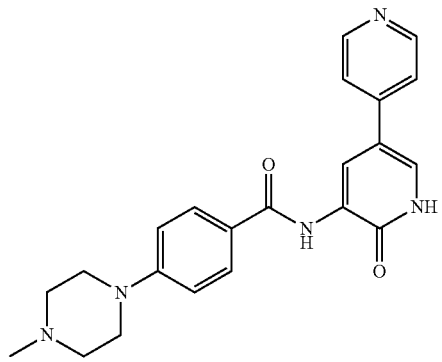
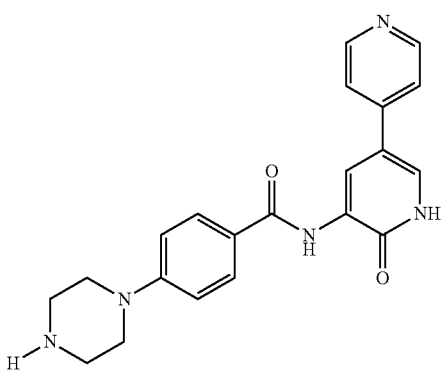
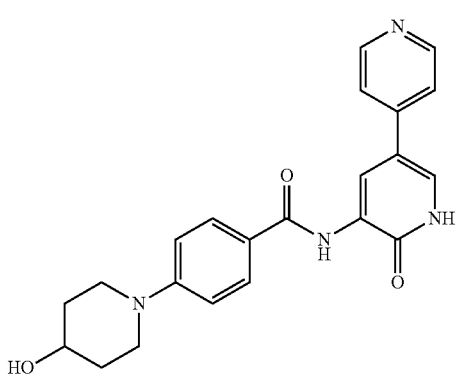
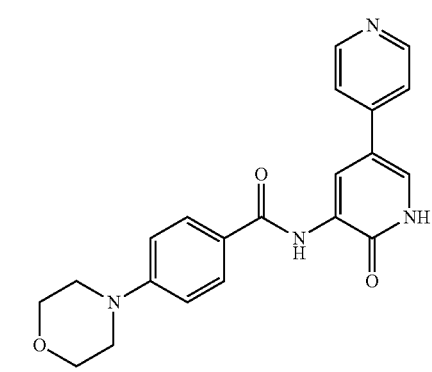
176
-continued
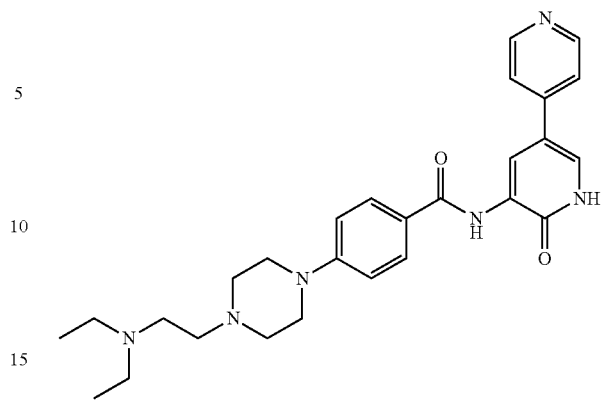
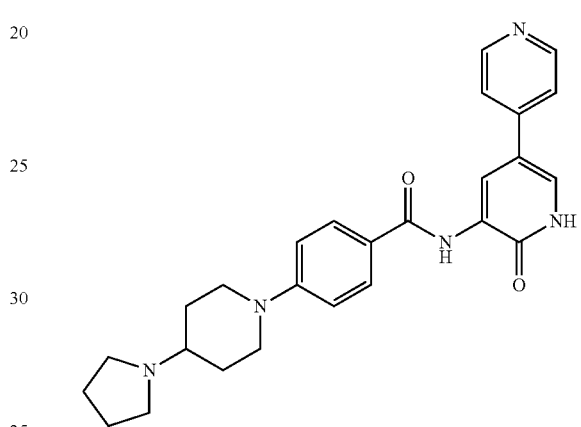
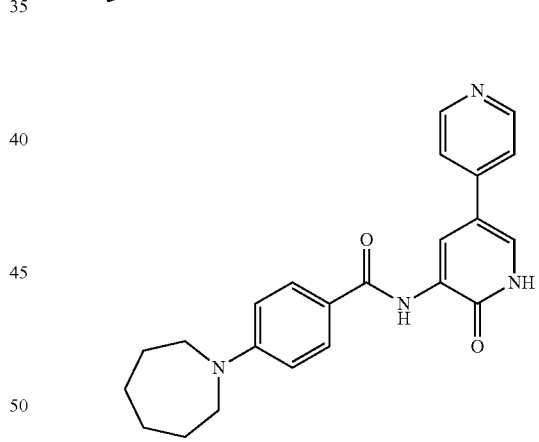
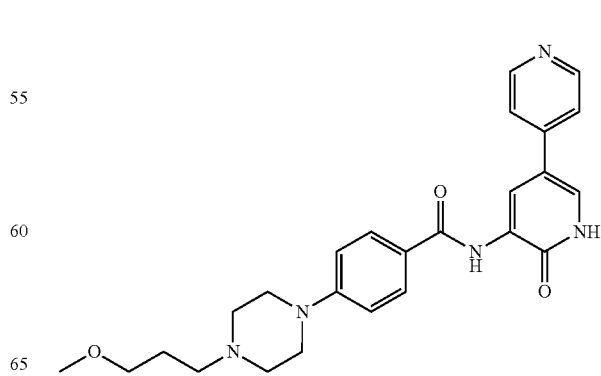

177
-continued
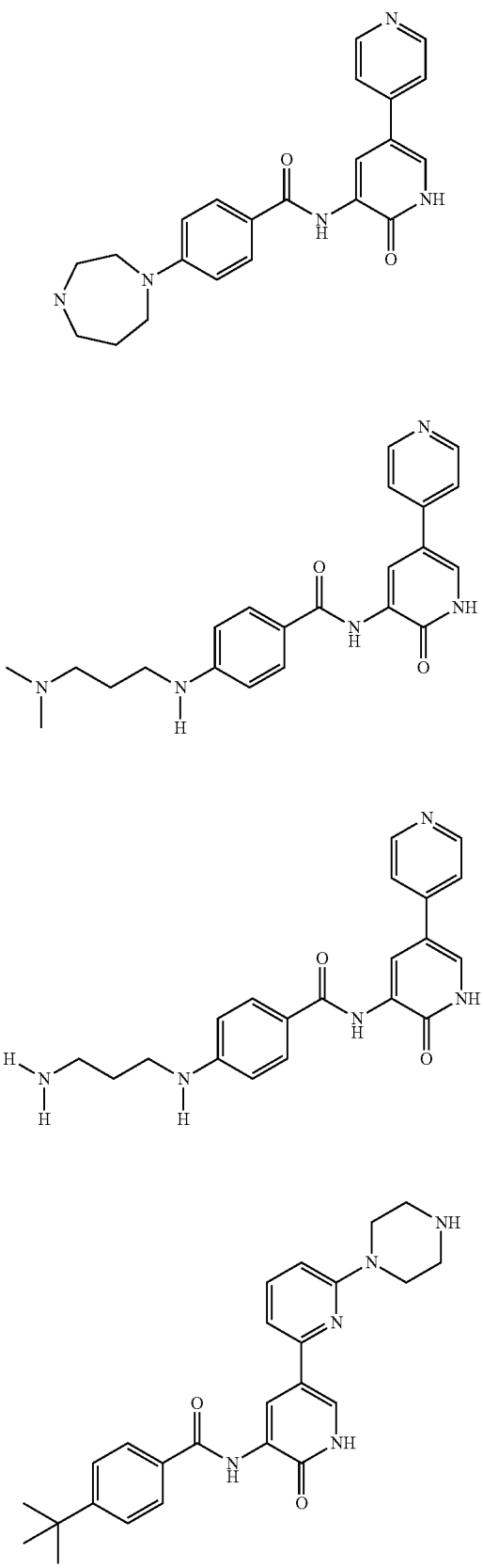
178
-continued
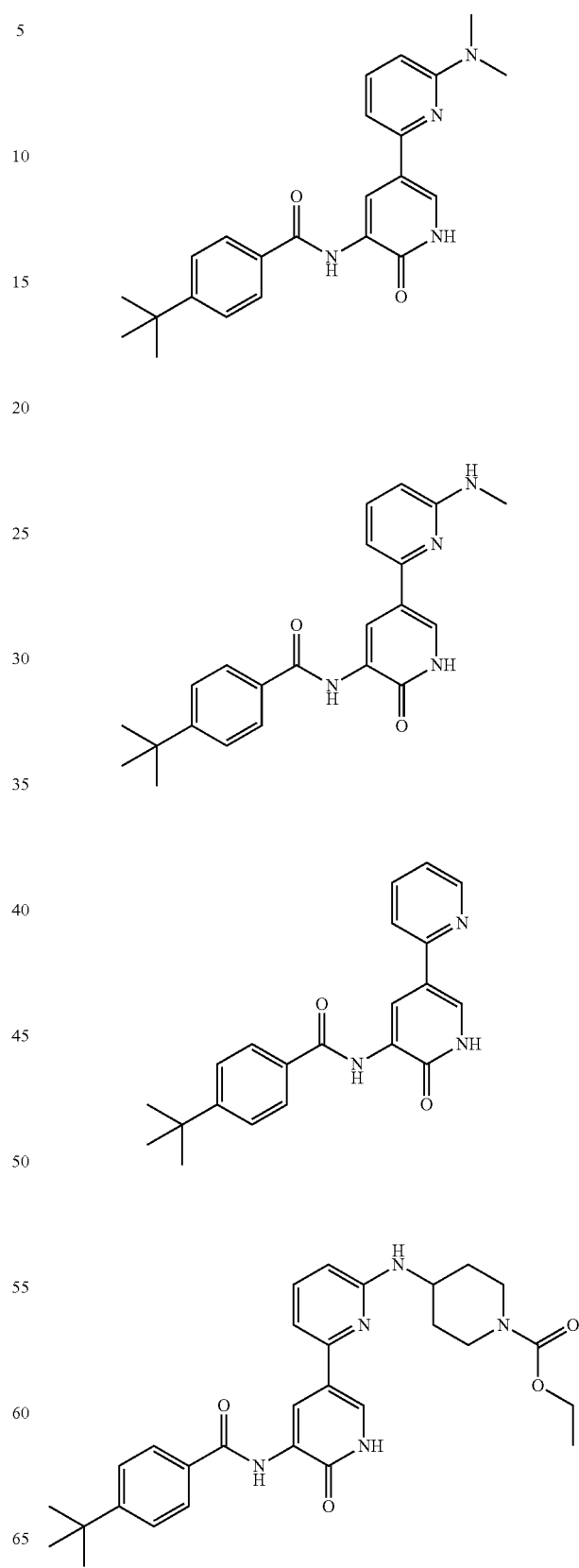

179
-continued
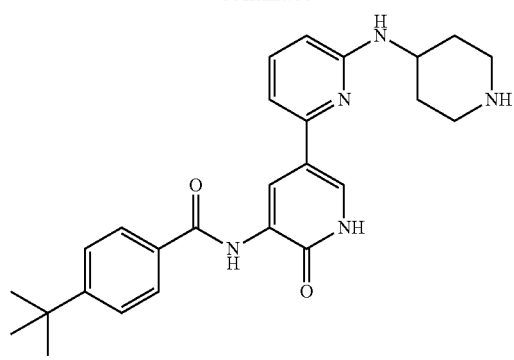
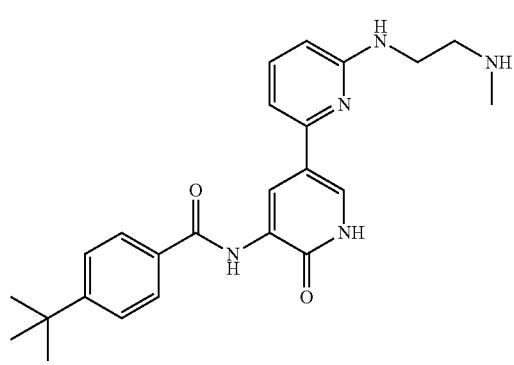
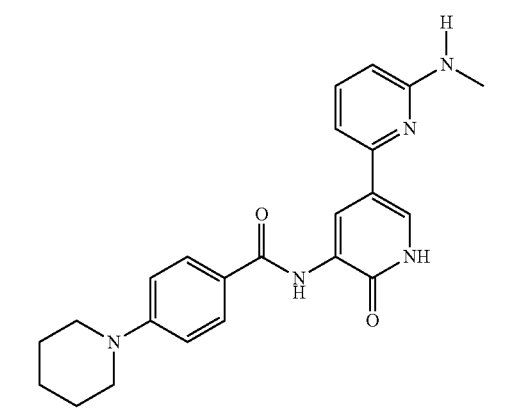
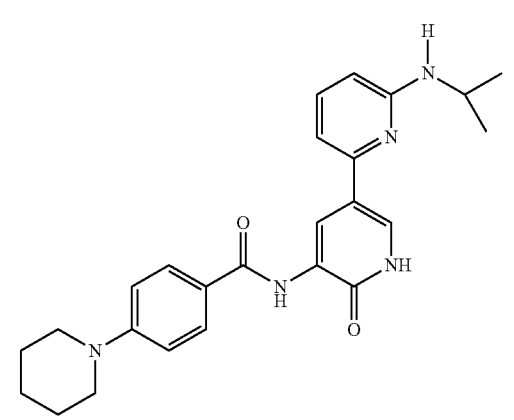
180
-continued
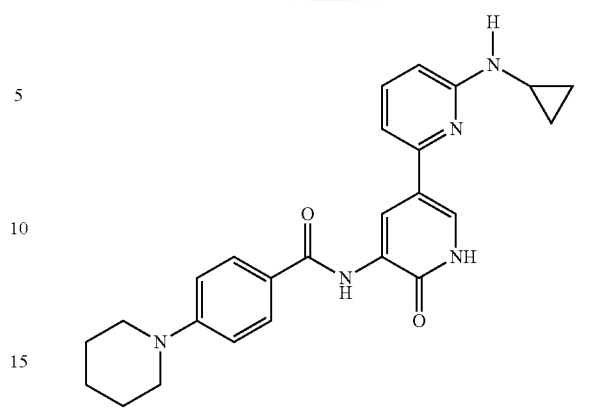
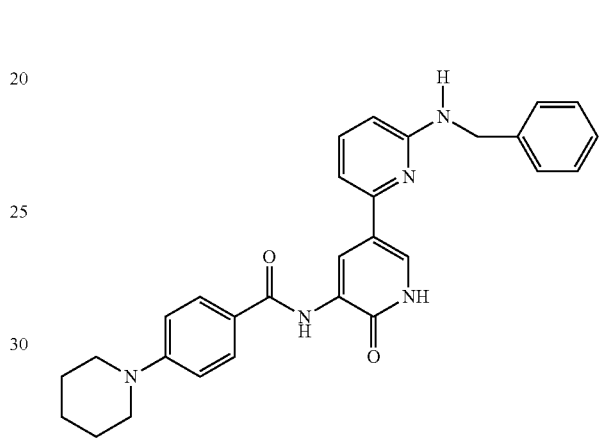
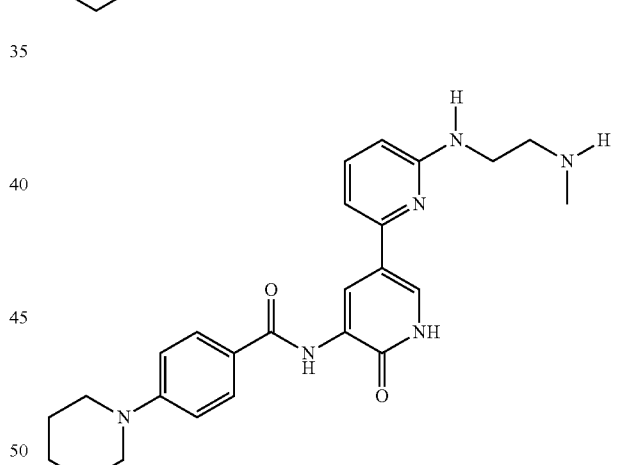
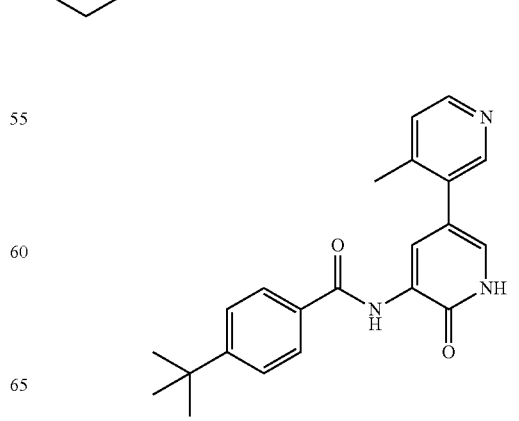

181
-continued
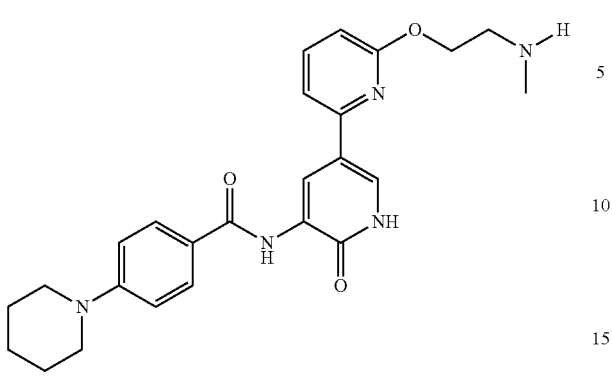
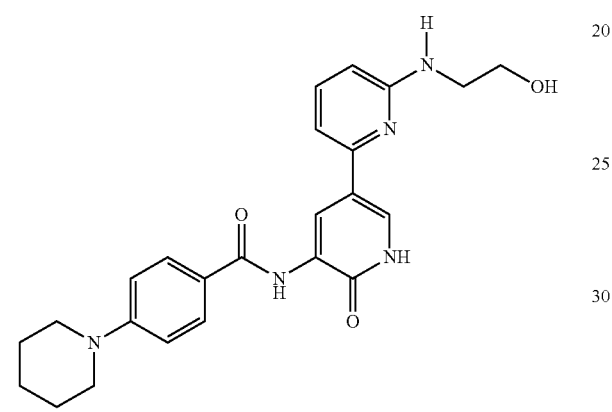
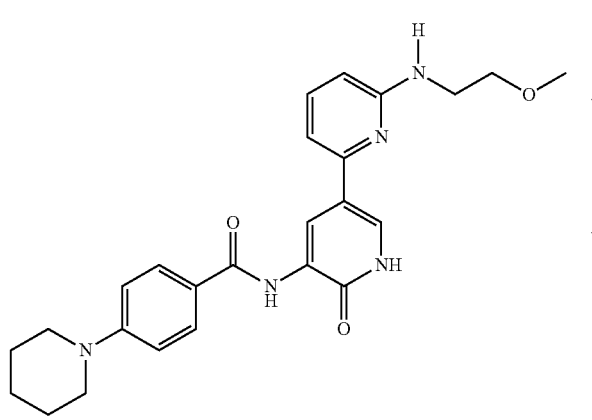
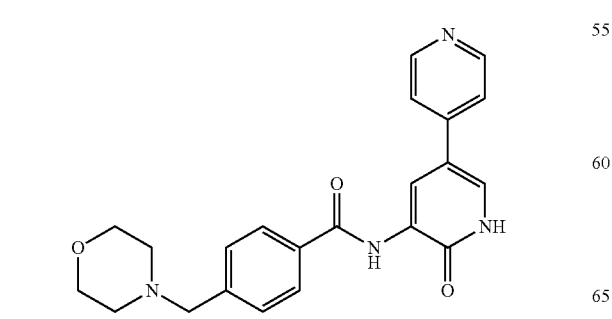
182
-continued
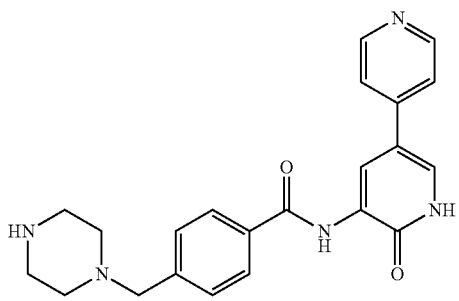
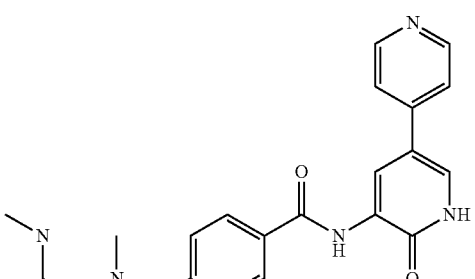
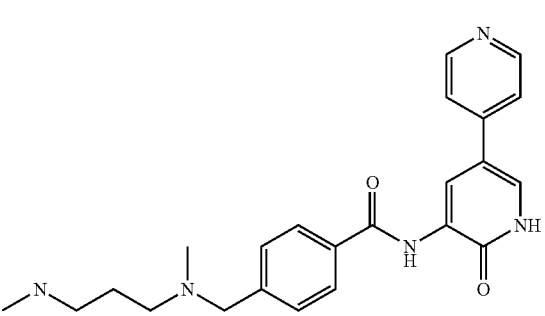
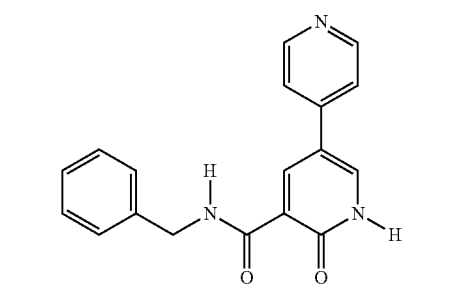
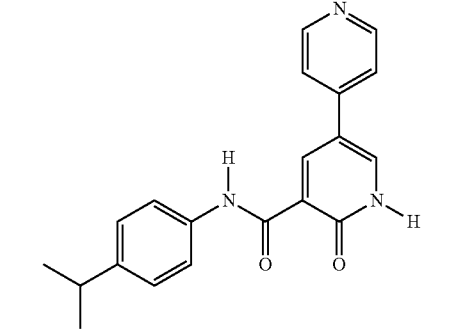

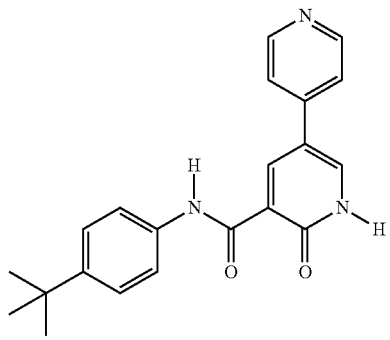
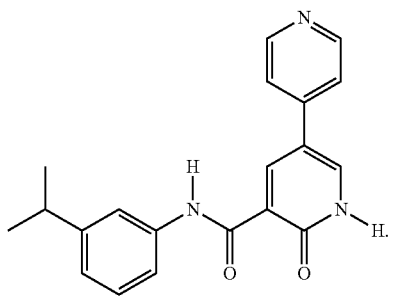
23. The compound according to claim 1, wherein the compound is selected from the following:
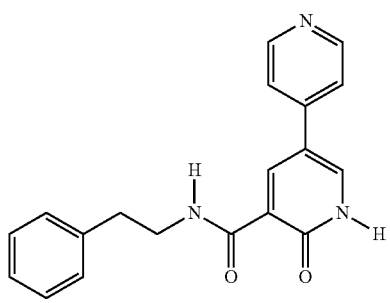
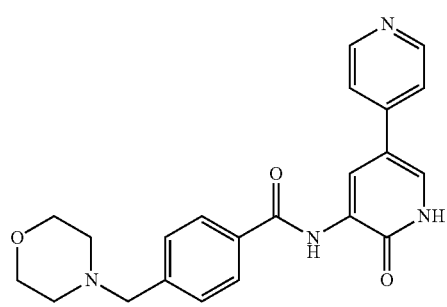
I-82
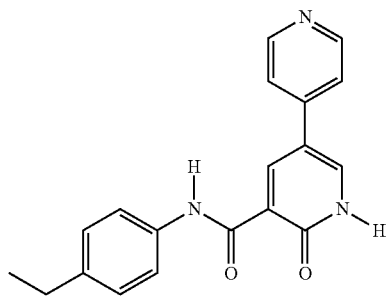
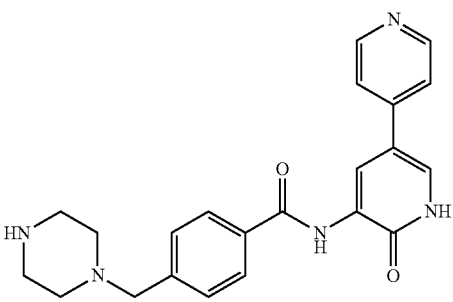
I-83
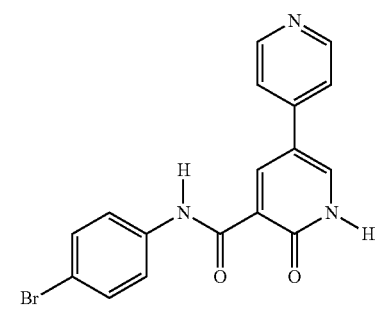
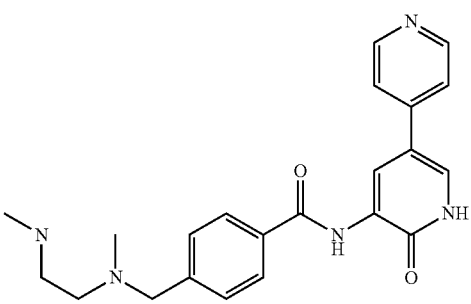
I-84
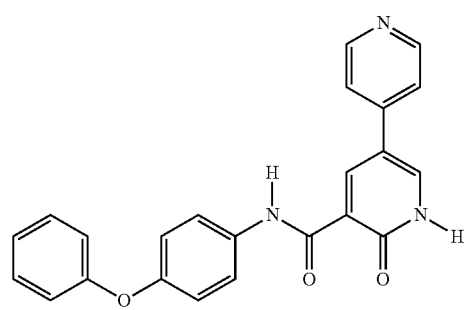
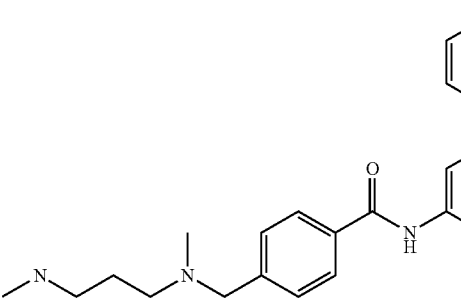
I-85

-continued
II-90
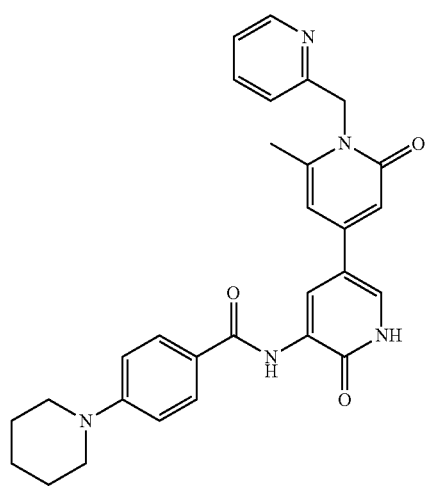
II-94
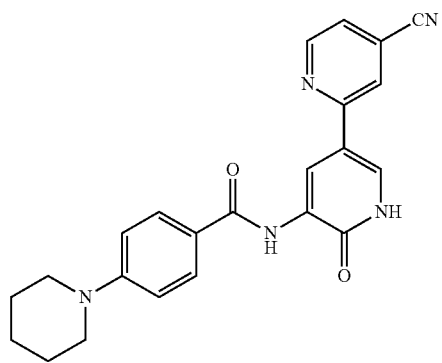
II-95
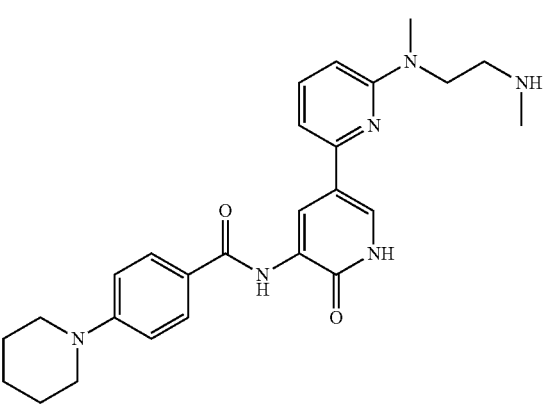
-continued
II-96
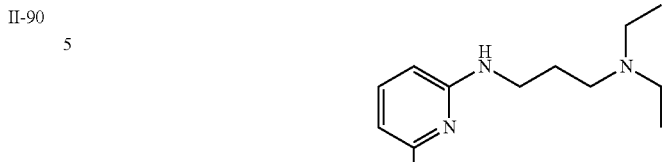
II-99
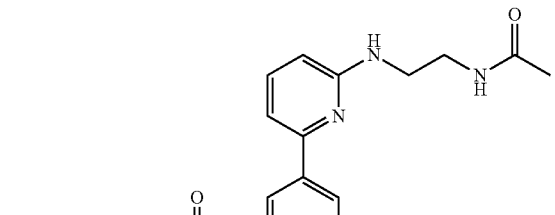
II-101
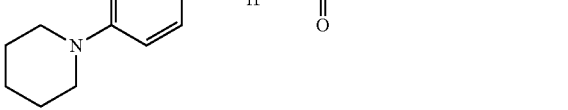
II-103
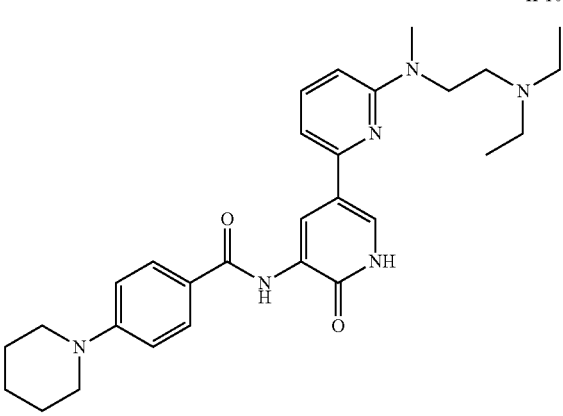

II-104
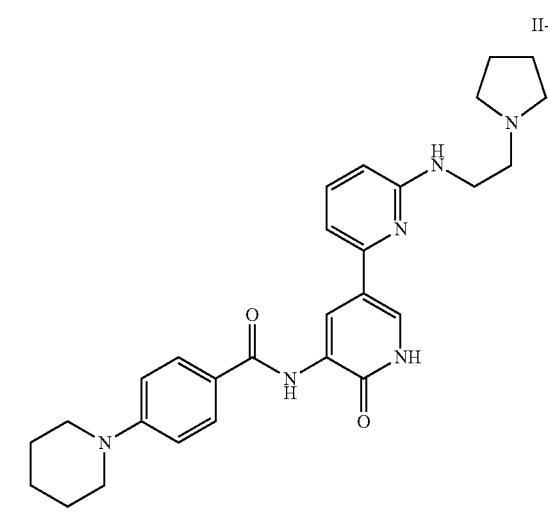
II-108
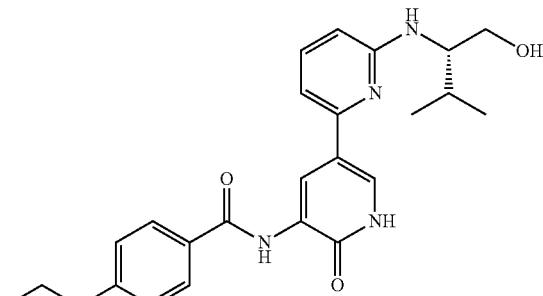
II-105
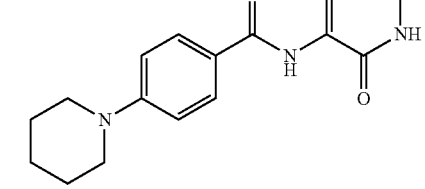
II-109
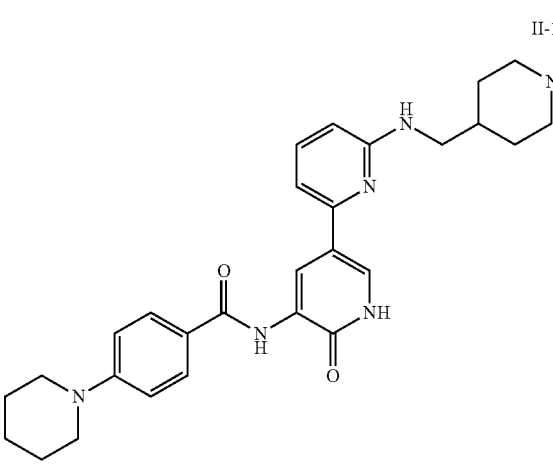
II-112
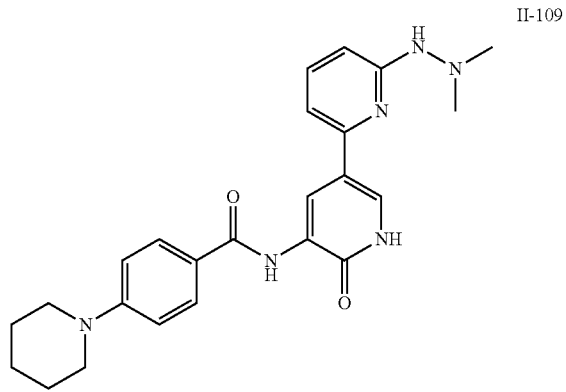
II-106
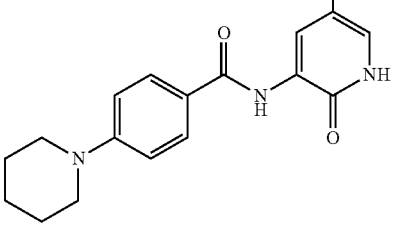
II-113
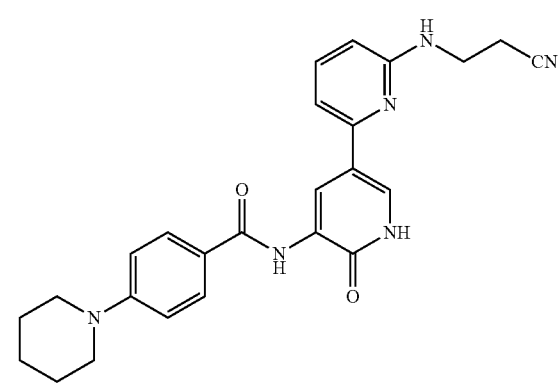
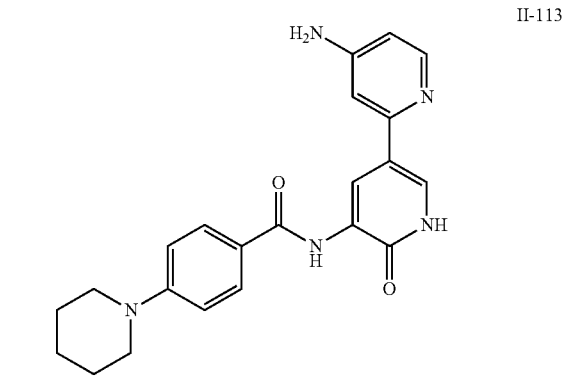

II-115
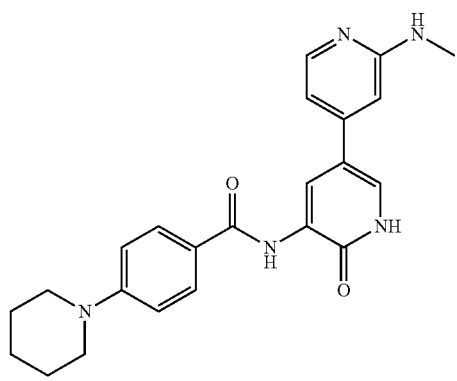
II-116
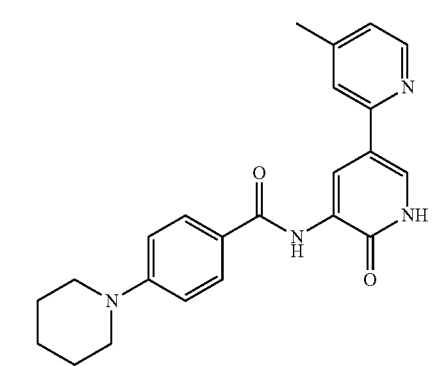
II-117
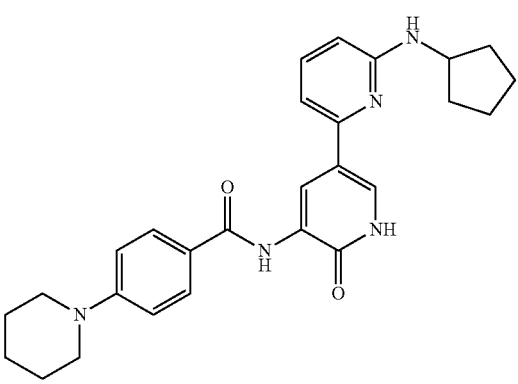
II-119
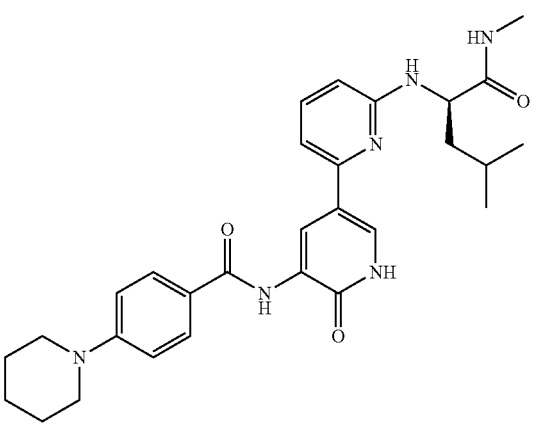
II-120
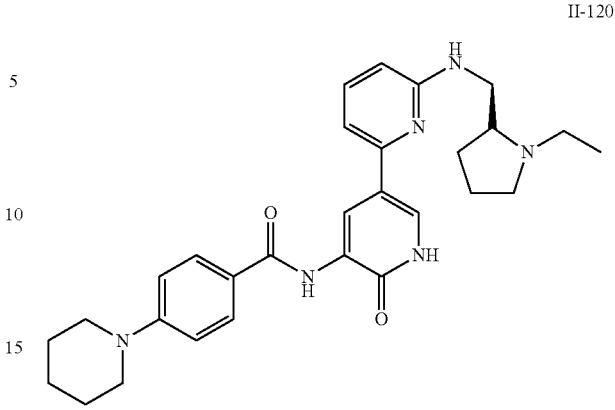
II-121
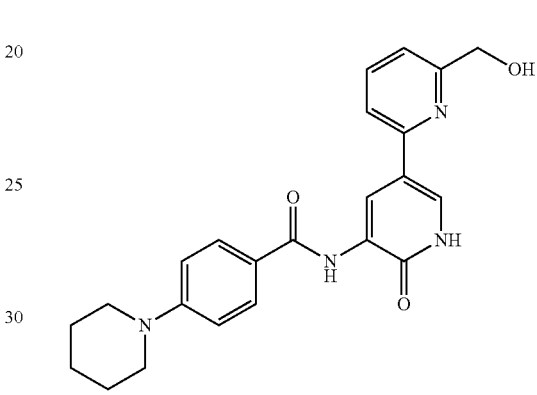
II-124
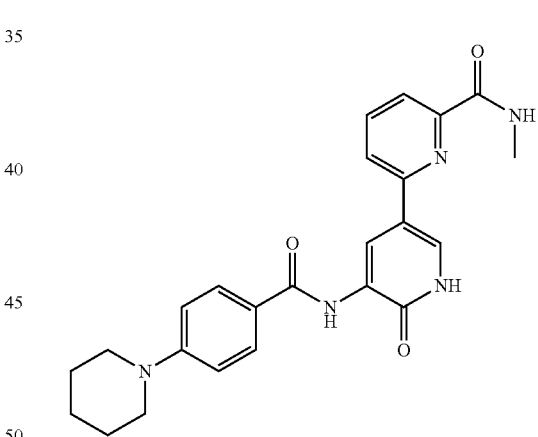
II-125
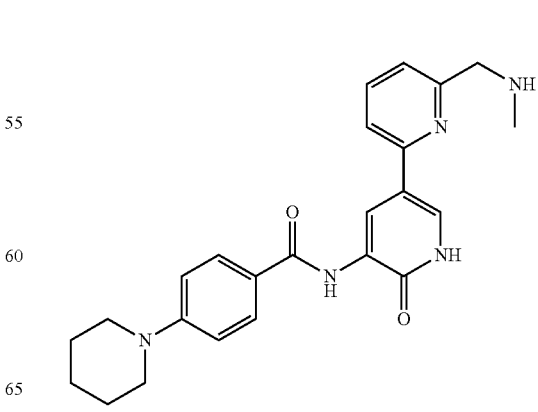

-continued
II-127
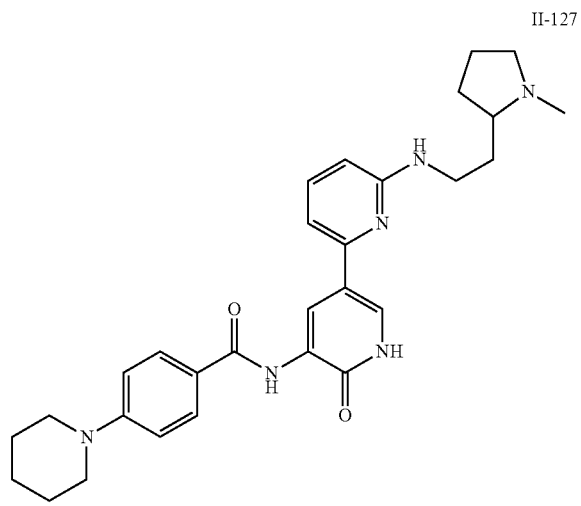
II-128
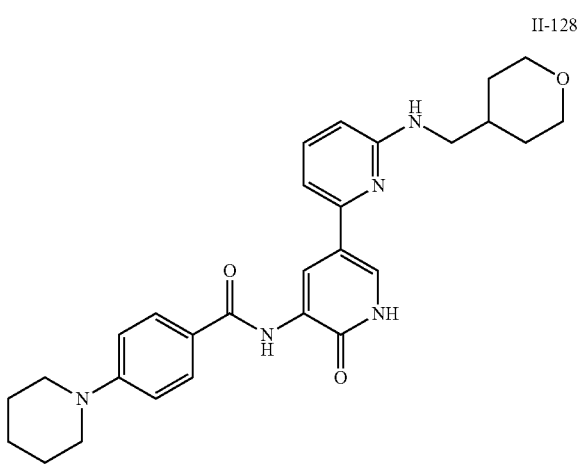
II-129
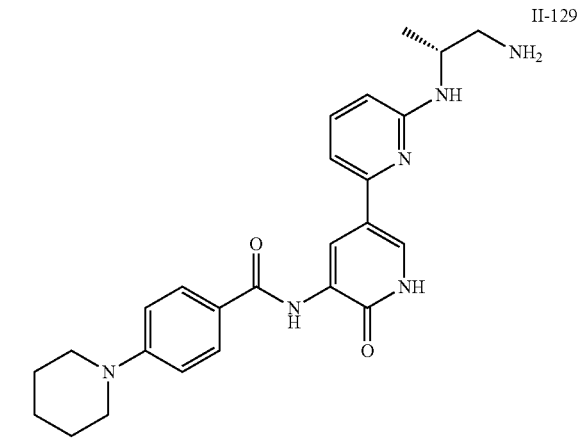
-continued
II-132
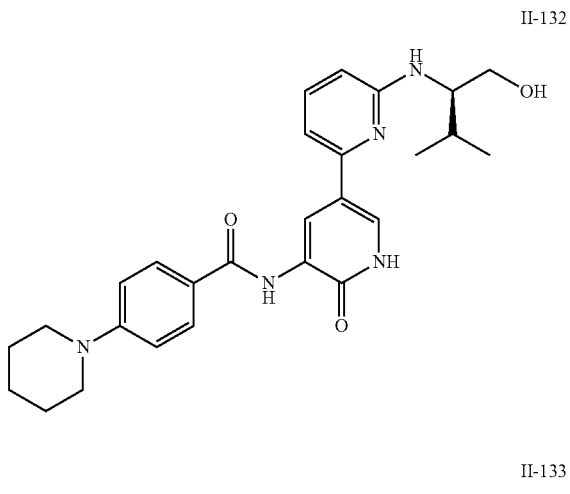
II-133
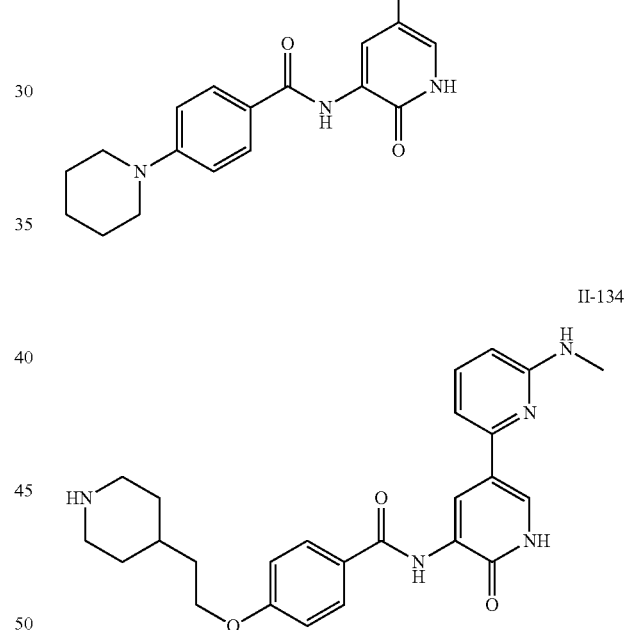
II-134
II-138
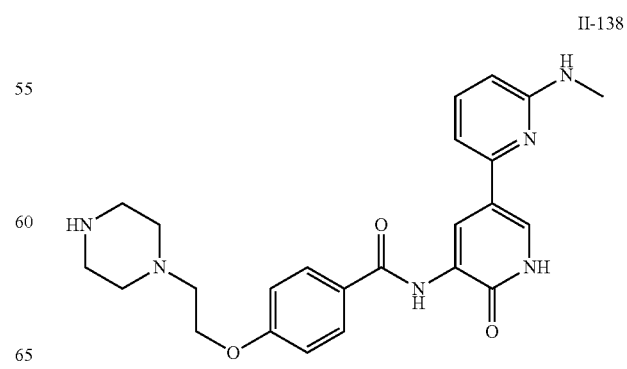

II-140
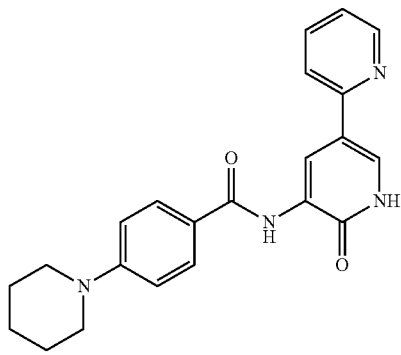
II-149
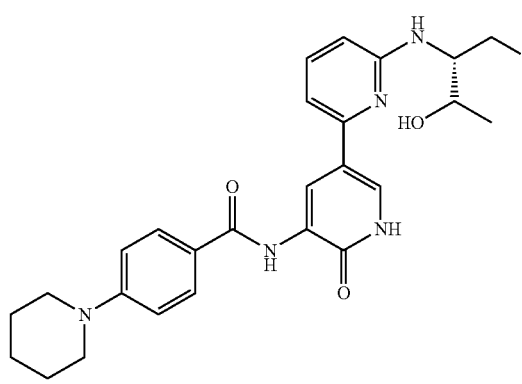
II-150
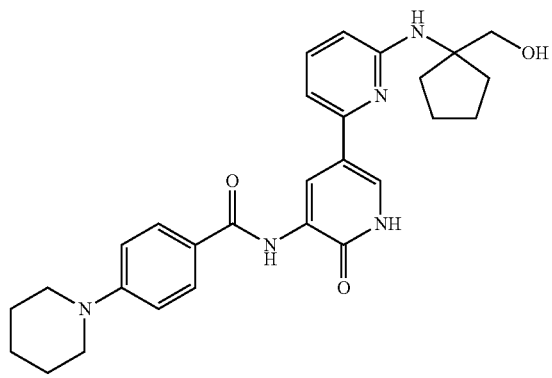
II-151
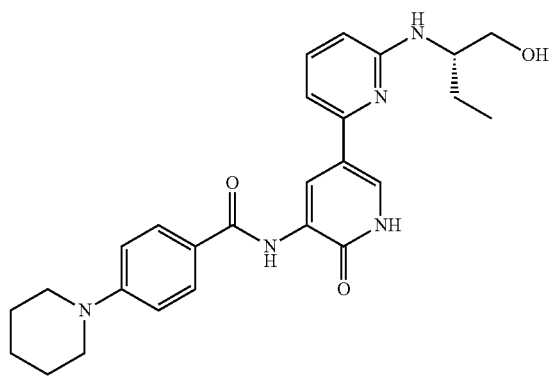
II-152
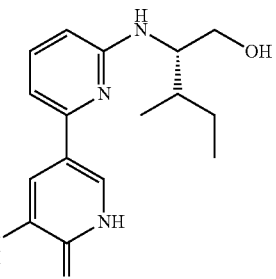
II-154
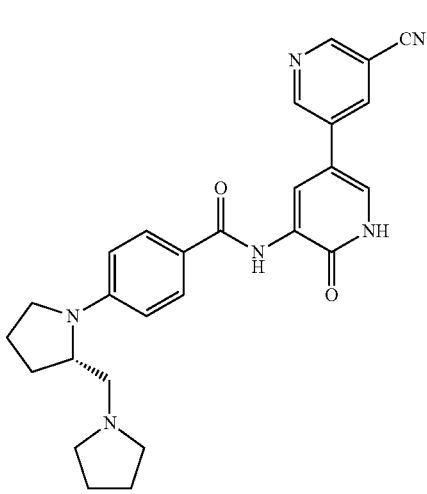
II-157
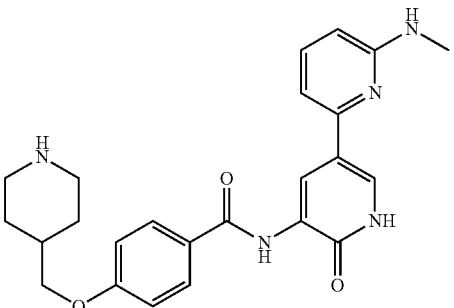
II-159
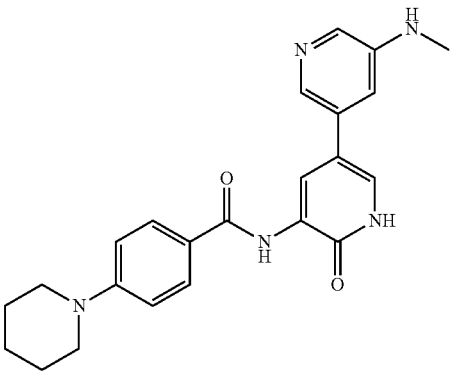

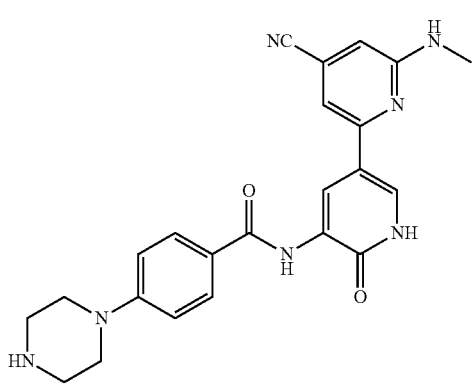
II-160
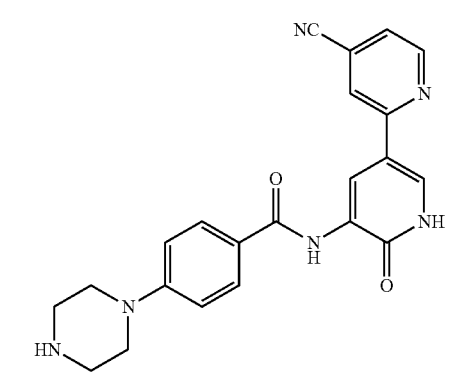
II-161
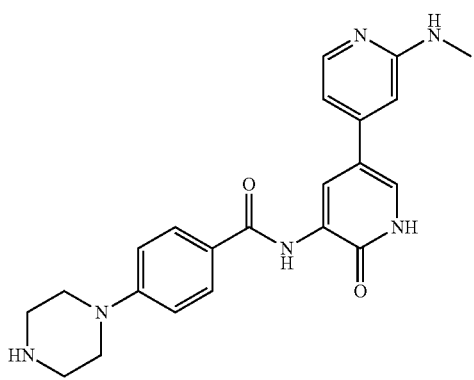
II-169
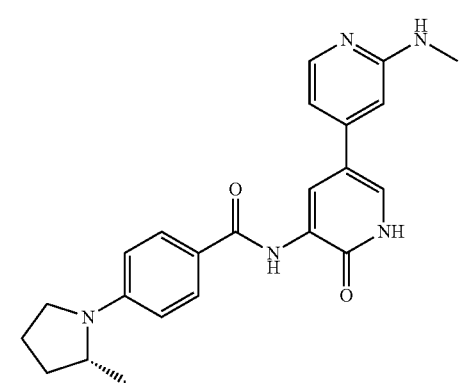
II-172
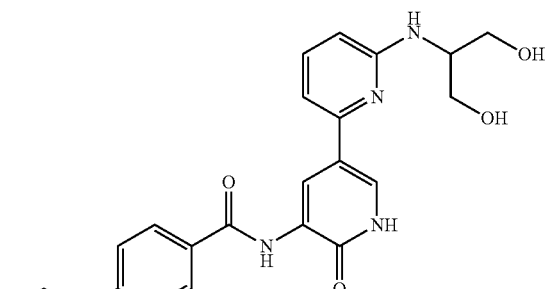
II-174
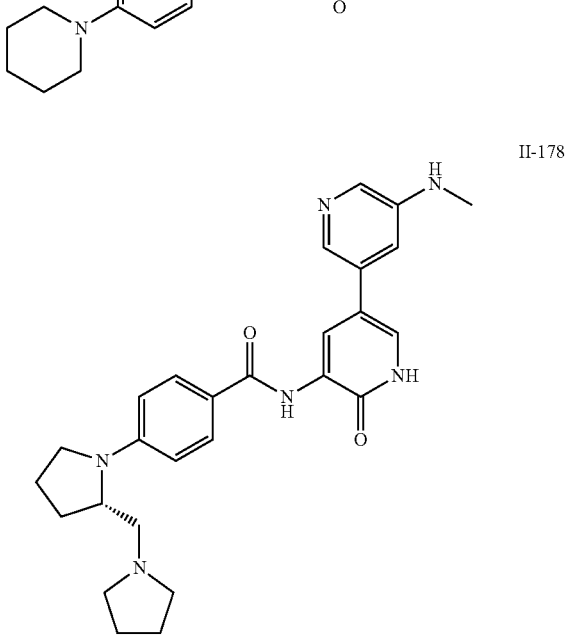
II-178
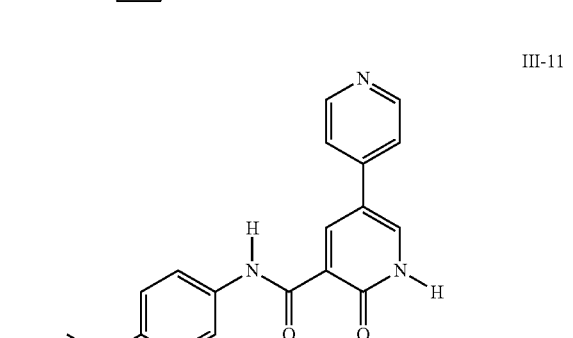
III-11
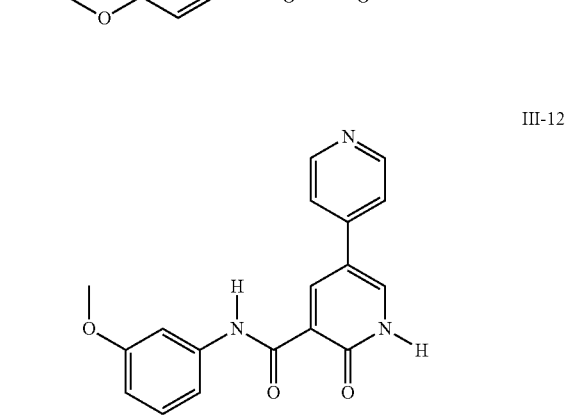
III-12

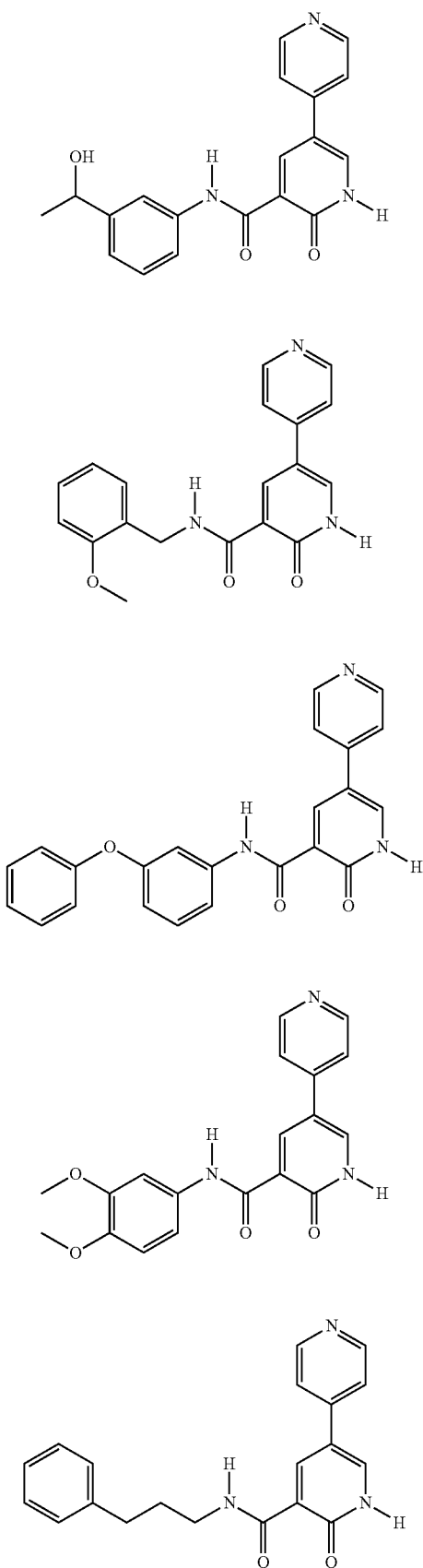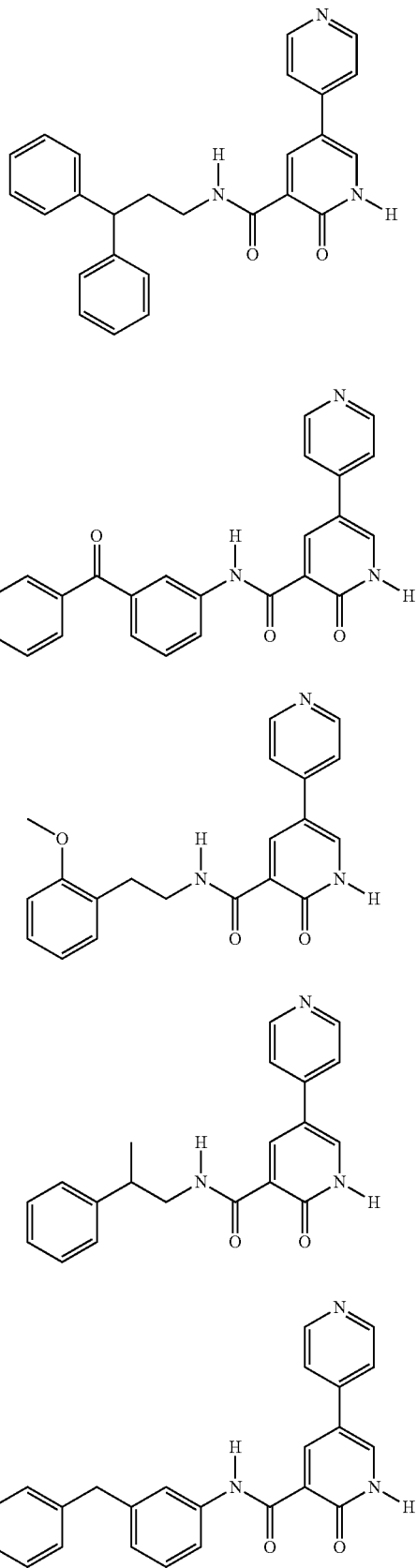

III-28
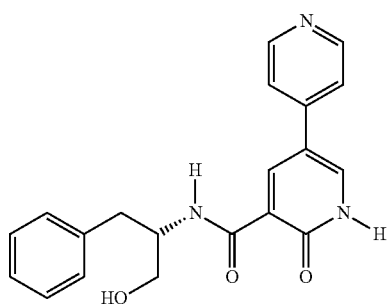
III-29
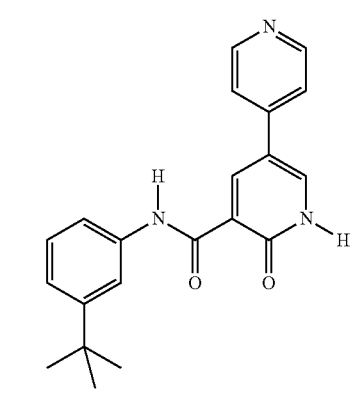
III-31
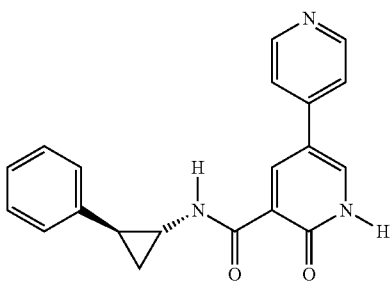
III-32
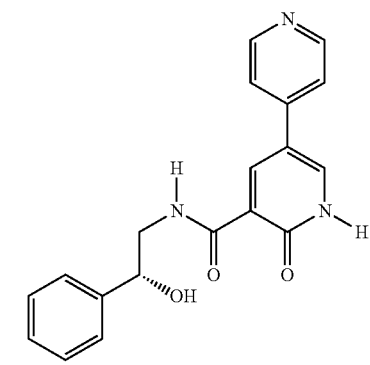
III-33
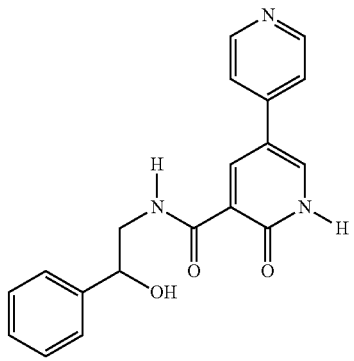
III-34
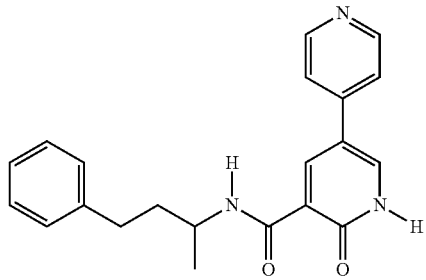
III-35
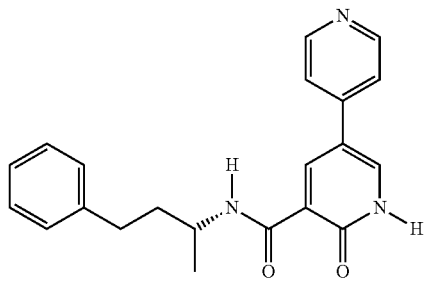
III-38
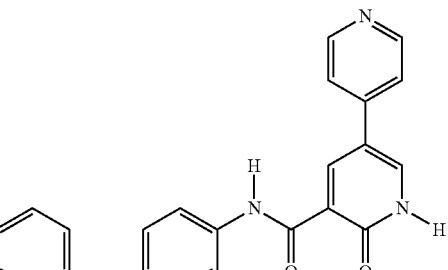
III-39
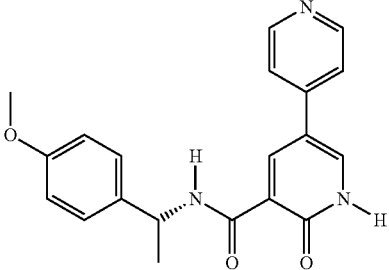

-continued
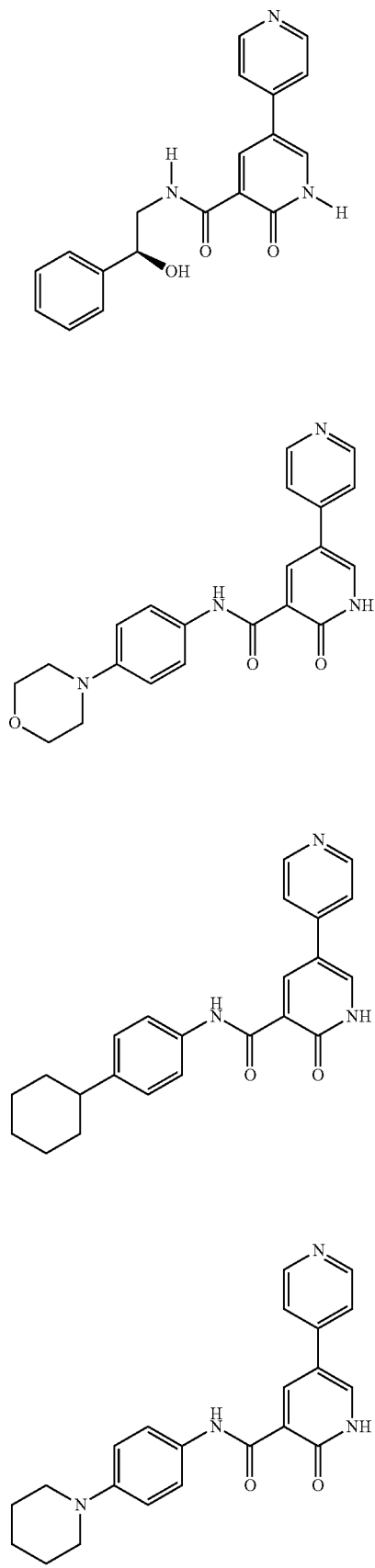
III-41
III-42
III-43
III-44
-continued
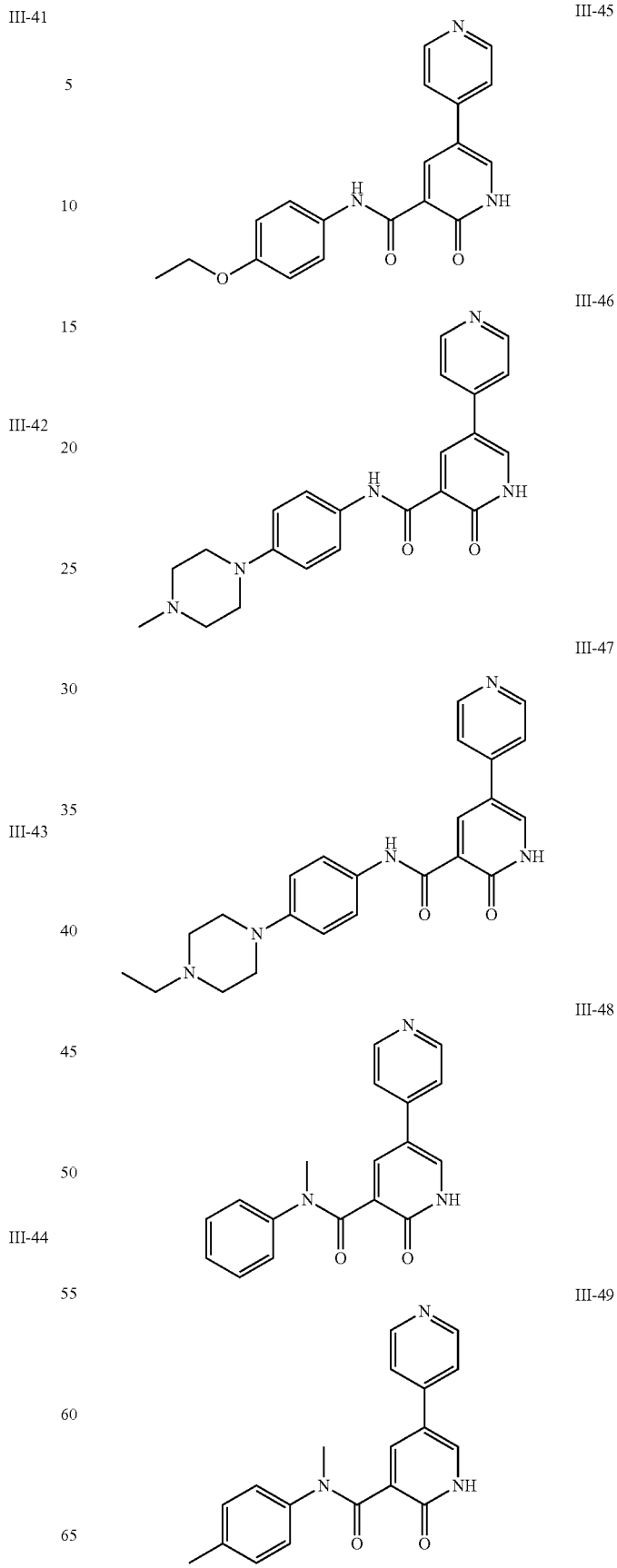
III-45
III-46
III-47
III-48
III-49

-continued

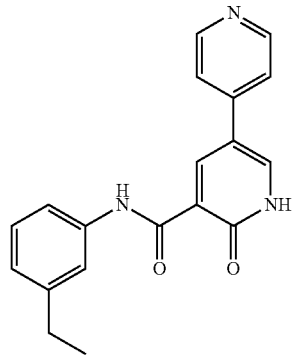
III-50

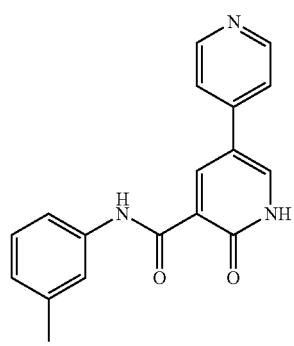
III-51

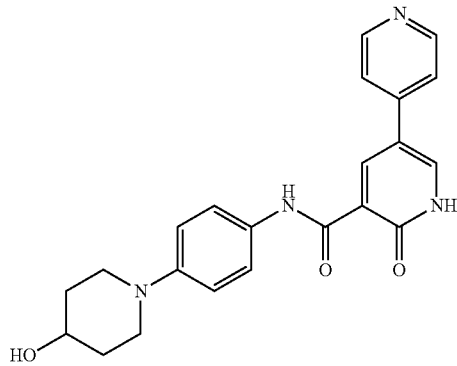
III-52

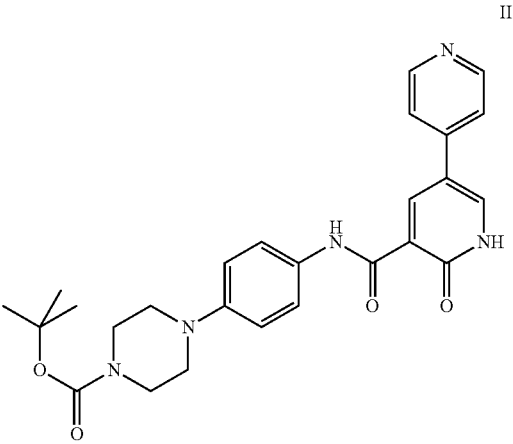
III-53

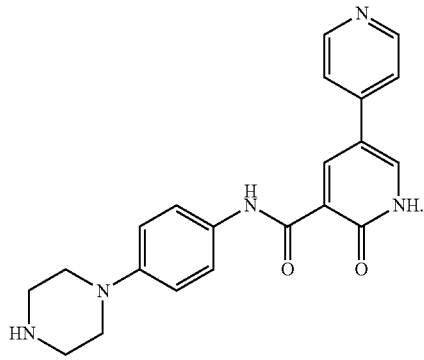
III-54

24. A pharmaceutical composition comprising a compound according to claim 1, and a pharmaceutically acceptable carrier, adjuvant, or vehicle.

25. A process for preparing a compound of formula I,

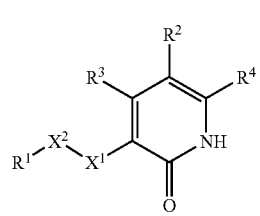
Formula I comprising reacting a compound of formula 22 with a compound $R^2$—X, wherein X is an appropriate leaving group to provide a compound of formula 23:

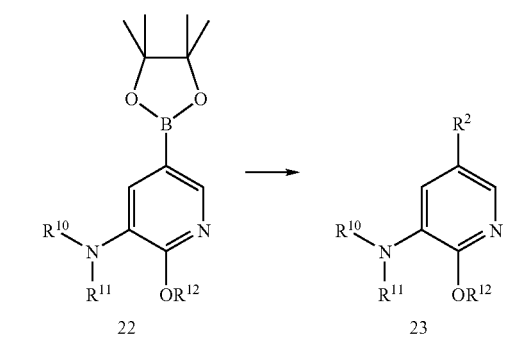

wherein:
$R^{10}$ is an amino protective group;
$R^{11}$ is H or $C_{1-6}$ alkyl or $R^{10}$ and $R^{11}$ together with the nitrogen atom to which they are bound form an amine protective group;
$R^{12}$ is a hydroxyl protecting group; and
$R^2$, $J^R$, and $R^o$ are as defined according to claim 1.

* * * * *